US011774442B2

(12) United States Patent
Spoonamore et al.

(10) Patent No.: US 11,774,442 B2
(45) Date of Patent: Oct. 3, 2023

(54) MOLECULE SENSOR SYSTEMS

(71) Applicant: enEvolv, Inc., Medford, MA (US)

(72) Inventors: James E. Spoonamore, Medford, MA (US); Noah D. Taylor, Medford, MA (US); Kristin J. Adolfsen, Medford, MA (US); Matthew R. Dunn, Medford, MA (US); Ilan N. Wapinski, Medford, MA (US); Jay H. Konieczka, Medford, MA (US)

(73) Assignee: enEvolv, Inc., Medford, MA (US)

( * ) Notice: Subject to any disclaimer, the term of this patent is extended or adjusted under 35 U.S.C. 154(b) by 1267 days.

(21) Appl. No.: 16/325,650

(22) PCT Filed: Aug. 15, 2017

(86) PCT No.: PCT/US2017/047012
§ 371 (c)(1),
(2) Date: Feb. 14, 2019

(87) PCT Pub. No.: WO2018/035159
PCT Pub. Date: Feb. 22, 2018

(65) Prior Publication Data
US 2019/0204303 A1 Jul. 4, 2019

Related U.S. Application Data

(60) Provisional application No. 62/379,002, filed on Aug. 24, 2016, provisional application No. 62/378,999, filed on Aug. 24, 2016, provisional application No. 62/375,305, filed on Aug. 15, 2016, provisional application No. 62/375,301, filed on Aug. 15, 2016.

(51) Int. Cl.
*G01N 33/531* (2006.01)
*C07K 14/195* (2006.01)
*G01N 33/53* (2006.01)
*C07K 14/00* (2006.01)
*C12N 15/00* (2006.01)
*G01N 33/68* (2006.01)
*G16B 15/30* (2019.01)
*G16B 35/20* (2019.01)
*C12N 15/63* (2006.01)
*G01N 33/50* (2006.01)
*C12N 15/64* (2006.01)
*G16B 15/00* (2019.01)

(52) U.S. Cl.
CPC ........... *G01N 33/531* (2013.01); *C07K 14/00* (2013.01); *C07K 14/195* (2013.01); *C12N 15/00* (2013.01); *C12N 15/635* (2013.01); *C12N 15/64* (2013.01); *G01N 33/5014* (2013.01); *G01N 33/5308* (2013.01); *G01N 33/68* (2013.01); *G16B 15/30* (2019.02); *G16B 35/20* (2019.02); *G16B 15/00* (2019.02)

(58) Field of Classification Search
CPC .................................................. G01N 33/531
See application file for complete search history.

(56) References Cited

U.S. PATENT DOCUMENTS

| 7,476,500 | B1 | 1/2009 | Liu et al. |
| 7,968,287 | B2 | 6/2011 | Griffiths et al. |
| 8,552,169 | B2 | 10/2013 | Dietrich et al. |
| 8,652,804 | B2 | 2/2014 | Dietrich et al. |
| 8,871,444 | B2 | 10/2014 | Griffiths et al. |
| 9,029,083 | B2 | 5/2015 | Griffiths et al. |
| 9,186,643 | B2 | 11/2015 | Griffiths et al. |
| 9,721,061 | B2 | 8/2017 | Raman et al. |
| 9,919,277 | B2 | 3/2018 | Griffiths et al. |
| 9,925,501 | B2 | 3/2018 | Griffiths et al. |
| 2003/0186281 | A1* | 10/2003 | Hillen ............... C07K 14/21 435/320.1 |
| 2009/0263853 | A1 | 10/2009 | Liu et al. |
| 2011/0287485 | A1 | 11/2011 | Bowers et al. |
| 2016/0202256 | A1 | 7/2016 | Church et al. |

FOREIGN PATENT DOCUMENTS

| WO | WO 02/074978 A2 | 9/2002 |
| WO | WO 2008/052303 A2 | 5/2008 |
| WO | WO 2008/303475 A3 | 8/2008 |
| WO | WO 2034/358594 A3 | 10/2014 |
| WO | WO 2035/037866 A3 | 2/2015 |
| WO | WO 2035/327242 A3 | 8/2016 |
| WO | WO 2036/368382 A3 | 10/2016 |

OTHER PUBLICATIONS

Wissmann et al. (Genetics Jun. 1991 128: 225-232) (Year: 1991).*
Hecht et al. (J. Bacteriology Feb. 1993 175: 1206-1210) (Year: 1993).*
Muller et al. (Nature Structural Biology Aug. 8, 1995 2(8): 693-703) (Year: 1995).*
Davis, et al., "Study of PcaV from Streptomyces coelicolor yields new insights into ligand-responsive MarR family transcription factors," Nucleic Acids Res. vol. 14, No. 6, pp. 3888-3900, Feb. 2013.
International Search Report & Written Opinion, PCT Appl. No. PCT/US17/47012, dated Dec. 22, 2017, 15 pages.
Taylor, et al.,"Engineering an allosteric transcription factor to respond to new ligands," Nature Methods, vol. 13, No. 2, pp. 177-183, Feb. 2016.
UNIPROT Accession Q9XAM6 Putative Transcriptional Regulator [Streptomyces coelicolor] [online], 4 pages, Nov. 1, 1999.
Georgi, et al., "On-chip automation of cell-free protein synthesis: new opportunities due to a novel reaction mode," Lab Chip 16 (2):269-281, Jan. 2016.
Glass, et al., "The coregulatory exchange in transcriptional functions of nuclear receptors," Genes Dev., vol. 14, No. 2, pp. 121-141, Jan. 15, 2000.

(Continued)

Primary Examiner — Peter J Reddig
(74) Attorney, Agent, or Firm — Morgan, Lewis & Bockius LLP

(57) ABSTRACT

The present described inventions relate, inter alia, to methods and compositions that provide for improved detection of target molecules.

9 Claims, 31 Drawing Sheets
Specification includes a Sequence Listing.

(56) References Cited

OTHER PUBLICATIONS

Gupta, et al., "Dynamic regulation of metabolic flux in engineered bacteria using a pathway—Independent quorum-sensing circuit," Nat. Bioteclmol, 35, 273-279 (2017).

Laskowski, et al., "The structural basis of allosteric regulation in proteins," FEBS Letters, vol. 583, No. 11, pp. 1692-1698, Jun. 2009.

Nielsen, et al, "Genetic circuit design automation," Science 352, aac7341 (2016).

Rogers, et al., "Biosensor-based engineering of biosynthetic pathways," Curr. Opin. Bioteclmol. 42, 84-91 (2016).

Strickland, et al., "Light-activated DNA binding in a designed allosteric protein," Proc Natl Acad Sci USA, vol. 105, No. 31, pp. 10709-10714, Aug. 2008.

Zhang, et al., "Design of a dynamic sensor—regulator system for production of chemicals and fuels derived from fatty acids," Nat. Biotechnol. 30, 354-359 (2012).

\* cited by examiner

```
gcatcaaattaagcagaggccatcctgacggatggccttttgcgtttctacaaactctgctagcaagtaaggccgactTCGACATTTATCCCTTGCGGC
                                                                          rrnB terminator  Automatically imported      Untitled      kosuri p49 partial cgtagtttaattcgtcttccggtaggactgcctaccggaaaaacgcaaagatgtttgagacgatcgttcattccggctgAGCTGTAAATAGGAACGCCG GATATAATGTGTGGAATCCTTATAGACCGATCGCACGGTCTATAACCATTATCTTAATTCTAGCGGGGAAGTTTCATatgctaaggtgaagaact
kosuri p49 partial     QacR operator                                                   kosuri-R90

CTATATTACACACCTATGAGGAATATCTGGCTAGCGTGCCAGATATTGGTAATAGAATTAGATCGCCCCTTCCAAAGTATacgcattccacttcttga
                                                                                                sfGFP
```

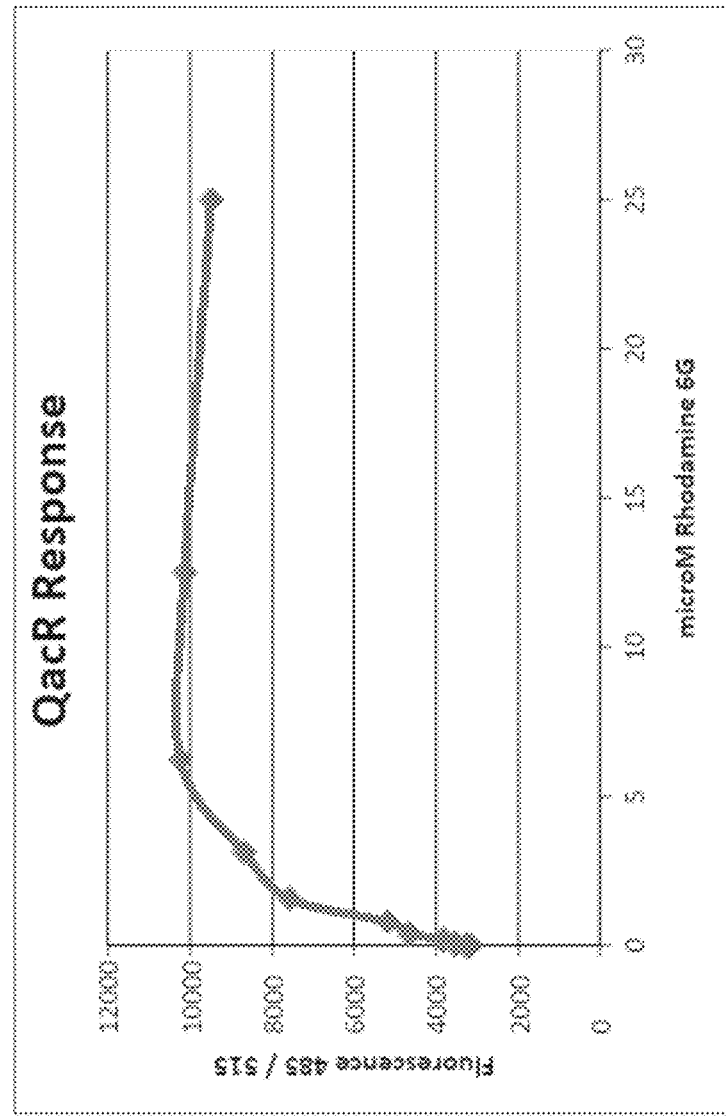

```
gcatcaaattaagcagagaaggccatcctgacggatggccttttgcgtttctacaaactctgtagcaagtaaggccgactGGACATTTATCCCTTGCGGGC cgtagttaattcgtctccggtagactgcctaccggaaaaacgcaaagatgttttgagacgatcgttcattcggctgAGCTGTAAATAGGAACGCCG
                              rrnB terminator Automatically imported        Untitled          Kosuri p49 partial GATATAATGTGTGGAATacgtcatcatgcccttgacccttggaacacagtattagccaATCTTAATTTACGGGGAAGTTTCATatgcgtaaagtgaagaactg CTATATTACACACCTTAtgcagtagtaccgggactggaacctttgtcataatcggtTAGAATTAGAATAtacgcattccacttcttgac
    Kosuri p49 partial        CviR operator            Kosuri-R90                 sfGFP
```

FIG. 6

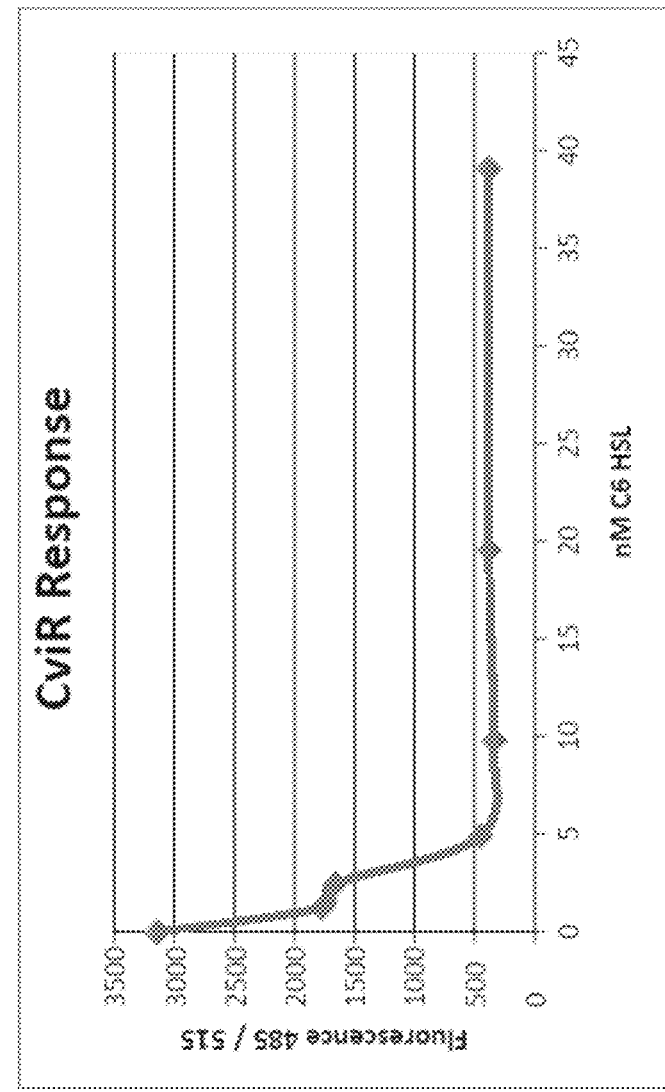

FIG. 7

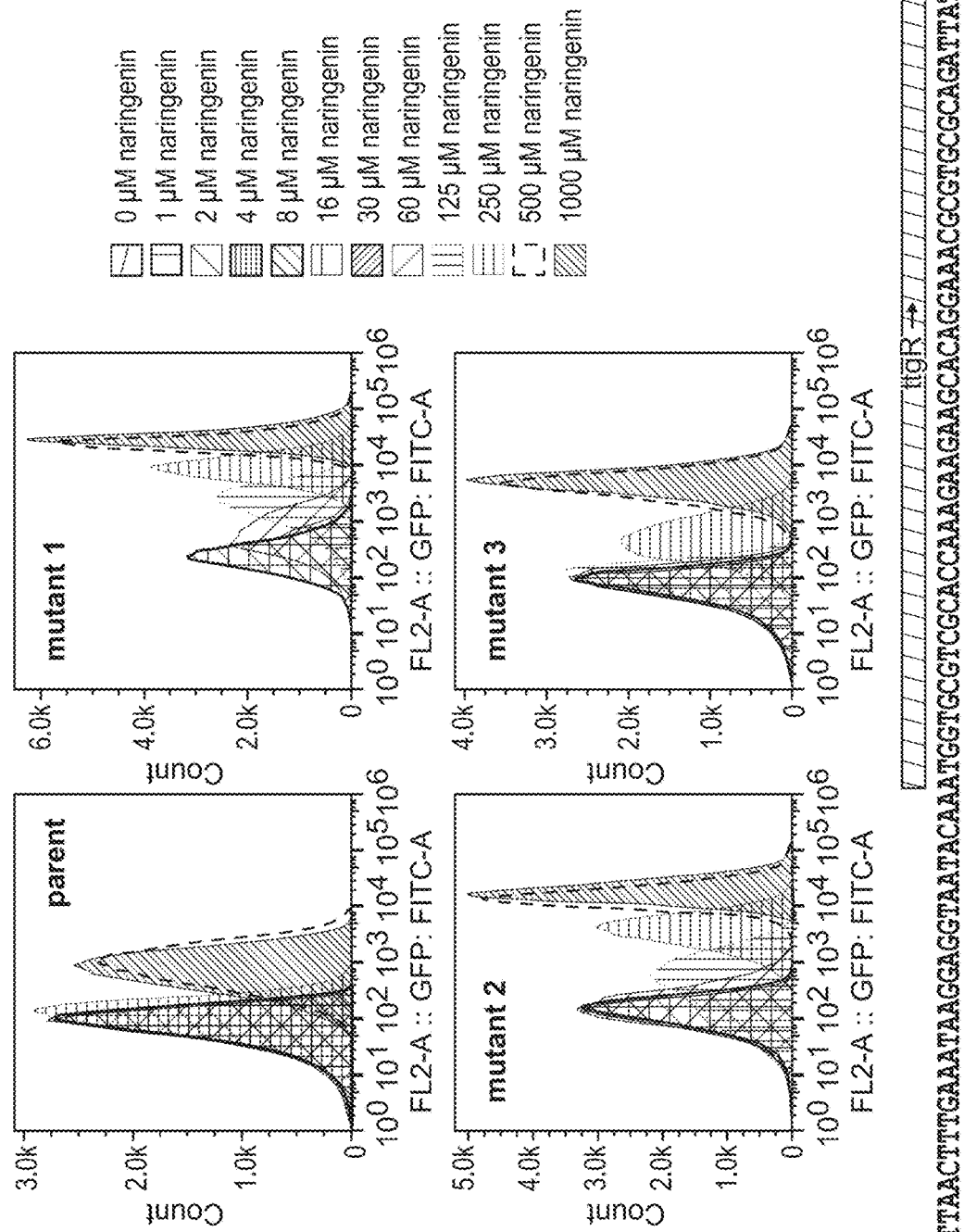

FIG. 24A

| | | | |
|---|---|---|---|
| EB463 | 1 | MSRLCKSKVINSALELLNEVGIEGLTTRKLAQKLGVEQPTLYWHVKNKRA | 50 |
| JE9 | 1 | MSRLCKSKVINSALELLNEVGIEGLTTRKLAQKLGVEQPTLYWHVKNKRA | 50 |
| EB463 | 51 | LLDALAIEMLDRHHTHFCPLEGESWQDFLRNNAKSFRCALLSHRDGAKVH | 100 |
| JE9 | 51 | LLDALAIEMLDRHHTHFCPLEGESWQDFLRNNAKSFRCALLSHRDGAKVH | 100 |
| EB463 | 101 | LGTRPTEKQYETLENQLAFLCQQGFSLENALYALSAVGHFTLGCVLEDQE | 150 |
| JE9 | 101 | LGTRPTEKQYETLENQLAFLCQQGFSLENALYALSAVGHFTLGCVLEDQE | 150 |
| EB463 | 151 | HQVAKEERETPTTQSHPPLLRQAIELFDHQGAEPAFLFGLELLIC------LLLIVCRHYYD | 195 |
| JE9 | 151 | HQVVKKKGK--------------------------------H------LLLIVCRHYYD | 171 |
| EB463 | 196 | GLEKQLKCESGS------------------------------------ | 267 |
| JE9 | 172 | KLSNYLITKVQSQPTYSALN-SYAD*KNNLNVKVGLNKRLKN* | 214 |

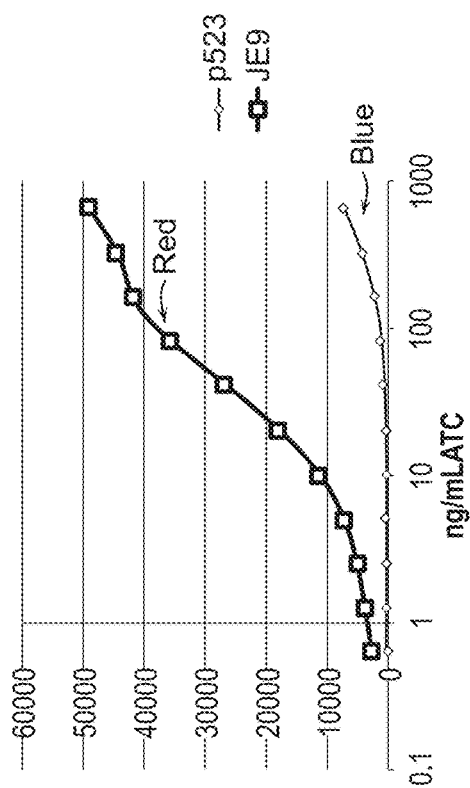
FIG. 24B
FIG. 24C
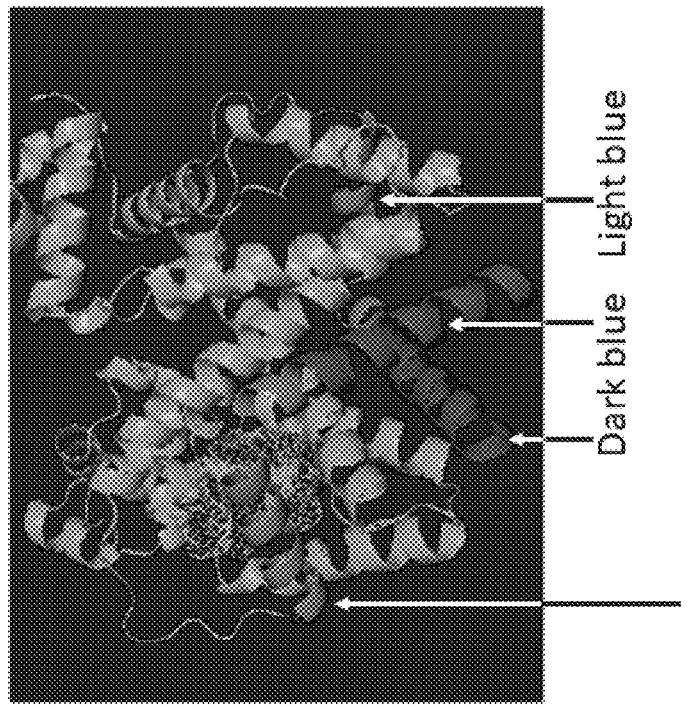
FIG. 25

```
           151
           LDVSDQTPIN SIIFSHEDGT RLGVEHLVAL GHQQIALLAG PLSSVSARLR
    TKN41  .......... .....T..A. .......... ........S. H....M....
    TKN87  NNT.N..... ..G..Q..A. .......... .......... ..........
```

```
            161
            SIIFSHEDGT RLGVEHLVAL GHQQIALLAG PLSSVSARLR
STL34       ..T.....EA .......... .......... N....GS...
```

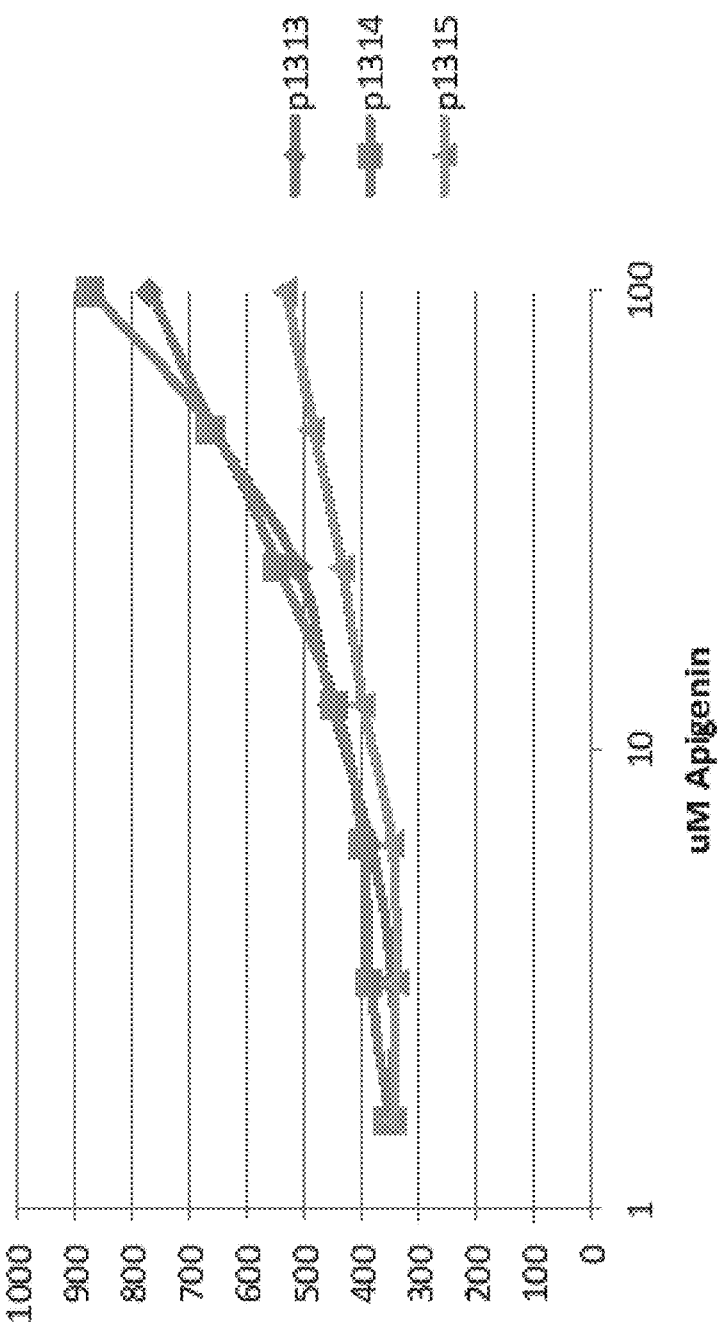

FIGURE 37
A
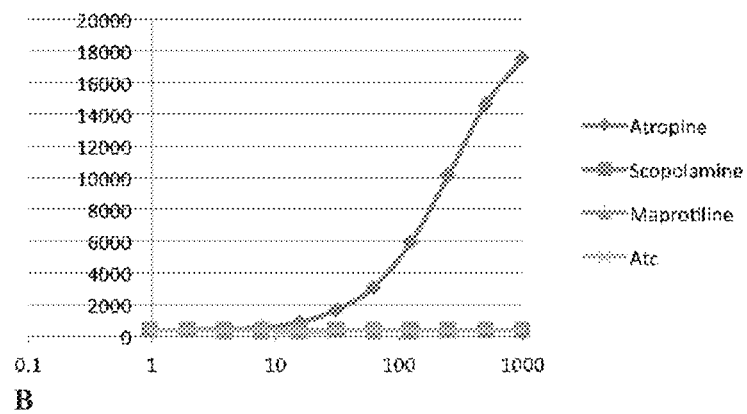
B
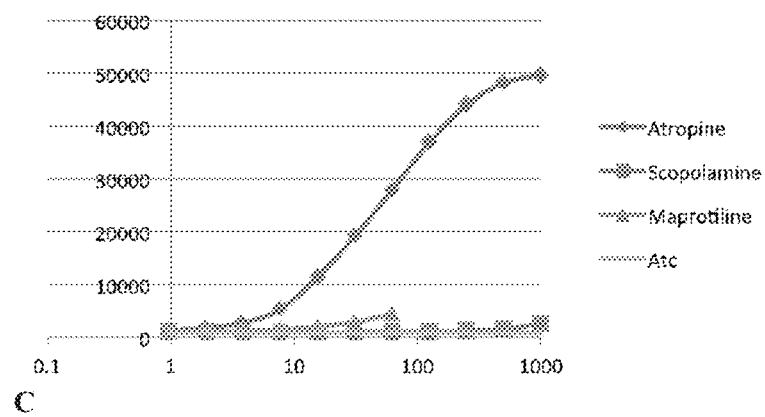
C
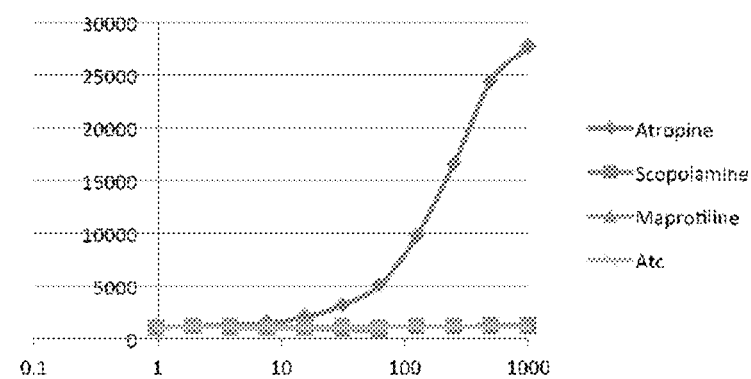

p1057 LB-carb p1057 LB p1057 + p674 LB Kan p1057 + p1174 LB Kan p1174 LB Kan p1057 – HERS, GFP, AmpR
p674 – RFP, KanR
p1174 – HE, RFP, KanR ~200,000x reduction in carb resistant plasmid

MOLECULE SENSOR SYSTEMS

CROSS-REFERENCE TO RELATED APPLICATIONS

This application claims the benefit of U.S. Provisional Application Nos. 62/375,305, filed Aug. 15, 2016; 62/375,301, filed Aug. 15, 2016; 62/378,999, filed Aug. 24, 2016; and 62/379,002, filed Aug. 24, 2016, the contents of which are hereby incorporated by reference herein in their entirety.

GOVERNMENT INTEREST

This invention was made with government support under Contract No. D16PC00132 and Contract No. D15PC00035, each awarded by the Defense Advanced Research Projects Agency (DARPA). The government has certain rights in the invention.

SEQUENCE LISTING SUBMISSION VIA EFS-WEB

The instant application contains a Sequence Listing which has been submitted in ASCII format via EFS-Web and is hereby incorporated by reference in its entirety. Said ASCII copy, created on Mar. 20, 2023 is named "ENV-005US_Sequence Listing_ST25.txt" and is 114,688 bytes in size.

FIELD

The present described inventions relate, inter alia, to methods and compositions that provide for allosteric sensor proteins.

BACKGROUND

A key objective of synthetic biology is the efficient production of high value target molecules. But, a significant unsolved bottleneck in the bioengineering design-build-test cycle is in the test phase due to screening limitations. One possible solution to this bottleneck is the use of molecular sensors. Indeed, sensors that recognize industrially important molecules are rapidly becoming part of metabolic engineering strategies to improve enzymatic bioproduction and detection. However, coupling a response to the detection of a specific target is an engineering challenge in itself.

The use of bacterial allosteric transcription factors (aTFs)—single proteins that directly couple the recognition of a small molecule to a transcriptional output—has been proposed (Taylor, et al. Nat. Methods 13(2): 177). Allostery is a common feature of proteins, in which the behavior at an 'active' site is altered by binding of an effector to a second or 'allosteric' site, often quite distant from the first (about 10A or more). The protein's conformational change caused by effector binding modulates its affinity for a specific operator DNA sequence, which alters gene expression by up to 5000-fold. Any strategy to engineer aTF sensors for new molecular recognition engineers both the sensing and actuation functions that are needed for a sensing device to operate within a cell. This makes aTF sensors an exciting paradigm to address the sense-and-respond challenge that is central to many applications of synthetic biology in a cell.

As there is a desire for the production and detection of expanded diversities of target molecules, there is a need for improved compositions and methods for sensing target molecules.

BRIEF DESCRIPTION OF THE FIGURES

Figure 1:
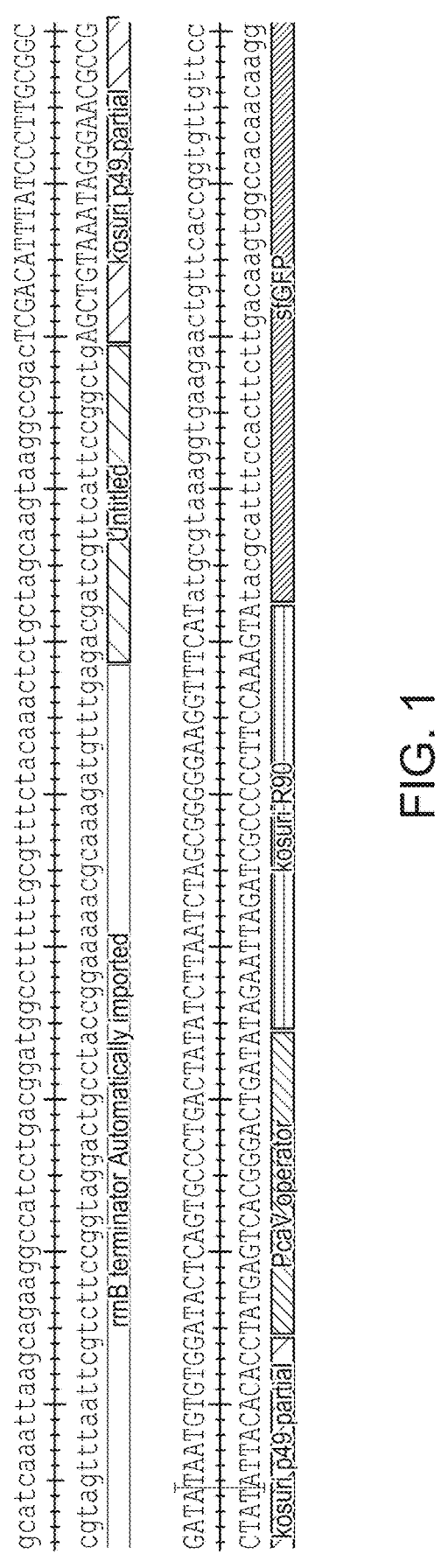

FIG. 1 shows an annotated PcaV synthetic promoter operator sequence (SEQ ID NO: 1 and SEQ ID NO: 84).

FIG. 4 shows an annotated QacR synthetic promoter operator sequence (SEQ ID NO: 2 and SEQ ID NO: 85).

FIG. 5 shows a dose response of QacR to rhodamine 6G.

FIG. 6 shows an annotated CviR synthetic promoter operator sequence (SEQ ID NO: 3 and SEQ ID NO: 86).

FIG. 7 shows a dose response of CviR to C6 HSL.

FIG. 10 shows GFP distributions for the TtgR-GFP parent system and mutants 1, 2 and 3 from FIG. 9. Right shifting of curves indicates binding in the mutants.

FIG. 11 shows the ribosome binding site and start codon mutations used to modulate sensitivity of the TtgR-GFP sensor-reporter system to naringenin in FIG. 9 and FIG. 10 (top row is SEQ ID NO: 4, second row from top is SEQ ID NO: 5, third row from top is SEQ ID NO: 6, and bottom row is SEQ ID NO: 7).

FIG. 24 shows improvement of TetR sensitivity and response level through deletion of a portion of the gene. Panel A shows an alignment of wild type (EB463) and truncated (JE9) TetR. Panel B highlights regions which are mutated (light blue) or deleted (dark blue) on a structural model of the wild type protein. Panel C shows the dose response of the truncated (red) and wild type (blue) TetRs to ATc. EB463 is SEQ ID NO: 8 and JE9 is SEQ ID NO: 9.

FIG. 25 shows region of TtgR mutated to sense apigenin (SEQ ID NO: 79, SEQ ID NO: 80, and SEQ ID NO: 81, from top to bottom).

FIG. 32 shows dose response of 3 TetR apigenin sensors.

FIG. 33 shows the region of TetR mutated to sense resveratrol (top row is SEQ ID NO: 16, p816 is SEQ ID NO: 17, p815 is SEQ ID NO: 18, p818 is SEQ ID NO: 19).

FIG. 37 shows molecular selectivity of TetR atropine sensors to atropine, scopolamine, maprotiline, and ATc (panels A, B, and C).

SUMMARY

Figure 2:
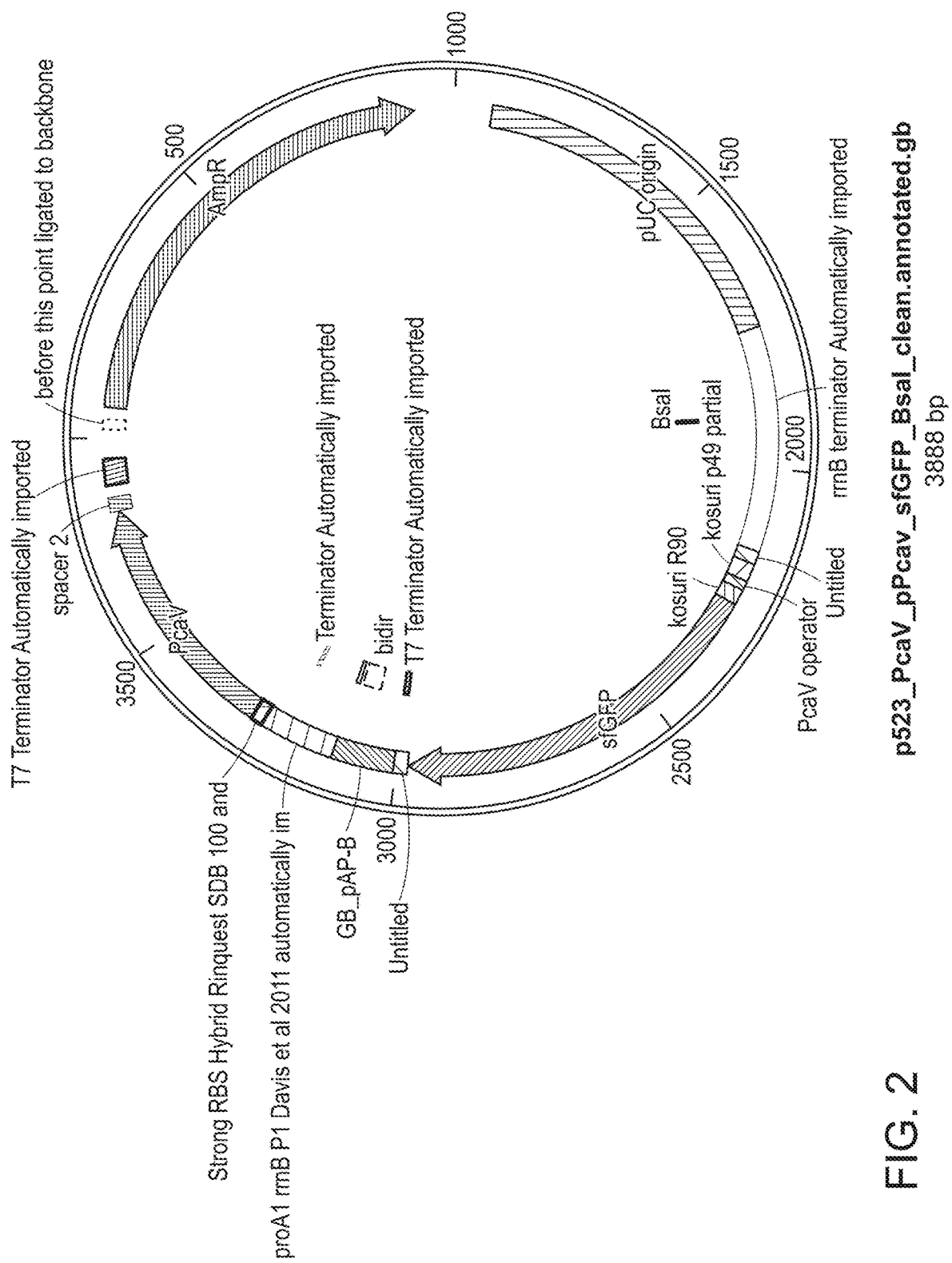
FIG. 2 shows a plasmid with GFP expression under control of PcaV.
Figure 3:
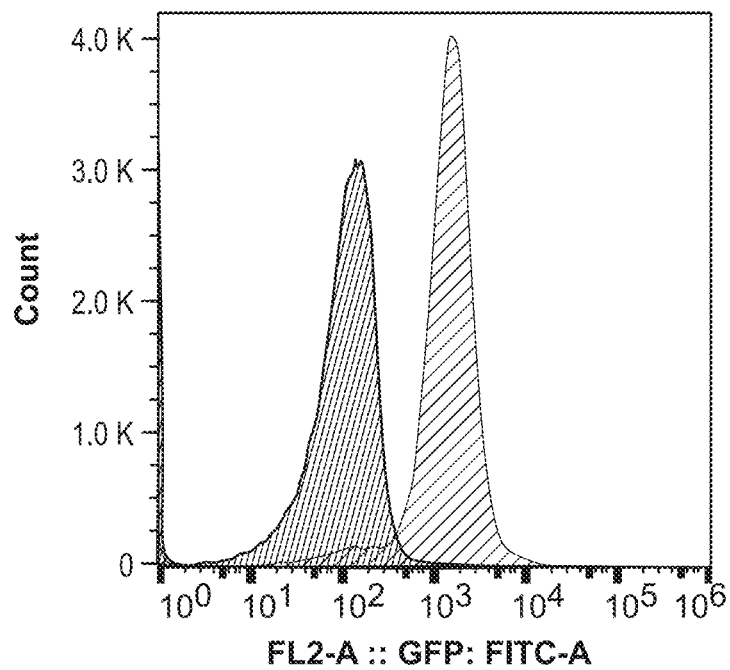
FIG. 3 shows a histogram overlay of FACS data showing GFP expression from E. coli harboring the PcaV plasmid grown without (left side) and with 1 mM 3,4-dihydroxybenzoic acid (right side) supplemented in the growth medium.

Accordingly, in general, methods and compositions which improve the detection and/or production of target molecules in cells using engineered protein sensors and/or switches, such as engineered aTFs, are provided.

In one aspect, the present invention relates to compositions and methods for making an engineered protein sensor and/or switch, e.g. from an allosteric protein, e.g. a transcription factor, that binds to and allows detection of a target molecule.

In various embodiments, there is provided a method of making an allosteric DNA-binding protein sensor and/or switch which binds to a target molecule, comprising (a) designing a candidate allosteric DNA-binding protein sensor and/or switch, the DNA-binding protein sensor and/or switch being designed for an ability to bind a target molecule and the designing optionally being in silico; (b) providing a host cell with a nucleic acid encoding the candidate allosteric DNA-binding protein sensor and/or switch and a reporter gene system and selecting for cells comprising a candidate allosteric DNA-binding protein sensor and/or switch and a reporter gene system; and (c) interrogating cells comprising a candidate allosteric DNA-binding protein sensor and/or switch and a reporter gene system for binding to the target molecule.

In some embodiments, the engineered protein sensor and/or switch, such as an aTF, detects target molecule binding via the production of a detectable reporter. For example, in some embodiments, the engineered protein sensor and/or switch, such as an aTF, is contacted with a target molecule and a reporter is generated in the cells. In other embodiments, a split reporter is used.

In some aspects, there is provided a method for making, and optionally isolating, a protein sensor and/or switch, e.g. an allosteric DNA-binding protein, e.g. an aTF, that binds to a target molecule that induces a conformation change comprising designing in silico candidate allosteric DNA-binding proteins having a binding pocket for a target molecule; providing nucleic acid sequences encoding the designed candidate protein sensor and/or switch, e.g. an allosteric DNA-binding protein, e.g. an aTF; introducing the nucleic acid sequences into host cells and expressing the designed candidate allosteric DNA-binding proteins; determining whether the designed candidate protein sensor and/or switch, e.g. an allosteric DNA-binding protein, e.g. an aTF, binds to DNA and inhibits expression of a gene by using negative selection to identify a first host cell population where the designed candidate protein sensor and/or switch, e.g. an allosteric DNA-binding protein, e.g. an aTF, has bound to DNA and inhibit expression of the gene; and determining whether the designed candidate protein sensor and/or switch, e.g. an allosteric DNA-binding protein, e.g.

an aTF, in the first host cell population binds to the target molecule using positive selection to identify a second host cell population where the designed candidate protein sensor and/or switch, e.g. an allosteric DNA-binding protein, e.g. an aTF, has bound to the target molecule.

In some embodiments, there is provided selection for cells, optionally in series, for cells which the designed candidate protein sensor and/or switch, e.g. an allosteric DNA-binding protein, e.g. an aTF, has bound to target DNA and/or the target molecule.

In certain embodiments, methods of negatively selecting a cell expressing a designed candidate protein sensor and/or switch that does not undergo an allosteric conformational change and/or that undergoes an undesired allosteric conformational change upon target binding are provided. In other embodiments, methods of positively selecting a microorganism expressing a designed candidate protein sensor and/or switch that undergoes an allosteric conformational change and/or binds a target molecule are provided.

In various embodiments, the allosteric DNA-binding protein sensor and/or switch finds use in a method for engineering a cell to produce a target molecule, for instance by engineering the cell to produce a target molecule and a DNA-binding protein sensor and/or switch that responds to the target molecule. For instance, the invention allows for selection of desired target molecule-producing cells based on the activity of the DNA-binding protein sensor and/or switch described herein.

In another aspect, the present invention relates to compositions and methods for detecting a target molecule using an engineered protein sensor and/or switch, such as an aTF as described herein.

DETAILED DESCRIPTION

The present invention is based, in part, on the surprising discovery that engineered protein sensors and/or switches, such as aTFs, can be designed to bind and detect a target molecule, including instances when the target molecule is distinct from the natural cognate ligand of the protein sensor and/or switch. Accordingly, the present methods allow for the development of a variety of engineered protein sensors and/or switches and the interrogation of a wide variety of target molecules.

In various embodiments, there is provided a method of making an allosteric DNA-binding protein sensor and/or switch which binds to a target molecule, comprising (a) designing a candidate allosteric DNA-binding protein sensor and/or switch, the DNA-binding protein sensor and/or switch being designed for an ability to bind a target molecule and the designing optionally being performed in silico; (b) providing a host cell with a nucleic acid encoding the candidate allosteric DNA-binding protein sensor and/or switch and a reporter gene system and selecting for cells comprising a candidate allosteric DNA-binding protein sensor and/or switch and a reporter gene system; and (c) interrogating cells comprising a candidate allosteric DNA-binding protein sensor and/or switch and a reporter gene system for binding to the target molecule.

In some embodiments, the engineered protein sensor and/or switch, such as an aTF, detects target molecule binding via the production of a detectable reporter product (see, e.g., FIGS. 2, 3, 5, 7, 8, 14-23). For example, in some embodiments, the engineered protein sensor and/or switch, such as an aTF, is contacted with a target molecule and a reporter signal is generated in the cells.

As described more fully herein, in various embodiments, the engineered protein sensor and/or switch may be first designed from an existing aTF (sometimes referred to as a "chassis"), for instance using in silico methods described herein or known in the art; assembling nucleic acids encoding designed engineered protein sensor and/or switch; using various screening mechanisms to remove non-functional or poorly functioning designs (e.g. via toxin/antidote and/or reporter systems or sorting, as described herein or known in the art), positively selecting for a desired engineered protein sensor and/or switch (e.g. using the target molecule against which the engineered protein sensor and/or switch is engineered as described herein or known in the art), and various maturations (e.g. for sensing or switching activity and/or for a specific use). In various embodiments, any of steps, or all of them, are employed. An illustrative embodiment is shown in FIG. 12, panel A.

Figure 12:
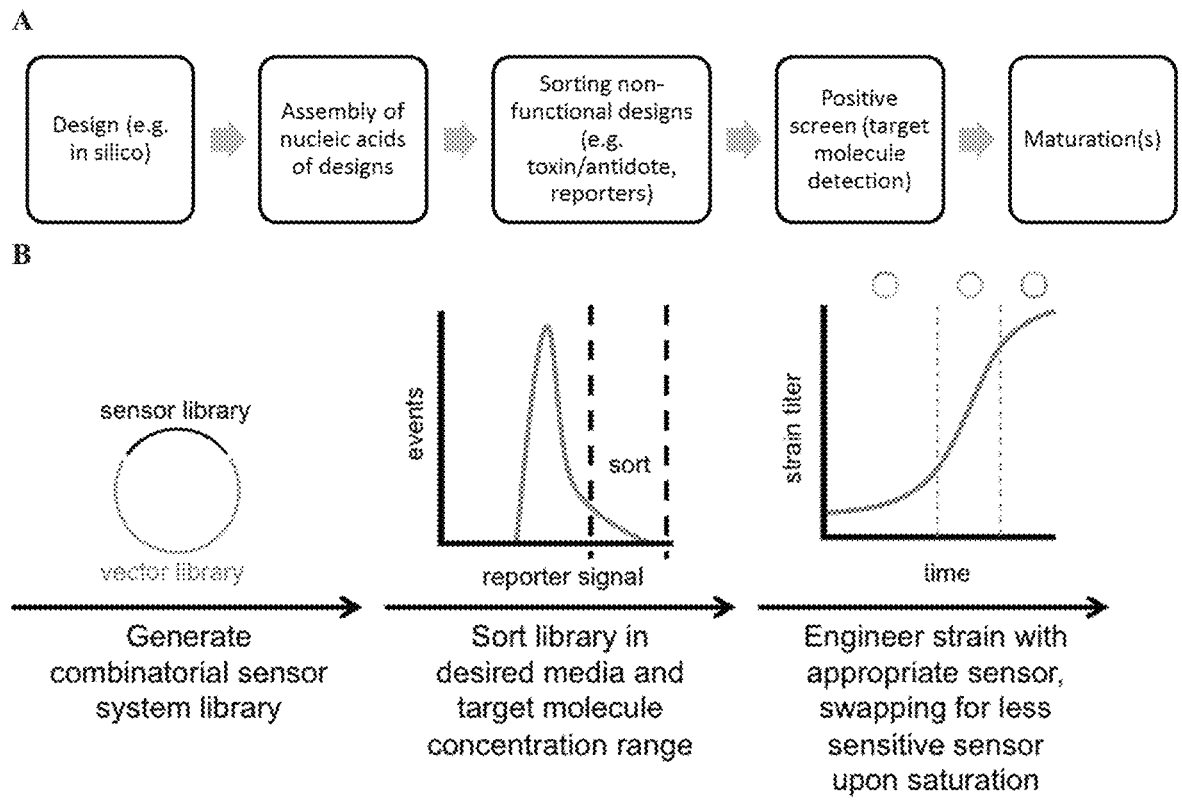
FIG. 12, panel A illustrates an embodiment of creating a sensor that responds to a target molecule; panel B shows another embodiment involving the sensor-reporter screening platform for the identification and use of sensor-reporter variants in screening production strains under desired conditions.

Further, as shown in the illustrative embodiment of FIG. 12, panel B, the present invention, as described more fully herein, allows for use of the present engineered sensors and/or switches in the context of engineering a cell to produce a target molecule. For example, a cell comprising an engineered sensor and/or switch responsive to a target molecule may be manipulated, e.g. using whole genome techniques (e.g. MAP), plasmid-based techniques (e.g. to produce the target molecule, and the engineered sensor and/or switch responsive to a target molecule finds use in allowing for selection of cells that produce the target molecule at a desirable level. Or, in some embodiments, the cells may be first manipulated and the sensor and/or switch added later to a population of manipulated cells.

In both the context of making an engineered sensor and/or switch responsive to a target molecule, the present invention encompasses both positive and negative selection methods to generate the desired engineered sensor and/or switch response to a target molecule.

Further, in the context of making a cell that produces a target molecule, using an engineered sensor and/or switch responsive to a target molecule, the present invention encompasses both positive and negative selection methods, at the level of the sensors and/or cells, to generate the desired engineered sensor and/or switch response to a target molecule and/or cell that produces a target molecule at desired levels.

In some embodiments, the engineered protein sensor and/or switch, e.g. transcription factor, library members and reporter gene system reside on a single plasmid. In another embodiment, the transcription factor library resides on one plasmid while the reporter gene system resides on a second plasmid. By having two separate plasmids, the effective concentration of reporter gene to sensor library members may be adjusted to facilitate identification of active library members. This is useful where simply using higher versus lower promoter strength is not enough control, for instance.

Figure 18:
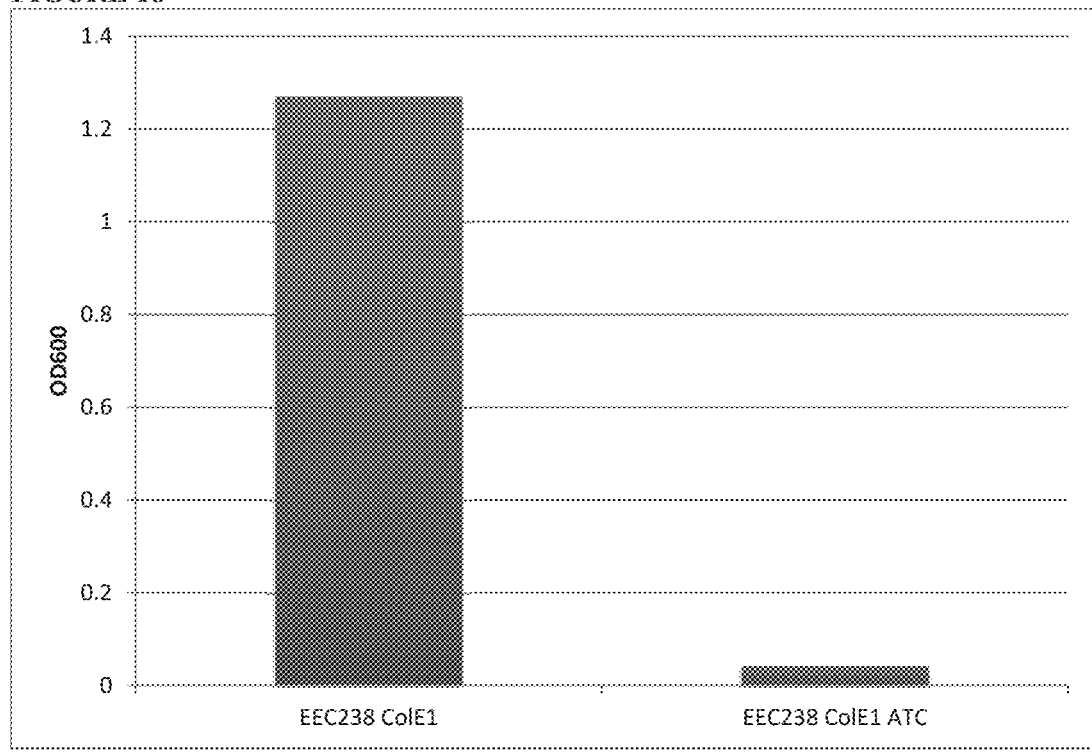
FIG. 18 shows TetR expressed off of a plasmid driving a genomically encoded selective marker (tolC).

In another embodiment, the reporter system and/or engineered protein sensor and/or switch is encoded in the host genome (see, e.g., FIG. 18).

In some aspects, there is provided a method for making, and optionally isolating, a protein sensor and/or switch, e.g. an allosteric DNA-binding protein, e.g. an aTF, that binds to a target molecule that induces a conformation change comprising designing in silico candidate allosteric DNA-binding proteins having a binding pocket for a target molecule, providing nucleic acid sequences encoding the designed candidate protein sensor and/or switch, e.g. an allosteric DNA-binding protein, e.g. an aTF; introducing the nucleic acid sequences into host cells and expressing the designed candidate allosteric DNA-binding proteins; determining whether the designed candidate protein sensor and/or switch, e.g. an allosteric DNA-binding protein, e.g. an aTF, binds to DNA and inhibits expression of a gene by using negative selection to identify a first host cell population where the designed candidate protein sensor and/or switch, e.g. an allosteric DNA-binding protein, e.g. an aTF, has bound to DNA and inhibit expression of the gene; and determining whether the designed candidate protein sensor and/or switch, e.g. an allosteric DNA-binding protein, e.g. an aTF, in the first host cell population binds to the target molecule using positive selection to identify a second host cell population where the designed candidate protein sensor and/or switch, e.g. an allosteric DNA-binding protein, e.g. an aTF, has bound to the target molecule.

In some aspects, the present invention allows for engineering or use of a protein sensor and/or switch for which the protein sensor and/or switch's natural promoter and/or operator does not function suitably in a host cell. In some embodiments, the invention provides transfer of a functional operator site from one organism to another. For instance, such transfer is applicable to the present sensor engineering and the use of an engineered sensor in a host cell (e.g. to detect production of a target molecule). In some embodiments, e.g. when deploying the present sensors (e.g. to detect production of a target molecule in a host cell), the present invention allows for the introduction of protein sensors and/or switches, e.g. aTFs, from a variety of organisms and the operation of the present sensing in a variety of host organisms, including those particularly desired for metabolic engineering, such as any of the host cells described herein.

An illustrative method to transfer a functional operator site from one organism to another, such organisms may be selected from the cells described herein, is to clone the intergenic region immediately upstream of a gene regulated by the protein sensor and/or switch, e.g. aTF, of interest immediately upstream of reporter gene that is carried in the desired host organism. This naïve approach assumes that the transcriptional promoter will also function in the host organism. If an active promoter is present, and no host repressors recognize the exogenous operator site once cloned, the reporter will be constitutively on until expression of the target regulator protein in a mode to bind its operator and repress the reporter signal. The basic approach has the advantage of, among others, not needing any information about the actual DNA sequence of the operator site but may suffer from the fact that the intergenic region cloned may have a promoter region incompatible with the new host organism.

To circumvent the problem of the host cell not being able to utilize the foreign promoter, an operator sequence may be cloned into a promoter region known to function in the host organism between the transcriptional promoter and ribosome binding site (RBS), or overlapping one or both of the promoter and/or RBS. Sometimes operator sequences are longer than the allowable sequence space between the promoter and RBS. In such cases the operator may be placed 5' or 3' to the promoter site. In some cases, the operator consists of two regions of DNA separated by some number of bases. In such cases, it may be advantageous to flank either or both the promoter and/or RBS site with the operator binding sequence.

Construction of synthetic promoter/operators allow the aTF to function in any organism for which the promoter/RBS paradigm is maintained, including eukaryotes such as yeast. This might comprise inserting an operator site, or a library of similar operator sites, into a promoter that functions in the new desired host organism, cloning the resulting promoter or promoters upstream of a reporter gene, and using the reporter gene to screen or select for promoters that allow the operator DNA site to functionally bind to the aTF. Depending on the expected mode of action of the aTF, this might yield promoters that become less active in the presence of the aTF (for repressor-mode aTFs) or more active in the presence of the aTF (for activator-mode aTFs). Optionally, in eukaryotes, the aTF may be expressed as a fusion with a nuclear localization signal and/or as a fusion with a known activator domain in the desired host organism (e.g. VP16 domain in S. cerevisiae).

In some embodiments, there is provided selection for cells, optionally in series, in which the designed candidate protein sensor and/or switch, e.g. an allosteric DNA-binding protein, e.g. an aTF, has bound to target DNA and/or the target molecule.

In some embodiments, the negative selection includes contacting the host cells with a toxin that is toxic to cells which express the gene (i.e. for which the gene is not repressed and/or the designed candidate protein sensor and/or switch has not bound to DNA, or has incorrectly bound to DNA, to inhibit expression of the gene). In various embodiments, the cell is optionally genetically modified to include DNA encoding an antidote to the toxin that is regulated by the protein sensor and/or switch. In some embodiments, the positive selection includes contacting the first host cell population with a toxin which is toxic to cells where the gene is not expressed, and the target molecule. In various embodiments, the positive selection includes detecting a detectable marker from, e.g., a reporter gene as described herein, that is expressed in cells in which designed the candidate protein sensor and/or switch has bound to DNA and is released when bound to the target molecule.

In certain embodiments, methods of negatively selecting a cell expressing a designed candidate protein sensor and/or switch that does not undergo an allosteric conformational change and/or that undergoes an incorrect allosteric conformational change upon target binding are provided. In other embodiments, methods of positively selecting a microorganism expressing a designed candidate protein sensor and/or switch that undergoes an allosteric conformational change and/or binds a target molecule are provided.

In some embodiments, a cell is genetically modified to include one or more exogenous nucleic acids encoding an antidote to a toxin. Toxin and antidote pairs are known to those of skill in the art and include, but are not limited to, SDS:tolC, kanamycin: kanamycin nucleotidyltransferase, chloramphenicol:chloramphenicol acyl tranferase, ampicillin:beta lactamase, tetracycline:tetracycline efflux pump tetA; analogous conditional toxins (enabling negative selection) known include but are not limited to: colicin:tolC, nickel chloride:tetracycline efflux pump tetA, 5-fluoroorotic acid:URA3. The transformed cell expresses the antidote under suitable conditions. The genes for production of any particular antidote are known to those of skill in the art. For example, the genes for the above antidotes are fully described in tetA (Postle et al. Nucleic Acid Research 1984 12(12)4849-4863, the contents of which are hereby incorporated by reference in their entirety), tolC (Fralick J. Bacteriol. 1996 178(19)5803-5805, the contents of which are hereby incorporated by reference in their entirety), Chloramphenicol acetyl tranfersase (Shaw et al. J. Bacteriol. 1970 104(3): 1095-1 105, the contents of which are hereby incorporated by reference in their entirety). Methods described herein can be used to insert the nucleic acids into the genome of the microorganism that are responsible for production of DNA-binding proteins or onto a plasmid to be maintained in the microorganism.

In some embodiments, the transformed, recombinant cell expresses a protein sensor and/or switch which regulates production of the antidote. When expressed, the protein sensor and/or switch prevents the cell from expressing the antidote gene, either by blocking the expression (repressor) or failing to activate the expression (activator) of the antidote unless the protein sensor and/or switch is bound by the target molecule, which leads to antidote expression by changing protein sensor and/or switch function. Several regulation mechanisms are possible. For a protein sensor and/or switch that is a repressor, the repressor protein may block transcription of the antidote gene by binding a region of DNA 5' to the antidote gene (or within the antidote gene sequence) unless the target molecule binds the repressor. For a protein sensor and/or switch that is an activator, the activator recruits RNA polymerase to a region of DNA 5' to the antidote gene only when the target molecule binds to the activator. For an attenuating protein sensor and/or switch, the protein sensor and/or switch is encoded in the 5' untranslated region of a repressor regulating the transcription of the antidote gene, and attenuates translation of this repressor when bound to the target molecule.

In some embodiments, the transformed, recombinant cell expresses a protein sensor and/or switch which regulates production of a metabolite required for growth, e.g. a cofactor, amino acid, or nucleotide, or a transporter for a required nutrient.

In some embodiments, the protein sensor and/or switch is used to control expression of one or more detectable markers in a microorganism, e.g. a reporter gene system, such as any of those described herein. In certain embodiments, the reporter is an expressed barcode sequence that is unique to each plasmid encoding a sensor gene library member, such that the abundance of each sensor library member can be ascertained by sequencing the expressed barcode sequences, once each sensor and barcode combination has been determined.

In certain embodiments, the reporter gene system is used in conjunction with toxin selection. In some embodiments, the reporter gene system is used as the only selection technique and cells are sorted with, e.g., a fluorescence activated cell sorting (FACS) apparatus or microbial colony picker (e.g., QPix), a microfluidics apparatus, optical tweezer, bead-based apparatus or the like, as described herein.

In another aspect, the present invention relates to compositions and methods for detecting a target molecule using an engineered protein sensor and/or switch, such as an aTF, as described herein. For instance, in some embodiments, the detection of a target molecule is in a cell, such as any of those described herein, that has been manipulated to produce the target molecule.

In various embodiments, the present invention allows for engineering a host cell to produce a target molecule and the target molecule is detected or detectable using one or more of the engineered protein sensor and/or switch. In various embodiments, cells are engineered with a multiplex genome engineering technique (e.g. Multiplexed Automated Genome Engineering (MAGE, see, e.g., Wang et al., Nature, 460:894-898 (2009); Church et al., U.S. Pat. No. 8,153,432, the contents of which are hereby incorporated by reference in their entireties), conjugative assembly genome engineering (CAGE, see, e.g., Isaacs, F. J. et al. Science 333, 348-353, the contents of which are hereby incorporated by reference in their entirety), a method involving a double-strand break (DSB) or single-strand break or nick which can be created by a site-specific nuclease such as a zinc-finger nuclease (ZFN) or TAL effector domain nuclease (TALEN) or BurrH binding domain (BuD)-derived nucleases, or CRISPR/Cas9 system with an engineered crRNA/tracrRNA (or synthetic guide RNA) to guide specific cleavage (see, e.g., U.S. Patent Publications 2003/0232410; 2005/0208489; 2005/0026157; 2005/0064474; 2006/0188987; 2009/0263900; 2009/0117617; 2010/0047805; 2011/0207221; 2011/0301073 and International Patent Publication WO 2007/014275, and Gaj, et al. *Trends in Biotechnology,* 31(7), 397-405 (2013), the contents of which are hereby incorporated by reference in their entireties, or utilizes the organism's native CRISPR system together with a recombinase (e.g. ssDNA recombinase system, which may include a single-stranded annealing protein (SSAP), such as the Lambda Red recombineering system (e.g., Beta protein) or RecET system (e.g., recT), or homologous system, including Rad52-like (of which Lambda Red Beta, Sak, and Erf are members), Rad51-like (e.g., Sak4), and Gp2.5-like, each with distinct sequence profiles and folds. Datta et al., PNAS USA, 105:1626-31 (2008); Lopes, A., *Nucleic Acids Research,* 38(12), 3952-3962, which are hereby incorporated by reference in their entireties, see also International Patent Publication WO/2015/017866, the contents of which are hereby incorporated by reference in its entirety), the disclosures of which are incorporated by reference in their entireties for all purposes)).

Figure 46:
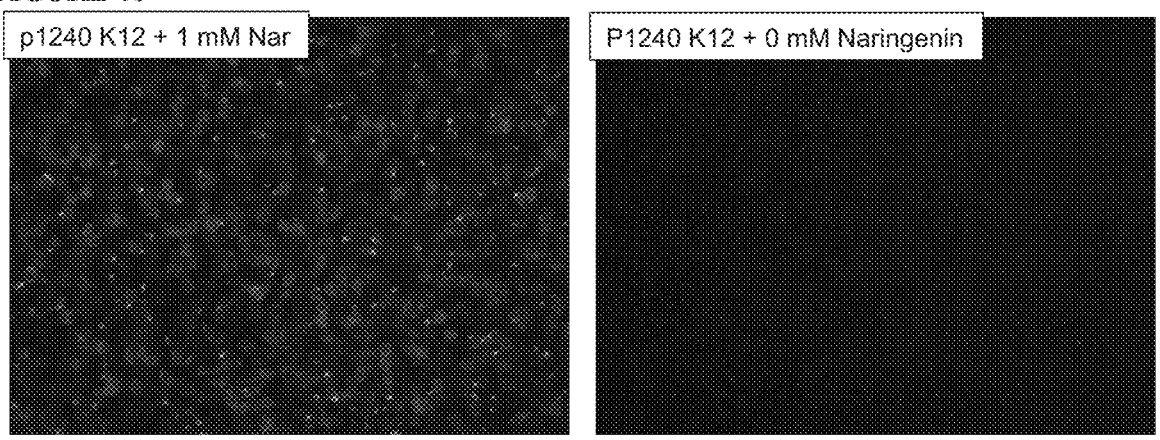
FIG. 46 shows encapsulated sensor strain reporting presence of naringenin through GFP.

In some embodiments, a cell or cells hosting the sensor system is coencaspulated with a metabolically engineered cell or cells, or "producing strain," having been engineered by one or more of the methods described herein, designed to produce the target molecule capable of being detected by the sensor system. This is useful, inter alia, if the producing strain constitutively exports the sensed molecule into its growth medium creating the case where a high producing and low producing strain both have the same intracellular concentration of the molecule of interest but the medium of the high producing strain has a greater concentration. In such cases, the detector strain may be used to discern high from low producers. In other embodiments, the present invention includes the use of multiple droplets containing whole or lysed cells from different hosts. For instance, in some embodiments, a first droplet comprises whole or lysed cells with an engineered sensor while a second droplet comprises whole or lysed cells, "producer strains", with the target molecule (e.g. host cells that are engineered to produce a target molecule as described elsewhere herein). For example, in some embodiments, the first droplet comprising whole or lysed cells with an engineered sensor is used to detect production of a target molecule in a different host (in the form of whole or lysed cells in a droplet). As such, inter alia, this permits detection of the target molecule at levels that are beyond what could be undertaken if the engineered sensor were present solely in the host cells that are engineered to produce a target molecule. In some embodiments transcription/translation of the sensor and/or the reporter it controls are driven by in vitro transcription and translation (IVTT), as described in Zubay. *Ann. Rev. Genet.* 1973.7: 267-287, the entire contents of which are hereby incorporated by reference in their entirety or TX-TL as described in Shin and Noireaux, *J Biol. Eng.* 4, 8 (2010) and US Patent Publication No. 2016/0002611, the entire contents of which are hereby incorporated by reference in their entireties. Microencapsulation of single producers, either harboring the sensor machinery or coencapsulated with sensor cells, is also a useful technique in cases where the molecule is highly diffusible across the cell membrane, making screening in batch liquid culture impossible (see, e.g., FIG. 46).

In some embodiments, the metabolically engineered cell or cells, or "producing strain," is grown on solid medium to spatially isolate each producer. This is useful if either the target molecule or any of its metabolic precursors is highly diffusible across the cell membrane. In some embodiments, the sensor system is harbored within the producing strain. In other embodiments, the sensor system is maintained within separate host cells. In some embodiments, growth of the sensor cells is induced by the target molecule (e.g. by inducing production of a toxin antidote, or by inducing production of a metabolite for which the sensor strain is auxotrophic, or by any other positive growth selection described herein or known in the art), such that the sensor cells grow only within the immediate vicinity of adequate target molecule producers. The magnitude of the sensor cell growth near producer colonies may report on their productivity. In other embodiments, motile sensor cells employ chemotaxis to move toward producer cells or producer cell colonies on or within solid growth medium.

In various embodiments, the engineered protein sensor and/or switch is an aTF, for instance a eukaryotic aTF. In various embodiments, engineered protein sensor and/or switch is an engineered version of a prokaryotic transcriptional regulator family such as a member of the LysR, AraC/XylS, TetR, LuxR, LacI, ArsR, MerR, AsnC, MarR, NtrC (EBP), OmpR, DeoR, Cold shock, GntR, and Crp families.

In various embodiments, engineered protein sensor and/or switch is an engineered version of a prokaryotic transcriptional regulator family such as a member of the AbrB, AlpA, AraC, ArgR, ArsR, AsnC, BetR, Bhl, CitT, CodY, ComK, Crl, Crp, CsoR, CtsR, DeoR, DnaA, DtxR, Ecf, FaeA, Fe_dep_repress, FeoC, Fis, FlhC, FlhD, Fur, GntR, GutM, Hns, HrcA, HxlR, IclR, KorB, LacI, LexA, Lsr2, LuxR, LysR, LytTR, MarR, MerR, MetJ, Mga, Mor, MtlR, NarL, NtrC, OmpR, PadR, Prd, PrrA, PucR, PuR, Rok, Ros_MucR, RpiR, RpoD, RpoN, Rrf2, RtcR, Sarp, SfsA, SinR, SorC, Spo0A, TetR, TrmB, TrpR, WhiB, Xre, YcbB, and YesN families.

In various embodiments, engineered protein sensor and/or switch is an engineered version of a member of the TetR family of receptors, such as AcrR, ActII, AmeR AmrR, ArpR, BpeR, EnvR E, EthR, HydR, IfeR, LanK, LfrR, LmrA, MtrR, Pip, PqrA, QacR, RifQ, RmrR, SimReg, SmeT, SrpR, TcmR, TetR, TtgR, TtgW, UrdK, VarR, YdeS, ArpA, Aur1B, BarA, CalR1, CprB, FarA, JadR, JadR2, MphB, NonG, PhlF, TylQ, VanT, TarA, TylP, BM1P1, Bm1P1, Bm3R1, ButR, CampR, CamR, CymR, DhaR, KstR, LexA-like, AcnR, PaaR, PsbI, ThlR, UidR, YDH1, BetI, McbR, MphR, PhaD, Q9ZF45, TtK, Yhgd or YixD, CasR, IcaR, LitR, LuxR, LuxT, OpaR, Orf2, SmcR, HapR, Ef0113, HlyIIR, BarB, ScbR, MmfR, AmtR, PsrA, and YjdC.

The engineered protein sensor and/or switch may be an engineered version of a two-component or hybrid two-component system that directly bind both a ligand and DNA or work through a protein cascade.

In various embodiments, the engineered protein sensor and/or switch is an aTF, for instance a eukaryotic aTF. In various embodiments, engineered protein sensor and/or switch is an engineered version of RovM (*Yersinia pseudotuberculosis*), HcaR (*Acinetobacter*), BlcR (*Agrobacterium tumefaciens*), HetR (*Anabaena* spp.), HetR (*Anabaena* spp.), DesR (*B. subtilis*), HyIIIR (*Bacillus cereus*), PlcR (*Bacillus cereus*), CcpA (*Bacillus megaterium*), YvoA (*Bacillus subtilis*), AhrR (*Bacillus subtilis*), MntR (*Bacillus subtilis*), GabR (*Bacillus subtilis*), SinR (*Bacillus subtilis*), CggR (*Bacillus subtilis*), FapR (*Bacillus subtilis*), OhrR (*Bacillus subtilis*), PurR (*Bacillus subtilis*), Rrf2 (*Bacillus subtilis*), BmrR (*Bacillus subtilis*), CcpN repressor (*Bacillus subtilis*), TreR (*Bacillus subtilis*), CodY (*Bacillus subtilis*), yfiR (*Bacillus subtilis*), OhrR (*Bacillus subtilis*), Rex (*Bacillus subtilis, Thermus thermophilus, Thermus aquaticus*), NprR (*Bacillus thuringiensis*), BtAraR (*Bacteroides thetaiotaomicron*), AraR (*Bacteroides thetaiotaomicron* VPI), DntR (*Burkholderia cepacia*), CmeR (*Camplylobacter jejuni*), CviR (*Chromobacterium violaceum*), TsaR (*Comamonas testosteroni*), CGL2612 (*Corynebacterium glatamicum*), ClgR (*Corynebacterium glutamicum*), LldR (CGL2915) (*Corynebacterium glutamicum*), NtcA (Cyanobacterium *Anabaena*), HucR (*Deinococcus radiodurans*), LacI (*E. coli*), PrgX (*Enterococcus faecalis*), NikR (*Helobacter pylori*), LmrR (*Lactococcus lactis*), CcpA (*Lactococcus lactis*), MtbCRP (*Mycobacterium tuberculosis*), EthR (*Mycobacterium tuberculosis*), MosR (*Mycobacterium tuberculosis*), PhoP (*Mycobacterium tuberculosis*), Rv1846c (*Mycobacterium tuberculosis*), EthR (*Mycobacterium tuberculosis*), LysR (*Neisseria meningitdis*), NMB0573/AsnC (*Neisseria meningitidis*), TetR-class H (*Pasteurella multocida*), MexR (*Pseudomonas aeruginosa*), DNR (*Pseudomonas aeruginosa*), PA01 (*Pseudomonas aeruginosa*), PA2196 (*Pseudomonas aeruginosa*), ttgR (*Pseudomonas putida*), Cra (*Pseudomonas putida*), QscR (*Psudemonas aeruginosa*), ActR (*S. coelicolor*), SC00520 (*S. coelicolor*), CprB (*S. coelicolor*), SlyA (*Salmonella enterica* SlyA), FapR (*Staphylococcus aureus*), QacR (*Staphylococcus aureus*), SarZ (*Staphylococcus aureus*), IcaR (*Staphylococcus aureus*), LcaR (*Staphylococcus epidermidis*), SM ET (*Stenotrophomonas maltophilia*), PcaV (SC06704) (*Streptomyces coelicolor*), SC04008 (*Streptomyces coelicolor*), NdgR (*Streptomyces coelicolor*), CprB (*Streptomyces coelicolor*), SC00253 (*Streptomyces coelicolor*), TetR family (*Streptomyces coelicolor*), SC00520 (*Streptomyces coelicolor*), SC04942 (*Streptomyces coelicolor*), SC04313 (*Streptomyces coelicolor*), TetR family (*Streptomyces coelicolor*), SC07222 (*Streptomyces coelicolor*), SC03205 (*Streptomyces coelicolor*), SC03201 (*Streptomyces coelicolor*), ST1710 (*Sulfolobus tokodaii* ST1710), HrcA (*Thermotoga maritime*), TM1030 (*Thermotoga maritima*), tm1171 (*thermotoga* maritime), Id R (*Thermotoga maritima*), CarH (*Thermus thermophilus*), FadR (*Vibrio cholerae*), SmcR (*Vibrio vulnificus*), and RovA (*Yersinia pestis*).

In various embodiments, engineered protein sensor and/or switch is an engineered version of MphR, AlkS, AlkR, CdaR, BenM, RUNX1, MarR, AphA, Pex, CatM, AtzR, CatR, ClcR, CbbR, CysB, CbnR, OxyR, OccR, and CrgA.

In various embodiments, engineered protein sensor and/or switch is an engineered version of an *E. coli* TF, such as ArcA, AtoC, BaeR, BasR, CitB, CpxR, CreB, CusR, DcuR, DpiA, EvgA, KdpE, NarL, NarP, OmpR, PhoB, PhoP, QseB, RcsB, RstA, TorR, UhpA, UvrY, YedW, YehT, YfhK, YgiX, YpdB, ZraR, RssB, AgaR, AIIR (ybbU), ArsR, AscG, BetI, BglJ, CadC, CaiF, CelD, CueR, CynR, ExuR, FecR, FucR, Fur, GatR, GutM, GutR (SrlR), ModE, MtlR, NagC, NanR (yhcK), NhaR, PhnF, PutA, RbsR, RhaR, RhaS, RpiR (AlsR), SdiA, UidR, XapR, XylR, ZntR, AllS (ybbS), Arac, ArgR, AsnC, CysB, CytR, DsdC, GalR, GalS, GcvA, GcvR, GlcC, GlpR, GntR, IdnR, LctR, Lrp, LysR, MelR, MhpR, TdcA, TdcR, TetR, TreR, TrpR, and TyrR.

In various embodiments, the engineered protein sensor and/or switch is an engineered version of a plant transcriptional regulator family such as a member of the AP2, C2H2, Dof, LATA, HD-ZIP, M-type, NF-YA, S1Fa-like, TCP, YABBY, ARF, C3H, E2F/DP, GRAS, HRT-like, MIKC, NF-YB, SAP, Trihelix, ZF-HD, ARR-B, CAMTA, EIL, GRF, HSF, MYB, NF-YC, SBP, VOZ, bHLH, B3, CO-like, ERF, GeBP, LBD, MYB_related, NZZ/SPL, SRS, WOX, bZIP, BBR-BPC, CPP, FAR1, HB-PHD, LFY, NAC, Nin-like, STAT, WRKY, BES1, DBB, G2-like, HB-other, LSD, NF-X1, RAV, TALE, and Whirly families.

In various embodiments, the engineered protein sensor and/or switch is an engineered version of a yeast TF, such as Abf1p, Abf2p, Aca1p, Ace2p, Adr1p, Aft1p, Aft2p, Arg80p, Arg81p, Aro80p, Arr1p, Asg1p, Ash1p, Azf1p, Bas1p, Cad1p, Cat8p, Cbf1p, Cep3p, Cha4p, Cin5p, Crz1p, Cst6p, Cup2p, Cup9p, Dal80p, Dal81p, Dal82p, Dot6p, Ecm22p, Ecm23p, Eds1p, Ert1p, Fhl1p, Fkh1p, Fkh2p, Flo8p, Fzf1p, Gal4p, Gat1p, Gat3p, Gat4p, Gcn4p, Gcr1p, Gis1p, Gln3p, Gsm1p, Gzf3p, Haa1p, Hac1p, Hal9p, Hap1p, Hap2p, Hap3p, Hap4p, Hap5p, Hcm1p, Hmlalpha2p, Hmra2p, Hsf1p, Ime1p, Ino2p, Ino4p, Ixr1p, Kar4p, Leu3p, Lys14p, Mac1p, Mal63p, Matalpha2p, Mbp1p, Mcm1p, Met31p, Met32p, Met4p, Mga1p, Mig1p, Mig2p, Mig3p, Mot2p, Mot3p, Msn1p, Msn2p, Msn4p, Mss11p, Ndt80p, Nhp10p, Nhp6ap, Nhp6 bp, Nrg1p, Nrg2p, Oaf1p, Pdr1p, Pdr3p, Pdr8p, Phd1p, Pho2p, Pho4p, Pip2p, Ppr1p, Put3p, Rap1p, Rdr1p, Rds1p, Rds2p, Reb1p, Rei1p, Rfx1p, Rgm1p, Rgt1p, Rim101p, Rlm1p, Rme1p, Rox1p, Rph1p, Rpn4p, Rsc30p, Rsc3p, Rsf2p, Rtg1p, Rtg3p, Sfl1p, Sfp1p, Sip4p, Skn7p, Sko1p, Smp1p, Sok2p, Spt15p, Srd1p, Stb3p, Stb4p, Stb5p, Ste12p, Stp1p, Stp2p, Stp3p, Stp4p, Sum1p, Sut1p, Sut2p, Swi4p, Swi5p, Tbf1p, Tbs1p, Tea1p, Tec1p, Tod6p, Tos8p, Tye7p, Uga3p, Ume6p, Upc2p, Urc2p, Usv1p, Vhr1p, War1p, Xbp1p, YER064C, YER130C, YER184C, YGR067C, YKL222C, YLL054C, YLR278C, YML081W, YNR063W, YPR013C, YPR015C, YPR022C, YPR196W, Yap1p, Yap3p, Yap5p, Yap6p, Yap7p, Yox1p, Yrm1p, Yrr1p, and Zap1p.

In various embodiments, the engineered protein sensor and/or switch is an engineered version of a nematode TF, such as ada-2, aha-1, ahr-1, alr-1, ast-1, atf-2, atf-5, atf-6, atf-7, athp-1, blmp-1, bra-2, brc-1, cbp-1, ccr-4, cdk-9, ced-6, ceh-1, ceh-10, ceh-12, ceh-13, ceh-14, ceh-16, ceh-17, ceh-18, ceh-19, ceh-2, ceh-20, ceh-21, ceh-22, ceh-23, ceh-24, ceh-26, ceh-27, ceh-28, ceh-30, ceh-31, ceh-32, ceh-33, ceh-34, ceh-36, ceh-37, ceh-38, ceh-39, ceh-40, ceh-41, ceh-43, ceh-44, ceh-45, ceh-48, ceh-49, ceh-5, ceh-6, ceh-60, ceh-7, ceh-8, ceh-9, cep-1, ces-1, ces-2, cey-1, cey-2, cey-3, cey-4, cfi-1, chd-3, cky-1, cnd-1, cog-1, crh-1, daf-12, daf-14, daf-16, daf-19, daf-3, daf-8, dcp-66, die-1, dlx-1, dmd-3, dmd-4, dmd-5, dmd-6, dnj-11, dpi-1, dpr-1, dpy-20, dpy-22, dpy-26, dro-1, dsc-1, efl-1, efl-2, egl-13, egl-18, egl-27, egl-38, egl-43, egl-44, egl-46, egl-5, ekl-2, ekl-4, elc-1, elt-1, elt-2, elt-3, elt-4, elt-6, elt-7, end-1, end-3, eor-1, ets-4, ets-5, eya-1, fax-1, fkh-10, fkh-2, fkh-3, fkh-4, fkh-5, fkh-6, fkh-7, fkh-8, fkh-9, flt-1, fos-1, fozi-1, gei-11, gei-13, gei-3, gei-8, gfl-1, gla-3, ham-2, hbl-1, hif-1, hlh-1, hlh-10, hlh-11, hlh-12, hlh-13, hlh-14, hlh-15, hlh-16, hlh-17, hlh-19, hlh-2, hlh-25, hlh-26, hlh-27, hlh-28, hlh-29, hlh-3, hlh-30, hlh-4, hlh-6, hlh-8, hmg-1.1, hmg-1.2, hmg-11, hmg-12, hmg-3, hmg-4, hmg-5, hnd-1, hsf-1, irx-1, lag-1, let-381, let-418, lfi-1, lim-4, lim-6, lim-7, lin-1, lin-11, lin-22, lin-26, lin-28, lin-31, lin-32, lin-35, lin-39, lin-40, lin-41, lin-48, lin-49, lin-54, lin-59, lin-61, lpd-2, lsl-1, lss-4, lst-3, mab-23, mab-3, mab-5, mab-9, mbf-1, mbr-1, mbr-1, mdl-1, mec-3, med-1, med-2, mef-2, mes-2, mes-4, mes-6, mdl-1, mex-1, mex-5, mex-6, mgl-2, mls-1, mis-2, mml-1, mua-1, mxl-1, mxl-2, mxl-3, nfi-1, ngn-1, nhr-1, nhr-10, nhr-100, nhr-101, nhr-102, nhr-103, nhr-104, nhr-105, nhr-106, nhr-107, nhr-108, nhr-109, nhr-11, nhr-110, nhr-111, nhr-112, nhr-113, nhr-114, nhr-115, nhr-116, nhr-117, nhr-118, nhr-119, nhr-12, nhr-120, nhr-121, nhr-122, nhr-123, nhr-124, nhr-125, nhr-126, nhr-127, nhr-128, nhr-129, nhr-13, nhr-130, nhr-131, nhr-132, nhr-133, nhr-134, nhr-135, nhr-136, nhr-137, nhr-138, nhr-139, nhr-14, nhr-140, nhr-141, nhr-142, nhr-143, nhr-145, nhr-146, nhr-147, nhr-148, nhr-149, nhr-15, nhr-150, nhr-152, nhr-153, nhr-154, nhr-155, nhr-156, nhr-157, nhr-158, nhr-159, nhr-16, nhr-161, nhr-162, nhr-163, nhr-164, nhr-165, nhr-166, nhr-167, nhr-168, nhr-169, nhr-17, nhr-170, nhr-171, nhr-172, nhr-173, nhr-174, nhr-175, nhr-176, nhr-177, nhr-178, nhr-179, nhr-18, nhr-180, nhr-181, nhr-182, nhr-183, nhr-184, nhr-185, nhr-186, nhr-187, nhr-188, nhr-189, nhr-19, nhr-190, nhr-191, nhr-192, nhr-193, nhr-194, nhr-195, nhr-196, nhr-197, nhr-198, nhr-199, nhr-2, nhr-20, nhr-201, nhr-202, nhr-203, nhr-204, nhr-205, nhr-206, nhr-207, nhr-208, nhr-209, nhr-21, nhr-210, nhr-211, nhr-212, nhr-213, nhr-214, nhr-215, nhr-216, nhr-217, nhr-218, nhr-219, nhr-22, nhr-220, nhr-221, nhr-222, nhr-223, nhr-225, nhr-226, nhr-227, nhr-228, nhr-229, nhr-23, nhr-230, nhr-231, nhr-232, nhr-233, nhr-234, nhr-237, nhr-238, nhr-239, nhr-241, nhr-242, nhr-243, nhr-244, nhr-245, nhr-246, nhr-247, nhr-248, nhr-249, nhr-25, nhr-250, nhr-251, nhr-252, nhr-253, nhr-254, nhr-255, nhr-256, nhr-257, nhr-258, nhr-26, nhr-260, nhr-261, nhr-262, nhr-263, nhr-264, nhr-265, nhr-266, nhr-267, nhr-268, nhr-269, nhr-27, nhr-270, nhr-271, nhr-272, nhr-273, nhr-274, nhr-275, nhr-276, nhr-277, nhr-278, nhr-28, nhr-280, nhr-281, nhr-282, nhr-283, nhr-285, nhr-286, nhr-288, nhr-3, nhr-30, nhr-31, nhr-32, nhr-33, nhr-34, nhr-35, nhr-36, nhr-37, nhr-38, nhr-39, nhr-4, nhr-40, nhr-41, nhr-42, nhr-43, nhr-44, nhr-45, nhr-46, nhr-47, nhr-47, nhr-48, nhr-49, nhr-5, nhr-50, nhr-51, nhr-52, nhr-53, nhr-54, nhr-55, nhr-56, nhr-57, nhr-58, nhr-59, nhr-6, nhr-60, nhr-61, nhr-62, nhr-63, nhr-64, nhr-65, nhr-66, nhr-67, nhr-68, nhr-69, nhr-7, nhr-70, nhr-71, nhr-72, nhr-73, nhr-74, nhr-75, nhr-76, nhr-77, nhr-78, nhr-79, nhr-8, nhr-80, nhr-81, nhr-82, nhr-83, nhr-84, nhr-85, nhr-86, nhr-87, nhr-88, nhr-89, nhr-9, nhr-90, nhr-91, nhr-92, nhr-94, nhr-95, nhr-96, nhr-97, nhr-98, nhr-99, nob-1, ntl-2, ntl-3, nurf-1, odr-7, oma-1, oma-2, pag-3, pal-1, pax-1, pax-3, peb-1, pes-1, pha-1, pha-2, pha-4, php-3, pie-1, pop-1, pos-1, pqn-47, pqn-75, psa-1, rabx-5, rbr-2, ref-1, rnt-1, sbp-1, sdc-1, sdc-2, sdc-3, sea-1, sem-4, sex-1, skn-1, sknr-1, sma-2, sma-3, sma-4, smk-1, sop-2, sox-1, sox-2, sox-3, spr-1, sptf-2, sptf-3, srab-2, srt-58, srw-49, sta-1, tab-1, taf-4, taf-5, tag-153, tag-182, tag-185, tag-192, tag-295, tag-331, tag-347, tag-350, tag-68, tag-97, tbx-11, tbx-2, tbx-30, tbx-31, tbx-32, tbx-33, tbx-34, tbx-35, tbx-36, tbx-37, tbx-38, tbx-39, tbx-40, tbx-41, tbx-7, tbx-8, tbx-9, tra-1, tra-4, ttx-1, ttx-3, unc-120, unc-130, unc-3, unc-30, unc-37, unc-39, unc-4, unc-42, unc-55, unc-62, unc-86, vab-15, vab-3, vab-7, xbp-1, zag-1, zfp-1, zim-1, zip-1, zip-2, zip-3, zip-4, zip-5, and ztf-7.

In various embodiments, the engineered protein sensor and/or switch is an engineered version of a archeal TF, such as APE_0290.1, APE_0293, APE_0880b, APE_1602a, APE_2413, APE_2505, APE_0656a, APE_1799a, APE_1458a, APE_1495a, APE_2570.1, APE_0416b.1, APE_0883a, APE_0535, APE_0142, APE_2021.1, APE_0060.1, APE_0197.1, APE_0778, APE_2011.1, APE_0168.1, APE_2517.1, APE_0288, APE_0002, APE_1360.1, APE_2091.1, APE_0454, APE_1862.1, APE_0669.1, APE_2443.1, APE_0787.1, APE_2004.1, APE_0025.1, APE_0153.1, AF0653, AF1264, AF1270, AF1544, AF1743, AF1807, AF1853, AF2008, AF2136, AF2404, AF0529, AF0114, AF0396, AF1298, AF1564, AF1697, AF1869, AF2271, AF1404, AF1148, AF0474, AF0584, AF1723, AF1622, AF1448, AF0439, AF1493, AF0337, AF0743, AF0365, AF1591, AF0128, AF0005, AF1745, AF0569, AF2106, AF1785, AF1984, AF2395, AF2232, AF0805, AF1429, AF0111, AF1627, AF1787, AF1793, AF1977, AF2118, AF2414, AF0643, AF1022, AF1121, AF2127, AF0139, AF0363, AF0998, AF1596, AF0673, AF2227, AF1542, AF2203, AF1459, AF1968, AF1516, AF0373, AF1817, AF1299, AF0757, AF0213, AF1009, AF1232, AF0026, AF1662, AF1846, AF2143, AF0674, Cmaq_0146, Cmaq_0924, Cmaq_1273, Cmaq_1369, Cmaq_1488, Cmaq_1508, Cmaq_1561, Cmaq_1699, Cmaq_0215, Cmaq_1704, Cmaq_1956, Cmaq_0058, Cmaq_1637, Cmaq_0227, Cmaq_0287, Cmaq_1606, Cmaq_1720, Cmaq_0112, Cmaq_1149, Cmaq_1687, Cmaq_0411, Cmaq_1925, Cmaq_0078, Cmaq_0314, Cmaq_0768, Cmaq_1206, Cmaq_0480, Cmaq_0797, Cmaq_1388, Cmaq_0152, Cmaq_0601, Cmaq_1188, Mboo_0375, Mboo_0423, Mboo_0749, Mboo_1012, Mboo_1134, Mboo_1154, Mboo_1189, Mboo_1266, Mboo_1711, Mboo_1971, Mboo_0002, Mboo_0956, Mboo_1071, Mboo_1405, Mboo_1643, Mboo_0973, Mboo_1170, Mboo_0158, Mboo_0195, Mboo_0277, Mboo_1462, Mboo_1574, Mboo_1649, Mboo_2112, Mboo_0013, Mboo_0386, Mboo_0946, Mboo_0977, Mboo_1081, Mboo_2241, Mboo_0142, Mboo_0396, Mboo_0409, Mboo_0976, Mboo_2244, Mboo_0526, Mboo_0346, Mboo_1018, Mboo_0917, Mboo_0323, Mboo_0916, Mboo_1680, Mboo_1288, Mboo_2311, Mboo_2048, Mboo_1027, Mboo_2312, rrnAC0161, rrnAC0578, rrnAC0961, rrnAC3494, rrnB0118, pNG7045, pNG6160, rrnAC0867, rrnAC2723, rrnAC3399, rrnAC3447, rrnB0052, rrnAC1653, rrnAC2779, pNG7038, rrnAC1252, rrnAC3288, rrnAC3307, rrnAC0503, rrnAC1269, pNG6047, rrnAC2622, rrnAC3290, rrnAC3365, rrnAC2301, pNG6157, rrnAC2002, rrnAC1238, rrnAC3207, pNG2039, pNG7160, rrnAC2748, rrnB0134, rrnAC2283, rrnAC1714, rrnAC1715, rrnAC2338, rrnAC2339, rrnAC2900, rrnAC0341, rrnAC3191, rrnAC1825, rrnAC2037, rrnAC0496, rrnAC3074, rrnAC2669, rrnAC0019, rrnACO231, rrnAC0564, rrnAC0640, rrnAC1193, rrnAC1687, rrnAC1786, rrnAC1895, rrnAC1953, rrnAC1996, rrnAC2017, rrnAC2022, rrnAC2052, rrnAC2070, rrnAC2160, rrnAC2472, rrnAC2785, rrnAC2936, rrnAC3167, rrnAC3451, rrnAC3486, rrnAC3490, rrnB0253, rrnB0269, pNG7159, pNG7188, pNG7357, pNG6134, rrnAC0376, rrnAC1217, rrnAC1541, rrnAC1663, rrnAC3229, pNG7223, rrnAC0440, rrnAC0535, rrnAC1742, rrnAC2519, rrnAC1764, rrnAC1777, rrnAC2762, rrnAC3264, rrnAC0417, rrnAC1303, rrnB0301, pNG6155, pNG7021, pNG7343, rrnAC1964, pNG7171, rrnAC1338, pNG7344, rrnACO230, rrnAC1971, rrnB0222, rrnAC0385, rrnAC0312, pNG7133, rrnAC0006, rrnAC1805, rrnAC3501, pNG7312, rrnAC0435, rrnAC0768, rrnAC0992, rrnAC2270, rrnAC3322, rrnB0112, rrnB0157, rrnB0161, pNG6058, pNG6092, pNG5119, pNG5140, pNG4042, pNG2006, pNG1015, rrnAC0199, rrnAC0681, rrnAC1765, rrnAC1767, pNG5067, pNG7180, pNG7307, pNG7183, rrnAC3384, pNG5131, rrnAC2777, pNG5071, rrnAC1472, pNG7308, rrnAC0869, rrnB0148, rrnAC2051, rrnAC0016, rrnAC1875, pNG6072, pNG6123, rrnAC2769, rrnAC1357, rrnAC1126, rrnAC0861, rrnAC0172, rrnAC0420, rrnAC0914, rrnAC2354, rrnAC3310, rrnAC3337, pNG5013, pNG5133, rrnAC3082, rrnB0074, pNG6075, pNG5024, rrnAC0924, rrnB0235, pNG7146, VNG0462C, VNG7122, VNG7125, VNG2445C, VNG0591C, VNG1843C, VNG0320H, VNG1123Gm, VNG1237C, VNG1265G, VNG2094G, VNG1351G, VNG1377G, VNG1179C, VNG1922G, VNG1816G, VNG0134G, VNG0194H, VNG0147C, VNG6193H, VNG2163H, VNG0101G, VNG1836G, VNG0530G, VNG0536G, VNG0835G, VNG2579G, VNG6349C, VNG1394H, VNG0113H, VNG0156C, VNG0160G, VNG0826C, VNG0852C, VNG1207C, VNG1488G, VNG6065G, VNG6461G, VNG7048, VNG7161, VNG1464G, VNG1548C, VNG0247C, VNG0471C, VNG0878Gm, VNG1029C, VNG1616C, VNG2112C, VNG6009H, VNG7007, VNG0704C, VNG1405C, VNG6318G, VNG0142C, VNG6072C, VNG6454C, VNG7053, VNG7156, VNG0703H, VNG0258H, VNG0751C, VNG1426H, VNG2020C, VNG6048H, VNG6126H, VNG6239G, VNG6478H, VNG7102, VNG6027G, VNG7023, VNG1786H, VNG2629G, VNG1598a, VNG7031, VNG6037G, VNG7171, VNG7114, VNG7038, VNG2243G, VNG6140G, VNG7100, VNG6476G, VNG6438G, VNG6050G, VNG0726C, VNG1390H, VNG6351G, VNG2184G, VNG0869G, VNG0254G, VNG6389G, VNG0315G, VNG0734C, VNG0757G, VNG1451C, VNG1886C, VNG1903Cm, VNG0985H, VNG6377H, HQ2607A, HQ2612A, HQ2779A, HQ1740A, HQ1541A, HQ1491A, HQ2619A, HQ1811A, HQ3063A, HQ3354A, HQ3642A, HQ2773A, HQ1436A, HQ2221A, HQ1414A, HQ3339A, HQ2484A, HQ3265A, HQ3620A, HQ1268A, HQ1388A, HQ1866A, HQ1563A, HQ1710A, HQ1962A, HQ1084A, HQ1739A, HQ1861A, HQ1863A, HQ2750A, HQ2664A, HQ2869A, HQ3058A, HQ3361A, HQ1277A, HQ2225A, HQ1993A, HQ1937A, HQ1088A, HQ1724A, HQ1568A, HQ2167A, HQ1230A, HQ2407A, HQ3108A, HQ1973A, HQ3260A, HQ2527A, HQ3410A, HQ2369A, HQ2564A, HQ1153A, HQ1227A, HQ3654A, HQ1867A, HQ2571A, HQ1625A, HQ3408A, HQ1689A, HQ2491A, HQ2726A, HQ2987A, HQ1041A, HQ1898A, HQ1900A, HQ1118A, Hbut_1261, Hbut_0073, Hbut_0009, Hbut_0100, Hbut_0987, Hbut_1340, Hbut_0120, Hbut_0990, Hbut_0316, Hbut_0659, Hbut_0660, Hbut_0366, Hbut_0204, Hbut_1498, Hbut_1630, Hbut_1485, Hbut_1260, Hbut_0942, Hbut_0163, Hbut_0116, Hbut_0207, Hbut_1516, Hbut_0476, Hbut_1139, Hbut_0299, Hbut_0033, Hbut_0336, Hbut_1471, Hbut_1522, Hbut_0601, Hbut_0934, Hbut_0458, Hbut_0054, Hbut_1136, Hbut_0646, Hbut_0815, Igni_0122, Igni_0494, Igni_0706, Igni_1249, Igni_0226, Igni_0308, Igni_0658, Igni_0702, Igni_0486, Igni_0602, Igni_1394, Igni_0858, Igni_1361, Igni_0354, Igni_0989, Igni_1372, Igni_1124, Msed_0229, Msed_0717, Msed_1005, Msed_1190, Msed_1224, Msed_1970, Msed_2175, Msed_0166, Msed_0688, Msed_1202, Msed_1209, Msed_1765, Msed_1956, Msed_2295, Msed_0619, Msed_0621, Msed_2232, Msed_0140, Msed_2016, Msed_0767, Msed_1126, Msed_0856, Msed_0992, Msed_1773, Msed_1818, Msed_2183, Msed_1598, Msed_1725, Msed_2276, Msed_2293, Msed_1450, Msed_0265, Msed_0492, Msed_1279, Msed_1397, Msed_1563, Msed_1566, Msed_2027, Msed_0565, Msed_0868, Msed_1371, Msed_1483, Msed_1728, Msed_1351, Msed_1733, Msed_2209, Msed_2279, Msed_2233, MTH107, MTH517, MTH899, MTH1438, MTH1795, MTH163, MTH1288, MTH1349, MTH864, MTH1193, MTH254, MTH821, MTH1696, MTH739, MTH603, MTH214, MTH936, MTH659, MTH700, MTH729, MTH967, MTH1553, MTH1328, MTH1470, MTH1285, MTH1545, MTH931, MTH313, MTH1569, MTH281, MTH1488, MTH1521, MTH1627, MTH1063, MTH1787, MTH885, MTH1669, MTH1454, Msm_1107, Msm_1126, Msm_1350, Msm_1032, Msm_0213, Msm_0844, Msm_1260, Msm_0364, Msm_0218, Msm_0026, Msm_0329, Msm_0355, Msm_0453, Msm_1150, Msm_1408, Msm_0864, Msm_0413, Msm_1230, Msm_1499, Msm_1417, Msm_1250, Msm_1090, Msm_0720, Msm_0650, Msm_0424, Msm_0631, Msm_1445, Mbur_0656, Mbur_1148, Mbur_1658, Mbur_1965, Mbur_2405, Mbur_1168, Mbur_0166, Mbur_0946, Mbur_1817, Mbur_1830, Mbur_0231, Mbur_0234, Mbur_2100, Mbur_1375, Mbur_2041, Mbur_0776, Mbur_0783, Mbur_2071, Mbur_1477, Mbur_1871, Mbur_1635, Mbur_1221, Mbur_0292, Mbur_0512, Mbur_0609, Mbur_0661, Mbur_1211, Mbur_1719, Mbur_1811, Mbur_1931, Mbur_2112, Mbur_2130, Mbur_2048, Mbur_2144, Mbur_0368, Mbur_1483, Mbur_2274, Mbur_1359, Mbur_2306, Mbur_1647, Mbur_0631, Mbur_0378, Mbur_0085, Mbur_1496, Mbur_0963, Mbur_0372, Mbur_1140, Mbur_2097, Mbur_2262, Mbur_1532, Maeo_0092, Maeo_0872, Maeo_0888, Maeo_1298, Maeo_1146, Maeo_1061, Maeo_1147, Maeo_0865, Maeo_0659, Maeo_0679, Maeo_1305, Maeo_0977, Maeo_1182, Maeo_1472, Maeo_1362, Maeo_0019, Maeo_0277, Maeo_0356, Maeo_0719, Maeo_1032, Maeo_1289, Maeo_0698, Maeo_1183, Maeo_0223, Maeo_0822, Maeo_0218, Maeo_0186, Maeo_1155, Maeo_0575, Maeo_0728, Maeo_0696, Maeo_0664, MJ0432, MJ1082, MJ1325, MJ0229, MJ0361, MJ1553, MJ1563, MJ0774, MJ1398, MJ0723, MJ0151, MJ0589a, MJECL29, MJ1647, MJ1258, MJ0168, MJ0932, MJ0080, MJ0549, MJ0767, MJ1679, MJ0568, MJ1005, MJ0529, MJ0586, MJ0621, MJ1164, MJ1420, MJ1545, MJ0272, MJ0925, MJ0300, MJ1120, MJ0379, MJ0558, MJ1254, MJ0159, MJ0944, MJ0241, MJ0173, MJ0507, MJ0782, MJ0777, MJ1503, MJ1623, MmarC5_0244, MmarC5_1146, MmarC5_0136, MmarC5_1648, MmarC5_1124, MmarC5_0967, MmarC5_1647, MmarC5_0448, MmarC5_0231, MmarC5_0579, MmarC5_1252, MmarC5_1664, MmarC5_0974, MmarC5_0625, MmarC5_1666, MmarC5_0111, MmarC5_1039, MmarC5_0316, MmarC5_0131, MmarC5_1762, MmarC5_1579, MmarC5_0380, MmarC5_0898, MmarC5_0813, MmarC5_1143, MmarC5_1694, MmarC5_1294, MmarC5_1236, MmarC5_1150, MmarC5_1138, MmarC5_1543, MmarC5_0999, MmarC5_1507, MmarC5_0876, MmarC5_0202, MmarC5_1416, MmarC5_0612, MmarC5_0571, MmarC5_1100, MmarC5_1639, MmarC5_1644, MmarC5_0714, MmarC5_0484, MmarC5_0976, MmarC6_0024, MmarC6_0026, MmarC6_0104, MmarC6_0105, MmarC6_0128, MmarC6_0252, MmarC6_0566, MmarC6_0917, MmarC6_1231, MmarC6_0916, MmarC6_1531, MmarC6_0524, MmarC6_1326, MmarC6_1644, MmarC6_0165, MmarC6_0929, MmarC6_0258, MmarC6_0037, MmarC6_0055, MmarC6_1206, MmarC6_1606, MmarC6_0210, MmarC6_0325, MmarC6_0744, MmarC6_0850, MmarC6_1025, MmarC6_1226, MmarC6_1398, MmarC6_1462, MmarC6_1664, MmarC6_1175, MmarC6_0959, MmarC6_0931, MmarC6_0136, MmarC6_0425, MmarC6_0508, MmarC6_0285, MmarC6_0184, MmarC6_0443, MmarC6_0782, MmarC6_1297, MmarC6_0861, MmarC6_0696, MmarC6_1636, MmarC6_1817, MmarC6_0908, MmarC6_0913, MmarC6_0262, MmarC6_1567, MmarC6_1748, MmarC7_0274, MmarC7_0687, MmarC7_1029, MmarC7_1513, MmarC7_1661, MmarC7_1030, MmarC7_0388, MmarC7_0257, MmarC7_0592, MmarC7_1384, MmarC7_1017, MmarC7_1655, MmarC7_0306, MmarC7_0712, MmarC7_0235, MmarC7_0457, MmarC7_0521, MmarC7_0692, MmarC7_0743, MmarC7_0919, MmarC7_1096, MmarC7_1211, MmarC7_1587, MmarC7_1702, MmarC7_0987, MmarC7_1015, MmarC7_0031, MmarC7_1400, MmarC7_1790, MmarC7_1499, MmarC7_1629, MmarC7_1168, MmarC7_1727, MmarC7_0621, MmarC7_1085, MmarC7_1260, MmarC7_0085, MmarC7_0265, MmarC7_1461, MmarC7_1038, MmarC7_1033, MmarC7_0154, MmarC7_0352, MmarC7_1652, MmarC7_1455, MMP0499, MMP1442, MMP0480, MMP0752, MMP0032, MMP0460, MMP0637, MMP0033, MMP0217, MMP1137, MMP0386, MMP1347, MMP1015, MMP0719, MMP0020, MMP0631, MMP0742, MMP1467, MMP1052, MMP0097, MMP0209, MMP0568, MMP0674, MMP0678, MMP0993, MMP1210, MMP1275, MMP1447, MMP1646, MMP1499, MMP0018, MMP1712, MMP0402, MMP0787, MMP0607, MMP0168, MMP0700, MMP0465, MMP1376, MMP0086, MMP0257, MMP0840, MMP1023, MMP0791, MMP0799, MMP0041, MMP0036, MMP0907, MMP0629, MMP1100, Mevan_0753, Mevan_1029, Mevan_1232, Mevan_1560, Mevan_1502, Mevan_1030, Mevan_0459, Mevan_0343, Mevan_0658, Mevan_1373, Mevan_1201, Mevan_1594, Mevan_1567, Mevan_1203, Mevan_0375, Mevan_0778, Mevan_0320, Mevan_0525, Mevan_0587, Mevan_0758, Mevan_0808, Mevan_0951, Mevan_1109, Mevan_1444, Mevan_1514, Mevan_1517, Mevan_1014, Mevan_0136, Mevan_0295, Mevan_1389, Mevan_1479, Mevan_1173, Mevan_1578, Mevan_1653, Mevan_0686, Mevan_1098, Mevan_1270, Mevan_0270, Mevan_0282, Mevan_1620, Mevan_1668, Mevan_1038, Mevan_1044, Mevan_1050, Mevan_1056, Mevan_1033, Mevan_0014, Mevan_0425, Mevan_0095, Mlab_0303, Mlab_0817, Mlab_0821, Mlab_1236, Mlab_1381, Mlab_0824, Mlab_0002, Mlab_0494, Mlab_0162, Mlab_0744, Mlab_1629, Mlab_0854, Mlab_0909, Mlab_1549, Mlab_0037, Mlab_0071, Mlab_0160, Mlab_1173, Mlab_1603, Mlab_1630, Mlab_1666, Mlab_1628, Mlab_0070, Mlab_1522, Mlab_0331, Mlab_1259, Mlab_0324, Mlab_1366, Mlab_1576, Mlab_0353, Mlab_0010, Mlab_0295, Mlab_0588, Mlab_1668, Mlab_0447, Mlab_0440, Mlab_0197, Mlab_1697, Mlab_1694, Mlab_1710, Mlab_1511, Mlab_0458, Mlab_0497, Mlab_0762, Mlab_0988, Mlab_0826, Memar_0011, Memar_0013, Memar_1330, Memar_1512, Memar_1567, Memar_1770, Memar_2080, Memar_0129, Memar_0140, Memar_0431, Memar_1231, Memar_1756, Memar_2162, Memar_2068, Memar_1225, Memar_0002, Memar_1921, Memar_0834, Memar_2239, Memar_1448, Memar_0817, Memar_2411, Memar_2490, Memar_2264, Memar_1471, Memar_1420, Memar_0458, Memar_1291, Memar_1391, Memar_1410, Memar_1819, Memar_2218, Memar_2347, Memar_2360, Memar_2449, Memar_1304, Memar_0106, Memar_0096, Memar_0419, Memar_1120, Memar_0385, Memar_0555, Memar_1103, Memar_1319, Memar_2487, Memar_1252, Memar_1388, Memar_0473, Memar_1524, Memar_0459, Memar_0487, Memar_1209, Memar_1387, Memar_2116, MK0576, MK1025, MK0542, MK1515, MK0506, MK1677, MK1502, MK1190, MK0175, MK0800, MK0457, MK0449, MK1380, MK1430, MK0574, MK1482, MK0984, MK0337, MK1587, MK0839, MK0619, MK0858, MK0495, MK0253, Mthe_1108, Mthe_1291, Mthe_1230, Mthe_0612, Mthe_0503, Mthe_0879, Mthe_0047, Mthe_0598, Mthe_0023, Mthe_0662, Mthe_0543, Mthe_0154, Mthe_0459, Mthe_1389, Mthe_1446, Mthe_1633, Mthe_1233, Mthe_0669, Mthe_0067, Mthe_0404, Mthe_0982, Mthe_1201, Mthe_0152, Mthe_0265, Mthe_1650, Mthe_1683, Mthe_0889, MA0191, MA0342, MA0380, MA1458, MA2551, MA3784, MA3925, MA3940, MA3952, MA4076, MA4344, MA4484, MA4576, MA0207, MA0750, MA2499, MA3597, MA4479, MA2544, MA4480, MA0504, MA2921, MA0862, MA0205, MA0460, MA0622, MA0629, MA1953, MA4398, MA4560, MA0723, MA1529, MA1551, MA2421, MA1531, MA0924, MA0575, MA1588, MA0672, MA1395, MA4075, MA1763, MA2814, MA3468, MA0022, MA4338, MA2133, MA0971, MA1005, MA0067, MA1424, MA1815, MA4668, MA2914, MA3524, MA4040, MA4267, MA3984, MA0283, MA0333, MA0414, MA1339, MA3166, MA0176, MA0180, MA0743, MA1863, MA2051, MA2055, MA2206, MA2211, MA2771, MA3189, MA4167, MA1122, MA3015, MA0079, MA0989, MA4404, MA2093, MA1671, MA4106, MA4346, MA0278, MA4331, MA0179, MA2948, MA3586, MA2761, MA1487, MA1771, MA2746, MA0364, MA2951, MA0354, MA2902, MA0368, MA2764, MA2766, MA0178, MA2782, MA2493, MA0610, MA3871, MA0287, MA0359, MA1835, MA2057, MA2207, MA2212, MA3151, MA4622, MA0926, MA1664, MA4408, MA1868, Mbar_A0506, Mbar_A0581, Mbar_A0738, Mbar_A0909, Mbar_A1363, Mbar_A1705, Mbar_A1707, Mbar_A1708, Mbar_A1719, Mbar_A2323, Mbar_A2748, Mbar_A3221, Mbar_A3427, Mbar_A1541, Mbar_A1729, Mbar_A2416, Mbar_A3312, Mbar_A0803, Mbar_A3558, Mbar_A0794, Mbar_A2965, Mbar_A1070, Mbar_A1333, Mbar_A2865, Mbar_A1639, Mbar_A3371, Mbar_A0650, Mbar_A3377, Mbar_A3361, Mbar_A0654, Mbar_A3464, Mbar_A1460, Mbar_A2808, Mbar_A1584, Mbar_A2743, Mbar_A2250, Mbar_A0507, Mbar_A0992, Mbar_A1457, Mbar_A0588, Mbar_A0122, Mbar_A2068, Mbar_A0552, Mbar_A0621, Mbar_A0692, Mbar_A1033, Mbar_A2079, Mbar_A2171, Mbar_A2218, Mbar_A2819, Mbar_A2992, Mbar_A3339, Mbar_A1265, Mbar_A1377, Mbar_A1884, Mbar_A2294, Mbar_A3663, Mbar_A2575, Mbar_A2637, Mbar_A3146, Mbar_A3330, Mbar_A3493, Mbar_A2012, Mbar_A2036, Mbar_A2688, Mbar_A3560, Mbar_A1076, Mbar_A0340, Mbar_A0520, Mbar_A1497, Mbar_A3486, Mbar_A1949, Mbar_A0475, Mbar_A0579, Mbar_A1062, Mbar_A0595, Mbar_A3297, Mbar_A3442, Mbar_A3419, Mbar_A0834, Mbar_A0787, Mbar_A2740, Mbar_A1394, Mbar_A0196, Mbar_A1270, Mbar_A3331, Mbar_A3578, Mbar_A3670, Mbar_A1080, MM0272, MM0662, MM0841, MM1040, MM1257, MM1484, MM1796, MM2237, MM2242, MM2246, MM2247, MM2261, MM2525, MM2985, MM3068, MM3208, MM1882, MM1494, MM3092, MM1595, MM3173, MM0565, MM1492, MM0266, MM1080, MM1605, MM1650, MM2809, MM2861, MM2446, MM2441, MM2040, MM1728, MM1739, MM2416, MM1825, MM0666, MM0842, MM2657, MM1332, MM2573, MM1034, MM2606, MM0247, MM0444, MM0872, MM0927, MM1363, MM2394, MM2895, MM3179, MM1005, MM3233, MM1550, MM0359, MM0361, MM1586, MM1863, MM2851, MM2853, MM3117, MM0116, MM0289, MM0346, MM1903, MM3195, MM3170, MM1085, MM0386, MM2835, MM0811, MM1042, MM1027, MM2184, MM1028, MM0432, MM2546, MM1614, MM1772, MM0692, MM0146, MM0345, MM0369, MM1554, MM2854, MM1094, MM2042, MM3115, Msp_0061, Msp_0120, Msp_1519, Msp_0293, Msp_1556, Msp_0769, Msp_0168, Msp_0614, Msp_0518, Msp_0122, Msp_0383, Msp_1218, Msp_0446, Msp_0265, Msp_0608, Msp_1143, Msp_1207, Msp_0248, Msp_0512, Msp_0823, Msp_1188, Msp_0235, Msp_0194, Msp_1057, Msp_1097, Msp_0717, Msp_0971, Msp_1360, Msp_1272, Msp_1125, Msp_0149, Mhun_0040, Mhun_0316, Mhun_0873, Mhun_1073, Mhun_1644, Mhun_2448, Mhun_2633, Mhun_2472, Mhun_0365, Mhun_0919, Mhun_0576, Mhun_0165, Mhun_2458, Mhun_0842, Mhun_0941, Mhun_1324, Mhun_1346, Mhun_2089, Mhun_1313, Mhun_1731, Mhun_1706, Mhun_0152, Mhun_0501, Mhun_1037, Mhun_2548, Mhun_2928, Mhun_3036, Mhun_0241, Mhun_1541, Mhun_2190, Mhun_0646, Mhun_1347, Mhun_1533, Mhun_1553, Mhun_1866, Mhun_1954, Mhun_0253, Mhun_1259, Mhun_1451, Mhun_2502, Mhun_0684, Mhun_2259, Mhun_0763, Mhun_1327, Mhun_1530, Mhun_2935, Mhun_2804, Mhun_0568, Mhun_0593, Mhun_1236, Mhun_1656, Mhun_2481, Mhun_2797, Mhun_0497, Mhun_0575, Mhun_0588, NEQ328, NEQ229, NEQ348, NEQ288, NEQ453, NEQ143, NEQ039, NEQ276, NEQ098, NEQ541, NP1838A, NP2534A, NP3936A, NP6056A, NP2558A, NP1144A, NP0458A, NP2490A, NP2664A, NP3370A, NP0078A, NP5052A, NP4026A, NP6200A, NP0924A, NP4828A, NP2752A, NP6106A, NP2470A, NP2474A, NP0316A, NP0252A, NP5326A, NP1048A, NP2958A, NP5152A, NP4632A, NP3636A, NP3734A, NP4552A, NP5064A, NP1496A, NP4726A, NP2878A, NP0136A, NP0162A, NP0654A, NP1532A, NP1538A, NP1564A, NP2794A, NP4286A, NP4406A, NP5130A, NP5298A, NP6030A, NP6220A, NP4436A, NP1320A, NP2146A, NP3466A, NP4796A, NP5168A, NP3046A, NP2812A, NP3608A, NP2618A, NP6176A, NP3330A, NP7054A, NP2762A, NP4124A, NP3490A, NP1128A, NP1628A, NP2114A, NP0674A, NP2366A, NP3002A, NP3776A, NP4444A, NP1296A, NP1064A, NP4080A, NP4082A, NP0534A, NP2466A, NP3718A, NP5096A, NP2220A, NP5186A, NP1684A, NP2246A, NP4822A, NP4326A, NP4106A, NP2518A, NP5272A, NP6088A, NP4258A, PTO0457, PTO0754, PTO0795, PTO0420, PTO1287, PTO0595, PTO0891, PTO0200, PTO1201, PTO0428, PTO0376, PTO0514, PTO0375, PTO0781, PTO1148, PTO0979, PTO0276, PTO0843, PTO0557, PTO1105, PTO1211, PTO1517, PTO1052, PTO1150, PTO0114, PTO1041, PTO1176, PTO0063, PTO0799, PTO1388, PTO1389, PTO0914, PTO1110, PTO1216, PTO0675, PTO1123, PTO0506, PTO1258, PTO1372, PTO0363, PTO1340, PTO1338, PTO1067, PTO1454, PTO1523, PTO0576, PTO0198, PAE0731, PAE0738, PAE1612, PAE2042, PAE2911, PAE1948, PAE2655, PAE0385, PAE2225, PAE3116, PAE2186, PAE1103, PAE1592, PAE1848, PAE3387, PAE1507, PAE1986, PAE3469, PAE3471, PAE0659, PAE1443, PAE1484, PAE0296, PAE2022, PAE2357, PAE1544, PAE0640, PAE2309, PAE3163, PAE2449, PAE3605, PAE0783, PAE1627, PAE1638, PAE2071, PAE3208, PAE0019, PAE0813, PAE3327, PAE0146, PAE2679, PAE2684, PAE1218, PAE1760, PAE0013, PAE3437, PAE2640, PAE3378, PAE2164, PAE0171, PAE0170, PAE3329, PAE2120, PAE1645, PAE0781, PAE2282, Pars_0006, Pars_0433, Pars_0703, Pars_0836, Pars_0990, Pars_1924, Pars_2088, Pars_2298, Pars_0264, Pars_2028, Pars_0627, Pars_1855, Pars_2059, Pars_1853, Pars_0399, Pars_0425, Pars_1561, Pars_2084, Pars_0343, Pars_0668, Pars_2155, Pars_0438, Pars_1526, Pars_2364, Pars_1428, Pars_0037, Pars_1981, Pars_1988, Pars_2104, Pars_0057, Pars_0792, Pars_0504, Pars_0550, Pars_1742, Pars_1776, Pars_0311, Pars_0752, Pars_1087, Pars_1872, Pars_1005, Pars_0806, Pars_2186, Pars_2187, Pars_1743, Pars_2132, Pars_1649, Pars_1976, Pars_0035, Pars_1810, Pars_2125, Pcal_0142, Pcal_0905, Pcal_0946, Pcal_0412, Pcal_0495, Pcal_0687, Pcal_1273, Pcal_0822, Pcal_1595, Pcal_1185, Pcal_0610, Pcal_1183, Pcal_2085, Pcal_0796, Pcal_0536, Pcal_1689, Pcal_0008, Pcal_1198, Pcal_1653, Pcal_0295, Pcal_1924, Pcal_1927, Pcal_0200, Pcal_0589, Pcal_0596, Pcal_2145, Pcal_0791, Pcal_0023, Pcal_1415, Pcal_1735, Pcal_0266, Pcal_0346, Pcal_0543, Pcal_0792, Pcal_1032, Pcal_0159, Pcal_1078, Pcal_1890, Pcal_1316, Pcal_1055, Pcal_0584, Pcal_1734, Pcal_2147, Pcal_1638, Pcal_2070, Pisl_1759, Pisl_2001, Pisl_0858, Pisl_1838, Pisl_0307, Pisl_0653, Pisl_1426, Pisl_1248, Pisl_1639, Pisl_1808, Pisl_0995, Pisl_1590, Pisl_0997, Pisl_0709, Pisl_1563, Pisl_1834, Pisl_1578, Pisl_0622, Pisl_1613, Pisl_0725, Pisl_1023, Pisl_0410, Pisl_1076, Pisl_1655, Pisl_1662, Pisl_1854, Pisl_0045, Pisl_1100, Pisl_0810, Pisl_0572, Pisl_1971, Pisl_1303, Pisl_1717, Pisl_0038, Pisl_0979, Pisl_0565, Pisl_1878, Pisl_0807, Pisl_1975, Pisl_1974, Pisl_0573, Pisl_0955, Pisl_1667, Pisl_1074, Pisl_1008, Pisl_1250, PAB2298, PAB1869, PAB0625, PAB0751, PAB1002, PAB2328, PAB0125, PAB0208, PAB0619, PAB1229, PAB1227, PAB0108, PAB0322, PAB0392, PAB2312, PAB7115, PAB2062.1n, PAB1938, PAB1236, PAB2257, PAB7359, PAB2299, PAB0758a, PAB3089, PAB3117, PAB0960, PAB1522.1n, PAB2324, PAB0714, PAB2311, PAB1533, PAB0211, PAB2104, PAB2035, PAB0475, PAB0842, PAB0668, PAB7155, PAB3293, PAB0917, PAB0661, PAB0953, PAB1243, PAB1544, PAB0331, PAB1922, PAB7338, PAB0603, PAB1517, PAB1726, PAB1641, PAB1642, PAB0976, PAB1912, PAB0950, PAB0838, PF0007, PF0230, PF1072, PF1406, PF2051, PF0113, PF0232, PF1790, PF1088, PF0095, PF1734, PF0054, PF1543, PF1732, PF0250, PF0739, PF1231, PF1601, PF1022, PF1893, PF0607, PF0829, PF1722, PF1831, PF0322, PF0524, PF2053, PF0851, PF1194, PF0055, PF0505, PF0512, PF1386, PF1735, PF1794, PF1851, PF0691, PF0487, PF0988, PF1029, PF2062, PF0263, PF0709, PF1476, PF0584, PF1198, PF0535, PF1295, PF1338, PF1337, PF0687, PF1377, PF0491, PF0496, PF0661, PF1743, PF0124, PF0649, PH0062, PH1101, PH0199, PH0289, PH0825, PH1061, PH1406, PH1744, PH1930, PH1932, PH0977, PH0952, PH0180, PH1692, PH0045, PH1856.1n, PH0061, PHS045, PH1592, PH1916, PH0140, PH1519, PHS023, PH1055, PHS034, PHS051, PHS046, PH0601, PHS024, PH0468, PH1163, PH0046, PH0787, PH0783, PH1471, PH1691, PH1748, PH1808, PH0660, PH0804, PH0995, PH0614, PH0914, PH0718.1n, PH1080, PH0763, PH1009, PH1161, PH1160, PH1482, PH0864, PH0619, PH0751, PH0799, PH1034, PH0588, Smar_0567, Smar_0017, Smar_0429, Smar_1295, Smar_0048, Smar_0184, Smar_0954, Smar_1451, Smar_0205, Smar_0336, Smar_0366, Smar_1141, Smar_0476, Smar_0879, Smar_0338, Smar_0194, Smar_0612, Smar_0915, Smar_1254, Smar_1341, Smar_0279, Smar_1409, Smar_0319, Smar_0758, Smar_1442, Smar_1514, Smar_1075, Smar_1322, Smar_0054, Smar_1137, Smar_1250, Smar_0918, Smar_0086, Saci_0006, Saci_0446, Saci_1068, Saci_1787, Saci_1979, Saci_0800, Saci_1710, Saci_2236, Saci_2266, Saci_2136, Saci_0992, Saci_0731, Saci_0752, Saci_1304, Saci_1588, Saci_0944, Saci_0843, Saci_0942, Saci_0264, Saci_1391, Saci_0476, Saci_1223, Saci_0112, Saci_0048, Saci_1851, Saci_0455, Saci_2061, Saci_2116, Saci_2167, Saci_2183, Saci_2296, Saci_0655, Saci_1344, Saci_1505, Saci_2359, Saci_1192, Saci_2313, Saci_0161, Saci_0102, Saci_0133, Saci_0874, Saci_1219, Saci_1482, Saci_1670, Saci_1956, Saci_2112, Saci_0488, Saci_0483, Saci_1180, Saci_1171, Saci_1186, Saci_1242, Saci_0489, Saci_1005, Saci_2352, Saci_0380, Saci_1336, Saci_1230, Saci_2283, Saci_1107, Saci_0866, Saci_1341, Saci_0652, Saci_0842, Saci_1161, SSO0458, SSO0620, SSO9953, SSO2688, SSO0200, SSO1423, SSO2114, SSO2347, SSO3103, SSO5522, SSO0977, SSO0606, SSO2131, SSO10340, SSO0157, SSO6024, SSO0659, SSO5826, SSO10342, SSO3242, SSO0669, SSO2273, SSO2244, SSO1589, SSO1255, SSO0447, SSO0785, SSO1008, SSO1219, SSO1306, SSO1536, SSO2058, SSO3061, SSO3080, SSO1868, SSO3097, SSO2474, SSO3188, SSO0107, SSO0270, SSO0387, SSO0942, SSO1066, SSO0040, SSO1264, SSO1384, SSO1750, SSO1897, SSO2090, SSO2132, SSO2933, SSO2992, SSO2897, SSO3176, SSO0048, SSO0365, SSO1082, SSO1108, SSO1352, SSO1101, SSO1110, SSO2652, SSO1695, SSO1748, SSO2957, SSO2327, SSO0038, SSO0049, SSO0994, SSO2138, SSO2571, SSO0951, SSO2206, SSO2089, SSO2598, SSO2506, SSO0446, SSO0946, SSO0266, SSO0426, SSO2073, ST0236, ST1060, ST1064, ST1076, ST1486, ST1604, ST1889, STS229, ST0720, ST0173, STS095, ST2514, ST1022, ST2372, ST0193, ST0489, ST1115, ST1301, STS042, ST1473, STS071, STS074, STS163, STS072, STS250, STS248, ST2039, ST2236, ST2114, ST2562, ST0051, ST0164, ST0722, ST2550, ST1593, ST0256, ST0331, ST1268, ST2084, ST2190, ST1409, ST0808, STS035, ST0758, ST1043, ST1386, ST1710, ST1716, ST1867, ST1890, ST2388, STS086, ST0749, ST0837, ST0980, ST2050, ST0757, ST0766, ST2210, ST1773, ST1340, ST1054, ST1275, ST1007, ST1041, ST0684, ST0072, ST0349, ST1271, ST0334, ST1630, ST0371, TK0063, TK0559, TK1041, TK1261, TK1826, TK1881, TK2190, TK1086, TK1883, TK1955, TK2291, TK2134, TK1285, TK1487, TK0168, TK1331, TK0567, TK0834, TK1491, TK1210, TK2110, TK2052, TK0143, TK1413, TK2289, TK2270, TK1815, TK1439, TK0695, TK1259, TK0107, TK0448, TK1057, TK1058, TK1272, TK0697, TK0126, TK0539, TK1266, TK1688, TK2197, TK2218, TK1489, TK1339, TK0142, TK0169, TK1246, TK0770, TK1494, TK1924, TK2107, TK1143, TK1654, TK0151, TK0779, TK2151, TK0132, TK2287, TK1280, TK2024, TK0471, TK1769, TK1913, TK1050, Tpen_0466, Tpen_0552, Tpen_0860, Tpen_1509, Tpen_0232, Tpen_0836, Tpen_1499, Tpen_0577, Tpen_0018, Tpen_0579, Tpen_0150, Tpen_0366, Tpen_0869, Tpen_0668, Tpen_0348, Tpen_1236, Tpen_0124, Tpen_0102, Tpen_0973, Tpen_1621, Tpen_0378, Tpen_0538, Tpen_0707, Tpen_0776, Tpen_0069, Tpen_0090, Tpen_0173, Tpen_1796, Tpen_1358, Tpen_0115, Tpen_1464, Tpen_1595, Tpen_1401, Tpen_0901, Tpen_1818, Tpen_0293, Tpen_0690, Tpen_0374, Tpen_0710, Tpen_0070, Tpen_1551, Tpen_1591, Tpen_1154, Tpen_1562, Ta0472, Ta0731, Ta1110, Ta0115, Ta1173, Ta1443, Ta0185, Ta0678, Ta0608, Ta0257, Ta0981, Ta0093, Ta0550m, Ta0842, Ta0872, Ta1362m, Ta0736, Ta1394, Ta0166, Ta0675, Ta0748, Ta1231, Ta1186, Ta0106, Ta0948, Ta1282m, Ta1363, Ta0131, Ta0320m, Ta0411, Ta1064, Ta1166, Ta1218, Ta1503, Ta0201, Ta0346, Ta1496, Ta0868m, Ta1061m, Ta0825, Ta0795, Ta0199, Ta1485, Ta0945, Ta0940, Ta0134, Ta0685, Ta0890, Ta1324, TVN0192, TVN0983, TVN1251, TVN0658, TVN0295, TVN1196, TVN1337, TVN1127, TVN0160, TVN0945, TVN0938, TVN0292, TVN0236, TVN0364, TVN0447, TVN0906, TVN1422, TVN0185, TVN0291, TVN0514, TVN1093, TVN0210, TVN1272, TVN0519, TVN0603, TVN1246, TVN1408, TVN1203, TVN1162, TVN0516, TVN1265, TVN1392, TVN1493, TVN0934, TVN0728, TVN0704, TVN1394, TVN0084, TVN1083, TVN1089, TVN0213, TVN1149, TVN0972, TVN0377, LRC567, RCIX1274, RCIX1420, RCIX1655, RCIX1698, RCIX2213, RCIX2336, RRC298, RRC486, RRC76, RCIX1140, RCIX2193, RCIX670, RCIX684, RCIX808, RCIX820, LRC582, RCIX785, LRC109, RCIX103, RCIX105, RCIX106, RCIX1508, RCIX1739, RCIX2247, RRC465, RCIX1740, RCIX2328, RRC178, LRC575, RCIX1349, RCIX1520, LRC520, RCIX125, RCIX1430, RCIX148, RCIX1527, RCIX1743, RCIX2456, RCIX449, RCIX571, RRC212, RCIX960, LRC190, RCIX1230, RCIX414, RCIX1747, LRC319, RCIX1292, RCIX1376, RCIX2173, RCIX2196, RRC154, RCIX1238, RCIX1068, RCIX1190, RCIX1914, RCIX2177, RCIX824, RCIX989, RCIX2108, LRC274, LRC304, RCIX1189, RCIX1785, RCIX1790, and RCIX90.

In various embodiments, the engineered protein sensor and/or switch is an engineered version of a *B. subtilis* TF, such as Abh, AbrB, AcoR, AdaA, AhrC, AlaR, AlsR, AnsR, AraR, ArfM, ArsR, AzlB, BirA, BkdR, BltR, BmrR, CcpA, CcpB, CcpC, CggR, CheB, CheV, CheY, CitR, CitT, CodY, ComA, ComK, ComZ, CssR, CtsR, DctR, DegA, DegU, DeoR, DnaA, ExuR, FNR, FruR, Fur, GabR, GerE, GlcK, GlcR, GlcT, GlnR, GlpP, GltC, GltR, GntR, GutR, Hbs, Hpr, HrcA, HtrA, HutP, HxlR, IolR, Ipi, KdgR, KipR, LacR, LevR, LexA, LicR, LicT, LmrA, LrpA, LrpB, LrpC, LytR, LytT, ManR, MecA, Med, MntR, MsmR, Mta, MtlR, MtrB, NhaX, PadR, PaiA, PaiB, PerR, Phage PBSX transcriptional regulator, PhoP, PksA, PucR, PurR, PyrR, RbsR, ResD, Rho, RocR, Rok, RplT, RsfA, SacT, SacV, SacY, SenS, SigA, SigB, SigD, SigE, SigF, SigG, SigH, SigI, SigK, SigL, SigM, SigV, SigW, SigX, SigY, SigZ, SinR, Slr, SplA, Spo0A, Spo0F, SpoIIID, SpoVT, TenA, TenI, TnrA, TreR, TrnB-Gly1, TrnB-Phe, TrnD-Cys, TrnD-Gly, TrnD-Phe, TrnD-Ser, TrnD-Trp, TrnD-Tyr, TrnI-Gly, TrnI-Thr, TrnJ-Gly, TrnS-Leu2, TrnSL-Tyr1, TrnSL-Val2, Xpf, Xre, XylR, YacF, YazB, YbaL, YbbB, YbbH, YbdJ, YbfA, YbfI, YbfP, YbgA, YcbA, YcbB, YcbG, YcbL, YccF, YccH, YceK, YcgE, YcgK, YclA, YclJ, YcnC, YcnK, YcxD, YczG, YdcH, YdcN, YdeB, YdeC, YdeE, YdeF, YdeL, YdeP, YdeS, YdeT, YdfD, YdfF, YdfI, YdfL, YdgC, YdgG, YdgJ, YdhC, YdhQ, YdhR, YdiH, YdzF, YerO, YesN, YesS, YetL, YezC, YezE, YfhP, YfiA, YfiF, YfiK, YfiR, YfiV, YfmP, YhbI, YhcB, YhcF, YhcZ, YhdE, YhdI, YhdQ, YhgD, YhjH, YhjM, YisR, YisV, YjbD, YjdI, YkmA, YkoG, YkoM, YkvE, YkvN, YkvZ, YlaC, YlbO, YlpC, YmfC, YneI, YoaU, YobD, YobQ, YocG, YodB, YofA, YonR, YopO, YopS, YozA, YozG, YpbH, YpIP, YpoP, YpuH, YqaE, YqaF, YqaG, YqfL, YqzB, YraB, YraN, YrdQ, YrhI, YrhM, YrkP, YrxA, YrzC, YsiA, YsmB, YtcD, YtdP, YtlI, YtrA, YtsA, YttP, YtzE, YufM, YulB, YurK, YusO, YusT, YuxN, YvaF, YvaN, YvaO, YvaP, YvbA, YvbU, YvcP, YvdE, YvdT, YvfI, YvfU, YvhJ, YvkB, YvmB, YvnA, YvoA, YvqC, YvrH, YvrI, YvyD, YvzC, YwaE, YwbI, YwcC, YwfK, YwgB, YwhA, YwoH, YwqM, YwrC, YwtF, YxaD, YxaF, YxbF, YxdJ, YxjL, YxjO, YyaN, YybA, YybE, YybR, YycF, YydK, and Zur.

In various embodiments, the engineered protein sensor and/or switch is an engineered version of a *Arabidopsis thaliana* TF, such as AT1G01060, AT1G01380, AT1G01530, AT1G02340, AT1G04370, AT1G06160, AT1G07640, AT1G09530, AT1G09770, AT1G10170, AT1G12610, AT1G12860, AT1G12980, AT1G13960, AT1G14350, AT1G14920, AT1G15360, AT1G16490, AT1G18570, AT1G19220, AT1G19350, AT1G19850, AT1G21970, AT1G22070, AT1G23420, AT1G24260, AT1G24590, AT1G25560, AT1G26310, AT1G26870, AT1G26945, AT1G27730, AT1G28300, AT1G30210, AT1G30330, AT1G30490, AT1G32330, AT1G32540, AT1G32640, AT1G32770, AT1G33240, AT1G34370, AT1G34790, AT1G35515, AT1G42990, AT1G45249, AT1G46768, AT1G47870, AT1G51700, AT1G52150, AT1G52880, AT1G52890, AT1G53230, AT1G53910, AT1G54060, AT1G55580, AT1G55600, AT1G56010, AT1G56650, AT1G62300, AT1G62360, AT1G63650, AT1G65620, AT1G66350, AT1G66390, AT1G66600, AT1G67260, AT1G68640, AT1G69120, AT1G69180, AT1G69490, AT1G69600, AT1G70510, AT1G71030, AT1G71692, AT1G71930, AT1G73730, AT1G74930, AT1G75080, AT1G76420, AT1G77850, AT1G78600, AT1G79180, AT1G79580, AT1G79840, AT2G01500, AT2G01570, AT2G01930, AT2G02450, AT2G03340, AT2G16910, AT2G17950, AT2G20180, AT2G22300, AT2G22540, AT2G22630, AT2G22770, AT2G23760, AT2G24570, AT2G26150, AT2G27050, AT2G27300, AT2G27990, AT2G28160, AT2G28350, AT2G28550, AT2G28610, AT2G30250, AT2G30432, AT2G33810, AT2G33835, AT2G33860, AT2G33880, AT2G34710, AT2G36010, AT2G36270, AT2G36890, AT2G37260, AT2G37630, AT2G38470, AT2G40220, AT2G40950, AT2G42200, AT2G42830, AT2G43010, AT2G45190, AT2G45660, AT2G46270, AT2G46410, AT2G46680, AT2G46770, AT2G46830, AT2G46870, AT2G46970, AT2G47190, AT2G47460, AT3G01140, AT3G01470, AT3G02990, AT3G03450, AT3G04670, AT3G07650, AT3G10800, AT3G11440, AT3G12250, AT3G13540, AT3G13890, AT3G15170, AT3G15210, AT3G15500, AT3G15510, AT3G16770, AT3G16857, AT3G17609, AT3G18990, AT3G19290, AT3G20310, AT3G20770, AT3G22170, AT3G23130, AT3G23250, AT3G24650, AT3G25710, AT3G26744, AT3G26790, AT3G27785, AT3G27810, AT3G27920, AT3G28470, AT3G28910, AT3G44750, AT3G46640, AT3G48160, AT3G48430, AT3G49940, AT3G50410, AT3G51060, AT3G54220, AT3G54320, AT3G54340, AT3G54620, AT3G55370, AT3G56400, AT3G58070, AT3G58780, AT3G59060, AT3G61850, AT3G61890, AT3G61910, AT3G62420, AT4G00120, AT4G00180, AT4G00220, AT4G01250, AT4G01540, AT4G02560, AT4G04450, AT4G08150, AT4G09820, AT4G09960, AT4G15090, AT4G16110, AT4G16780, AT4G17750, AT4G18960, AT4G20380, AT4G21330, AT4G21750, AT4G23550, AT4G23810, AT4G24020, AT4G24240, AT4G24470, AT4G24540, AT4G25470, AT4G25480, AT4G25490, AT4G25530, AT4G26150, AT4G27330, AT4G27410, AT4G28110, AT4G28610, AT4G30080, AT4G31550, AT4G31800, AT4G31920, AT4G32730, AT4G32880, AT4G32980, AT4G34000, AT4G34590, AT4G34990, AT4G35900, AT4G36730, AT4G36870, AT4G36920, AT4G36930, AT4G37540, AT4G37650, AT4G37750, AT4G38620, AT5G01900, AT5G02030, AT5G02470, AT5G03150, AT5G03680, AT5G03790, AT5G04240, AT5G05410, AT5G06070, AT5G06100, AT5G06650, AT5G06950, AT5G06960, AT5G07100, AT5G07690, AT5G07700, AT5G08130, AT5G09750, AT5G10140, AT5G10510, AT5G11260, AT5G11510, AT5G12870, AT5G13790, AT5G14010, AT5G14750, AT5G14960, AT5G15840, AT5G15850, AT5G16560, AT5G16820, AT5G17300, AT5G17430, AT5G18560, AT5G18830, AT5G20240, AT5G20730, AT5G21120, AT5G22220, AT5G22570, AT5G23000, AT5G23260, AT5G26660, AT5G35550, AT5G35770, AT5G37020, AT5G37260, AT5G40330, AT5G40350, AT5G40360, AT5G41315, AT5G41410, AT5G42630, AT5G43270, AT5G45980, AT5G47220, AT5G48670, AT5G51990, AT5G52830, AT5G53200, AT5G53210, AT5G53950, AT5G54070, AT5G56110, AT5G56270, AT5G56860, AT5G59570, AT5G59820, AT5G60690, AT5G60890, AT5G60910, AT5G61270, AT5G61420, AT5G61850, AT5G62000, AT5G62020, AT5G62380, AT5G62430, AT5G65050, AT5G66870, AT5G67300, and AT5G67420.

In various embodiments, the engineered protein sensor and/or switch is an engineered version of a *Drosophila melanogaster* TF, such as CG10325, CG11648, CG6093, CG3796, CG9151, CG15845, CG3935, CG3166, CG8376, CG3258, CG6677, CG3629, CG1034, CG3578, CG11491, CG12653, CG1759, CG6384, CG11924, CG4881, CG8367, CG17894, CG8669, CG2714, CG5893, CG9745, CG5102, CG2189, CG33183, CG9908, CG10798, CG1897, CG11094, CG2711, CG10604, CG32346, CG5714, CG1765, CG7383, CG32180, CG8127, CG1007, CG2988, CG9015, CG14941, CG8365, CG2328, CG8933, CG10488, CG6502, CG10002, CG2707, CG10034, CG2047, CG4059, CG33133, CG9656, CG2692, CG3388, CG7952, CG6494, CG11607, CG9786, CG4694, CG9768, CG1619, CG5748, CG17117, CG17835, CG2275, CG33956, CG10197, CG4717, CG4761, CG3340, CG3647, CG3758, CG4158, CG4148, CG7664, CG10699, CG5954, CG17743, CG1264, CG3839, CG32120, CG1689, CG8346, CG6096, CG8361, CG1705, CG14548, CG8328, CG8333, CG2050, CG18740, CG9045, CG10250, CG11450, CG6534, CG3851, CG1133, CG7467, CG6824, CG5109, CG12212, CG3978, CG17077, CG9610, CG8246, CG6716, CG7230, CG6348, CG10393, CG1849, CG9495, CG1030, CG8544, CG7734, CG1641, CG16738, CG3956, CG3836, CG11121, CG7847, CG3992, CG7938, CG17958, CG6993, CG8573, CG8599, CG8409, CG8068, CG11502, CG4216, CG16778, CG1378, CG6883, CG8651, CG1374, CG1856, CG10619, CG2956, CG10388, CG2762, CG4380, CG6172, CG7803, CG1046, CG1048, CG3411, CG12154, CG7895, CG3827, CG11387, CG17950, CG12287, CG7450, CG2368, CG6143, CG6338, CG2939, CG6464, CG17228, CG1322, CG1449, CG7672, CG14307, CG7771, CG5403, CG3497, CG5488, CG4220, CG2125, CG18412, CG7902, CG7937, CG18023, CG9097, CG2102, CG1130, CG3242, CG10021, CG1132, CG3668, CG11921, CG11922, CG9310, CG8887, CG3114, CG6634, CG1464, CG11049, CG14513, CG3090, CG8404, CG3886, CG12052, CG4354, CG1454, CG7018, CG5583, CG2914, CG4952, CG5683, CG4491, CG33152, CG9930, CG5441, CG6570, CG3905, CG8704, CG17921, CG4817, CG7562, CG2851, CG5965, CG7508, CG5580, CG5557, CG6964, CG5575, CG6794, CG2655, CG3052, CG6545, CG7187, CG17161, CG8625, CG12399, CG1775, CG1429, CG31240, CG7260, CG5529, CG4654, CG12223, CG6376, CG5247, CG11494, CG33261, CG12296, CG8103, CG1072, CG7959, CG7960, CG8567, CG18389, CG11992, CG5069, CG12245, CG10601, CG6103, CG1864, CG2678, CG5264, CG11987, CG6215, CG8522, CG7199, CG11783, CG8396, CG11798, CG9019, CG4029, CG10036, CG7951, CG7659, CG1650, CG10159, CG15319, CG5838, CG9398, CG7413, CG5393, CG10571, CG10605, CG14029, CG6604, CG17888, CG13598, CG4257, CG13951, CG9648, CG11186, CG3858, CG9696, CG5799, CG14938, CG1343, CG6312, CG5201, CG10052, CG8013, CG1447, CG32788, CG11202, CG9415, CG1507, CG10270, CG3998, CG5005, CG10269, CG7391, CG8667, CG8727, CG5206, CG13316, CG7807, CG2819, CG3848, CG16902, CG6269, CG10016, CG7760, CG9653, CG1414, CG15552, CG4013, CG8524, CG1071, CG5649, CG2712, CG1605, CG11182, CG18455, CG4303, CG9102, CG17829, CG2932, CG11551, CG2262, CG8474, CG6352, CG6121, CG7958, CG4143, CG11354, CG5935, CG8290, CG32575, CG9418, CG11352, CG3871, CG6627, CG1024, CG8108, CG2790, CG1966, CG11194, CG9776, CG7758, CG8208, CG2244, CG5067, CG5229, CG18783, CG18124, CG15286, CG11405, CG3268, CG11902, CG5133, CG15269, CG3491, CG17328, CG4185, CG16863, CG12630, CG32904, CG17594, CG1922, CG13906, CG18024, CG9233, CG12690, CG2875, CG17592, CG4136, CG12236, CG3726, CG3815, CG3847, CG14441, CG14438, CG3075, CG4575, CG3032, CG4617, CG9650, CG2116, CG2120, CG2129, CG15336, CG10959, CG18262, CG11294, CG12075, CG15365, CG7041, CG7055, CG2889, CG9817, CG2202, 0G11122, CG11696, 0G11695, CG11085, CG4404, CG4318, CG15749, CG1716, 0G11172, CG11071, CG6211, CG9215, CG8119, CG8944, CG8578, CG8909, CG8924, CG9609, CG6769, CG5927, CG6470, CG7101, CG7556, CG14200, CG9571, CG11710, CG1529, CG11617, CG4133, CG31670, CG11723, CG17257, CG3407, CG17612, CG15435, CG15436, CG9088, CG13775, CG9200, CG4496, CG3838, CG13123, CG18619, CG18144, CG5034, CG12299, CG4621, CG6686, CG6792, CG9932, CG5204, CG9305, CG7099, CG5953, CG17912, CG5545, CG10348, CG10431, CG10446, CG17568, CG10263, CG10366, CG10462, CG10447, CG10631, CG10949, CG9342, CG18362, CG15216, CG1832, CG3136, CG2682, CG1845, CG1621, CG1620, CG1603, CG1602, CG12769, CG11641, CG8643, CG8216, CG1663, CG18446, CG12744, CG1407, CG18011, CG12942, CG12391, CG13204, CG12370, CG8821, CG8819, CG3850, CG4676, CG6061, CG6701, CG17385, CG17390, CG10209, CG8089, CG8092, CG16801, CG8314, CG8388, CG7786, CG4282, CG15710, CG17287, CG18468, CG4903, CG15073, CG11906, CG13424, CG9954, CG10543, CG9437, CG10321, CG10318, CG13493, CG11301, CG10344, CG9895, CG9890, CG9876, CG3941, CG5591, CG3065, CG3328, CG11414, CG4707, CG6905, CG1233, CG17181, CG13897, CG9139, CG2199, CG12104, CG1244, CG15812, CG14962, CG14965, CG12029, CG12605, CG15011, CG5249, CG17334, CG13287, CG13296, CG10274, CG7386, CG10147, CG8591, CG7404, CG7015, CG6683, CG6765, CG5093, CG5187, CG3891, CG3445, CG3654, CG7839, CG6272, CG11799, CG7368, CG4328, CG10704, CG10654, CG14117, CG17361, CG17359, CG7345, CG3919, CG6854, CG13458, CG7372, CG15715, CG9705, CG32171, CG18265, CG7271, CG4076, CG8765, CG11456, CG10565, CG7204, CG11247, CG14451, CG14655, CG14667, CG12162, CG10979, CG10296, CG9727, CG10267, CG33323, CG2702, CG9638, CG7963, CG8145, CG11762, CG8159, CG9793, CG9797, CG8359, CG11966, CG11984, CG11033, CG12952, CG16779, CG8301, CG8319, CG16899, CG8478, CG8484, CG6254, CG4570, CG4820, CG6689, CG6791, CG14710, CG6808, CG14711, CG6813, CG18476, CG6913, CG10042, CG5196, CG5245, CG33976, CG7518, CG15889, CG3143, CG7987, CG14860, CG6654, CG6276, CG5083, CG10278, CG5952, CG10309, CG3995, CG17803, CG17806, CG17802, CG17801, CG7357, CG7785, CG18599, CG7691, CG17186, CG4424, CG4854, CG4413, CG4936, CG4360, CG4217, CG15696, CG5737, CG7056, CG7045, CG7046, CG6990, CG4677, CG33336, CG4374, CG6129, CG5669, CG13617, CG13624, CG6892, CG11375, CG10669, CG4553, CG4730, CG17198, CG17197, CG17195, CG4956, CG32474, CG3350, CG5586, CG1647, CG14514, CG15504, CG15514, CG7928, CG2229, CG12071, CG11317, CG12054, CG1792, CG2052, CG11093, CG11152, CG11153, CG17172, CG6889, CG3743, CG13475, CG3526, CG11398, CG12767, CG15367, CG33473, CG14767, CG3576, CG12659, CG13109, CG12809, CG8817, CG8254, CG16910, CG3274, CG18764, CG32139, CG32577, CG2380, CG15736, CG13399, CG4427, CG12219, CG18647, CG31753, CG33720, CG30011, CG30020, CG30077, CG30401, CG30403, CG30420, CG30431, CG30443, CG31169, CG31224, CG31365, CG31388, CG31392, CG31441, CG31460, CG31481, CG31510, CG31612, CG31632, CG31642, CG31782, CG31835, CG31875, CG31955, CG32006, CG32050, CG32105, CG32121, CG32264, CG32296, CG32532, CG32719, CG32767, CG32772, CG32778, CG32830, CG33695, CG32982, CG33178, CG33213, CG33221, CG33520, CG33525, CG33557, CG33936, CG33980, CG34031, CG12632, CG17469, CG34100, CG34145, CG34149, CG34340, CG34346, CG34367, CG34376, CG34395, CG34403, CG34406, CG34407, CG34415, CG34419, CG34421, CG34422, CG8961, CG9397, CG10037, CG31258, CG31666, CG12196, CG6930, CG12238, CG33546, CG42234, CG34360, CG42267, CG42277, CG42281, CG42311, CG42332, CG42344, CG4807, CG7752, CG12701, CG17100, CG11971, CG42516, CG42515, CG6667, CG1028, CG3281, CG12124, CG42599, CG8506, CG17836, CG1070, and CG8676.

In various embodiments, the engineered protein sensor and/or switch is an engineered version of a mouse TF, such as mouse loci 11538, 11568, 11569, 11614, 11622, 11624, 11632, 11634, 11694, 11695, 11733, 11736, 11819, 11835, 11859, 11863, 11864, 11865, 11878, 11906, 11908, 11909, 11910, 11911, 11920, 11921, 11922, 11923, 11924, 11925, 11991, 12013, 12014, 12020, 12021, 12022, 12023, 12029, 12051, 12053, 12142, 12151, 12173, 12180, 12189, 12192, 12224, 12265, 12326, 12355, 12387, 12393, 12394, 12395, 12399, 12400, 12416, 12417, 12418, 12454, 12455, 12566, 12567, 12572, 12578, 12579, 12580, 12581, 12590, 12591, 12592, 12606, 12607, 12608, 12609, 12611, 12653, 12677, 12705, 12753, 12785, 12848, 12912, 12913, 12914, 12915, 12916, 12951, 13017, 13018, 13047, 13048, 13134, 13163, 13170, 13172, 13180, 13196, 13198, 13345, 13390, 13392, 13393, 13394, 13395, 13396, 13433, 13435, 13486, 13494, 13496, 13555, 13557, 13559, 13560, 13591, 13592, 13593, 13626, 13653, 13654, 13655, 13656, 13661, 13709, 13710, 13711, 13712, 13713, 13714, 13716, 13796, 13797, 13798, 13799, 13813, 13819, 13864, 13865, 13871, 13872, 13875, 13876, 13982, 13983, 13984, 14008, 14009, 14011, 14013, 14025, 14028, 14029, 14030, 14055, 14056, 14085, 14105, 14106, 14154, 14155, 14200, 14233, 14234, 14235, 14236, 14237, 14238, 14239, 14240, 14241, 14247, 14281, 14282, 14283, 14284, 14359, 14390, 14391, 14457, 14460, 14461, 14462, 14463, 14464, 14465, 14472, 14489, 14531, 14534, 14536, 14581, 14582, 14605, 14632, 14633, 14634, 14659, 14797, 14815, 14836, 14842, 14843, 14884, 14885, 14886, 14896, 14912, 15110, 15111, 15161, 15163, 15181, 15182, 15183, 15184, 15185, 15193, 15205, 15206, 15207, 15208, 15209, 15213, 15214, 15218, 15220, 15221, 15223, 15227, 15228, 15229, 15242, 15248, 15251, 15258, 15260, 15273, 15284, 15285, 15331, 15353, 15354, 15361, 15364, 15370, 15371, 15372, 15373, 15375, 15376, 15377, 15378, 15379, 15384, 15394, 15395, 15396, 15397, 15398, 15399, 15400, 15401, 15402, 15403, 15404, 15405, 15407, 15408, 15410, 15412, 15413, 15414, 15415, 15416, 15417, 15421, 15422, 15423, 15424, 15425, 15426, 15427, 15429, 15430, 15431, 15432, 15433, 15434, 15436, 15437, 15438, 15460, 15499, 15500, 15563, 15569, 15900, 15901, 15902, 15903, 15904, 15951, 15976, 16150, 16151, 16201, 16348, 16362, 16363, 16364, 16371, 16372, 16373, 16391, 16392, 16476, 16477, 16478, 16596, 16597, 16598, 16599, 16600, 16601, 16656, 16658, 16761, 16764, 16814, 16815, 16825, 16826, 16842, 16869, 16870, 16871, 16872, 16873, 16874, 16875, 16876, 16909, 16911, 16917, 16918, 16969, 17095, 17119, 17121, 17122, 17125, 17126, 17127, 17128, 17129, 17130, 17131, 17132, 17133, 17134, 17135, 17172, 17173, 17187, 17188, 17191, 17192, 17215, 17216, 17217, 17218, 17219, 17220, 17257, 17258, 17259, 17260, 17261, 17268, 17274, 17283, 17285, 17286, 17300, 17301, 17318, 17341, 17342, 17344, 17354, 17355, 17420, 17425, 17428, 17480, 17536, 17537, 17681, 17684, 17692, 17701, 17702, 17703, 17749, 17764, 17765, 17859, 17863, 17864, 17865, 17869, 17870, 17876, 17877, 17878, 17927, 17928, 17932, 17933, 17936, 17937, 17938, 17977, 17978, 17979, 17984, 18002, 18012, 18013, 18014, 18018, 18019, 18020, 18021, 18022, 18023, 18024, 18025, 18027, 18028, 18029, 18030, 18032, 18033, 18034, 18036, 18037, 18038, 18044, 18045, 18046, 18071, 18072, 18088, 18089, 18091, 18092, 18094, 18095, 18096, 18109, 18124, 18128, 18129, 18131, 18132, 18140, 18142, 18143, 18171, 18181, 18185, 18193, 18198, 18227, 18291, 18292, 18393, 18412, 18420, 18423, 18424, 18426, 18432, 18503, 18504, 18505, 18506, 18507, 18508, 18509, 18510, 18511, 18514, 18515, 18516, 18519, 18572, 18606, 18609, 18612, 18616, 18617, 18626, 18627, 18628, 18667, 18676, 18685, 18736, 18740, 18741, 18742, 18771, 18789, 18854, 18933, 18935, 18983, 18985, 18986, 18987, 18988, 18990, 18991, 18992, 18993, 18994, 18995, 18996, 18997, 18998, 18999, 19009, 19013, 19014, 19015, 19016, 19017, 19018, 19049, 19056, 19060, 19084, 19099, 19127, 19130, 19182, 19184, 19202, 19213, 19231, 19290, 19291, 19326, 19330, 19377, 19401, 19411, 19434, 19645, 19650, 19651, 19664, 19668, 19687, 19696, 19697, 19698, 19708, 19712, 19724, 19725, 19726, 19727, 19763, 19820, 19822, 19826, 19883, 19885, 20016, 20017, 20018, 20019, 20020, 20021, 20022, 20024, 20128, 20174, 20181, 20182, 20183, 20185, 20186, 20204, 20218, 20220, 20230, 20231, 20232, 20289, 20371, 20375, 20384, 20409, 20429, 20439, 20464, 20465, 20466, 20467, 20471, 20472, 20473, 20474, 20475, 20476, 20480, 20481, 20583, 20585, 20586, 20587, 20589, 20591, 20592, 20602, 20613, 20638, 20664, 20665, 20666, 20667, 20668, 20669, 20670, 20671, 20672, 20673, 20674, 20675, 20677, 20678, 20679, 20680, 20681, 20682, 20683, 20687, 20688, 20689, 20728, 20787, 20788, 20807, 20819, 20833, 20841, 20842, 20846, 20847, 20848, 20849, 20850, 20851, 20852, 20893, 20901, 20904, 20922, 20923, 20924, 20997, 21339, 21340, 21341, 21343, 21349, 21350, 21374, 21375, 21380, 21382, 21383, 21384, 21385, 21386, 21387, 21388, 21389, 21399, 21400, 21401, 21405, 21406, 21407, 21408, 21410, 21411, 21412, 21413, 21414, 21415, 21416, 21417, 21418, 21419, 21420, 21422, 21423, 21425, 21426, 21427, 21428, 21429, 21652, 21674, 21676, 21677, 21678, 21679, 21685, 21780, 21781, 21783, 21804, 21807, 21815, 21833, 21834, 21835, 21843, 21847, 21848, 21849, 21869, 21885, 21886, 21887, 21888, 21907, 21908, 21909, 21917, 21929, 21945, 21981, 22025, 22026, 22051, 22057, 22059, 22061, 22062, 22088, 22160, 22200, 22221, 22255, 22259, 22260, 22278, 22282, 22286, 22326, 22337, 22383, 22385, 22431, 22433, 22608, 22632, 22634, 22639, 22640, 22642, 22646, 22654, 22658, 22661, 22666, 22668, 22678, 22680, 22685, 22691, 22694, 22695, 22696, 22697, 22698, 22700, 22701, 22702, 22704, 22709, 22710, 22712, 22715, 22717, 22718, 22719, 22722, 22750, 22751, 22754, 22755, 22756, 22757, 22758, 22759, 22761, 22762, 22764, 22767, 22768, 22770, 22771, 22772, 22773, 22775, 22776, 22778, 22779, 22780, 23808, 23827, 23849, 23850, 23856, 23857, 23871, 23872, 23885, 23894, 23942, 23957, 23958, 23989, 23994, 24068, 24074, 24075, 24113, 24116, 24135, 24136, 26356, 26371, 26379, 26380, 26381, 26386, 26404, 26413, 26417, 26419, 26423, 26424, 26427, 26461, 26465, 26573, 26754, 26927, 26939, 27049, 27056, 27057, 27059, 27081, 27140, 27217, 27223, 27224, 27274, 27386, 28019, 29806, 29808, 29813, 29861, 29871, 30046, 30051, 30794, 30841, 30923, 30927, 30928, 30942, 30944, 30946, 30951, 50496, 50524, 50721, 50754, 50777, 50783, 50794, 50796, 50817, 50868, 50887, 50907, 50913, 50914, 50916, 50996, 51792, 51813, 52024, 52040, 52231, 52502, 52609, 52615, 52705, 52708, 52712, 52897, 53314, 53317, 53357, 53380, 53415, 53417, 53626, 53868, 53869, 53970, 53975, 54006, 54123, 54131, 54132, 54139, 54169, 54343, 54352, 54388, 54422, 54446, 54562, 54601, 54633, 54678, 54711, 55927, 55942, 55994, 56030, 56070, 56196, 56198, 56218, 56220, 56222, 56233, 56275, 56309, 56312, 56314, 56321, 56353, 56380, 56381, 56404, 56406, 56449, 56458, 56469, 56484, 56490, 56501, 56503, 56505, 56522, 56523, 56525, 56613, 56642, 56707, 56736, 56771, 56784, 56787, 56805, 56809, 56856, 56869, 57080, 57230, 57246, 57314, 57316, 57376, 57737, 57745, 57748, 57756, 57765, 57782, 58172, 58180, 58198, 58202, 58206, 58234, 58805, 59004, 59021, 59024, 59026, 59035, 59057, 59058, 60345, 60406, 60611, 64050, 64144, 64290, 64379, 64383, 64384, 64406, 64453, 64685, 65020, 65247, 65255, 65256, 65257, 66056, 66118, 66136, 66213, 66233, 66277, 66352, 66376, 66420, 66464, 66491, 66505, 66556, 66596, 66622, 66634, 66642, 66671, 66698, 66729, 66799, 66867, 66880, 66923, 66930, 66959, 66970, 66980, 66985, 67057, 67065, 67122, 67150, 67151, 67155, 67199, 67235, 67260, 67279, 67288, 67367, 67370, 67379, 67381, 67389, 67419, 67439, 67575, 67657, 67673, 67692, 67710, 67815, 67847, 67873, 67949, 67985, 67993, 68040, 68153, 68196, 68268, 68346, 68479, 68558, 68701, 68705, 68776, 68839, 68842, 68854, 68910, 68911, 68992, 69020, 69125, 69167, 69168, 69188, 69234, 69241, 69257, 69260, 69299, 69317, 69389, 69539, 69606, 69656, 69716, 69790, 69833, 69890, 69920, 69944, 70073, 70122, 70127, 70315, 70350, 70392, 70408, 70428, 70459, 70497, 70508, 70601, 70625, 70637, 70650, 70673, 70779, 70796, 70797, 70823, 70859, 70981, 71041, 71063, 71131, 71137, 71163, 71176, 71241, 71280, 71371, 71375, 71409, 71458, 71468, 71592, 71597, 71702, 71722, 71752, 71767, 71777, 71782, 71793, 71828, 71834, 71838, 71839, 71939, 71949, 71990, 71991, 72057, 72074, 72135, 72180, 72195, 72199, 72290, 72293, 72323, 72325, 72388, 72459, 72465, 72475, 72556, 72567, 72615, 72720, 72727, 72739, 72823, 72949, 72958, 73178, 73181, 73340, 73389, 73451, 73469, 73503, 73610, 73614, 73844, 73845, 73945, 74007, 74068, 74106, 74120, 74123, 74149, 74164, 74168, 74197, 74282, 74318, 74322, 74326, 74335, 74352, 74377, 74481, 74533, 74561, 74570, 74838, 75196, 75199, 75210, 75291, 75305, 75339, 75387, 75480, 75482, 75507, 75572, 75599, 75605, 75646, 75725, 75901, 76007, 76022, 76294, 76308, 76365, 76389, 76467, 76572, 76580, 76793, 76803, 76804, 76834, 76893, 76900, 77057, 77114, 77117, 77264, 77286, 77318, 77480, 77683, 77889, 77907, 77913, 78020, 78088, 78246, 78251, 78284, 78455, 78469, 78541, 78619, 78656, 78699, 78703, 78783, 78829, 78910, 78912, 78921, 78929, 79221, 79233, 79362, 79401, 80283, 80509, 80720, 80732, 80859, 80902, 81601, 81630, 81703, 81845, 81879, 83383, 83395, 83396, 83557, 83602, 83925, 83993, 84653, 93674, 93681, 93686, 93691, 93759, 93760, 93761, 93762, 93837, 93871, 94047, 94112, 94187, 94275, 96979, 97064, 97165, 98053, 98403, 99377, 99730, 100090, 100563, 100710, 100978, 101095, 101206, 102162, 102209, 102334, 103136, 103806, 103889, 104328, 104349, 104360, 104383, 104384, 104394, 104886, 105377, 105594, 105859, 106795, 106894, 107351, 107433, 107499, 107503, 107568, 107586, 107751, 107765, 107771, 107889, 107932, 107951, 108060, 108098, 108143, 108655, 108672, 108857, 109113, 109115, 109575, 109594, 109663, 109676, 109889, 109910, 109958, 109972, 109973, 109995, 110052, 110061, 110068, 110109, 110147, 110506, 110521, 110616, 110641, 110647, 110648, 110784, 110796, 110805, 110913, 112077, 114142, 114565, 114606, 114642, 114774, 114889, 116810, 116848, 116870, 116871, 116912, 117168, 117198, 117590, 118445, 140477, 140490, 140500, 140577, 140743, 170574, 170644, 170729, 170740, 170767, 170787, 170791, 170826, 170938, 192195, 192231, 192285, 192651, 192657, 193796, 195333, 208076, 208258, 208266, 208292, 208439, 208677, 208715, 209011, 209357, 209361, 209416, 209446, 209448, 209707, 210135, 210162, 211378, 212168, 212276, 212391, 212712, 213010, 213990, 214105, 214162, 214384, 214669, 214899, 215031, 216151, 216154, 216285, 216456, 216558, 216578, 217031, 217082, 217127, 217166, 217558, 218030, 218440, 218490, 218624, 218772, 218989, 219150, 223227, 223690, 223701, 223922, 224419, 224585, 224656, 224694, 224829, 224902, 224903, 225876, 225895, 225998, 226049, 226182, 226442, 226641, 226747, 226896, 227099, 227644, 227656, 227940, 228136, 228598, 228731, 228775, 228790, 228829, 228839, 228852, 228869, 228876, 228880, 228980, 229004, 229534, 229663, 229906, 230073, 230162, 230587, 230674, 230700, 230753, 230908, 230936, 230991, 231044, 231051, 231329, 231386, 231986, 231991, 232232, 232337, 232807, 232853, 232854, 232878, 232906, 233056, 233410, 233490, 233863, 233887, 233890, 233908, 233987, 234725, 234959, 235028, 235041, 235050, 235320, 235442, 235582, 235623, 235682, 236193, 237052, 237336, 237409, 237615, 237758, 237960, 238247, 239099, 239546, 239652, 240064, 240120, 240263, 240427, 240442, 240476, 240590, 240690, 241066, 241447, 241520, 242523, 242620, 242705, 243187, 243833, 243906, 243931, 243963, 243983, 244349, 244713, 244813, 244954, 245572, 245583, 245596, 245688, 245841, 246086, 246196, 246198, 246791, 252829, 260298, 268281, 268301, 268396, 268448, 268564, 268741, 268903, 268932, 269252, 269713, 269870, 270076, 270627, 271278, 271305, 272347, 272359, 272382, 277353, 319196, 319207, 319535, 319594, 319599, 319601, 319615, 319695, 319785, 320067, 320376, 320429, 320586, 320595, 320790, 320799, 320875, 320995, 328572, 330301, 330361, 330502, 332937, 338353, 347691, 353187, 353208, 378435, 381319, 386626, and 386655.

Illustrative aTFs are found in Ramos, et al. *Microbiology and Molecular Biology Reviews*, June 2005, p. 326-356 and Tropell, et al. *Microbiol Mol Biol Rev.* 2004 September;68 (3):474-500, the contents of which are hereby incorporated by reference in their entireties.

Protein sensor and/or switch amino acid sequences upon which engineering is to occur may, in various embodiments, be selected by sequence homology using one or more of BLASTP, PSI-BLAST, DELTA-BLAST, OR HMMER, JackHMMER, or the corresponding nucleotide sequences selected by sequence homology search.

Methods of identifying protein sequences that can be candidate protein sensors and/or switches are found in US 2016/0063177, the entire contents of which are hereby incorporated by reference in its entirety.

Various protein sensor and/or switches are engineered as part of the invention and can be interrogated with target molecules. Illustrative engineering approaches include mutagenesis that alters the binding activity of an allosteric protein, e.g. making the allosteric protein suitable for binding the target molecule at the expense of the allosteric proteins cognate ligand (i.e. the ligand that binds to the wild type allosteric protein). In some embodiments, mutagenesis comprises introducing one or more amino acid mutations, e.g. independently selected from substitutions, insertions, deletions, and truncations.

In some embodiments, the amino acid mutations are amino acid substitutions, and may include conservative and/or non-conservative substitutions.

"Conservative substitutions" may be made, for instance, on the basis of similarity in polarity, charge, size, solubility, hydrophobicity, hydrophilicity, and/or the amphipathic nature of the amino acid residues involved. The 20 naturally occurring amino acids can be grouped into the following six standard amino acid groups: (1) hydrophobic: Met, Ala, Val, Leu, Ile; (2) neutral hydrophilic: Cys, Ser, Thr; Asn, Gln; (3) acidic: Asp, Glu; (4) basic: His, Lys, Arg; (5) residues that influence chain orientation: Gly, Pro; and (6) aromatic: Trp, Tyr, Phe.

As used herein, "conservative substitutions" are defined as exchanges of an amino acid by another amino acid listed within the same group of the six standard amino acid groups shown above. For example, the exchange of Asp by Glu retains one negative charge in the so modified polypeptide. In addition, glycine and proline may be substituted for one another based on their ability to disrupt α-helices.

As used herein, "non-conservative substitutions" are defined as exchanges of an amino acid by another amino acid listed in a different group of the six standard amino acid groups (1) to (6) shown above.

In various embodiments, the substitutions may also include non-classical amino acids (e.g. selenocysteine, pyrrolysine, N-formylmethionine β-alanine, GABA and δ-Aminolevulinic acid, 4-aminobenzoic acid (PABA), D-isomers of the common amino acids, 2,4-diaminobutyric acid, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosme, citrulline, homocitrulline, cysteic acid, t-butylglycine, t-butylalanine, phenylglycine, cyclohexylalanine, β-alanine, fluoro-amino acids, designer amino acids such as 3 methyl amino acids, C α-methyl amino acids, N α-methyl amino acids, and amino acid analogs in general).

In various embodiments, regions or domains are swapped between proteins. For instance, the ligand binding domain of an aTF or other protein is swapped to the DNA binding domain of another aTF. In another example, domains or secondary structure features or primary sequence regions of aTFs are swapped or shuffled, including between two or more mutants of the same aTF chassis.

The present invention pertains to various target molecules, for which a protein sensor and/or switch may be engineered. Illustrative target molecules include one or more of the compounds described in WO 2015/017866, e.g. at paragraphs [00107]-[00112], the entire contents of which are hereby incorporated by reference in its entirety. Additionally, illustrative target molecules can include one or more of 1,8-cineole, s-perillic acid, r-perillic acid, alpha-humulene, Nootkatone, Valencene, resveratrol, niacin, atropine, glyphosate, glufosinate, rebadioside A, rebadioside B, rebadioside C, rebaudioside D, rebaudioside E, rebaudioside M, petrosellinic acid, aleuritic acid, 1,5-pentane diamine 1,6-hexane diamine, 1,7-heptane diamine, 1,8-octane diamine. Additionally, illustrative target molecules include Polysaccharides, Sulfonated polysaccharides, molecules such as Heparin, Heparosan, Chondroitin, PAPS (3'-Phosphoadenosine-5'-phosphosulfate), ATP-glucose, CTP-glucose, GTP-glucose, TTP-glucose, or UDP-glucose. In various embodiments, the protein sensor and/or switch is selected based on its cognate ligand identity and any commonality the cognate ligand may have with a target molecules. For example, a shared chemical group between a cognate ligand and a target molecule may direct one to the protein sensor and/or switch which binds to the cognate ligand and lead to the engineering of the protein sensor and/or switch so it can bind to the target molecule.

In some embodiments, the present invention relates to antibiotics. To circumvent toxicity of antibiotics, various resistance mechanisms may be introduced into a producing cell. Without limitation, these may include enzymes which degrade or chemically render the antibiotic less toxic to the producing cell. Resistance to the antibiotics mechanism of action may be conferred by alterations introduced into the cellular context of the producing cell. For instance, the ribosome may be altered to avoid antibiotic binding and relieve inhibition of protein synthesis. A cell wall biosynthetic enzyme may be mutated to ablate antibiotic binding and relieve inhibition of cell wall biosynthesis. A pump which lowers the intracellular concentration may be expressed. A specific antibiotic binding protein may be expressed.

In some embodiments, the target molecule is an antibiotic (e.g. one which is lethal to a host cell). In some embodiments, the antibiotic is a beta-lactam antibiotic, such as a penicillin, e.g., Penicillin, Amoxicillin, Ampicillin, Azlocillin, Carbenicillin, Cloxacillin, Dicloxacillin, Flucloxacillin, Mezlocillin, Methicillin, Nafcillin, Oxacillin, Penicillin G, Penicillin V, Piperacillin, Penicillin G, Temocillin, Ticarcillin. In some embodiments, the antibiotic is an Aminoglycoside, e.g., Amikacin, Gentamicin, Kanamycin, Neomycin, Netilmicin, Tobramycin, Paromomycin, Streptomycin, or Spectinomycin. In some embodiments, the antibiotic is an Ansamycin, e.g., Geldanamycin, Herbimycin, or Rifaximin. In other embodiments, the antibiotic is a penem such as faropenem or Ritipenem; or a Carbacephem such as Loracarbef; or a carbapenem such as Ertapenem, Doripenem, Imipenem/Cilastatin, or Meropenem. In other embodiments, the antibiotic is an Cephalosporin, e.g., Cefadroxil, Cefazolin, Cefalotin or Cefalothin, Cefalexin (or cephalexin), Cefaclor, Cefamandole, Cefoxitin, Cefprozil, Cefuroxime, Cefixime, Cefdinir, Cefditoren, Cefoperazone, Cefotaxime, Cefpodoxime, Ceftazidime, Ceftibuten, Ceftizoxime, Ceftriaxone (IV and IM), Cefepime, Ceftaroline fosamil, Ceftobiprole, Ceftiofur, Cefquinome, or Cefovecin. In yet other embodiments, the antibiotic is a 3-lactamase inhibitor, such as, for example, Penam (Sulbactam Tazobactam), Clavam (Clavulanic acid), Avibactam, or Vaborbactam. In other embodiments, the antibiotic is a glycopeptide such as Teicoplanin, Vancomycin, Telavancin, Dalbavancin, or Oritavancin. In some embodiments, the antibiotic is a lincosamides such as, e.g., Clindamycin or Lincomycin. In yet other embodiments, the antibiotic is a lipopeptide such as Daptomycin. In some embodiments, the antibiotic is a Macrolide such as, e.g., Azithromycin, Clarithromycin, Dirithromycin, Erythromycin, Roxithromycin, Troleandomycin, Telithromycin, or Spiramycin. In some embodiments, the antibiotic is a Monobactam such as Aztreonam, Tigemonam, Carumonam, or Nocardicin A. In some embodiments, the antibiotic is a nitrofuran, such as, e.g., Furazolidone or Nitrofurantoin. In some other embodiments, the antibiotic is an oxazolidinones such as, e.g., Linezolid, Posizolid, Radezolid, or Torezolid. In other embodiments, the antibiotic is a polypeptide, such as Bacitracin, Colistin, or Polymyxin B. In yet other embodiments, the antibiotic is a Quinolone or Fluoroquinolone such as, e.g., Ciprofloxacin, Enoxacin, Gatifloxacin, Gemifloxacin, Levofloxacin, Lomefloxacin, Moxifloxacin, Nalidixic acid, Norfloxacin, Ofloxacin, Trovafloxacin, Grepafloxacin, Sparfloxacin, or Temafloxacin. In some embodiments, the antibiotic is a sulfonamide such as Mafenide, Sulfacetamide, Sulfadiazine, Silver sulfadiazine, Sulfadimethoxine, Sulfamethizole, Sulfamethoxazole, Sulfanilimide (archaic), Sulfasalazine, Sulfisoxazole, Trimethoprim, Trimethoprim-Sulfamethoxazole(Cotrimoxazole) (TMP-SMX), or Sulfonamidochrysoidine. In some embodiments, the antibiotic is a Tetracycline, e.g., Demeclocycline, Doxycycline, Minocycline, Oxytetracycline, or Tetracycline. In some embodiments, the antibiotic is a drug against mycobacteria, such as Clofazimine, Dapsone, Capreomycin, Cycloserine, Ethambutol(Bs), Ethionamide, Isoniazid, Pyrazinamide, Rifampicin (Rifampin in US), Rifabutin, Rifapentine, Streptomycin. In some embodiments, the antibiotic is Arsphenamine, Chloramphenicol (Bs), Fosfomycin, Fusidic acid, Metronidazole, Mupirocin, Platensimycin, Quinupristin/Dalfopristin, Thiamphenicol, Tigecycline(Bs), Tinidazole. In yet other embodiments the antibiotic is teixobactin, or related molecules in this new class of antibiotics, which harm bacteria by binding lipid II and/or lipid III, which are important cell wall precursors.

In various embodiments, the protein sensor and/or switch is engineered using design from existing allosteric proteins, e.g. aTFs. In various embodiments, the designing comprises in silico design. Illustrative design principles are found in US 2016/0063177, the entire contents of which are hereby incorporated by reference in their entirety.

For example, in various embodiments, molecular modeling is used to predict mutations in an allosteric protein which may render the allosteric protein able to bind one or more target molecules. In various embodiments, reference to an experimentally derived three-dimensional protein structure, typically obtained through experimental methods including, but not limited to, x-ray crystallography, nuclear magnetic resonance (NMR), scattering, or diffraction techniques, is employed to model and/or predict mutations in an allosteric protein which may render the allosteric protein able to bind one or more target molecule. In various embodiments, the ROSETTA software suite is employed to assist with modelling (see Kaufmann et al. Biochemistry. 2010 Apr. 13; 49(14):2987-98, the entire contents of which are hereby incorporated by reference in its entirety). Alternatively, or in combination, a homology modeling algorithm such as ROBETTA, TASSER, I-TASSER, HHpred, HHsearch, or MODELLER, or SWISS-MODEL can be used. In some embodiments, such as (without limitation) those in which allosteric protein lacks an experimentally derived three-dimensional protein structure, a homology modeling algorithm can be used to build the sequence homology models. In various embodiments, one or more sequence or structural homologs have less than 90% amino acid sequence identity, less than 85% amino acid sequence identity, less than 80% amino acid sequence identity, less than 75% amino acid sequence identity, less than 70% amino acid sequence identity, less than 65% amino acid sequence identity, less than 60% amino acid sequence identity, less than 55% amino acid sequence identity, less than 50% amino acid sequence identity, less than 45% amino acid sequence identity, less than 40% amino acid sequence identity, less than 35% amino acid sequence identity, less than 30% amino acid sequence identity, less than 25% amino acid sequence identity, or less amino acid sequence identity to the amino acid sequence of the three-dimensional protein structure. Illustrative homology modelling methods and principles are found in US 2016/0063177, e.g. at paragraphs [0085]-[0093], the entire contents of which are hereby incorporated by reference in its entirety.

In some embodiments, a structure of an allosteric protein is evaluated for alterations which may render the allosteric protein able to bind one or more target molecules (e.g. by docking a one or more target molecules into the structure of an allosteric protein). Illustrative docking methods and principles are found in US 2016/0063177, e.g. at paragraphs [0095]-[0101], the entire contents of which are hereby incorporated by reference in its entirety.

In various embodiments, engineering may use the technique of computational protein design (as disclosed in U.S. Pat. Nos. 7,574,306 and 8,340,951, which are hereby incorporated by reference in their entirety) directed evolution techniques, rational mutagenesis, or any suitable combination thereof.

In other embodiments, mutation techniques such as gene shuffling, homologous recombination, domain swapping, deep mutation scanning, and/or random mutagenesis may be employed.

Mutated allosteric proteins that may be protein sensors and/or switches able to bind one or more target molecules can be screened using standard binding assays (e.g. fluorescent, radioactive assays, surface plasmon resonance, etc.).

In various embodiments, the protein sensor and/or switch is engineered as described in Taylor, et al. Nat. Methods 13(2): 177, the entire contents of which are hereby incorporated by reference in its entirety.

In various embodiments, the following table provides illustrative sensors that may be designed in accordance with various embodiments of the present invention. For instance, in various embodiments, one may select an aTF ("Chassis") and/or native ligand and make reference to a provided representative structure (PDB) to, in accordance with the disclosure herein, design a senor to a target molecule or class of target molecules (see Target Molecule Property column).

TABLE 1

| aTF ("Chassis") | Native Ligand | Native Host | Representative Structure (PDB) | Target Molecule Property |
| --- | --- | --- | --- | --- |
| QscR | Bound to N-3-oxo-dodecanoyl-L-Homoserine Lactone | Psudemonas aeruginosa | 3SZT | long chain fatty acids and homoserine lactones |
| NtcA | 2-oxoglutarate, 2,2-difluoropentanoic acid | Anabaena cyanobacterium | 3LA2, LA3, 3LA7 | 3-7 carbon acids/alcohols |
| CarH | adenosylcobalamin | Thermus thermophilus | 5C8A, 5C8D, 5C8E, 5C8F | cobalamine |

TABLE 1-continued

| aTF ("Chassis") | Native Ligand | Native Host | Representative Structure (PDB) | Target Molecule Property |
|---|---|---|---|---|
| CcpN repressor | ADP | *Bacillus subtilis* | 3FV6, 3FWR, 3FWS | nucleotides, nucleosides |
| BtAraR | arabinose | *Bacteriodes thetaiotaomicron* | 5BS6, 5DD4, 5DDG, 5DEQ | saccharides |
| AraR | arabinose | *Bacteroides thetaiotaomicron* VPI | 5BS6, 5DD4, 5DDG, 5DEQ | saccharides |
| AhrR | Arginine | *Bacillus subtilis* | 2P5L 2P5M | charged amino acids, quanidino groups |
| Rv1846c | *betalactams* | *Mycobacterium tuberculosis.* | 2G9W | betalactams |
| CviR | C6 HSL | *Chromobacterium violaceum* | 3QP1, 3QP2, 3QP4, 3QP5, 3QP6, 3QP8 | short chain fatty acids and homoserine lactones |
| MtbCRP | cAMP | *Myco tuberculosis* | 3I54 | cyclic nucleotides |
| BmrR | cationic antibiotics, dyes, and disinfectants | *Bacillus subtilis* | 3Q1M, 3Q2Y, 3Q3D, 3Q5P, 3Q5R, 3Q5S | cationic multirings |
| Rrf2 | cysteine | *Bacillus subtilis* | 2Y75 | hydrophobic amino acids, sulfur containing molecules |
| CGL2612 | drugs | *Corynebacterium glatamicum* | 1V7B, 2ZOY | rigid multiring molecules |
| ttgR | drugs | *Pseudomonas putida* | 2UXH, 2UXI, 2UXO 2UXP, 2UXU | rigid multiring molecules |
| QacR | Ethidium, rhodamine, | *Staphylococcus Aureus* | 3BR3 3BR6 2DTZ 2HQ5 | chemically rigid, bivalent compounds. |
| Cra | fructose 1 phosphate | *Pseudomonas putida* | 3O74, 3O75 | sugar phosphates |
| GabR | gamma-aminobutyric acid | *Bacillus subtilis* | 4N0B | short chain amines and acids |
| YvoA | glucosamine-6-phosphate, acetylglucosamine-6-phosphate | *Bacillus subtilis* | 4U0V, 4U0W, 4U0Y, 4WWC | C5, C6 sugars |
| CggR | glucose-6-phosphate and fructose-6-phosphate | *Bacillus subtilis* | 2OKG, 3BXE, 3BXF, 3BXG, 3BXH Also Cited By: 4OQP, 4OQQ | C5, C6 sugars |
| CodY | GTP, Isoleucine | *Bacillus subtilis* | 2B0L, 2B18, 2GX5, 2HGV | hydrophobic amino acids nucleosids, nucleotides, nucleotide phosphates |
| HrcA | heat | *Thermotoga maritima* | 1STZ | temperature, useful for circular permutation/stability measurements |
| RovA | heat | *Yersinia pestis* | 4AIH, 4AIJ, 4AIK | temperature, useful for circular permutation/stability measurements |
| LldR (CGL2915) | lactose | *Corynebacterium glutamicum* | 2DI3 | saccharides |
| LacI | Lactose/IPTG | *E. coli* | 2p9h | saccharides |
| NMB0573/AsnC | leucine methionine | *Neisseria meningitidis* | 2P5V, 2P6S, 2P6T | hydrophobic amino acids, sulfer containing compounds |
| FapR | malonyl-CoA | *Bacillus subtilis* | 2F3X, 2F41 | c3-c7 molecules, CoA cofactors |
| FapR | malonyl-CoA | *Staphylococcus Aureus* | 4A0X, 4A0Y, 4A0Z, 4A12 | c3-c7 molecules, CoA cofactors |
| LmrR | MDR pump controller | *Lactococcus lactis* | 3F8B, 3F8C, 3F8F | rigid multiring molecules |
| SMET | MDR pump controller | *Stenotrophomonas maltophilia* | 2W53 | rigid multiring molecules |
| SCO4008 | methylene blue, crystal violetcationic antibiotics, dyes, and disinfectants | *Streptomyces coelicolor* | 2D6Y | |
| MntR | Mn2+ | *Bacillus subtilis* | 4hv6 | metals and cations |
| Rex | NADH | *Bacillus subtilis, Thermus thermophilus, Thermus aquaticus* | 2VT2, 2VT3 | cofactors |
| NikR | Nickle | *Helobacter pylori* | 3PHT, 3QSI, 2WVB | |
| DNR | NO (via heme) | *Pseudomonas aeruginosa* | 2Z69 | metals and cations |
| FadR | oleoyl-CoA | *Vibrio cholerae* | 4P96, 4P9U, 4PDK | long chain fatty acids and cofactors |

TABLE 1-continued

| aTF ("Chassis") | Native Ligand | Native Host | Representative Structure (PDB) | Target Molecule Property |
|---|---|---|---|---|
| MosR | oxidative state | Mycobacterium tuberculosis. | 4FX0, 4FX4 | oxidative state, useful for circular permutation |
| OhrR | oxidative state (cys) | Bacillus subtilis | 1Z91, 1Z9C | oxidative state, useful for circular permutation |
| SarZ | oxidative stress | Staphylococcus Aureus | 3HRM, 3HSE, 3HSR | oxidative state, useful for circular permutation |
| TsaR | para-toluensulfonate | Comamonas testosteroni | 3FXQ, 3FXR, 3FXU, 3FZJ | c6-c12 aromatics |
| HetR | PatS | Anabaena sp. | 4YNL, 4YRV | peptides and proteins |
| NprR | peptide | Bacillus thuringiensis | 4GPK | peptides and proteins |
| MexR | peptide | Pseudomonas aeruginosa | 3ECH | peptides and proteins |
| PhoP | PhoR | Mycobacterium tuberculosis. | 2PMU | peptides and proteins |
| PurR | Phosphoribosylpyrophosphate | Bacillus subtilis | 1P4A | phosphorilated sugars |
| PcaV (SCO6704) | protocatechuate (a dihyroxy benzoic acid) | Streptomyces coelicolor | 4FHT, 4G9Y | aromatic acids, c4-c10 acids |
| DesR | self His-PO4 | Bacillus subtilis | 4LDZ, 4LE0, 4LE1, 4LE2 | useful for circular permutation |
| SinR | sinL dimer | Bacillus subtilis | 2YAL, 3QQ6 | peptides and proteins |
| EthR | something hydrophobic | Mycobacterium tuberculosis. | 1T56 | c4-c20 hydrophobic molecules |
| BlcR | succinate semialdehyde | Agrobacterium tumefaciens | 3MQ0 | short chain aldehydes |
| TetR-class H | Tet | Pasteurella multocida | 2VPR | rigid multiring molecules |
| TetR | Tetracycline | E. coli Tn10 | 4AC0 | rigid multiring molecules |
| TreR | trehalose | Bacillus subtilis | 2OGG | saccharides |
| DntR | TsaR type LTTR | Burkholderia cepacia | 5AE3, 5AE4 | c6-c12 aromatics |
| HyIIIR | unknown large molecule | Bacillus cereus | 2FX0 | large moledules |
| CprB | γ-butyrolactones | Streptomyces coelicolor | 4PXI | short chain lactones |
| AcuR | acrylic acid | Rhodobacter sphaeroides | 3BRU | Short chain acid and hydrocarbons |

In various embodiments, the amino acids targeted for mutation or in silico design are those within about 3, or about 5, or about 7, or about 10, or about 12 Angstroms (e.g. between about 3 to about 12 Angstroms, or between about 5 to about 12 Angstroms, or between about 7 to about 12 Angstroms, or between about 10 to about 12 Angstroms, or between about 3 to about 5 Angstroms, or between about 3 to about 7 Angstroms, or between about 3 to about 10 Angstroms) of a ligand modeled into a binding pocket either through docking or by experimental methods such as X-ray crystallography.

In various embodiments, the allosteric DNA-binding protein sensor and/or switch is one or more of those of Table 1 and has about 1, or 2, or 3, or 4, or 5, or 10 mutations (e.g. 1, or 2, or 3, or 4, or 5, or 6, or 7, or 8, or 9, or 10). The nature of such mutations is reflected elsewhere in this document.

In various embodiments, the allosteric DNA-binding protein sensor and/or switch comprises mutations at the positions outlined below. The nature of such mutations is reflected elsewhere in this document.

In some embodiments, the PcaV chassis (wild type is SEQ ID NO: 29) is engineered, e.g. by mutation(s), to sense a target molecule which is not a native ligand of the wild type PcaV aTF. For example, in various embodiments, the sensor comprises an amino acid sequence of about 90%, or about 93%, or about 95%, or about 97%, or about 98%, or about 99% identity to wild type PcaV chassis (SEQ ID NO: 29). In some embodiments, the wild type PcaV chassis (SEQ ID NO: 29) is mutated at one or more of GLN18, HIS21, TYR22, LEU24, TRP25, VAL29, THR34, SER35, PRO36, GLN37, TYR38, ALA39, VAL40, LEU41, ASN42, ALA43, ARG58, VAL59, GLY60, LEU61, LEU106, GLY107, ARG109, ILE110, ALA111, ARG112, MET113, ASN114, PHE117, VAL4, ASP5, LEU6, ALA7, THR8, HIS9, PRO10, GLY11, HIS12, LEU13, ALA14, ARG15, and ARG16. Such mutations can be of any type described elsewhere herein. In various embodiments, one or more mutations at GLN18, HIS21, TYR22, LEU24, TRP25, VAL29, THR34, SER35, PRO36, GLN37, TYR38, ALA39, VAL40, LEU41, ASN42, ALA43, ARG58, VAL59, GLY60, LEU61, LEU106, GLY107, ARG109, ILE110, ALA111, ARG112, MET113, ASN114, PHE117, VAL4, ASP5, LEU6, ALA7, THR8, HIS9, PRO10, GLY11, HIS12, LEU13, ALA14, ARG15, and ARG16, confer loss of binding to its cognate ligand dihyroxybenzoic acid.

In some embodiments, the QacR chassis (wild type is SEQ ID NO: 30) is engineered, e.g. by mutation(s), to sense a target molecule which is not a native ligand of the wild type QacR aTF. For example, in various embodiments, the sensor comprises an amino acid sequence of about 90%, or about 93%, or about 95%, or about 97%, or about 98%, or about 99% identity to wild type QacR chassis (SEQ ID NO: 30). In some embodiments, the wild type QacR chassis (SEQ ID NO: 30) is mutated at one or more of GLY158, ILE159, THR161, PHE162, THR163, HIS164, GLU165, GLN166, LEU54, ASN55, ILE56, GLU57, GLU58, SER59, LYS60, TRP61, GLN62, GLU63, GLN64, TRP65, TYR82, ASN83, LEU85, SER86, LEU87, THR88, THR89, GLU90, TYR91, TYR92, TYR93, PRO94, LEU95, GLN96, ASN113, MET116, ASN117, LYS118, LEU119, GLU120, ASN121, LYS122, TYR123, ILE124, SER149, LYS150, ILE151, ALA152, ALA153, ASN154, ALA155, VAL156, ASN157, GLY158, VAL160, and THR161. Such mutations can be of any type described elsewhere herein.

In some embodiments, the CviR chassis (wild type is SEQ ID NO: 31) is engineered, e.g. by mutation(s), to sense a target molecule which is not a native ligand of the wild type CviR aTF. For example, in various embodiments, the sensor comprises an amino acid sequence of about 90%, or about 93%, or about 95%, or about 97%, or about 98%, or about 99% identity to wild type CviR chassis (SEQ ID NO: 31). In some embodiments, the wild type CviR chassis (SEQ ID NO: 31) is mutated at one or more of ARG55, LEU56, LEU57, LEU58, ALA59, LEU60, LEU72, ARG74, VAL75, LEU76, ASN77, TYR80, PRO81, TRP84, LEU85, ASP86, GLN87, TYR88, MET89, ASN92, TYR93, ALA94, HIS96, ASP97, PRO98, ILE99, LEU100, ARG101, ILE102, MET110, TRP111, GLU112, ARG114, PHE115, PHE126, ILE127, ALA128, GLU129, ALA130, THR131, ASN133, GLY134, MET135, GLY136, SER137, GLY138, ILE139, THR140, PHE141, ILE153, LEU154, SER155, ILE156, and ALA157. Such mutations can be of any type described elsewhere herein.

In some embodiments, the TtgR chassis (wild type is SEQ ID NO: 32) is engineered, e.g. by mutation(s), to sense a target molecule which is not a native ligand of the wild type TtgR aTF. For example, in various embodiments, the sensor comprises an amino acid sequence of about 90%, or about 93%, or about 95%, or about 97%, or about 98%, or about 99% identity to wild type TtgR chassis (SEQ ID NO: 32). In some embodiments, the wild type TtgR chassis (SEQ ID NO: 32) is mutated at one or more of GLY173, LEU63, LEU66, HIS67, HIS70, ASP71, LEU73, ALA74, ARG75, SER77, GLU78, LEU86, CYS88, MET89, ARG90, LYS91, LEU92, LEU93, LEU94, GLN95, VAL96, PHE97, GLU99, LEU100, THR106, ARG107, ILE109, ASN110, GLU111, LEU113, HIS114, ALA133, VAL134, CYS137, HIS138, GLY140, ILE141, THR142, ALA144, LEU145, ALA163, ALA164, VAL165, ALA166, MET167, PHE168, ALA169, TYR170, VAL171, ASP172, GLY173, LEU174, ILE175, ARG176, LEU179, VAL195, GLY198, LEU199, and LEU202. Such mutations can be of any type described elsewhere herein. In various embodiments, mutations at H67 and H72 (or one or more of H67 and H72) confer binding of apigenin. Such mutations can be of any type described elsewhere herein. In various embodiments mutations at M167, F168, Y170, V171, and D172 (or one or more of M167, F168, Y170, V171, and D172) confer binding of apigenin. Such mutations can be of any type described elsewhere herein. In various embodiments, the present sensors based on the TtgR chassis comprise an amino acid sequence of about 90%, or about 93%, or about 95%, or about 97%, or about 98%, or about 99% identity to one or more of SEQ ID NOs: 33, 34, 35, 36, 37, and 38. In some embodiments, the engineered sensor based on TtgR is capable of binding naringenin.

In some embodiments, the AcuR chassis (wild type is SEQ ID NO: 39) is engineered, e.g. by mutation(s), to sense a target molecule which is not a native ligand of the wild type AcuR aTF. For example, in various embodiments, the sensor comprises an amino acid sequence of about 90%, or about 93%, or about 95%, or about 97%, or about 98%, or about 99% identity to wild type AcuR chassis (SEQ ID NO: 39). In some embodiments, the wild type AcuR chassis (SEQ ID NO: 39) is mutated at one or more of GLY44, TYR45, SER46, CYS125, LEU126, VAL127, GLY128, ASN129, LEU130, GLY131, GLN132, GLU133, MSE134, GLY135, ALA136, LEU137, ARG142, LEU145, GLU187, GLY188, LEU191, ARG192, LEU40, THR41, GLU42, LYS43, GLY44, ARG122, ARG123, GLY124, CYS125, LEU126, VAL127, GLY128, ASN129, LEU130, GLY131, GLN132, GLU133, TRP186, GLU187, GLY188, ALA189, ILE190, LEU191, ARG192, ALA193, LYS194, LEU195, and GLN132. Such mutations can be of any type described elsewhere herein. In various embodiments, the present sensors based on the AcuR chassis comprise an amino acid sequence of about 90%, or about 93%, or about 95%, or about 97%, or about 98%, or about 99% identity to any one of SEQ ID NOs: 40, 41, 42, 43, and 44. In some embodiments, the engineered sensor based on AcuR is capable of binding methylacrylate.

In some embodiments, the MphR chassis (wild type is SEQ ID NO: 45) is engineered, e.g. by mutation(s), to sense a target molecule which is not a native ligand of the wild type MphR aTF. For example, in various embodiments, the sensor comprises an amino acid sequence of about 90%, or about 93%, or about 95%, or about 97%, or about 98%, or about 99% identity to wild type MphR chassis (SEQ ID NO: 45). In some embodiments, the wild type MphR chassis (SEQ ID NO: 45) is mutated at one or more of TYR103, TRP107, ALA151, GLY152, ALA153, MET155, GLN156, VAL159, GLU14, ALA16, THR17, VAL18, VAL19, LEU20, LYS21, ARG22, ARG22, GLY24, PRO25, LEU55, MET58, MET58, MET59, GLU60, ARG61, GLY62, VAL63, GLU64, GLN65, VAL66, ARG67, HIS68, TYR69, LEU70, LEU86, VAL88, LEU89, VAL90, ARG91, ARG91, SER92, MET93, ASN94, THR95, PHE99, SER100, VAL101, ASN102, TYR103, LEU104, ILE105, SER106, SER106, TRP107, TYR108, GLU109, LEU118, ALA119, ILE120, GLN121, ARG122, ASN123, ARG124, ALA125, VAL126, VAL127, GLY129, LEU146, HIS147, SER148, VAL149, ILE150, ALA151, GLY152, ALA153, THR154, MET155, MET155, and ALA158.

In some embodiments, the TetR chassis (wild type is SEQ ID NO: 46) is engineered, e.g. by mutation(s), to sense a target molecule which is not a native ligand of the wild type TetR aTF. For example, in various embodiments, the sensor comprises an amino acid sequence of about 90%, or about 93%, or about 95%, or about 97%, or about 98%, or about 99% identity to wild type TetR chassis (SEQ ID NO: 46). In some embodiments, the wild type TetR chassis (SEQ ID NO: 46) is mutated at one or more of ALA56, ILE57, LEU60, ASP61, HIS64, THR65, HIS66, PHE67, CYS68, PRO69, PHE78, LEU79, ARG80, ASN81, ASN82, ALA83, LYS84, SER85, PHE86, ARG87, ALA89, LEU90, HIS100, LEU101, GLY102, THR103, ARG104, PRO105, THR106, LYS108, GLN109, TYR110, GLU111, THR112, LEU113, GLU114, ASN115, GLN116, LEU117, LEU127, GLU128, ALA130, LEU131, TYR132, ALA133, LEU134, SER135, ALA136, VAL137, GLY138, HIS139, PHE140, THR141, and LEU142. Such mutations can be of any type described elsewhere herein. In various embodiments, the engineered sensor based on TetR is capable of binding one or more of apigenin, resveratrol, humulene, and atropine. In various embodiments, mutations at S135A, G138I, H139M, and E147W confer binding to apigenin. In various embodiments, mutations at S135H, G138A, H139M, T141A, E147Y, and H151L confer binding to apigenin. In various embodiments, mutations at L131M, Y132R, S135A, G138H, H139L, E147Y, D148A, and H151L confer binding to apigenin. In various embodiments, mutations at S135A, G138I, H139M, and E147W confer binding to apigenin. In various embodiments, mutations at S135H, G138A, H139M, T141A, E147Y, and H151L confer binding to apigenin. In various embodiments, mutations at F65W, C66K, N82R, F86L, L90A, H100M, T103A confer binding to resveratrol. In various embodiments, mutations at R104Y confer binding to resveratrol. In various embodiments, mutations at R104Y, P105G, Q109L, T1121, L113A, E114R, Q116R, and L117A confer binding to resveratrol. In various embodiments, mutations at R104Y confer binding to resveratrol. In various embodiments, mutations at L131S, S135A, G138W, E147H, H151S confer binding to humulene. In various embodiments, mutations at L131S, Y137K, S135A, G138W, L142I, E147A, and H151R confer binding to humulene. In various embodiments, mutations at G124V, G138W, E147H, and H151L confer binding to humulene. In various embodiments, mutations at L131S, Y137K, S135A, G138W, L142I, E147A, and H151R confer binding to humulene. In various embodiments, mutations at H100A, R104T, P105G, Q109L, Y110R, T111V, L112G, E113A, Q115I, and G138L confer binding to atropine. In various embodiments, mutations at H100A, R104T, P105G, T106F, Q109L, Y110L, T111V, L112G, E113A, Q115N, and G138L confer binding to atropine. In various embodiments, mutations at H100A, R104T, P105G, Q109L, Y110L, T1111, L112G, E113A, Q115N, and G138L confer binding to atropine. In various embodiments, the present sensors based on the TetR chassis comprise an amino acid sequence of about 90%, or about 93%, or about 95%, or about 97%, or about 98%, or about 99% identity to any one of SEQ ID NOs: 47, 48, 49, 50, 51, 52, 53, 54, 55, 56, 57, 58, 59, 60, 61, 62, 63, and 64.

In some embodiments, the FapR chassis (wild type is SEQ ID NO: 65) is engineered, e.g. by mutation(s), to sense a target molecule which is not a native ligand of the wild type FapR aTF. For example, in various embodiments, the sensor comprises an amino acid sequence of about 90%, or about 93%, or about 95%, or about 97%, or about 98%, or about 99% identity to wild type FapR chassis (SEQ ID NO: 65). In some embodiments, the wild type FapR chassis (SEQ ID NO: 65) is mutated at one or more of SER101, VAL102, PHE103, THR106, ILE108, ALA109, ARG110, GLY111, HIS112, VAL113, LEU114, PHE115, GLN139, PHE140, ILE141, GLU142, LYS143, VAL144, LYS145, VAL177, PHE178, SER72, ILE73, GLU74, GLU77, PHE78, ILE79, PHE115, ALA116, GLN117, ALA118, ASN119, SER120, LEU121, CYS122, VAL123, ALA124, PRO129, THR130, VAL131, LEU132, THR133, HIS134, GLU135, SER136, ALA161, LYS162, HIS163, PHE182, LYS183, MET184, PHE185, TYR186, ASP187, LYS188, and ARG189. Such mutations can be of any type described elsewhere herein.

In some embodiments, the FadR chassis (wild type is SEQ ID NO: 66) is engineered, e.g. by mutation(s), to sense a target molecule which is not a native ligand of the wild type FadR aTF. For example, in various embodiments, the sensor comprises an amino acid sequence of about 90%, or about 93%, or about 95%, or about 97%, or about 98%, or about 99% identity to wild type FadR chassis (SEQ ID NO: 66). In some embodiments, the wild type FadR chassis (SEQ ID NO: 66) is mutated at one or more of GLY79, LEU80, HIS81, ILE82, LEU83, MET87, LEU89, ASP90, ALA94, SER96, ILE97, VAL98, GLU99, ASP100, LEU101, LEU102, ALA103, ALA104, ARG105, THR106, ASN107, ILE108, SER109, SER123, ALA124, ARG126, ILE127, MET128, ILE129, ASN130, VAL131, ILE132, GLU133, SER134, CYS135, SER151, PRO152, TYR153, ALA154, GLU155, LYS156, ILE157, GLN158, GLN159, HIS160, THR180, PHE181, ASN182, PHE183, TYR184, ASP185, TYR186, MET187, LEU188, PHE189, GLN190, ARG191, LEU192, ALA193, PHE194, HIS195, GLY197, ASN198, GLN199, ILE200, TYR201, GLY202, LEU203, ILE204, PHE205, ASN206, GLY207, LEU208, LYS209, LYS210, LEU211, TYR212, ASP213, ARG214, VAL215, GLY216, SER217, TYR218, TYR219, PHE220, SER221, ALA225, ARG226, LEU228, ALA229, PRO249, GLN250, ILE252, ARG253, GLN254, TYR255, GLY256, ILE257, ALA258, SER259, GLY260, HIS261, ILE262, TRP263, ASN264, ILE17, GLU18, SER19, ILE20, TRP21, ASN22, GLY23, PRO26, PRO27, GLY28, GLY59, TRP60, VAL71, ASN72, GLN73, PHE74, MET75, GLU76, THR77, SER78, GLY79, LEU80, HIS81, ILE82, LEU83, ASP84, LEU86, MET87, ASN93, ALA94, ILE97, VAL98, ASP100, LEU101, ALA104, ARG105, ASN107, ILE108, ILE111, PHE112, ARG114, TYR115, LYS118, LEU119, GLY197, ASN198, GLN199, ILE200, TYR201, GLY202, LEU203, ILE204, GLY207, LEU208, LEU211, and ARG245. Such mutations can be of any type described elsewhere herein.

In some embodiments, the AraR chassis (wild type is SEQ ID NO: 67) is engineered, e.g. by mutation(s), to sense a target molecule which is not a native ligand of the wild type AraR aTF. For example, in various embodiments, the sensor comprises an amino acid sequence of about 90%, or about 93%, or about 95%, or about 97%, or about 98%, or about 99% identity to wild type AraR chassis (SEQ ID NO: 67). In some embodiments, the wild type AraR chassis (SEQ ID NO: 67) is mutated at one or more of TYR12, LEU13, LEU13, GLY14, ILE15, ASP16, CYS17, LEU32, ARG34, ASN35, PHE36, GLU37, PRO38, ALA39, MSE40, TRP43, SER44, LEU45, MSE46, MSE46, GLY47, GLY48, PHE49, VAL50, VAL63, PHE81, GLY82, ASP85, ARG86, ASP87, PRO88, GLY89, GLU90, ARG91, VAL92, VAL93, SER94, ILE95, ALA96, LEU127, ILE128, PHE129, ASP130, HIS131, MSE134, TYR4, and TYR5. Such mutations can be of any type described elsewhere herein.

In some embodiments, the LmrR chassis (wild type is SEQ ID NO: 68) is engineered, e.g. by mutation(s), to sense a target molecule which is not a native ligand of the wild type LmrR aTF. For example, in various embodiments, the sensor comprises an amino acid sequence of about 90%, or about 93%, or about 95%, or about 97%, or about 98%, or about 99% identity to wild type LmrR chassis (SEQ ID NO: 68). In some embodiments, the wild type LmrR chassis (SEQ ID NO: 68) is mutated at one or more of ILE4, PRO5, GLU7, MET8, LEU9, ARG10, ALA11, GLN12, THR13, ASN14, VAL15, ILE16, LEU17, LEU18, ASN19, GLY85, HIS86, GLU87, ASN88, MET89, ARG90, LEU91, ALA92, PHE93, GLU94, SER95, TRP96, SER97, ARG98, VAL99, ASP100, GLU7, MET8, LEU9, ARG10, ALA11, GLN12, THR13, ASN14, VAL15, ILE16, LEU18, ASN88, MET89, ARG90, LEU91, ALA92, PHE93, GLU94, SER95, TRP96, SER97, VAL99, ASP100, LYS101, ILE103, and GLU104. Such mutations can be of any type described elsewhere herein.

In some embodiments, the LacI chassis (wild type is SEQ ID NO: 69) is engineered, e.g. by mutation(s), to sense a target molecule which is not a native ligand of the wild type LacI aTF. For example, in various embodiments, the sensor comprises an amino acid sequence of about 90%, or about 93%, or about 95%, or about 97%, or about 98%, or about 99% identity to wild type LacI chassis (SEQ ID NO: 69). In some embodiments, the wild type LacI chassis (SEQ ID NO: 69) is mutated at one or more of THR68, SER69, SER70, LEU71, ALA72, LEU73, HIS74, ALA75, PRO76, SER77, GLN78, ILE79, SER102, ILE124, ASN125, TYR126, PRO127, LEU128, PHE147, LEU148, ASP149, VAL150, SER151, ILE159, ILE160, PHE161, HIS163, GLY187, PRO188, SER190, SER191, VAL192, SER193, ALA194, LEU196, ARG197, ASP219, TRP220, SER221, VAL244, ALA245, ASN246, ASP247, GLN248, MET249, ALA250, GLY272, TYR273, ASP274, ASP275, THR276, ILE289, LYS290, GLN291, PHE293, LEU296, THR68, SER69, SER70, LEU71, ALA72, LEU73, HIS74, ALA75, PRO76, SER77, GLN78, ILE79, ILE124, ASN125, TYR126, PRO127, LEU128, PHE147, LEU148, ASP149, VAL150, SER151, ILE159, ILE160, PHE161, HIS163, GLY187, PRO188, SER190, SER191, VAL192, SER193, ALA194, LEU196, ARG197, ASP219, TRP220, SER221, VAL244, ALA245, ASN246, ASP247, GLN248, MET249, ALA250, GLY272, TYR273, ASP274, ASP275, THR276, ILE289, LYS290, GLN291, ASP292, PHE293, and LEU296. Such mutations can be of any type described elsewhere herein. In various embodiments, mutations at H166T, G169A, A189S, P191H, and S196M (e.g. one or more of H166T, G169A, A189S, P191H, and S196M) confer binding to nootkatone. In various embodiments, mutations at L151N, D152N, V153I, D155N, I163G, H166Q, and G169A (e.g. one or more of L151N, D152N, V153I, D155N, I163G, H166Q, and G169A) confer binding to nootkatone. In various embodiments, the present sensors based on the LacI chassis comprise an amino acid sequence of about 90%, or about 93%, or about 95%, or about 97%, or about 98%, or about 99% identity to any one of SEQ ID NOs: 70, 71, and 72.

In various embodiments, the allosteric DNA-binding protein sensor and/or switch is one or more of those of Table 2.

In various embodiments, randomized nucleotides may be included in targeted locations of the sensor sequence, or anywhere within the sensor sequence. These may be used in conjunction with any rational or structure-guided design approaches here mentioned.

In various embodiments, libraries of potential mutations to the allosteric protein are made and selection, positive or negative, is used to screen desired mutants. For instance, by way of non-limitation, even after designing, candidate protein sensors and/or switches, some of these candidates may be non-functional and therefore are selected away by negative screening as described herein or known in the art. Further, by way of non-limitation, candidate protein sensors and/or switches also may retain function but not produce desirable target molecule interactions and, as such, may be selected away by positive screening.

In certain embodiments, the negative selection technique is any of those described herein or known in the art, including antidote/toxin and/or reporter strategies.

In certain embodiments, the present invention provides sorting of cells, for either reporter negative (e.g. dark) or reporter positive (e.g. bright) cells, for their inability to either correctly repress the reporter gene system or remain inactive, depending on the logic of the gene reporter system, using, e.g., a reporter gene system and a fluorescence activated cell sorting (FACS) apparatus or microbial colony picker (e.g., QPix), or a microfluidics apparatus, or a bead-based apparatus or the like, as described herein. For example, for a protein sensor and/or switch that is a repressor, the repressor protein may fail to block transcription of the reporter gene system in the absence of any inducer molecule, target or otherwise, by failing to bind to a region of DNA adjacent (operator site) to the reporter gene system. In such a case, cells expressing the reporter gene system will represent failure to repress and the negative selection will involve sorting for cells that are dark, demonstrating either no expression or low or weak expression of the reporter gene system, and therefore capability to repress in the absence of any inducer molecule. Such cells would then be sorted and retained for positive screening or selection as described herein. For a protein sensor and/or switch that is an activator, the activator would normally recruit RNA polymerase to a region of DNA 5' to the reporter gene system only when the target molecule binds to the activator. Similarly in this case, cells that are not expressing the reporter gene system, demonstrating either no expression or low or weaker expression, in the absence of any induction, are sorted and retained for positive screening or selection as described herein. For an attenuating protein sensor and/or switch, the protein sensor and/or switch is encoded in the 5' untranslated region of a repressor regulating the transcription of the reporter gene system, and attenuates translation of this repressor only when bound to the target molecule, would similarly be sorted for those cells demonstrating either no expression or low or weak expression of the reporter gene system. Such cells would then be sorted and retained for positive screening or selection as described herein.

In certain embodiments the positive selection is performed by sorting cells with a reporter gene system as described herein. For example, the transformed, recombinant cell expresses a protein sensor and/or switch which regulates production of the reporter gene system. When expressed, the protein sensor and/or switch prevents the cell from expressing the reporter gene system, either by blocking the expression (repressor) or failing to activate the expression (activator) of the reporter gene system unless the protein sensor and/or switch is bound by the desired target molecule, which leads to reporter gene system expression by changing protein sensor and/or switch function. Several regulation mechanisms are possible as described above. Cells correctly expressing the reporter gene system in the presence of the desired target molecule are then sorted and maintained.

In certain embodiments, the positive selection is toxin/antidote selection, as described elsewhere herein.

In certain embodiments the cells are sorted by both a negative and a positive selection, in either order, for the selection.

In certain embodiments, the negative selection precedes the positive selection system described herein. In certain other embodiments, the positive selection precedes the negative selection described herein. In certain other embodiments, libraries of sensors for diverse designs are pooled together and have already undergone negative selection as described herein, prior to positive selection, and vice versa.

In embodiments, engineered protein sensor and/or switch, even after selection (e.g. one or more of positive and negative), may undergo maturations steps to improve functionality. Such maturation steps may improve general functionality of the engineered protein sensor and/or switch and/or be tailored to better suitability for a particular use.

Figure 44:
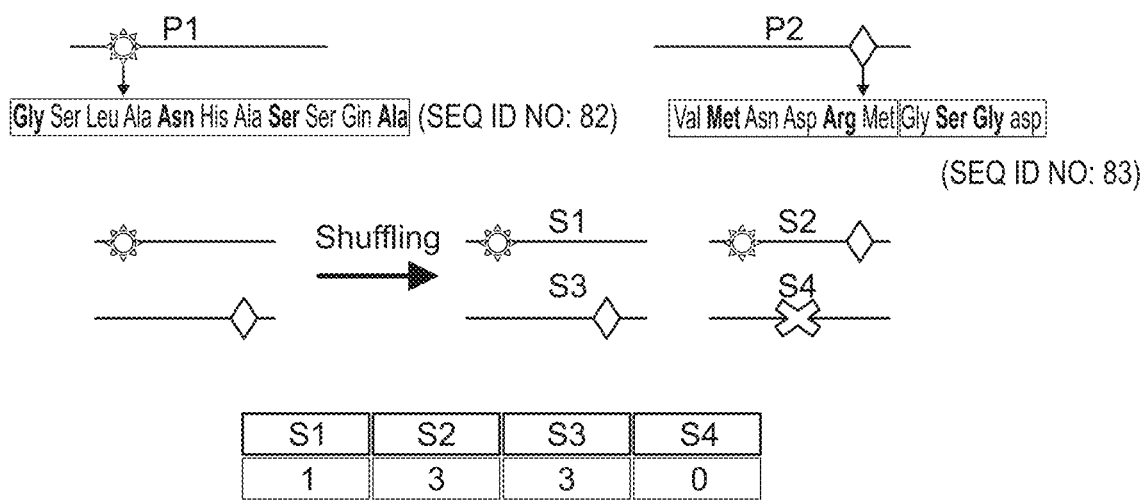
FIG. 44 shows a schematic of shuffling two mutation regions (P1 (SEQ ID NO: 82) and P2 (SEQ ID NO: 83)) can lead to four possible outcomes. 3/4 were observed in shuffling LacI glyphosate sensors.
Figure 45:
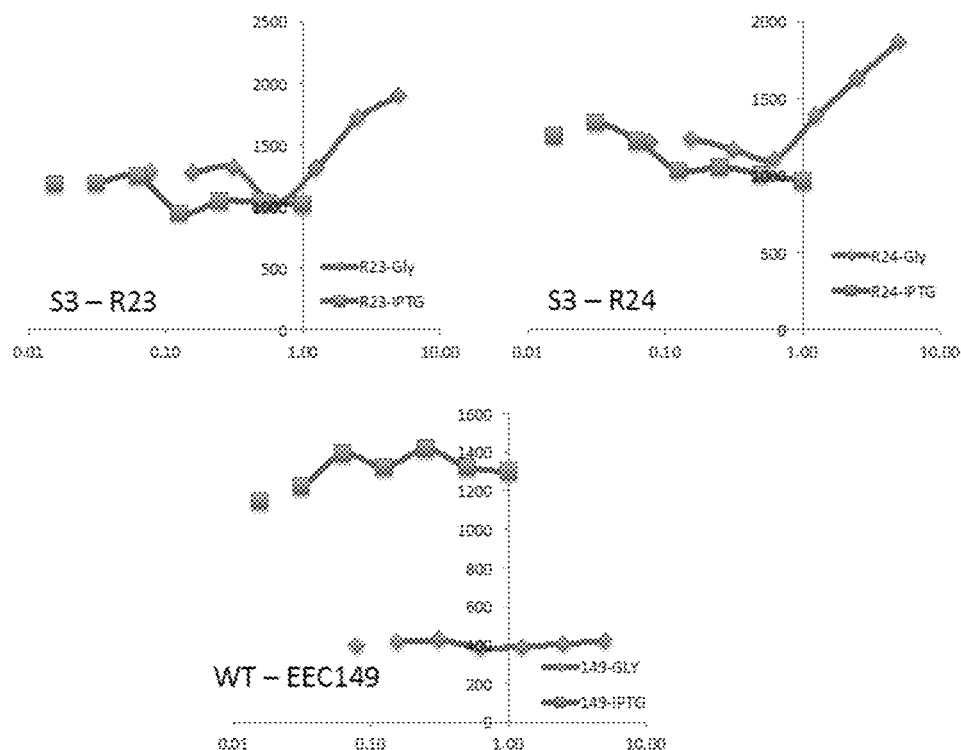
FIG. 45 shows dose response of two LacI shuffled sensors (S3-R23 and S3-R24) and wild type LacI (WT-EEC149) to glyphosate and IPTG.

In some embodiments, an engineered protein sensor and/or switch from, for instance molecular modeling as described herein, may not have the desired sensitivity to the target molecule, or may have other undesired response characteristics, such as, for example, response to other molecules. Additional, subsequent mutations may then be introduced into the engineered protein sensor and/or switch to improve them. In some embodiments, DNA shuffling among multiple engineered or non-engineered sensors is used to generate a library of new sensor proteins, which is then screened as described herein for sensors with improved characteristics (see, e.g., FIGS. 44 and 45). In other embodiments, domain swapping is used. In other embodiments, random mutations are introduced into the engineered sensor protein using techniques common in the art such as error-prone PCR, or inclusion of degenerate bases in synthetic DNA, etc., to produce a library of sensor candidates which may be screened for members with improved characteristics. In other embodiments, in silico design methods as outlined herein are used to determine additional mutations in the engineered sensor protein, which preserve some or all of the mutations that cause the protein sensor response to the target molecule. For example, engineered protein sensor and/or switch recognizing a new target molecule carry mutations, which relative to the wild type protein, frequently localize to a specific region of the protein such as a binding pocket or a dimer interface. Redesigning an engineered sensor protein through a subsequent round of in silico modeling to its target molecule can permit the maintenance of the critical mutations for the new function uncovered in the previous round(s) of engineering, and allows for improvements to either the same region or a region of the protein not mutated in the previous design cycle. This iterative approach may be applied until the engineered sensor protein has the desired response and specificity to the target molecule(s).

In some embodiments, the responsive range of the sensor-reporter system can be tuned to the molecule concentration range of interest, in the appropriate conditions needed to engineer strains for production of the desired target molecule, by various mechanisms. For example, without wishing to be bound by theory, expression of the allosteric DNA binding sensor can be modulated, e.g. by mutating the allosteric DNA binding sensor promoter, ribosome binding site, start codon, and/or gene sequence (e.g. to affect mRNA structure or codon choice). Other approaches include mutating the amino acid sequence of the sensor (FIG. 24), using for example, methods described herein and others known in the art, to increase or decrease affinity of the sensor for the DNA binding site and/or target molecule, or mutating the sensor DNA binding site(s) or sites to increase or decrease DNA binding affinity of the sensor, or combinations thereof (FIG. 11). Together, these techniques allow for construction of separate sensor-reporter systems for a given molecule that are responsive to specific concentration ranges, e.g. low micromolar range or millimolar range.

The dynamic range of the sensor-reporter system may be affected by the experimental conditions (e.g. rich versus minimal medium), so screening is, in some embodiments, performed under production conditions. In some embodiments, various screening techniques are used to recover mutants of the sensor gene or variants of the combined sensor-reporter system that exhibit different desired response characteristics from among collections or libraries of sensor-reporter systems that may contain mutations to one or more of these elements: the sensor gene; the regulatory sequences (e.g. promoter, ribosome binding site, transcriptional terminator, 5'-untranslated region, riboswitch, and/or degradation signal) controlling the expression of the sensor gene; the reporter gene; the regulatory sequences controlling the reporter gene (as above); the sensor DNA binding site; the origin of replication (e.g. if the system is contained on a replicative plasmid); the genomic integration location (e.g. if the system is genomically integrated). See Example 1 and FIGS. 8-13.

In embodiments, sensor variants or sensor-reporter system variant libraries are screened to uncover variants with desired response characteristics including, without wishing to be bound by theory: higher or lower sensitivity to the target molecule; higher or lower reporter expression without the target molecule present; higher or lower reporter expression with maximally-inducing concentration of the target molecule present; increased or reduced total responsive range of the sensor systems (e.g. through changes in cooperativity of binding between sensor dimers, trimers, tetramers or higher-order multimers); a change in the DNA binding sequence recognized by the sensor; a change in response of the sensor system in different media conditions or feedstock formulations suitable to the strain engineering goals (e.g. minimal medium, rich medium, anaerobic or microaerobic conditions); or a change in response of the sensor-reporter system in different growth phases (e.g. lag phase, log phase, or stationary phase). See Example 1 and FIG. 12.

The library members passing this initial screen may then be subjected to one or a range of induction conditions. For example, without wishing to be bound by theory, target inducer chemical concentration, growth media and growth phase, and members with desired reporter behavior are collected and characterized individually or as an ensemble. Where a range of reporter expression phenotypes are observed for a single set of induction parameters, several collection gate conditions may be used to sort the population into several bins of reporter expression, which may be sequenced, or subjected to further induction conditions, or both. By identifying subsets of a large library or collection of sensor or system variants that match the desired induction characteristics, and repeating the process of introducing new induction conditions, followed by further subset identification, sensor system variants with a vast range of induction behaviors suitable to the desired applications can be found. See Example 1 and FIG. 12.

During the strain improvement process, it can be useful to rapidly swap from one sensor plasmid to another sensor plasmid. For instance, a highly sensitive plasmid required for initial strain improvement may saturate as the strain or strain library is improved. Rapidly swapping the sensitive sensor plasmid for another harboring a less sensitive plasmid facilitates further strain improvement. Another instance could be that the desired molecule to be sensed for further strain improvement may change. To facilitate swapping between sensors, a sensor plasmid may additionally express a method directing the restriction of another sensor plasmid. By having three or more unique targets it allow at will restriction of any plasmid for another, i.e. Type A restriction targets Type B, Type B restriction targets Type C, and Type C targets Type A.

Figure 41:
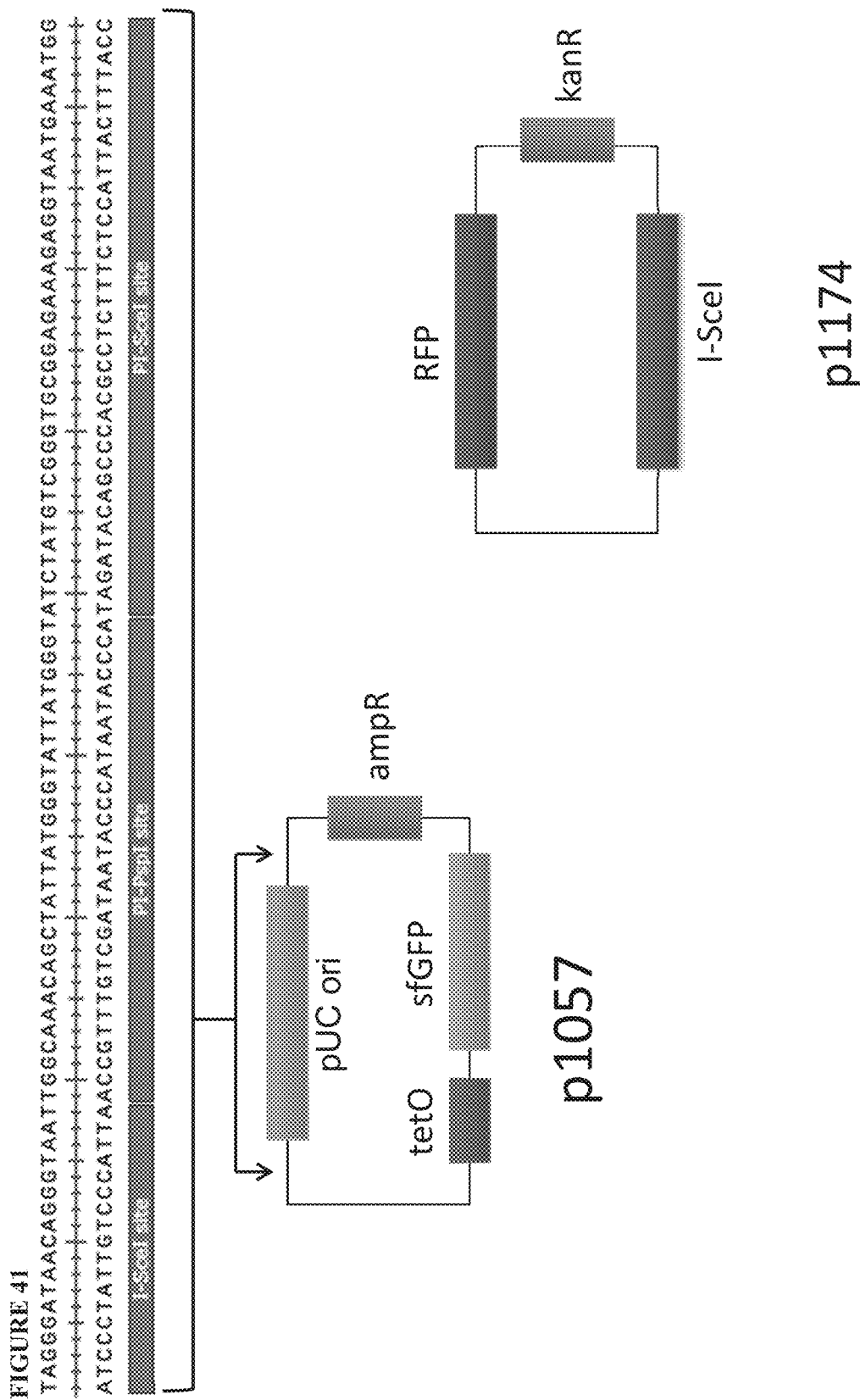
FIG. 41 shows the strategy of flanking a plasmid origin with restriction sites so that a second plasmid expressing a restriction enzyme can cure the stain, allowing rapid transition between various sensor plasmids (SEQ ID NO: 28 and SEQ ID NO: 87).
Figure 42:
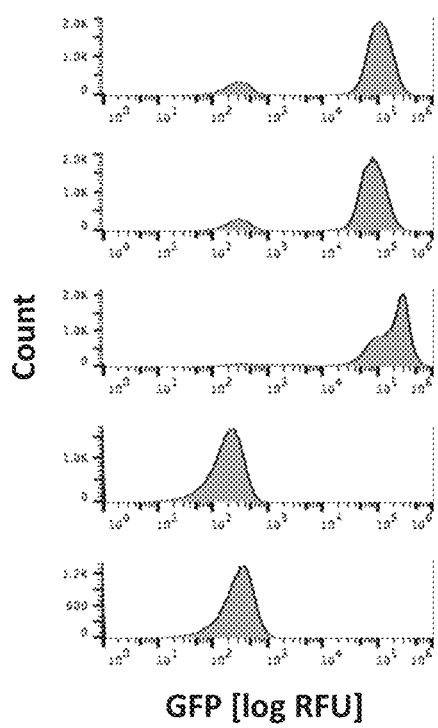
FIG. 42 shows flow cytometry data of p1174 plasmid causing loss of the p1057 target plasmid.
Figure 43:
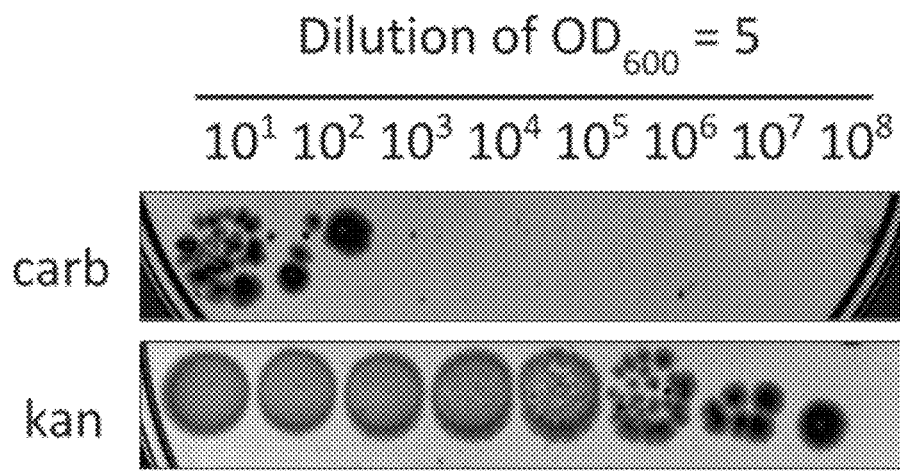
FIG. 43 shows dilutions of cultures on selective media for either p1174 or p1057 to estimate loss of carb plasmid.

In some embodiments, a vector (or plasmid), vector 1, conferring all or part of the natural or engineered sensor system contains a sequence that can be targeted by a crRNA or synthetic-guide RNA, such that a new vector (or plasmid), vector 2, conferring an identical or a different sensor system can be transformed into the same cell line or culture, whereby vector 2 also confers all or part of the CRISPR/Cas components necessary to target vector 1 for destruction. In other embodiments, vector 1 contains one or more restriction enzyme recognition sites, and vector 2 confers the restriction endonuclease necessary for vector 1 destruction (FIGS. 41-43). In embodiments, vector 2 contains a different selectable marker than vector 1, such that following transformation, the cell line or culture can be selected for cells possessing vector 2 and can be subsequently confirmed to be absent vector 1 by methods familiar to those skilled in the art. In certain embodiments, the cell line contains part of the components, e.g., but not wishing to be bound by theory, genes encoding the Cas proteins, are expressed from the genome or are expressed from another plasmid that has been previously transformed or can be subsequently transformed. In certain embodiments, vector 1 confers a sensor system that is more sensitive to the target molecule than the sensor system on vector 2, and the response profile of the sensor system on vector 1 demonstrates saturation at a lower concentration of the target. In these embodiments, the sensor system conferred by vector 2 may be less sensitive to the desired target molecule but demonstrates saturation at a higher concentration of the target, such that further strain engineering as described herein can be done to engineer strains with increasingly higher titer with vector 2 installed. In certain other embodiments, there is a vector 3 which confers a different selection marker than vector 2 and similarly expresses a crRNA or sgRNA to target vector 2, such that vector 2 can be supplanted by vector 2 in the same culture. In certain embodiments, the reporter gene (e.g., fluorescent protein or selection marker or others described herein) is different in vector 2 than vector 1, such that the reporter system present on vector 2 can be distinguished from vector 1, by for example but not wishing to be bound by theory, FACS analysis, in the case of the reporter system expressing a fluorescent protein. In certain embodiments, there is a vector 4, 5, 6, 7, 8, 9, 10, etc. In certain embodiments, the vector supplanting the previous vector in this way confers a sensor system that senses the same target molecule. In certain embodiments, the vector supplanting the previous confers a sensor system that targets a different molecule. In certain embodiments, the vector supplanting the previous contains multiple sensor systems. In certain embodiments, the vector conferring the sensor system is designed to integrate into the genome with or without the selection marker also integrating. In certain embodiments, the DNA conferring the sensor system, with or without the selection marker and with or without the crRNA or restriction enzyme, target the previous vector (or DNA) conferring the sensor system (with or without an accompanying selectable marker), is linear dsDNA. See Example 1 and FIG. 12.

In various embodiments, one or more of the present sensors and/or switches can be used (e.g. one, or two, or three, or four, or five, or ten). For instance, multiple sensors and/or switches can be used in the same cell, e.g. a cell being engineered to produce a target molecule.

In some embodiments, separate production cells are engineered for production of target molecule precursors using sensors specific for the precursor of interest. This is useful, inter alia, in cases where the precursors are highly diffusible or exported into the medium, and allows for optimization of the production of each precursor in separate strains. The optimized precursor producers can then be co-cultured for optimal target molecule production.

In general, each sensor protein chassis for each sensor system recognizes a specific DNA sequence, such that each sensor-DNA pair is distinct. However, in some embodiments, a single sensor protein chassis can be modified to recognize a new DNA binding sequence, allowing more than one derivative of a single sensor chassis to be employed in a single cell without interaction. Such new sensor-DNA binding site combinations can be generated by creating a collection of sensor protein mutants, and a collection of DNA binding sites, with combinations of the two collections made in single cells. Where the mutant sensor protein can bind to the new DNA binding site, a reporter gene will be repressed, allowing the identification of useful new sensor and binding site combinations. The original binding site can also be incorporated into the same cell controlling a second reporter, allowing the identification of new sensor protein sequences that bind to a new DNA sequence but not to the original binding site.

In various embodiments, multiple engineered sensors from diverse sensor systems or chassis can be utilized simultaneously within the same strain to diversify and engineer novel strains as described herein.

In various embodiments, one, several, or all operator sites for the engineered sensor are removed from the host organism with the exception of one or more operators controlling the reporter system and/or another desirable gene or set of genes which provides a desirable phenotype.

In various embodiments, the host cells of the present invention include eukaryotic and/or prokaryotic cells, including bacterial, yeast, algal, plant, insect, mammalian cells (human or non-human), and immortal cell lines.

For example, the host cell may be *Escherichia coli*, *Saccharomyces cerevisiae*, *Pichia pastoris*, *Saccharomyces castellii*, *Kluyveromyces lactis*, *Pichia stipitis*, *Schizosaccharomyces pombe*, *Chlamydomonas reinhardtii*, *Arabidopsis thaliana*, or *Caenorhabditis elegans*. In some embodiments the host cell is a bacterial cell, such as *Escherichia* spp., *Streptomyces* spp., *Zymonas* spp., *Acetobacter* spp., *Citrobacter* spp., *Synechocystis* spp., *Rhizobium* spp., *Clostridium* spp., *Corynebacterium* spp., *Streptococcus* spp., *Xanthomonas* spp., *Lactobacillus* spp., *Lactococcus* spp., *Bacillus* spp., *Pedobacter* spp., *Bacteroides* spp., *Alcaligenes* spp., *Pseudomonas* spp., *Aeromonas* spp., *Azotobacter* spp., *Comamonas* spp., *Mycobacterium* spp., *Rhodococcus* spp., *Gluconobacter* spp., *Ralstonia* spp., *Acidithiobacillus* spp., *Microlunatus* spp., *Geobacter* spp., *Geobacillus* spp., *Arthrobacter* spp., *Flavobacterium* spp., *Serratia* spp., *Saccharopolyspora* spp., *Thermus* spp., *Stenotrophomonas* spp., *Chromobacterium* spp., *Sinorhizobium* spp., *Saccharopolyspora* spp., *Agrobacterium* spp. and *Pantoea* spp. The bacterial cell can be a Gram-negative cell such as an *E. coli*, or a Gram-positive cell such as a species of *Bacillus*.

In other embodiments, the cell is a fungal cell such as a yeast cell, e.g., *Saccharomyces* spp., *Schizosaccharomyces* spp., *Pichia* spp., *Paffia* spp., *Kluyveromyces* spp., *Candida* spp., *Talaromyces* spp., *Brettanomyces* spp., *Pachysolen* spp., *Debaryomyces* spp., *Yarrowia* spp., and industrial polyploid yeast strains. Preferably the yeast strain is a *S. cerevisiae* strain or a *Yarrowia* spp. strain. Other examples of fungi include *Aspergillus* spp., *Pennicilium* spp., *Fusarium* spp., *Rhizopus* spp., *Acremonium* spp., *Neurospora* spp., *Sordaria* spp., *Magnaporthe* spp., *Allomyces* spp., *Ustilago* spp., *Botrytis* spp., and *Trichoderma* spp.

In other embodiments, the cell is an algal cell or a plant cell (e.g., *A. thaliana*, *C. reinhardtii*, *Arthrospira*, *P. tricomutum*, *T. suecica*, *P. carterae*, *P. tricomutum*, *Chlorella* spp., such as *Chlorella vulgaris*).

Target cells can include transgenic and recombinant cell lines. In addition, heterologous cell lines can be used, such as Chinese Hamster Ovary cells (CHO).

In some embodiments, the host cell is an Actinomycetes spp. cell. Actinomycetes are a heterogeneous collection of bacteria that form branching filaments which include, for example, *Actinomyces*, *Actinomadura*, *Nocardia*, *Streptomyces* and related genera. In some embodiments, *Actinomyces* comprise *Streptomyces*. In some embodiments, the Actinomycetes spp. cell is a *Streptomyces* cell. (e.g. *S. coelicolor*). *Streptomyces* include, by way of non-limiting example, *S. noursei*, *S. nodosus*, *S. natalensis*, *S. venezuelae*, *S. roseosporus*, *S. fradiae*, *S. lincolnensis*, *S. alboniger*, *S. griseus*, *S. rimosus*, *S. aureofaciens*, *S. clavuligerus*, *S. avermitilis*, *S. platensis*, *S. verticillus*, *S. hygroscopicus*, and *S. viridochromeogenes*.

In some embodiments, the host cell is a *Bacillus* spp. cell. In some embodiments, the *Bacillus* spp. cell is selected from *B. alcalophilus*, *B. alvei*, *B. aminovorans*, *B. amyloliquefaciens*, *B. aneurinolyticus*, *B. anthracis*, *B. aquaemaris*, *B. atrophaeus*, *B. boroniphilus*, *B. brevis*, *B. caldolyticus*, *B. centrosporus*, *B. cereus*, *B. circulans*, *B. coagulans*, *B. firmus*, *B. flavothermus*, *B. fusiformis*, *B. galliciensis*, *B. globigii*, *B. infernus*, *B. larvae*, *B. laterosporus*, *B. lentus*, *B.*

*licheniformis, B. megaterium, B. mesentericus, B. mucilaginosus, B. mycoides, B. natto, B. pantothenticus, B. polymyxa, B. pseudoanthracis, B. pumilus, B. schlegelii, B. sphaericus, B. sporothermodurans, B. stearothermophilus, B. subtilis, B. thermoglucosidasius, B. thuringiensis, B. vulgatis*, and *B. weihenstephanensis*.

In various embodiments, the nucleic acid is provided to host cell by one or more of by electroporation, chemical transformation, ballistic transformation, pressure induced transformation, electrospray injection, mechanical shear forces induced, for example, in microfluids, and carbon nanotubes, nanotube puncture, induced natural competence mechanisms of an organism, merging of protoplasts, and conjugation with *Agrobacterium*.

The present invention includes a reporter gene system, which comprises a protein having a unique spectral signature and/or assayable enzymatic activity. Reporters also include, without limitation, spectral signatures based on absorbance, physical properties such as magnetism and impedence, changes in redox state, assayable enzymatic activities, such as a phosphatase, beta-galactosidase, peroxidase, luciferase, or gas generating enzymes. Illustrative reporter systems detection methods include, but are not limited to, those using chemiluminescent or fluorescent proteins, such as, for example, green fluorescent protein (GFP), enhanced green fluorescent protein (EGFP), *Renilla Reniformis* green fluorescent protein, GFPmut2, GFPuv4, yellow fluorescent protein (YFP), enhanced yellow fluorescent protein (EYFP), cyan fluorescent protein (CFP), enhanced cyan fluorescent protein (ECFP), enhanced blue fluorescent protein (EBFP), citrine and red fluorescent protein from discosoma (dsRED), infrared fluorescent proteins, luciferase, phycoerythrin, and the like. Examples of detectable bioluminescent proteins include, but are not limited to, luciferase (e.g., bacterial, firefly, click beetle and the like), luciferin, aequorin and the like. Examples of detectable enzyme systems include, but are not limited to, galactosidases, glucorinidases, phosphatases, peroxidases, cholinesterases, proteases, and the like. In certain other embodiments, the reporter systems detection methods include an enzyme.

In certain embodiments, the reporter is composed of two or more components which when present together produce the functional reporter. Examples include split GFPs, and enzymes such as luciferase, beta galactosidase, beta lactamase, and dihydrofolate reductase. One or more components of a split reporter may be introduced exogenously allowing detection of cellular production of fewer components. The split reporter may be can be used to detect split reporter-fused to another protein allowing detection either inside the cell, outside the cell, or both. For instance, a split GFP fusion protein may be excreted by a cell encapsulated with the complementing reporter component such that the producing cell does not have the capacity to produce a functional reporter until encapsulated with its complement. In certain other embodiments, the detectable marker is a non-essential gene that can be assayed rapidly for genetic variation by qPCR. In certain other embodiments, the detectable marker is a drug resistance marker that can be readily assessed for functionality by reverse selection. In certain other embodiments, the detectable marker is a nutritional marker, e.g. production of a required metabolite in an auxotrophic strain, ability to grow on a sole carbon source, or any other growth selection strategy known in the art.

In certain embodiments, two reporters may be used simultaneously in the same system. This can include the co-expression with one reporter of a gene or gene product that reduces the expression (e.g. negative regulator, antisens transcript, guide RNA directing CRISPR-Cas9, RNAi, etc.) of a constitutively expressed reporter upon detection of a target molecule by the aTF controlling the first reporter. This strategy allows for the detection of ratiometric differences between the two reporters, rather than magnitude differences between one or more reporters, upon detection of a target molecule. This system may reduce reporter noise for enhanced detection of target molecule binding to aTFs within a large population with high cell-to-cell variation in reporter expression. This can also include one reporter fused to a negative regulator of a second constitutive reporter. The second reporter can also be regulated by the aTF to be reduced in expression upon binding of the aTF to a target molecule.

In various embodiments, the present methods include various detection techniques, e.g. for reporter signal. Such detection techniques may involve a microscope, a spectrophotometer, a fluorometer, a tube luminometer or plate luminometer, x-ray film, magnetic fields, a scintillator, a fluorescence activated cell sorting (FACS) apparatus, a microbial colony picker (e.g., QPix), a microfluidics apparatus, a bead-based apparatus or the like.

In various embodiments, the nucleic acid encoding the candidate allosteric DNA-binding protein sensor and/or switch and a reporter gene system comprises a single nucleic acid vector.

In various embodiments, the nucleic acid encoding the candidate allosteric DNA-binding protein sensor and/or switch and a reporter gene system comprises two nucleic acid vectors. In an illustrative embodiment, the protein sensor and/or switch, e.g. transcription factor library, resides on a first plasmid while the reporter gene system resides on a second plasmid. By having two separate plasmids, the effective concentration of reporter gene to sensor library members may be adjusted to facilitate identification of active library members. This is useful, for example where simply using higher versus lower promoter strength is not enough control.

As used herein, a vector (or plasmid) refers to discrete elements that are used to, for example, introduce heterologous nucleic acid into cells for expression or replication thereof. The vectors can remain episomal or can be designed to effect integration of a gene or portion thereof into a chromosome of the genome. Also contemplated are vectors that are artificial chromosomes, such as yeast artificial chromosomes and mammalian artificial chromosomes. Selection and use of such vehicles are well known to those of skill in the art. Included are vectors capable of expressing DNA that is operatively linked with regulatory sequences, such as promoter regions, that are capable of effecting expression of such DNA fragments (e.g. expression vectors). Thus, a vector refers to a recombinant DNA or RNA construct, such as a plasmid, a phage, recombinant virus or other vector that, upon introduction into an appropriate host cell, results in expression of the DNA. Appropriate vectors are well known to those of skill in the art and include those that are replicable in eukaryotic cells and/or prokaryotic cells and those that remain episomal or those that integrate into the host cell genome.

In some embodiments, the present compositions and methods can include vectors based and/or generated using commercially available expression constructs, which can optionally be adapted or optimized for use in certain species and/or cell types. Examples of such expression constructs include the GATEWAY cloning vector available from INVITROGEN, which is available for multiple species. Examples of other expression constructs suitable for use in various species are known in the art. By way of example, expression constructs suitable for use in, for example, *Pichia pastoris* include, for example, pAO815, pGAPZ, pGAPZa, pHIL-D2, pHIL-S1, pPIC3.5K, pPIC9K, pPICZ, and pPICZa. By way of example, expression constructs suitable for episomal maintenance in for example, *Kluyveromyces lactis* include, for example, pKD1. Expression constructs suitable for integration in *Kluyveromyces lactis* include, for example, pGB-HSb20 vector (Swinkels et al. *Antonie van Leeuwenhoek,* 64:187-201 (1993); Bergkamp et al., *Current Genetics,* 21(4-5):365-370 (1992); Rossolini et al. Gene, 21; 119(1):75-81 (1992); Dominguez et al., the *Official Journal of the Spanish Society for Microbiology,* 1:131-142 (1998)), pKLAC1 or pKLAC2 (Paul A. Colussi and Christopher H. Taron, Appl Environ Microbiol. 71(11): 7092-7098 (2005)).

The art provides a variety of vectors that find use in the present invention. By way of non-limiting illustration, phage vectors, plasmid vectors, phagemid vectors, phasmid vectors, cosmid vectors, virus vectors and YAC vectors may be used in the present invention.

Illustrative vectors are found in WO 2015/017866, e.g. at paragraphs [00154]-[00160], the entire contents of which are hereby incorporated by reference in its entirety.

Certain embodiments require the use of cloning methods, which are known in the art and include, by way of non-limiting example, fusion PCR and assembly PCR see, e.g. Stemmer et al. *Gene* 164(1): 49-53 (1995), inverse fusion PCR see, e.g. Spiliotis et al. *PLoS ONE* 7(4): 35407 (2012), site directed mutagenesis see, e.g. Ruvkun et al. *Nature* 289(5793): 85-88 (1981), Gibson assembly (see, e.g. Gibson et al. *Nature Methods* 6 (5): 343-345, (2009), the contents of which are hereby incorporated by reference in their entirety), Quickchange see, e.g. Kalnins et al. *EMBO* 2(4): 593-7 (1983), Gateway see, e.g. Hartley et al. *Genome Res.* 10(11): 1788-95 (2000), Golden Gate see, e.g. Engler et al. *Methods Mol Biol.* 1116:119-31 (2014), restriction digest and ligation including but not Limited to blunt end, sticky end, and TA methods see, e.g. Cohen et al. PNAS 70 (11): 3240-4 (1973).

The invention is further described with reference to the following non-limiting examples.

EXAMPLES

Example 1: Transfer of a Functional Operator Site from One Organism to Another As an example, *Streptomyces coelicolor* harbors an aTF, PcaV (SC06704), a member of the MarR family, which relieves repression on its operator in the presence of 3,4-dihydroxybenzoic acid. When the intergenic region between PcaV and Pcal was cloned into position to promote the expression of GFP on a plasmid which can be maintained in *E. coli*, no GFP expression was observed even though no known protein was present which could bind the operator site. When the palindromic repeat which has been shown to bind with PcaV (Davis et al) was cloned between a synthetic promoter/RBS pair (Kosuri et al) (FIG. 1, FIG. 2) a functional promoter was formed and GFP expression was observed. Upon the introduction of the PcaV protein under a constitutive promoter, the GFP expression was suppressed. Furthermore, expression of GFP was observed when *E. coli* harboring the plasmid were grown in medium supplemented with 3,4-dihydroxybenzoic acid. See FIG. 1, FIG. 2, FIG. 3, FIG. 21.

Further examples of this synthetic operator approach include QacR from *Staphylococcus aureus* (Grkovic et al), CviR from *Chromobacterium violaceum* (Stauff et al), and TtgR from *Psuedomonas putida* (Krell et al), whose DNA binding sites have been identified. QacR is an multidrug resistance gene which releases repression on its operator in response to various rigid bivalent compounds such as rhodamine or ethidium. When the QacR operator was cloned between a promoter and rbs element a functional operator results. See FIG. 4, FIG. 5.

CviR responds to the quorum sensing molecule C6 homoserine lactone (C6HSL) and in its native context binds to its operator and recruits transcription factors thus acting as an activator. In the case of the synthetic operator promoter, it has used in such a way that it binds its operator and represses GFP expression in *E. coli* so the observed fluorescence goes down with increasing concentration of C6HSL until the system is fully repressed. See FIG. 6, FIG. 7.

Figure 8:
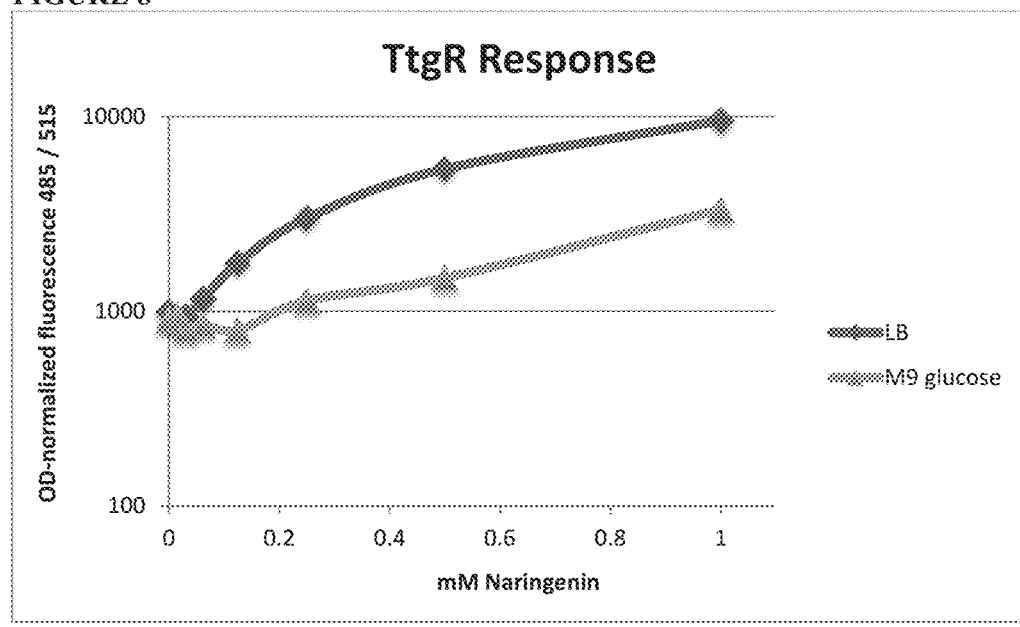
FIG. 8 shows a dose response of TtgR to naringenin in LB and in M9 minimal medium with 1% glucose.
Figure 9:
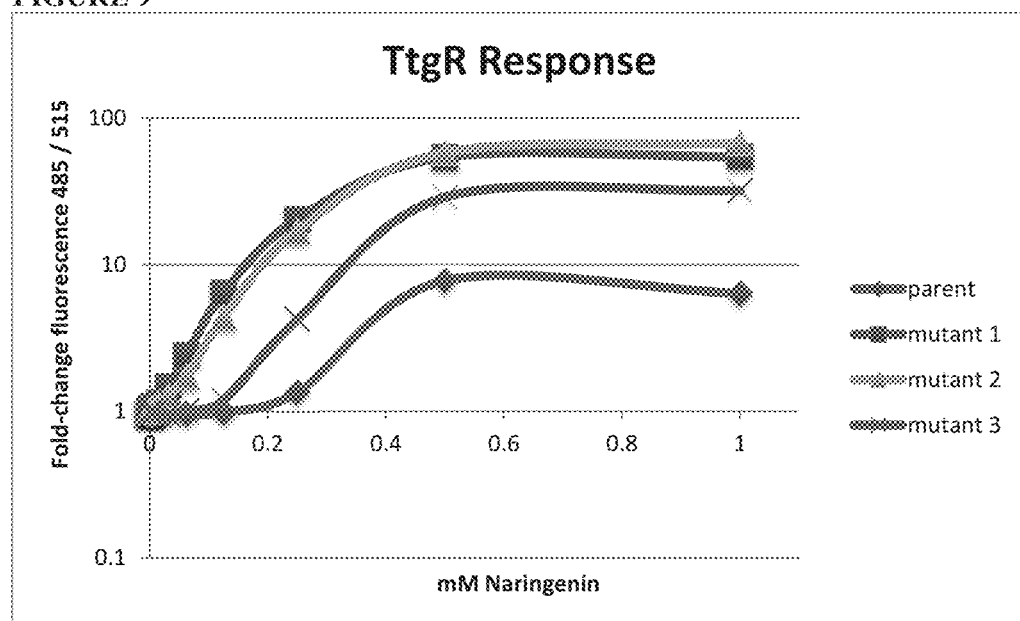
FIG. 9 shows a dose response of TtgR and TtgR expression variants to naringenin in M9 minimal medium with 1% glucose. Mutants 1, 2, and 3 represent strains in which TtgR expression has been modulated.

TtgR regulates the TtgABC efflux pump in *Pseudomonas putida*, and responds to antibiotics such as chloramphenicol (Teran, et al) as well as the flavanones such as naringenin (Raman, et al). In this example, a TtgR-binding synthetic operator promoter was used to drive GFP expression in *E. coli* in response to naringenin (FIG. 8, FIG. 9, FIG. 10). A distinct difference in the dynamic range and magnitude of signal of this sensor-reporter system was observed in rich (LB) versus minimal (M9 minimal salts with 1% glucose) medium, as shown in FIG. 8.

Figure 13:
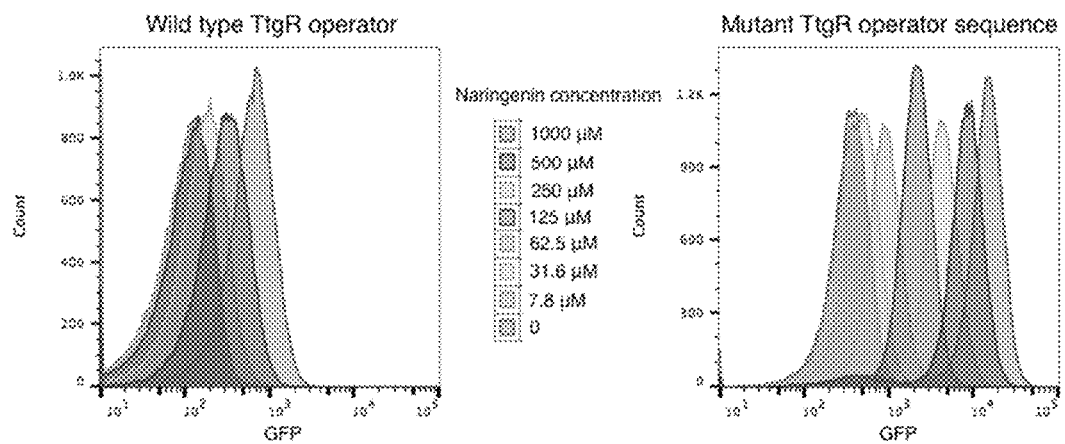
FIG. 13 shows GFP distributions for the wild-type TtgR-regulated operator and an operator with mutated TtgR binding sites. Right shifting of curves indicates binding in the mutant.

It was in the context of the lower sensitivity minimal medium environment that the ability to vary the dynamic range of a sensor-reporter system by modulating expression of the allosteric DNA-binding sensor was demonstrated (FIG. 9 and FIG. 10), where mutations which attenuated TtgR expression (mutants 1, 2, and 3, sequences in FIG. 11) were shown to substantially lower the limit of detection of naringenin. Mutations to the DNA binding site of TtgR (the operator site) also were shown to substantially lower the limit of detection of naringenin (FIG. 13). See FIG. 8, FIG. 9, FIG. 10, FIG. 11, FIG. 13.

The variety of sensor-reporter behavior across different media conditions and with different TtgR expression platforms led to the development of the sensor-reporter screening platform shown in FIG. 12. In this platform, a combinatorial sensor-reporter library varying in the sensor sequence as well as the vector sequence (e.g. the sensor or reporter promoter or terminator sequences) is constructed. This library is screened for the desired sensitivity in the appropriate environmental conditions. During strain engineering, the sensor can be swapped for a sensor with a higher dynamic range to allow strain library screening until a maximal yield is reached, alleviating issues with sensor saturation. See FIG. 12.

Figure 14:
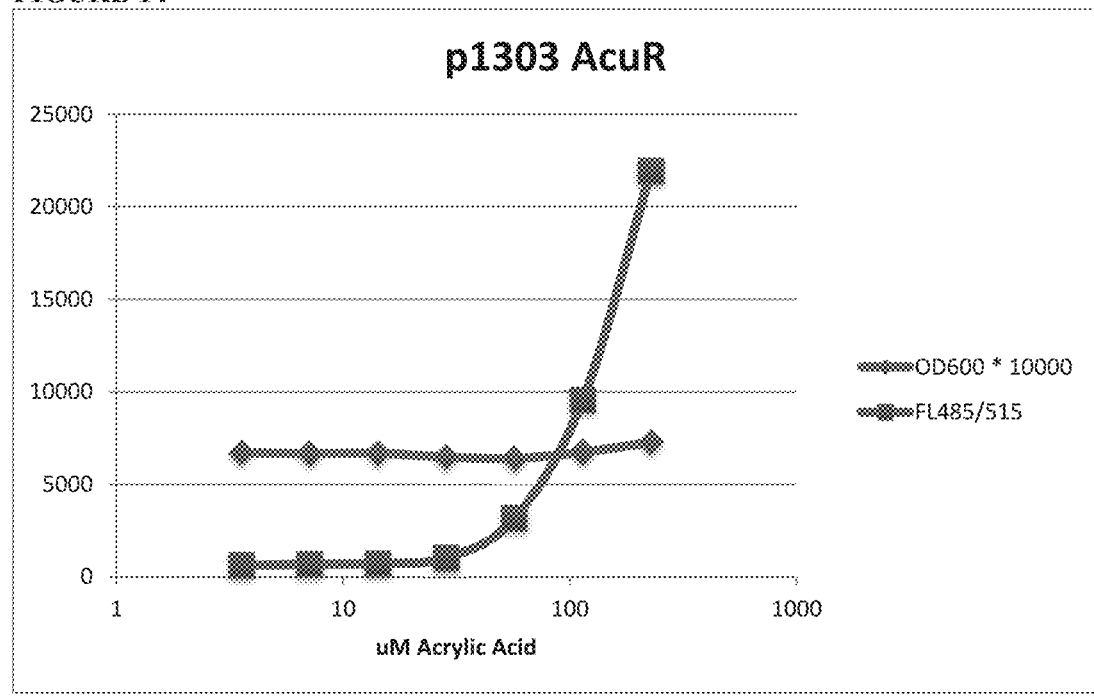
FIG. 14 shows the AcuR chassis dose response to acrylic acid.

AcuR responds to acrylic acid in *Rhodobacter sphaeroides*. In this example the native AcuR promoter has been cloned to regulate expression of GFP on an AcuR expression plasmid hosted in *E. coli*. (FIG. 14)

Figure 15:
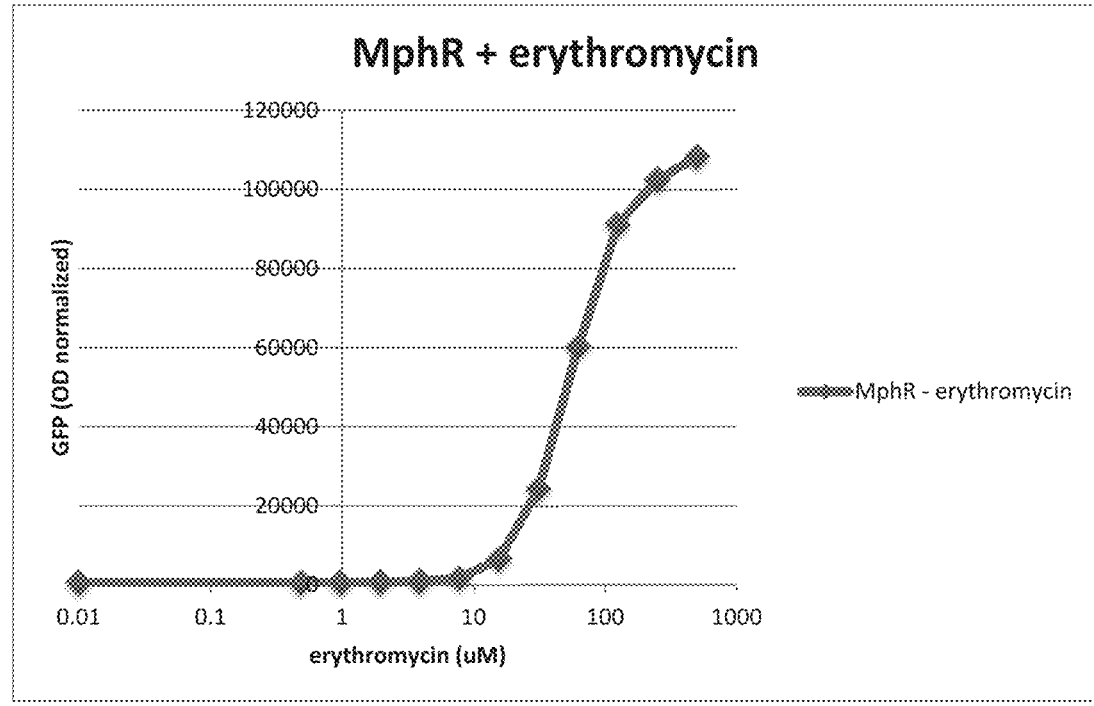
FIG. 15 shows the MphR chassis dose response to erythromycin.
Figure 16:
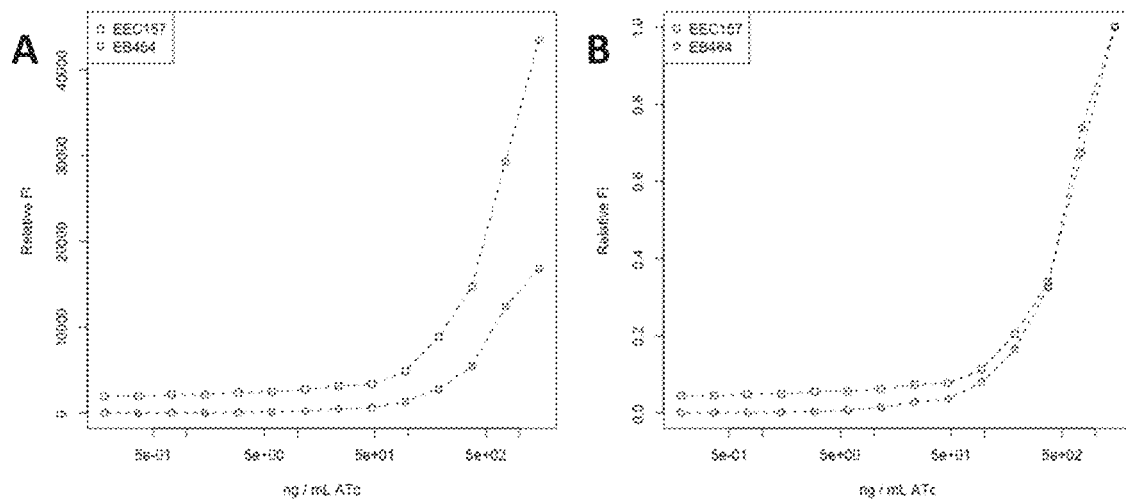
FIG. 16 panel A shows the TetR chassis dose response through two reporters, GFP (EEC157) and RFP (EB464). Panel B shows the normalized response of TetR is identical through both reporters.
Figure 17:
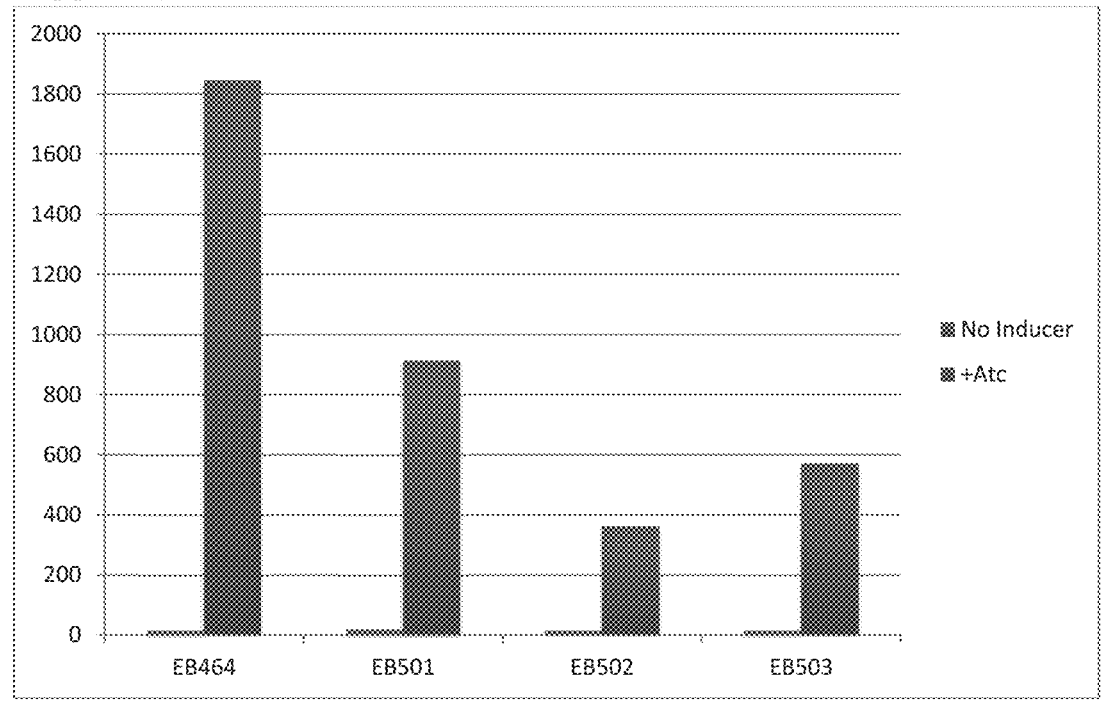
FIG. 17 shows induced and uninduced RFP reporter response of TetR sensor overnight cultures. SSRA degradation tags cause expressed proteins to be targeted for digestion by Clp protease thus altering expression level. Depending on the sequence of the SSRA tag, they may be weakly or strongly degraded. RFP is expressed with no degradation tag (EB464), a weak degradation tag (EB501) or a strong degradation tag (EB502 and EB503. In each series, the left bar is no inducer and the right bar is +Atc.

MphR controls expression of resistance systems to erythromycin and other antibiotics. In this example MphR has been cloned to regulate expression of GFP on an MphR expression plasmid hosted in *E coli* (FIG. 15). TetR controls expression of tetracycline resistance genes. In this example, it is being used to control the expression of two different fluorescent reporter proteins, GFP and RFP in *E coli* (FIG. 16, panel A). The normalized response of both reporters is identical (FIG. 16, panel B). Overall reporter response of the TetR RFP system can be modulated by using an SSRA degradation tag to decrease the level of reporter observed in overnight cultures (FIG. 17). TetR can be expressed off of a plasmid and control a genomically integrated selection marker (tolC) (FIG. 18).

Figure 19:
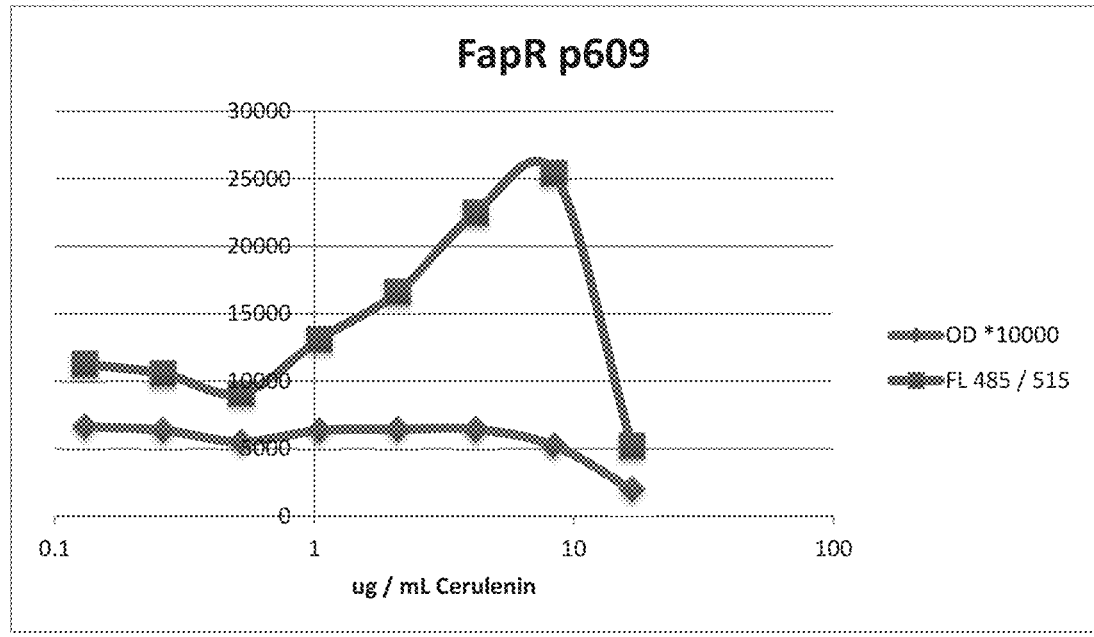
FIG. 19 shows the FapR chassis dose response to cerulenin. Note toxicity at highest concentration in OD600 and fluorescence channels.

*Staphylococcus aureus* FapR responds to intracellular levels of malonyl-CoA. Cerulenin is an inhibitor of fatty acid biosynthesis and is known to increase the intracellular pool of malonyl-CoA at subtoxic concentrations. FapR is shown driving the increased expression of a GFP reporter in *E coli* with increasing concentrations of cerulenin (FIG. 19).

Figure 20:
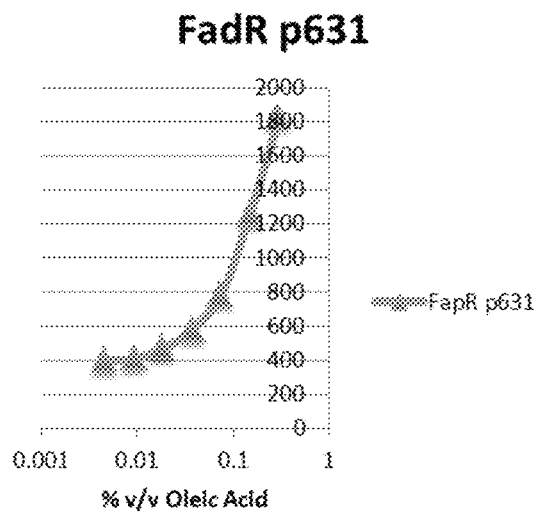
FIG. 20 shows the FadR chassis dose response to oleic acid.
Figure 21:
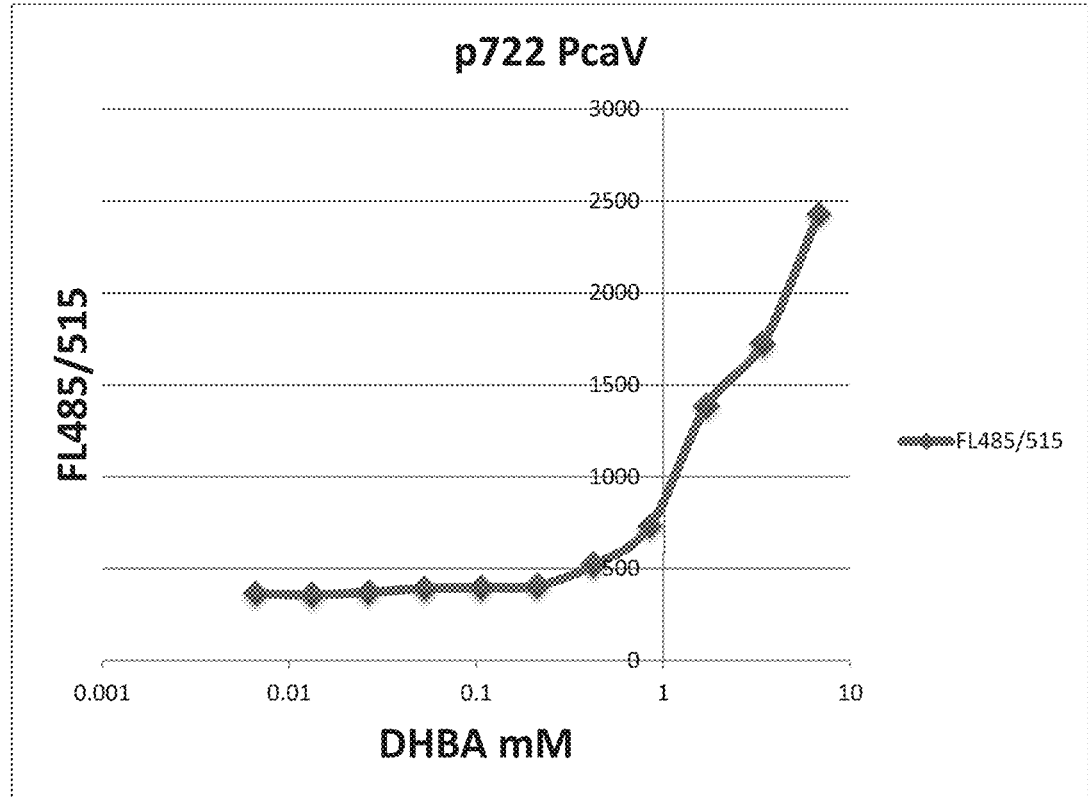
FIG. 21 shows the PcaV chassis dose response to dihyroxybenzoic acid (DHBA).
Figure 22:
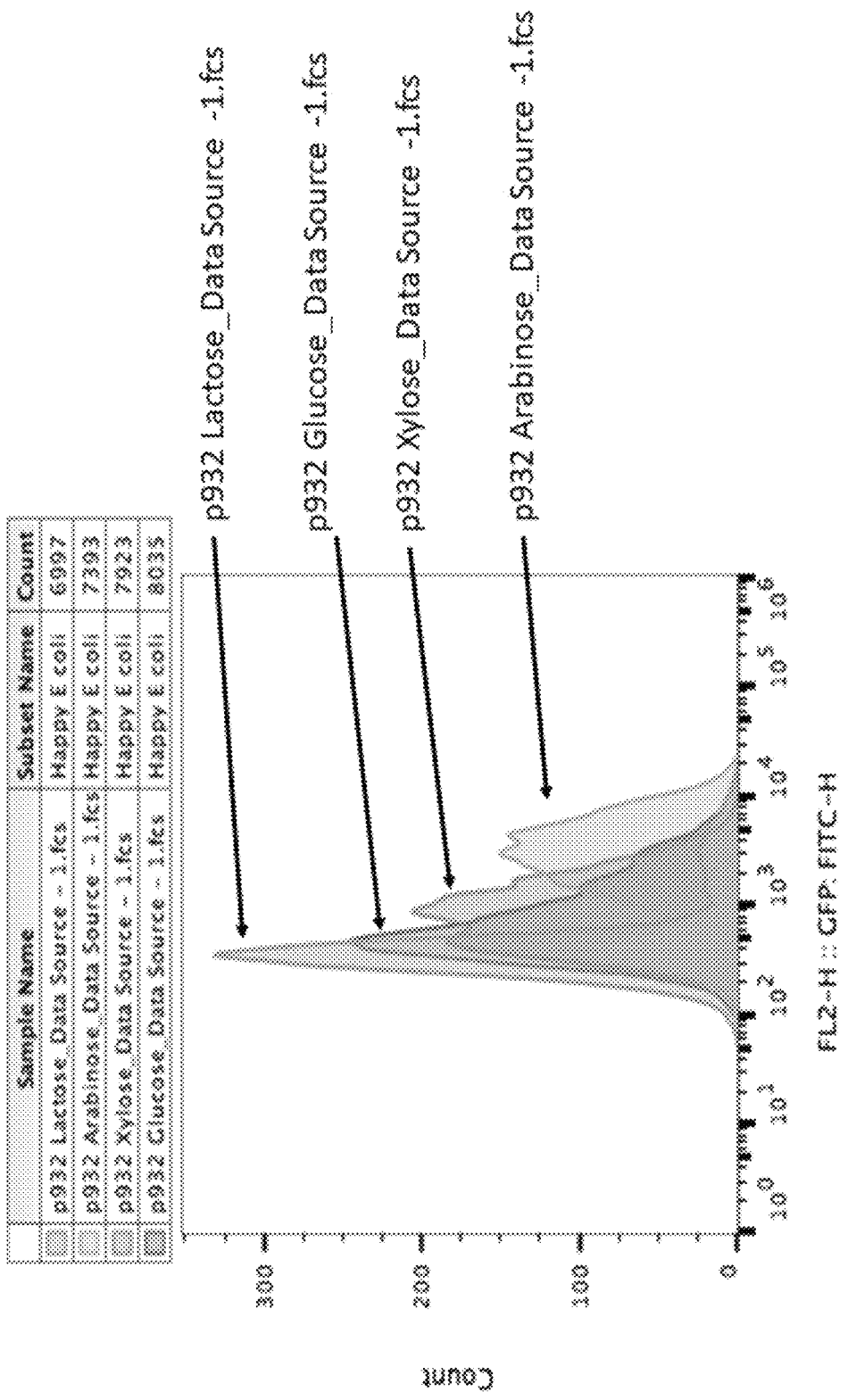
FIG. 22 shows the AraR chassis response to growth with various sugars as the carbon source.

*Vibrio cholerae* FadR regulates gene expression through modulation with oleoyl-CoA. FadR is shown driving expression of a GFP reporter in response to increased levels of oleic acid in *E coli* (FIG. 20).

*Bacteroides* thetaiotaomicron VPI AraR controls expression of genes related to arabinose metabolism. Shown is GFP reporter expression being driven by AraR controlled GFP in *E coli* cultures grown in minimal medium with glucose, xylose, arabinose, or lactose as the sole carbon source.

Figure 23:
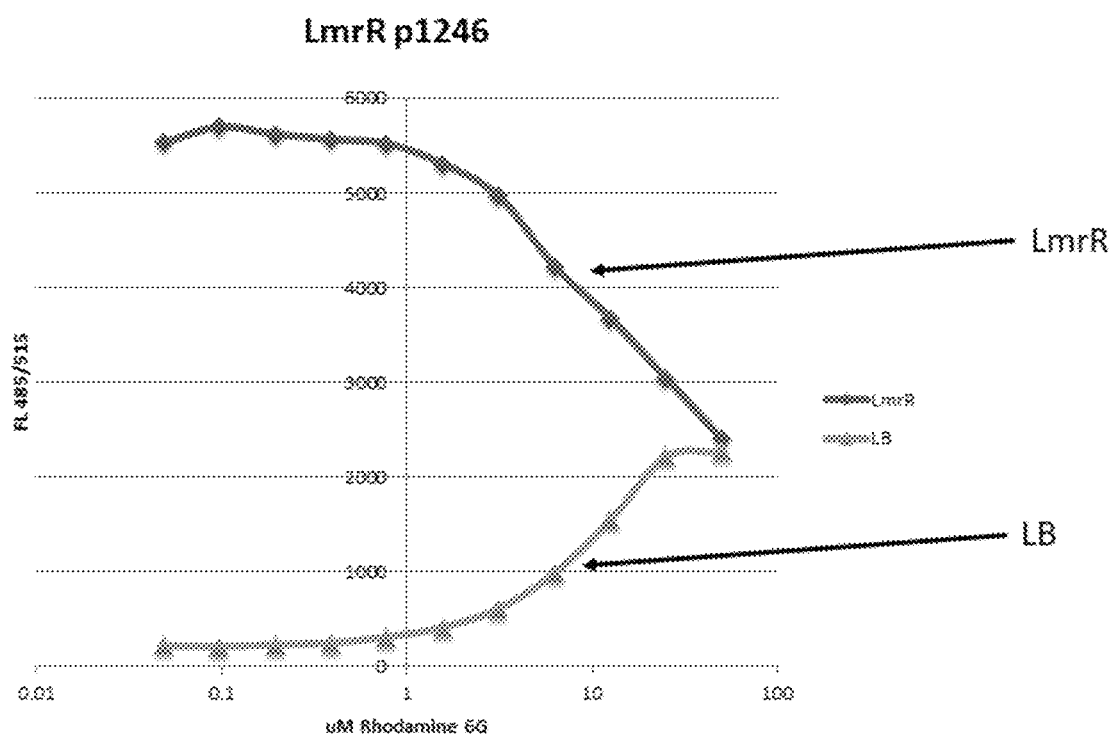
FIG. 23 shows the LmrR chassis dose response to rhodamine 6G and fluorescence in the growth medium caused by the rhodamine dye.
Figures 26, 27:
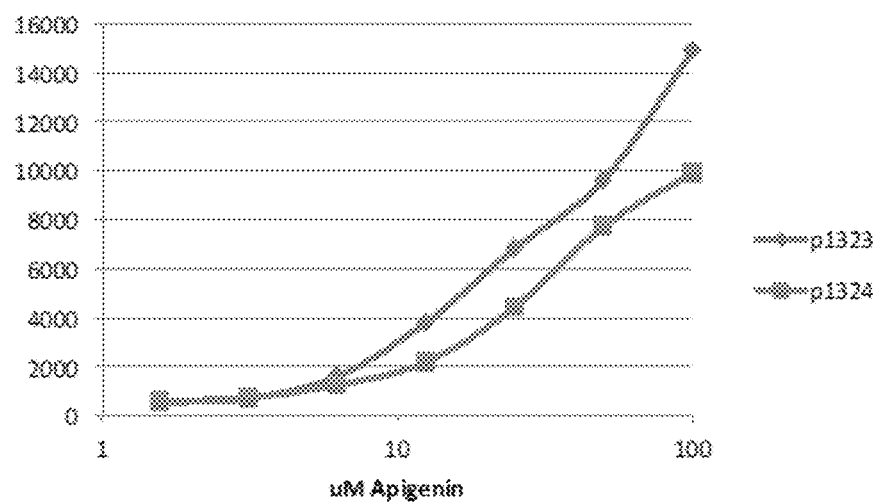
FIG. 26 shows dose response of TtgR based apigenin sensors.
FIG. 27 shows region of LacI mutated to sense nootkatone in sensors 41 and 87 (top row is SEQ ID NO: 10).

LmrR is a MDR pump regulator in *Lactococcus lactis*. Here it is shown driving the repression of GFP expression with increasing concentrations of rhodamine 6G (FIG. 23). Note that rhodamine fluoresces in the same channel so a medium and ligand only control is included.

Figures 28, 29:
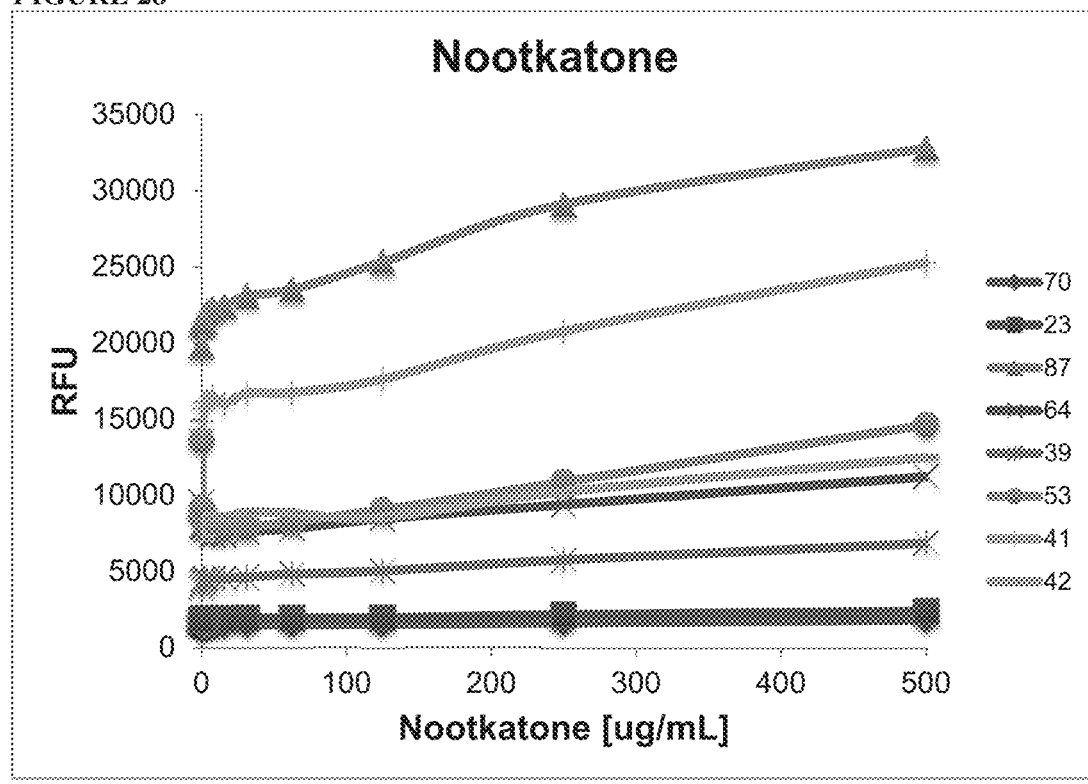
FIG. 28 shows dose response of 8 LacI nootkatone sensors.
FIG. 29 shows a region of LacI mutated to sense resveratrol (top row is SEQ ID NO: 11).
Figures 30, 31:
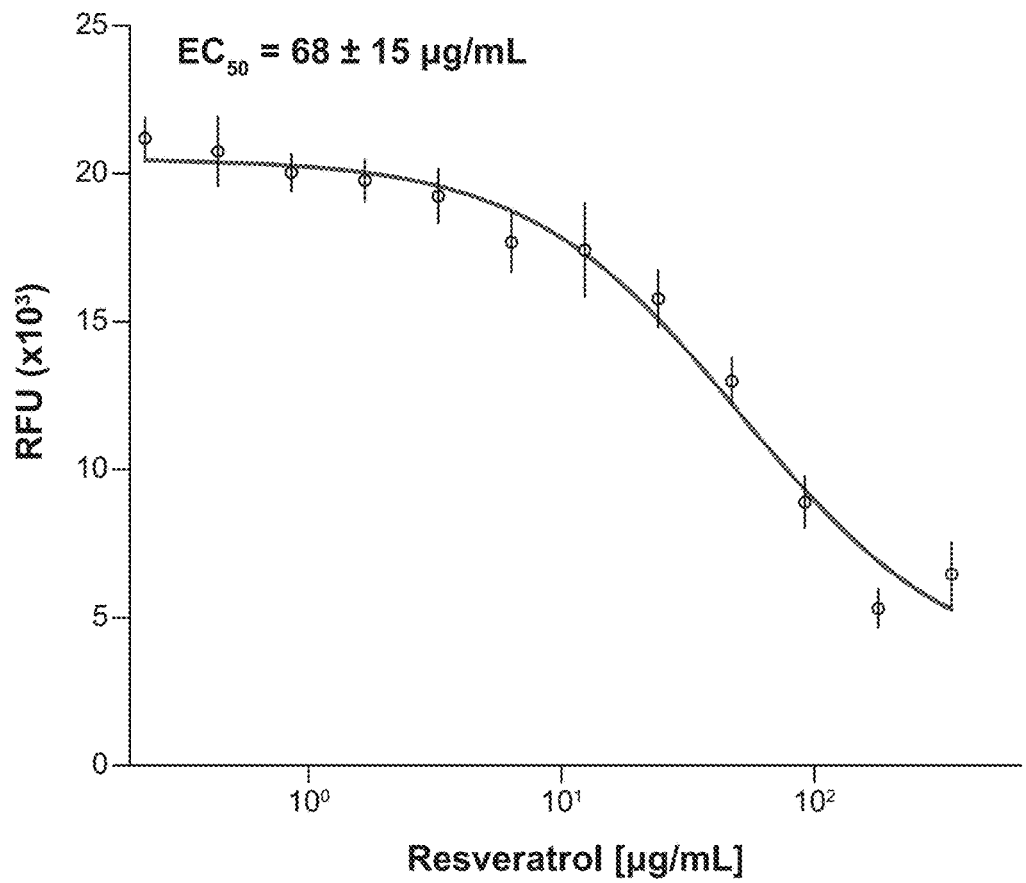
FIG. 30 shows dose response of the LacI resveratrol sensor.
FIG. 31 shows the region of TetR mutated to sense apigenin (top row is SEQ ID NO: 12, p1313 is SEQ ID NO: 13, p1314 is SEQ ID NO: 14, p1315 is SEQ ID NO: 15).
Figure 34:
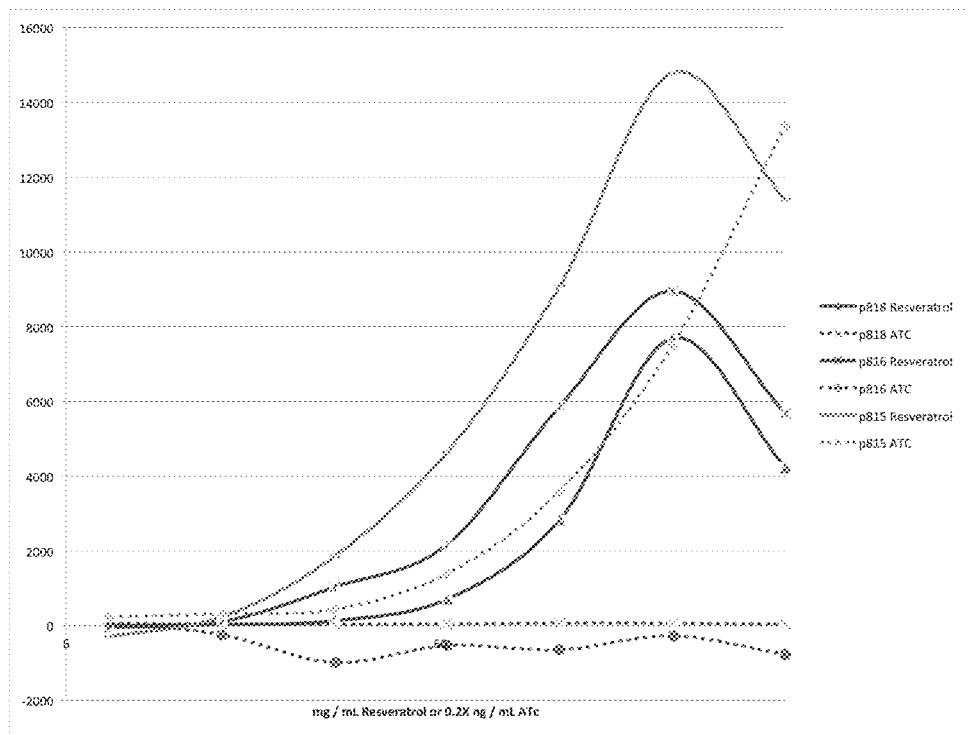
FIG. 34 shows dose response of 3 TetR resveratrol sensors to resveratrol and ATc.
Figure 35:
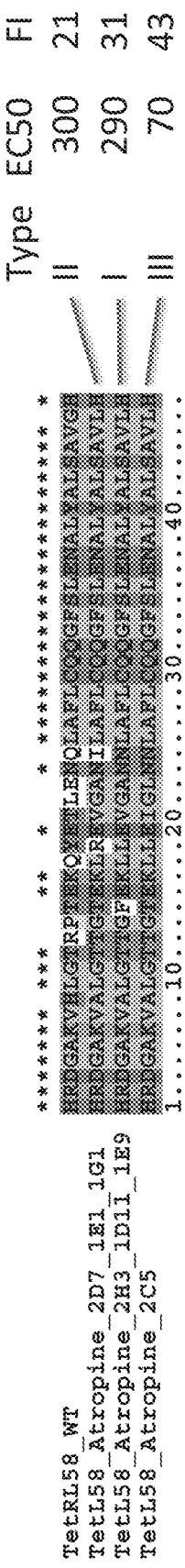
FIG. 35 shows region of TetR mutated to sense atropine, EC50 (uM) and maximum fold induction (top row is SEQ ID NO: 20, second row from top is SEQ ID NO: 21, third row from top is SEQ ID NO: 22, and bottom row is SEQ ID NO: 23).
Figure 36:
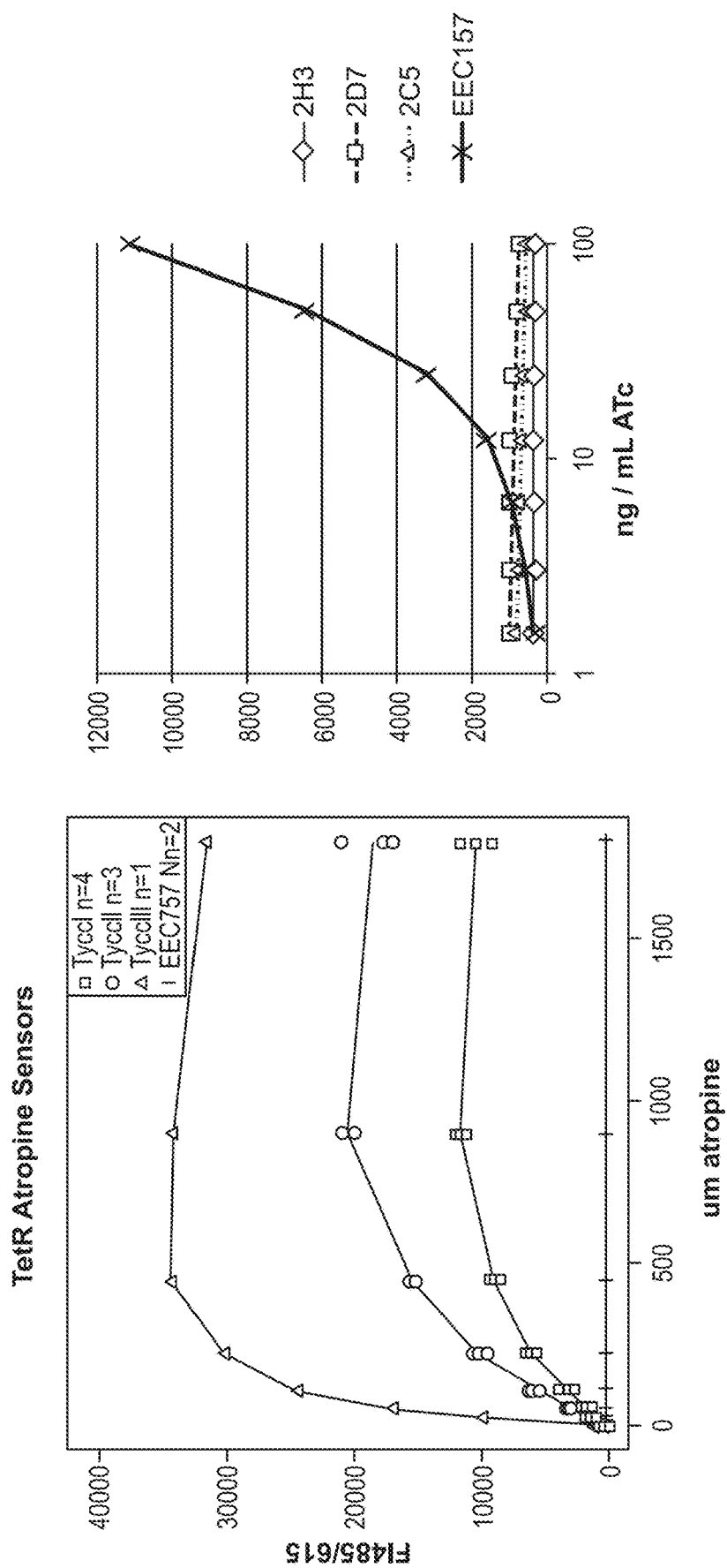
FIG. 36 left panel shows dose response curves of wild type (EEC157), p537 (TypeII), p538 (Type I) and p539 (Type III) TetR atropine sensors to atropine. Right panel shows response of same sensors p537 (2C5), p538 (2D7), p539 (2H3) to ATc.
Figures 38, 39:
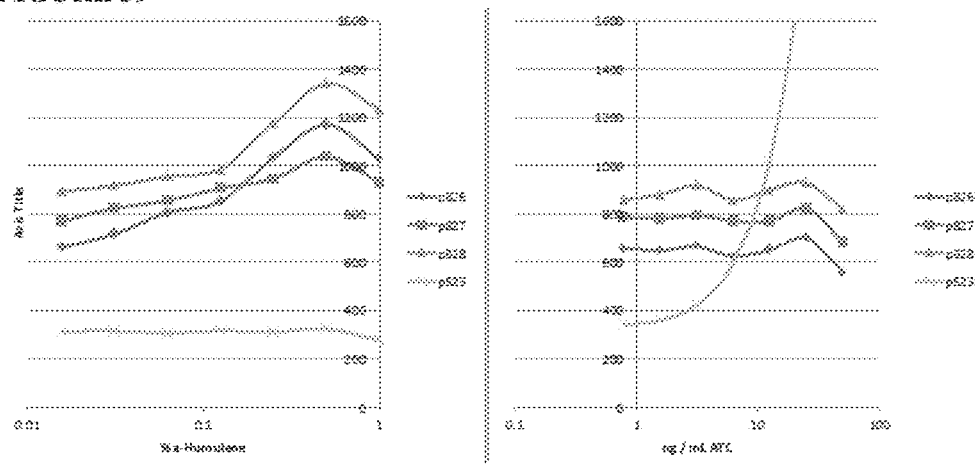
FIG. 38 shows the region of TetR mutated to sense humulene (top row is SEQ ID NO: 24, second row from top is SEQ ID NO: 25, third row from top is SEQ ID NO: 26, and bottom row is SEQ ID NO: 27).
FIG. 39 shows the dose response of 3 TetR humulene sensors (p826, p827, and p828) and wild type TetR (p523) to humulene and ATc.
Figure 40:
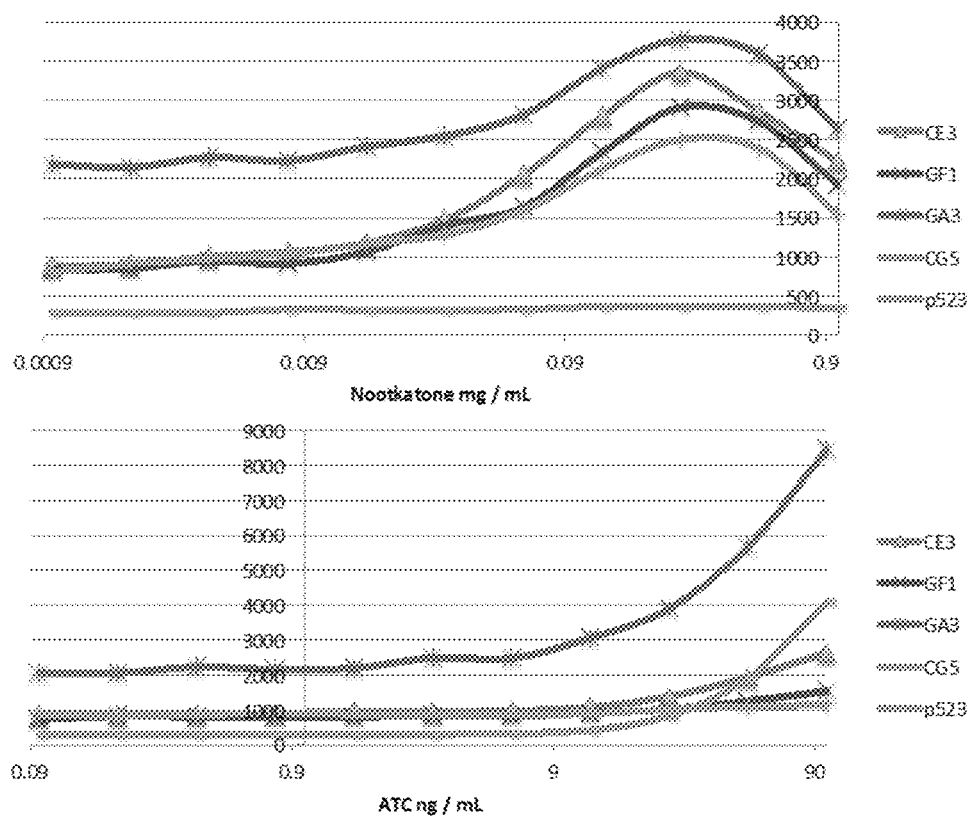
FIG. 40 shows the dose response of 4 TetR nootkatone sensors (CE3, GF1, GA3, and CG5) and wild type TetR (p523) to nootkatone and ATc.

Various chassis have been engineered to recognize ligands of interest. The mutated regions of TtgR, LacI, and TetR aligned with the wild type sequence are shown in FIGS. 25, 27, 29, 31, 33, 35, and 38. Dose response to apigenin sensed by chassis TtgR and TetR (FIGS. 25, 32). Nootkatone is sensed by LacI, and TetR chassis based sensors (FIGS. 28, 40). Resveratrol sensors based on the LacI and TetR chassis are shown (FIGS. 30, 34). Atropine sensors based on the TetR chassis as well as their specificity to the cognate ligand and structurally related molecules is shown (FIGS. 36 and 37). Humulene TetR based sensor response is shown (FIG. 38).

Figure 47:
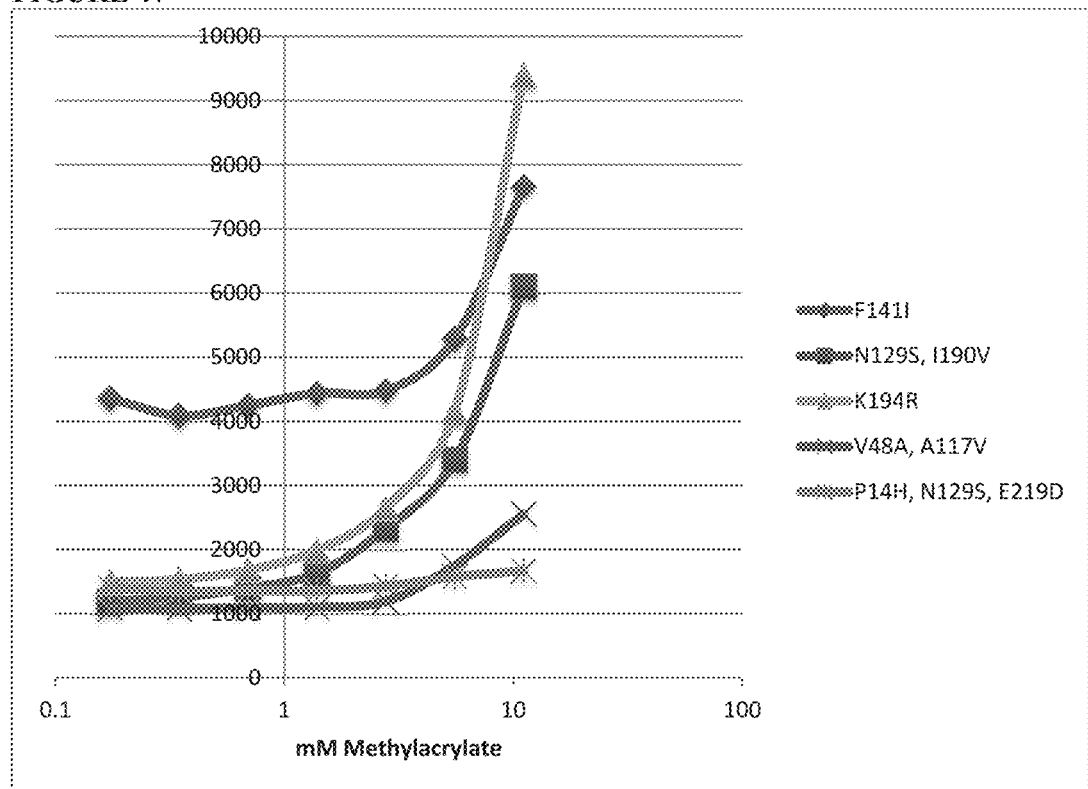
FIG. 47 shows dose response of 5 AcuR chassis methylacrylate sensors legend indicates mutations to wild type.

AcuR chassis has been mutated to respond to methylacrylate as a ligand (FIG. 47)

Example 2: Swapping a Primary Sensor Plasmid for a Secondary Sensor Plasmid

As an example, a population of cells was generated with a primary sensor plasmid harboring a single I-SceI restriction enzyme cut site and an ampicillin selection marker and expressing GFP (p1057). A secondary sensor plasmid was generated containing an expression cassette for the I-SceI enzyme and a kanamycin resistance cassette and RFP (p1174). Removal of the ampicillin from the selective medium did not result in a stochastic removal of the primary sensor plasmid. Based on flow cytometry, no difference was observed between a clean background strain transformed only with p1174 and the strain harboring the p1057 plasmid. However, introduction of the secondary sensor plasmid and subsequent growth on kanamycin selective medium resulted in a 200,000-fold reduction in cells harboring the primary plasmid in the population (FIGS. 42 and 43).

TABLE 2

Selected Chassis and Sensors

| Description | SEQ ID NO: | Amino Acid Sequence |
|---|---|---|
| Wild type of PcaV chassis P722 used to make sensors (See, e.g., Figures 1-3, 21) | 29 | MAAVDLATHPGHLARRLQQAHYLLWNTMVSEETTSPQYAVLNALVAEPGLD QRTVGERVGLDRSTIAEVVSRLGRRGLLDKVRDPQDGRRSLLRLTDEGLRVH RRLGVRIARMNQVFLAPLAADEQAVFFDLIRRVADAAEGLRNPAEPAVAPG |
| Wild type of QacR chassis P661 used to make sensors (See, e.g., Figures 4-5) | 30 | MNLKDKILGVAKELFIKNGYNATTTGEIVKLSESSKGNLYYHFKTKENLFLEILNI EESKWQEQWKKEQIKAKTNREKFYLYNELSLTTEYYYPLQNAIIEFYTEYYKTN SINEKMNKLENKYIDAYHVIFKEGNLNGEWSINDVNAVSKIAANAVNGIVTFTH EQNINERIKLMNKFSQIFLNGLSK |
| Wild type of CviR chassis P658 used to make sensors (See, e.g., Figures 6-7) | 31 | MVISKPINARPLPAGLTASQQWTLLEWIHMAGHIETENELKAFLDQVLSQAPS ERLLLALGRLNNQNQIQRLERVLNVSYPSDWLDQYMKENYAQHDPILRIHLGQ GPVMWEERFNRAKGAEEKRFIAEATQNGMGSGITFSAASERNNIGSILSIAGR EPGRNAALVAMLNCLTPHLHQAAIRVANLPPASPSNMPLSQREYDIFHWMSR GKTNWEIATILDISERTVKFHVANVIRKLNANNRTHAIVLGMHLAMPPSTVANE |
| Wild type of TtgR chassis P524 used to make sensors (See, e.g., Figures 8-11 and 13, 25, 26) | 32 | MVRRTKEEAQETRAQIIEAAERAFYKRGVARTTLADIAELAGVTRGAIYWHFN NKAELVQALLDSLHETHDHLARASESEDELDPLGCMRKLLLQVFNELVLDART RRINEILHHKCEFTDDMCEIRQQRQSAVLDCHKGITLALANAVRRGQLPGELD VERAAVAMFAYVDGLIGRWLLLPDSVDLLGDVEKWVDTGLDMLRLSPALRK |
| Mutant 1 of TtgR chassis used to make sensors (See, e.g., Figures 8-11) | 33 | MVRRTKEEAQETRAQIIEAAERAFYKRGVARTTLADIAELAGVTRGAIYWHFN NKAELVQALLDSLHETHDHLARASESEDELDPLGCMRKLLLQVFNELVLDART RRINEILHHKCEFTDDMCEIRQQRQSAVLDCHKGITLALANAVRRGQLPGELD VERAAVAMFAYVDGLIGRWLLLPDSVDLLGDVEKWVDTGLDMLRLSPALRK |
| Mutant 2 of TtgR chassis used to make sensors (See, e.g., Figures 8-11) | 34 | MVRRTKEEAQETRAQIIEAAERAFYKRGVARTTLADIAELAGVTRGAIYWHFN NKAELVQALLDSLHETHDHLARASESEDELDPLGCMRKLLLQVFNELVLDART RRINEILHHKCEFTDDMCEIRQQRQSAVLDCHKGITLALANAVRRGQLPGELD VERAAVAMFAYVDGLIGRWLLLPDSVDLLGDVEKWVDTGLDMLRLSPALRK |
| Mutant 3 of TtgR chassis used to make sensors (See, e.g., Figures 8-11) | 35 | MVRRTKEEAQETRAQIIEAAERAFYKRGVARTTLADIAELAGVTRGAIYWHFN NKAELVQALLDSLHETHDHLARASESEDELDPLGCMRKLLLQVFNELVLDART RRINEILHHKCEFTDDMCEIRQQRQSAVLDCHKGITLALANAVRRGQLPGELD VERAAVAMFAYVDGLIGRWLLLPDSVDLLGDVEKWVDTGLDMLRLSPALRK |

TABLE 2-continued

Selected Chassis and Sensors

| Description | SEQ ID NO: | Amino Acid Sequence |
|---|---|---|
| Engineered sensor based on TtgR responding to naringenin (See, e.g., Figures 8-9 and 13) | 36 | MVRRTKEEAQETRAQIIEAAERAFYKRGVARTTLADIAELAGVTRGAIYWHFN NKAELVQALLDSLHETHDHLARASESEDELDPLGCMRKLLLQVFNELVLDART RRINEILHHKCEFTDDMCEIRQQRQSAVLDCHKGITLALANAVRRGQLPGELD VERAAVAMFAYVDGLIGRWLLLPDSVDLLGDVEKWVDTGLDMLRLSPALRK |
| Engineered sensor p1323 based on TtgR responding to apigenin (see, e.g., Figures 8-11, 25, and 26) | 37 | MVRRTKEEAQETRAQIIEAAERAFYKRGVARTTLADIAELAGVTRGAIYWHFN NKAELVQALLDSLIETIDHLARASESEDELDPLGCMRKLLLQVFNELVLDARTR RINEILHHKCEFTDDMCEIRQQRQSAVLDCHKGITLALANAVRRGQLPGELDV ERAAVAMFAYVDGLIGRWLLLPDSVDLLGDVEKWVDTGLDMLRLSPALRK |
| Engineered sensor p1324 based on TtgR responding to apigenin (See, e.g., Figures 8-11, 25, and 26) | 38 | MVRRTKEEAQETRAQIIEAAERAFYKRGVARTTLADIAELAGVTRGAIYWHFN NKAELVQALLDSLHETHDHLARASESEDELDPLGCMRKLLLQVFNELVLDART RRINEILHHKCEFTDDMCEIRQQRQSAVLDCHKGITLALANAVRRGQLPGELD VERAAVASLAFTWGLIGRWLLLPDSVDLLGDVEKWVDTGLDMLRLSPALRK |
| Wild type of AcuR chassis P1303 used to make sensors (See, e.g., Figure 14) | 39 | MPLTDTPPSVPQKPRRGRPRGAPDASLAHQSLIRAGLEHLTEKGYSSVGVDE ILKAARVPKGSFYHYFRNKADFGLALIEAYDTYFARLLDQAFLDGSLAPLARLR LFTRMAEEGMARHGFRRGCLVGNLGQEMGALPDDFRAALIGVLETWQRRTA QLFREAQACGELSADHDPDALAEAFWIGWEGAILRAKLELRPDPLHSFTRTFG RHFVTRTQE |
| Engineered sensor based on AcuR responding to methylacrylate (See, e.g., Figure 47) | 40 | MPLTDTPPSVPQKPRRGRPRGAPDASLAHQSLIRAGLEHLTEKGYSSVGVDE ILKAARVPKGSFYHYFRNKADFGLALIEAYDTYFARLLDQAFLDGSLAPLARLR LFTRMAEEGMARHGFRRGCLVGNLGQEMGALPDDIRAALIGVLETWQRRTA QLFREAQACGELSADHDPDALAEAFWIGWEGAILRAKLELRPDPLHSFTRTFG RHFVTRTQE |
| Engineered sensor based on AcuR responding to methylacrylate (See, e.g., Figure 47) | 41 | MPLTDTPPSVPQKPRRGRPRGAPDASLAHQSLIRAGLEHLTEKGYSSVGVDE ILKAARVPKGSFYHYFRNKADFGLALIEAYDTYFARLLDQAFLDGSLAPLARLR LFTRMAEEGMARHGFRRGCLVGSLGQEMGALPDDFRAALIGVLETWQRRTA QLFREAQACGELSADHDPDALAEAFWIGWEGAVLRAKLELRPDPLHSFTRTF GRHFVTRTQE |
| Engineered sensor based on AcuR responding to methylacrylate (See, e.g., Figure 47) | 42 | MPLTDTPPSVPQKPRRGRPRGAPDASLAHQSLIRAGLEHLTEKGYSSVGVDE ILKAARVPKGSFYHYFRNKADFGLALIEAYDTYFARLLDQAFLDGSLAPLARLR LFTRMAEEGMARHGFRRGCLVGNLGQEMGALPDDFRAALIGVLETWQRRTA QLFREAQACGELSADHDPDALAEAFWIGWEGAILRARLELRPDPLHSFTRTF GRHFVTRTQE |
| Engineered sensor based on AcuR responding to methylacrylate (See, e.g., Figure 47) | 43 | MPLTDTPPSVPQKPRRGRPRGAPDASLAHQSLIRAGLEHLTEKGYSSAGVDE ILKAARVPKGSFYHYFRNKADFGLALIEAYDTYFARLLDQAFLDGSLAPLARLR LFTRMAEEGMVRHGFRRGCLVGNLGQEMGALPDDFRAALIGVLETWQRRTA QLFREAQACGELSADHDPDALAEAFWIGWEGAILRAKLELRPDPLHSFTRTFG RHFVTRTQE |
| Engineered sensor based on AcuR responding to methylacrylate (See, e.g., Figure 47) | 44 | MPLTDTPPSVPQKHRRGRPRGAPDASLAHQSLIRAGLEHLTEKGYSSVGVDE ILKAARVPKGSFYHYFRNKADFGLALIEAYDTYFARLLDQAFLDGSLAPLARLR LFTRMAEEGMARHGFRRGCLVGSLGQEMGALPDDFRAALIGVLETWQRRTA QLFREAQACGELSADHDPDALAEAFWIGWEGAILRAKLELRPDPLHSFTRTFG RHFVTRTQD |
| Wild type of MphR chassis P521 used to make sensors (See, e.g., Figure 15) | 45 | MPRPKLKSDDEVLEAATVVLKRCGPIEFTLSGVAKEVGLSRAALIQRFTNRDTL LVRMMERGVEQVRHYLNAIPIGAGPQGLWEFLQVLVRSMNTRNDFSVNYLIS WYELQVPELRTLAIQRNRAVVEGIRKRLPPGAPAAAELLLHSVIAGATMQWAV DPDGELADHVLAQIAAILCLMFPEHDDFQLLQAHA |
| Wild type of TetR chassis P523, EEC157, EB464, EB501, EB502, EB503, EEC238 used to make sensors (See, e.g., Figures 16-18, 24, 31-40) | 46 | MSRLDKSKVINSALELLNEVGIEGLTTRKLAQKLGVEQPTLYWHVKNKRALLD ALAIEMLDRHHTHFCPLEGESWQDFLRNNAKSFRCALLSHRDGAKVHLGTRP TEKQYETLENQLAFLQQGFSLENALYALSAVGHFTLGCVLEDQEHQVAKEE RETPTTDSMPPLLRQAIELFDHQGAEPAFLFGLELIICCGLEKQLKCESGS |
| Engineered sensor based on TetR (JE9, p1074) responding to anhydrotetracycline (See, e.g., Figure 24) | 47 | MSRLDKSKVINSALELLNEVGIEGLTTRKLAQKLGVEQPTLYWHVKNKRALLD ALAIEMLDRHHTHFCPLEGESWQDFLRNNAKSFRCALLSHRDGAKVHLGTRP TEKQYETLENQLAFLCQQGFSLENALYALSAVGHFTLGCVLEDQEHQVVKKK GKLLLIVCRHYYDKLSNYLITKVQSQPTYSALN |

TABLE 2-continued

Selected Chassis and Sensors

| Description | SEQ ID NO: | Amino Acid Sequence |
|---|---|---|
| Engineered sensor p1313 based on TetR responding to apigenin (See, e.g., Figure 31 and 32) | 48 | MSRLDKSKVINSALELLNEVGIEGLTTRKLAQKLGVEQPTLYWHVKNKRALLD ALAIEMLDRHHTHFCPLEGESWQDFLRNNAKSFRCALLSHRDGAKVHLGTRP TEKQYETLENQLAFLCQQGFSLENALYALAAIMHFTLGCVLWDQEHQVAKEE RETPTTDSMPPLLRQAIELFDHQGAEPAFLFGLELIICGLEKQLKCESGS |
| Engineered sensor p1314 based on TetR responding to apigenin (See, e.g., Figure 31 and 32) | 50 | MSRLDKSKVINSALELLNEVGIEGLTTRKLAQKLGVEQPTLYWHVKNKRALLD ALAIEMLDRHHTHFCPLEGESWQDFLRNNAKSFRCALLSHRDGAKVHLGTRP TEKQYETLENQLAFLCQQGFSLENALYALHAVAMFALGCVLYDQELQVAKEE RETPTTDSMPPLLRQAIELFDHQGAEPAFLFGLELIICGLEKQLKCESGS |
| Engineered sensor p1315 based on TetR responding to apigenin (See, e.g., Figure 31 and 32) | 51 | MSRLDKSKVINSALELLNEVGIEGLTTRKLAQKLGVEQPTLYWHVKNKRALLD ALAIEMLDRHHTHFCPLEGESWQDFLRNNAKSFRCALLSHRDGAKVHLGTRP TEKQYETLENQLAFLCQQGFSLENALRALAAVHLFTLGCVLYAQELQVAKEER ETPTTDSMPPLLRQAIELFDHQGAEPAFLFGLELIICGLEKQLKCESGS |
| P815 based on TetR responding to resveratrol (Se,, e.g., Figure 33 and 34) | 52 | MSRLDKSKVINSALELLNEVGIEGLTTRKLAQKLGVEQPTLYWHVKNKRALLD ALAIEMLDRHHTHFCPLEGESWQDFLRNNAKSFRCALLSHRDGAKVHLGTYP TEKQYETLENQLAFLCQQGFSLENAMRALAAVAMFTLGCVLEDQEHQVAKEE RETPTTDSMPPLLRQAIELFDHQGAEPAFLFGLELIICGLEKQLKCESGS |
| P816 based on TetR responding to resveratrol (See, e.g., Figure 33 and 34) | 53 | MSRLDKSKVINSALELLNEVGIEGLTTRKLAQKLGVEQPTLYWHVKNKRALLD ALAIEMLDRHHTHWKPLEGESWQDFLRNNAKSLRCAALSHRDGAKVMLGAR PTEKQYETLENQLAFLCQQGFSLENALYALSAVGHFTLGCVLEDQEHQVAKE ERETPTTDSMPPLLRQAIELFDHQGAEPAFLFGLELIICGLEKQLKCESGS |
| P818 based on TetR responding to resveratrol (See, e.g., Figure 33 and 34) | 54 | MSRLDKSKVINSALELLNEVGIEGLTTRKLAQKLGVEQPTLYWHVKNKRALLD ALAIEMLDRHHTHFCPLEGESWQDFLRNNAKSFRCALLSHRDGAKVHLGTHG TEKLYEIARNRAAFLCQQGFSLENALYALSAVGHFTLGCVLEDQEHQVAKEER ETPTTDSMPPLLRQAIELFDHQGAEPAFLFGLELIICGLEKQLKCESGS |
| P537, Type II, 2D7 based on TetR responding to atropine (See, e.g., Figure 35-37) | 55 | MSRLDKSKVINSALELLNEVGIEGLTTRKLAQKLGVEQPTLYWHVKNKRALLD ALAIEMLDRHHTHFCPLEGESWQDFLRNNAKSFRCALLSHRDGAKVALGTTG TEKLREVGANILAFLCQQGFSLENALYALSAVLHFTLGCVLEDQEHQVAKEER ETPTTDSMPPLLRQAIELFDHQGAEPAFLFGLELIICGLEKQLKCESGS |
| P538, Type III, 2H3 based on TetR responding to atropine (See, e.g., Figure 35-37) | 56 | MSRLDKSKVINSALELLNEVGIEGLTTRKLAQKLGVEQPTLYWHVKNKRALLD ALAIEMLDRHHTHFCPLEGESWQDFLRNNAKSFRCALLSHRDGAKVALGTTG TEKLLEIGLNNLAFLCQQGFSLENALYALSAVLHFTLGCVLEDQEHQVAKEER ETPTTDSMPPLLRQAIELFDHQGAEPAFLFGLELIICGLEKQLKCESGS |
| P539, Type I, 2C5 based on TetR responding to atropine (See e.g., Figure 35-37) | 57 | MSRLDKSKVINSALELLNEVGIEGLTTRKLAQKLGVEQPTLYWHVKNKRALLD ALAIEMLDRHHTHFCPLEGESWQDFLRNNAKSFRCALLSHRDGAKVALGTTG FEKLLEVGANNLAFLCQQGFSLENALYALSAVLHFTLGCVLEDQEHQVAKEER ETPTTDSMPPLLRQAIELFDHQGAEPAFLFGLELIICGLEKQLKCESGS |
| P826 based on TetR responding to a-humulene (See, e.g., Figure 38-39) | 58 | MSRLDKSKVINSALELLNEVGIEGLTTRKLAQKLGVEQPTLYWHVKNKRALLD ALAIEMLDRHHTHFCPLEGESWQDFLRNNAKSFRCALLSHRDGAKVHLGTRP TEKQYETLENQLAFLCQQGFSLENASYALAAVWHFTLGCVLHDQESQVAKEE RETPTTDSMPPLLRQAIELFDHQGAEPAFLFGLELIICGLEKQLKCESGS |
| P827 based on TetR responding to a-humulene (See, e.g., Figure 38-39) | 59 | MSRLDKSKVINSALELLNEVGIEGLTTRKLAQKLGVEQPTLYWHVKNKRALLD ALAIEMLDRHHTHFCPLEGESWQDFLRNNAKSFRCALLSHRDGAKVHLGTRP TEKQYETLENQLAFLCQQGFSLENASKALAAVWHFTIGCVLADQERQVAKEE RETPTTDSMPPLLRQAIELFDHQGAEPAFLFGLELIICGLEKQLKCESGS |
| P819 (CE3) based on TetR responding to Nootkatone (see, e.g., Figure 40) | 61 | MSRLDKSKVINSALELLNEVGIEGLTTRKLAQKLGVEQPTLYHVKNKRALLD ALAIEMLDRHHTHFCPLEGESWQDFLRNNAKSFRCALLSHRDGAKVHLGTRP TEKQYETLENQLAFLCQQGFSLENALYAMTAVLWFTLGCVLDDQERQVAKEE RETPTTDSMPPLLRQAIELFDHQGAEPAFLFGLELIICGLEKQLKCESGS |
| P820 (GF1) based on TetR responding to Nootkatone (see, e.g., Figure 40) | 62 | MSRLDKSKVINSALELLNEVGIEGLTTRKLAQKLGVEQPTLYWHVKNKRALLD ALAIEMLDRHHTHFCPLEGESWQDFLRNNAKSFRCALLSHRDGAKVHLGTRP TEKQYETLENQLAFLCQQGFSLENALYALTAVFLFTLGCVLQDQEAQVAKEER ETPTTDSMPPLLRQAIELFDHQGAEPAFLFGLELIICGLEKQLKCESGS |

TABLE 2-continued

Selected Chassis and Sensors

| Description | SEQ ID NO: | Amino Acid Sequence |
|---|---|---|
| P821 (CG5) based on TetR responding to Nootkatone (see, e.g., Figure 40) | 63 | MSRLDKSKVINSALELLNEVGIEGLTTRKLAQKLGVEQPTLYWHVKNKRALLD ALAIEMLDRHHTHFCPLEGESWQDFLRNNAKSFRCALLSHRDGAKVHLGTRP TEKQYETLENQLAFLCQQGFSLENAMRALAAVIHFTLGCVLDDQERQVAKEE RETPTTDSMPPLLRQAIELFDHQGAEPAFLFGLELIICGLEKQLKCESGS |
| P822 (GA3) based on TetR responding to Nootkatone (see, e.g., Figure 40) | 64 | MSRLDKSKVINSALELLNEVGIEGLTTRKLAQKLGVEQPTLYWHVKNKRALLD ALAIEMLDRHHTHFCPLEGESWQDFLRNNAKSFRCALLSHRDGAKVHLGTRP TEKQYETLENQLAFLCQQGFSLENAMRNLAAVWHFTLGCVLEDQEHQVAKE ERETPTTDSMPPLLRQAIELFDHQGAEPAFLFGLELIICGLEKQLKCESGS |
| Wild type of FapR chassis P609 used to make sensors (See, e.g., Figure 19) | 65 | MRGETLKLKKDKRREAIRQQIDSNPFITDHELSDLFQVSIQTIRLDRTYLNIPEL RKRIKLVAEKNYDQISSIEEQEFIGDLIQVNPNVKAQSILDITSDCVFHKTGIARG HVLFAQANSLCVALIKQPTVLTHESSIQFIEKVKLNDTVRAEARVVNQTAKNYY VEVKSYVKHALVFKGNFKMFYDKRG |
| Wild type of FadR P631 chassis used to make sensors (See, e.g., Figure 20) | 66 | MVIKAQSPAGFAEEYIIESIWNNRFPPGTILPAERELSELIGVTRTTLREVLQRL ARDGWLTIQHGKPTKVNNFWETSGLNILETLARLDHESVPQLIDNLLSVRTNIS TIFIRTAFRQHPDKAQEVLATANEVADHADAFAELDYNIFRGLAFASGNPIYGLI LNGMKGLYTRIGRHYFANPEARSLALGFYHKLSALCSEGAHDQVYETVRRYG HESGEIWHRMQKNLPGDLAIQGR |
| Wild type of AraR chassis P932 used to make sensors (See, e.g., Figure 22) | 67 | MKNYYSSNPTFYLGIDCIIFGFNEGEISLLLLKRNFEPAMGEWSLMGGFVQKD ESVDDAAKRVLAELTGLENVYMEQVGAFGAIDRDPGERVVSIAYYALININEYD RELVQKHNAYWVNINELPALIFDHPEMVDKAREMMKQKASVEPIGFNLLPKLF TLSQLQSLYEAIYGEPMDKRNFRKRVAEMDFIEKTDKIDKLGSKRGAALYKFN GKAYRKDPKFKL |
| Wild type of LmrR chassis P1246 used to make sensors (See, e.g., Figure 23) | 68 | MAEIPKEMLRAQTNVILLNVLKQGDNYVYGIIKQVKEASNGEMELNEATLYTIF KRLEKDGIISSYWGDESQGGRRKYYRLTEIGHENMRLAFESWSRVDKIIENLE ANKKSEAIK |
| Wild type of LacI chassis P1068 used to make sensors (See, e.g., Figure 27-30) | 69 | MKPVTLYDVAEYAGVSYQTVSRVVNQASHVSAKTREKVEAAMAELNYIPNRV AQQLAGKQSLLIGVATSSSLALHAPSQIVAAIKSRADQLGASVVVSMVERSGVE ACKAAVHNLLAQRVSGLIINYPLDDQDAIAVEAACTNVPALFLDVSDQTPINSIF SHEDGTRLGVEHLVALGHQQIALLAGPLSSVSARLRLAGWHKYLTRNQIQPIA EREGDWSAMSGFQQTMQMLNEGIVPTAMLVANDQMALGAMRAITESGLRV GADISVVGYDDTEDSSCYIPPLTTIKQDFRLLGQTSVDRLLQLSQGQAVKGNQ LLPVSLVKRKTTLAPNTQTASPRALADSLMQLARQVSRLESGQ |
| Engineered sensor based on LacI responding to nootkatone (See, e.g., Figure 27-28) | 70 | MKPVTLYDVAEYAGVSYQTVSRVVNQASHVSAKTREKVEAAMAELNYIPNRV AQQLAGKQSLLIGVATSSSLALHAPSQIVAAIKSRADQLGASVVVSMVERSGVE ACKAAVHNLLAQRVSGLIINYPLDDQDAIAVEAACTNVPALFLDVSDQTPINSIF STEDATRLGVEHLVALGHQQIALLSGHLSSVMARLRLAGWHKYLTRNQIQPIA EREGDWSAMSGFQQTMQMLNEGIVPTAMLVANDQMALGAMRAITESGLRV GADISVVGYDDTEDSSCYIPPLTTIKQDFRLLGQTSVDRLLQLSQGQAVKGNQ LLPVSLVKRKTTLAPNTQTASPRALADSLMQLARQVSRLESGQ |
| Engineered sensor based on LacI responding to nootkatone (See, e.g., Figure 27-28) | 71 | MKPVTLYDVAEYAGVSYQTVSRVVNQASHVSAKTREKVEAAMAELNYIPNRV AQQLAGKQSLLIGVATSSSLALHAPSQIVAAIKSRADQLGASVVVSMVERSGVE ACKAAVHNLLAQRVSGLIINYPLDDQDAIAVEAACTNVPALFNNTSNQTPINSIG FSQEDATRLGVEHLVALGHQQIALLAGPLSSVSARLRLAGWHKYLTRNQIQPI AEREGDWSAMSGFQQTMQMLNEGIVPTAMLVANDQMALGAMRAITESGLRV GADISVVGYDDTEDSSCYIPPLTTIKQDFRLLGQTSVDRLLQLSQGQAVKGNQ LLPVSLVKRKTTLAPNTQTASPRALADSLMQLARQVSRLESGQ |
| Engineered sensor based on LacI responding to resveratrol (See, e.g., Figure 29-30) | 72 | MKPVTLYDVAEYAGVSYQTVSRVVNQASHVSAKTREKVEAAMAELNYIPNRV AQQLAGKQSLLIGVATSSSLALHAPSQIVAAIKSRADQLGASVVVSMVERSGVE ACKAAVHNLLAQRVSGLIINYPLDDQDAIAVEAATNVPALFLDVSDQTPINSIT FSHEDEARLGVEHLVALGHQQIALLAGNLSSVGSRLRLAGWHKYLTRNQIQPI AEREGDWSAMSGFQQTMQMLNEGIVPTAMLVANDQMALGAMRAITESGLRV GADISVVGYDDTEDSSCYIPPLTTIKQDFRLLGQTSVDRLLQLSQGQAVKGNQ LLPVSLVKRKTTLAPNTQTASPRALADSLMQLARQVSRLESGQ |

The following references are incorporated by reference in their entireties:

J. R. Davis et al. Study of PcaV from *Streptomyces coelicolor* yields new insights into ligand-responsive MarR family transcription factors. 2013, Nucleic Acids Research, 41(6) 3888-3900

S. Kosuri, et al. Composability of regulatory sequences controlling transcription and translation in *Escherichia coli*. 2013, PNAS 110(34) 14024-14029

D. L. Stauff and B. L. Bassler. Quorum Sensing in Chromobacterium *violaceum*: DNA Recognition and Gene Regulation by the CviR Receptor. 2011 Journal of Bacteriology 193(15) 3871-3878

S. Grkovic, et al. The Staphylococcal QacR Multidrug Regulator Binds a Correctly Spaced Operator as a Pair of Dimers. 2001 Journal of Bacteriology 183(24) 7102-7109

T. Krell, et al. Optimization of the Palindromic Order of the TtgR Operator Enhances Binding Cooperativity. 2007 Journal of Molecular Biology 369 1188-1199

W. Teran, et al. Antibiotic-Dependent Induction of Psuedomonas *putida* DOT-T1E TtgABC Efflux Pump is Mediated by the Drug Binding Repressor TtgR. 2003 Antimicrobial Agents and Chemotherapy 47(10) 3067-3072

S. Raman, et al. Evolution-Guided Optimization of Biosynthetic Pathways. 2014 Proceedings of the National Academy of Sciences 111(50) 17803-17808

All of the numerical ranges, amounts, values and percentages, such as those for amounts of materials, elemental contents, times and temperatures of reaction, ratios of amounts, and others, in the following portion of the specification and attached claims may be read as if prefaced by the word "about" even though the term "about" may not expressly appear with the value, amount, or range. Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains error necessarily resulting from the standard deviation found in its underlying respective testing measurements. Furthermore, when numerical ranges are set forth herein, these ranges are inclusive of the recited range end points (e.g., end points may be used). When percentages by weight are used herein, the numerical values reported are relative to the total weight.

Also, it should be understood that any numerical range recited herein is intended to include all sub-ranges subsumed therein. For example, a range of "1 to 10" is intended to include all sub-ranges between (and including) the recited minimum value of 1 and the recited maximum value of 10, that is, having a minimum value equal to or greater than 1 and a maximum value of equal to or less than 10. The terms "one," "a," or "an" as used herein are intended to include "at least one" or "one or more," unless otherwise indicated.

Any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for detecting a target molecule that binds to an allosteric DNA-binding protein sensor and/or switch, comprising:
   (a) providing a host cell with a nucleic acid encoding the allosteric DNA-binding protein sensor and/or switch, the allosteric DNA-binding protein sensor and/or switch comprising an amino acid sequence of about 97% identity to TetR (SEQ ID NO: 46) is capable of binding apigenin, and a reporter gene system;
   (b) selecting for a cell comprising the TetR sequence and the reporter gene system; and
   (c) interrogating cells comprising the TetR sequence and the reporter gene system for reporter response,
   the reporter response being indicative of target molecule binding to the allosteric DNA-binding protein sensor and/or switch.

2. The method of claim 1, wherein the allosteric DNA-binding protein sensor and/or switch has one or more mutations S135A, G138I, H139M, and E147W.

3. The method of claim 1, wherein the allosteric DNA-binding protein sensor and/or switch has one or more mutations S135H, G138A, H139M, T141A, E147Y, and H151L.

4. The method of claim 1, wherein the allosteric DNA-binding protein sensor and/or switch has one or more mutations L131M, Y132R, S135A, G138H, H139L, E147Y, D148A, and H151L.

5. The method of claim 2, wherein the allosteric DNA-binding protein sensor and/or switch comprises an amino acid sequence having about 97% identity to one or more of SEQ ID NOs: 48, 50, and 51.

6. A method for detecting a target molecule that binds to an allosteric DNA-binding protein sensor and/or switch, comprising:
   (a) providing a host cell with a nucleic acid encoding the allosteric DNA-binding protein sensor and/or switch, the allosteric DNA-binding protein sensor and/or switch comprising an amino acid sequence of about 97% identity to TetR (SEQ ID NO: 46) is capable of binding resveratrol and has the mutation R104Y, and a reporter gene system;
   (b) selecting for a cell comprising the TetR sequence and the reporter gene system; and
   (c) interrogating cells comprising the TetR sequence and the reporter gene system for reporter response,
   the reporter response being indicative of target molecule binding to the allosteric DNA-binding protein sensor and/or switch.

7. A method for detecting a target molecule that binds to an allosteric DNA-binding protein sensor and/or switch, comprising:
   (a) providing a host cell with a nucleic acid encoding the allosteric DNA-binding protein sensor and/or switch, the allosteric DNA-binding protein sensor and/or switch comprising an amino acid sequence of about 97% identity to TetR (SEQ ID NO: 46) is capable of binding humulene and has one or more mutations G124V, G138W, E147H, and H151L, and a reporter gene system;
   (b) selecting for a cell comprising the TetR sequence and the reporter gene system; and
   (c) interrogating cells comprising the TetR sequence and the reporter gene system for reporter response,
   the reporter response being indicative of target molecule binding to the allosteric DNA-binding protein sensor and/or switch.

8. A method for detecting a target molecule that binds to an allosteric DNA-binding protein sensor and/or switch, comprising:
   (a) providing a host cell with a nucleic acid encoding the allosteric DNA-binding protein sensor and/or switch, the allosteric DNA-binding protein sensor and/or switch comprising an amino acid sequence of about 97% identity to TetR (SEQ ID NO: 46) is capable of binding nootkatone, and a reporter gene system;
   (b) selecting for a cell comprising the TetR sequence and the reporter gene system; and
   (c) interrogating cells comprising the TetR sequence and the reporter gene system for reporter response,
   the reporter response being indicative of target molecule binding to the allosteric DNA-binding protein sensor and/or switch.

9. The method of claim 8, wherein the allosteric DNA-binding protein sensor and/or switch comprises an amino acid sequence having about 97% identity to one or more of SEQ ID NOs: 61, 62, 63, and 64.

* * * * *

SEQUENCE LISTING

```
<160> NUMBER OF SEQ ID NOS: 87

<210> SEQ ID NO 1
<211> LENGTH: 200
<212> TYPE: DNA
<213> ORGANISM: Artificial Sequence
<220> FEATURE:
<223> OTHER INFORMATION: Synthetic Sequence

<400> SEQUENCE: 1
gcatcaaatt aagcagaagg ccatcctgac ggatggcctt tttgcgtttc tacaaactct      60
gctagcaagt aaggccgact cgacatttat cccttgcggc gatataatgt gtggatactc     120
agtgccctga ctatatctta atctagcggg ggaaggtttc atatgcgtaa aggtgaagaa     180
ctgttcaccg gtgttgttcc                                                 200

<210> SEQ ID NO 2
<211> LENGTH: 200
<212> TYPE: DNA
<213> ORGANISM: Artificial Sequence
<220> FEATURE:
<223> OTHER INFORMATION: Synthetic Sequence
```

<400> SEQUENCE: 2
gcatcaaatt aagcagaagg ccatcctgac ggatggcctt tttgcgtttc tacaaactct    60
gctagcaagt aaggccgact cgacatttat cccttgcggc gatataatgt gtggataatc    120
cttatagacc gatcgcacgg tctataacca ttatcttaat ctagcggggg aaggtttcat    180
atgcgtaaag gtgaagaact                                                200

<210> SEQ ID NO 3
<211> LENGTH: 200
<212> TYPE: DNA
<213> ORGANISM: Artificial Sequence
<220> FEATURE:
<223> OTHER INFORMATION: Synthetic Sequence

<400> SEQUENCE: 3
gcatcaaatt aagcagaagg ccatcctgac ggatggcctt tttgcgtttc tacaaactct    60
gctagcaagt aaggccgact cgacatttat cccttgcggc gatataatgt gtggatacgt    120
catgccctga cccttggaac agtattagcc aatcttaatc tagcggggga aggtttcata    180
tgcgtaaagg tgaagaactg                                                200

<210> SEQ ID NO 4
<211> LENGTH: 83
<212> TYPE: DNA
<213> ORGANISM: Artificial Sequence
<220> FEATURE:
<223> OTHER INFORMATION: Synthetic Sequence

<400> SEQUENCE: 4
tttgtttaac tttgaaataa ggaggtaata caaatggtgc gtcgcaccaa agaagaagca    60
caggaaacgc gtgcgcagat tat                                            83

<210> SEQ ID NO 5
<211> LENGTH: 82
<212> TYPE: DNA
<213> ORGANISM: Artificial Sequence
<220> FEATURE:
<223> OTHER INFORMATION: Synthetic Sequence

<400> SEQUENCE: 5
tttgtttaac tttgaaataa ggaggtatac aactggtgcg tcgcaccaaa gaagaagcac    60
aggaaacgcg tgcgcagatt at                                             82

<210> SEQ ID NO 6
<211> LENGTH: 83
<212> TYPE: DNA
<213> ORGANISM: Artificial Sequence
<220> FEATURE:
<223> OTHER INFORMATION: Synthetic Sequence

<400> SEQUENCE: 6
tttgtttaac tttgaaataa ggaggtaata caattggtgc gtcgcaccaa agaagaagca    60
caggaaacgc gtgcgcagat tat                                            83

<210> SEQ ID NO 7
<211> LENGTH: 83
<212> TYPE: DNA
<213> ORGANISM: Artificial Sequence
<220> FEATURE:
<223> OTHER INFORMATION: Synthetic Sequence -continued

<400> SEQUENCE: 7
tttgtttaac tttgaaataa ggaggtaata caagtggtgc gtcgcaccaa agaagaagca    60
caggaaacgc gtgcgcagat tat    83

<210> SEQ ID NO 8
<211> LENGTH: 207
<212> TYPE: PRT
<213> ORGANISM: Artificial Sequence
<220> FEATURE:
<223> OTHER INFORMATION: Synthetic Sequence

<400> SEQUENCE: 8

Met Ser Arg Leu Asp Lys Ser Lys Val Ile Asn Ser Ala Leu Glu Leu
1               5                   10                  15

Leu Asn Glu Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
        35                  40                  45

Arg Ala Leu Leu Asp Ala Leu Ala Ile Glu Met Leu Asp Arg His His
    50                  55                  60

Thr His Phe Cys Pro Leu Glu Gly Glu Ser Trp Gln Asp Phe Leu Arg
65                  70                  75                  80

Asn Asn Ala Lys Ser Phe Arg Cys Ala Leu Leu Ser His Arg Asp Gly
                85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125

Asn Ala Leu Tyr Ala Leu Ser Ala Val Gly His Phe Thr Leu Gly Cys
    130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Ser
        195                 200                 205

<210> SEQ ID NO 9
<211> LENGTH: 211
<212> TYPE: PRT
<213> ORGANISM: Artificial Sequence
<220> FEATURE:
<223> OTHER INFORMATION: Synthetic Sequence

<400> SEQUENCE: 9

Met Ser Arg Leu Asp Lys Ser Lys Val Ile Asn Ser Ala Leu Glu Leu
1               5                   10                  15

Leu Asn Glu Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
        35                  40                  45

Arg Ala Leu Leu Asp Ala Leu Ala Ile Glu Met Leu Asp Arg His His
    50                  55                  60

Thr His Phe Cys Pro Leu Glu Gly Glu Ser Trp Gln Asp Phe Leu Arg
65                  70                  75                  80

Asn Asn Ala Lys Ser Phe Arg Cys Ala Leu Leu Ser His Arg Asp Gly
            85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
            115                 120                 125

Asn Ala Leu Tyr Ala Leu Ser Ala Val Gly His Phe Thr Leu Gly Cys
    130                 135                 140

Val Leu Glu Asp Gln Glu His Gln Val Val Lys Lys Gly Lys His
145                 150                 155                 160

Leu Leu Leu Ile Val Cys Arg His Tyr Tyr Asp Lys Leu Ser Asn Tyr
            165                 170                 175

Leu Ile Thr Lys Val Gln Ser Gln Pro Thr Tyr Ser Ala Leu Asn Ser
            180                 185                 190

Tyr Ala Asp Lys Asn Asn Leu Asn Val Lys Val Gly Leu Asn Lys Arg
            195                 200                 205

Leu Lys Asn
    210

<210> SEQ ID NO 10
<211> LENGTH: 50
<212> TYPE: PRT
<213> ORGANISM: Artificial Sequence
<220> FEATURE:
<223> OTHER INFORMATION: Synthetic Sequence

<400> SEQUENCE: 10

Leu Asp Val Ser Asp Gln Thr Pro Ile Asn Ser Ile Phe Ser His
1               5                   10                  15

Glu Asp Gly Thr Arg Leu Gly Val Glu His Leu Val Ala Leu Gly His
            20                  25                  30

Gln Gln Ile Ala Leu Leu Ala Gly Pro Leu Ser Ser Val Ser Ala Arg
        35                  40                  45

Leu Arg
    50

<210> SEQ ID NO 11
<211> LENGTH: 40
<212> TYPE: PRT
<213> ORGANISM: Artificial Sequence
<220> FEATURE:
<223> OTHER INFORMATION: Synthetic Sequence

<400> SEQUENCE: 11

Ser Ile Ile Phe Ser His Glu Asp Gly Thr Arg Leu Gly Val Glu His
1               5                   10                  15

Leu Val Ala Leu Gly His Gln Gln Ile Ala Leu Leu Ala Gly Pro Leu
            20                  25                  30

Ser Ser Val Ser Ala Arg Leu Arg
        35                  40

<210> SEQ ID NO 12
<211> LENGTH: 37
<212> TYPE: PRT
<213> ORGANISM: Artificial Sequence
<220> FEATURE:
<223> OTHER INFORMATION: Synthetic Sequence

<400> SEQUENCE: 12

Phe Leu Cys Gln Gln Gly Phe Ser Leu Glu Asn Ala Leu Tyr Ala Leu
1               5                   10                  15

Ser Ala Val Gly His Phe Thr Leu Gly Cys Val Leu Glu Asp Gln Glu
            20                  25                  30

His Gln Val Ala Lys
        35

<210> SEQ ID NO 13
<211> LENGTH: 37
<212> TYPE: PRT
<213> ORGANISM: Artificial Sequence
<220> FEATURE:
<223> OTHER INFORMATION: Synthetic Sequence

<400> SEQUENCE: 13

Phe Leu Cys Gln Gln Gly Phe Ser Leu Glu Asn Ala Leu Tyr Ala Leu
1               5                   10                  15

Ala Ala Val Ile Met Phe Thr Leu Gly Cys Val Leu Trp Asp Gln Glu
            20                  25                  30

His Gln Val Ala Lys
        35

<210> SEQ ID NO 14
<211> LENGTH: 37
<212> TYPE: PRT
<213> ORGANISM: Artificial Sequence
<220> FEATURE:
<223> OTHER INFORMATION: Synthetic Sequence

<400> SEQUENCE: 14

Phe Leu Cys Gln Gln Gly Phe Ser Leu Glu Asn Ala Leu Tyr Ala Leu
1               5                   10                  15

His Ala Val Ala Met Phe Ala Leu Gly Cys Val Leu Tyr Asp Gln Glu
            20                  25                  30

Leu Gln Val Ala Lys
        35

<210> SEQ ID NO 15
<211> LENGTH: 37
<212> TYPE: PRT
<213> ORGANISM: Artificial Sequence
<220> FEATURE:
<223> OTHER INFORMATION: Synthetic Sequence

<400> SEQUENCE: 15

Phe Leu Cys Gln Gln Gly Phe Ser Leu Glu Asn Ala Met Arg Ala Leu
1               5                   10                  15

Ala Ala Val His Leu Phe Thr Leu Gly Cys Val Leu Tyr Ala Gln Glu
            20                  25                  30

Leu Gln Val Ala Lys
        35

<210> SEQ ID NO 16
<211> LENGTH: 82
<212> TYPE: PRT
<213> ORGANISM: Artificial Sequence
<220> FEATURE:
<223> OTHER INFORMATION: Synthetic Sequence

<400> SEQUENCE: 16

```
Asp Arg His His Thr His Phe Cys Pro Leu Glu Gly Glu Ser Trp Gln
1               5                   10                  15
Asp Phe Leu Arg Asn Asn Ala Lys Ser Phe Arg Cys Ala Leu Leu Ser
            20                  25                  30
His Arg Asp Gly Ala Lys Val His Leu Gly Thr Arg Pro Thr Glu Lys
        35                  40                  45
Gln Tyr Glu Thr Leu Glu Asn Gln Leu Ala Phe Leu Cys Gln Gln Gly
    50                  55                  60
Phe Ser Leu Glu Asn Ala Leu Tyr Ala Leu Ser Ala Val Gly His Phe
65                  70                  75                  80
Thr Leu
```

<210> SEQ ID NO 17
<211> LENGTH: 82
<212> TYPE: PRT
<213> ORGANISM: Artificial Sequence
<220> FEATURE:
<223> OTHER INFORMATION: Synthetic Sequence

<400> SEQUENCE: 17

```
Asp Arg His His Thr His Trp Lys Pro Leu Glu Gly Glu Ser Trp Gln
1               5                   10                  15
Asp Phe Leu Arg Asn Arg Ala Lys Ser Leu Arg Cys Ala Ala Leu Ser
            20                  25                  30
His Arg Asp Gly Ala Lys Val Met Leu Gly Ala Arg Pro Thr Glu Lys
        35                  40                  45
Gln Tyr Glu Thr Leu Glu Asn Gln Leu Ala Phe Leu Cys Gln Gln Gly
    50                  55                  60
Phe Ser Leu Glu Asn Ala Leu Tyr Ala Leu Ser Ala Val Gly His Phe
65                  70                  75                  80
Thr Leu
```

<210> SEQ ID NO 18
<211> LENGTH: 82
<212> TYPE: PRT
<213> ORGANISM: Artificial Sequence
<220> FEATURE:
<223> OTHER INFORMATION: Synthetic Sequence

<400> SEQUENCE: 18

```
Asp Arg His His Thr His Phe Cys Pro Leu Glu Gly Glu Ser Trp Gln
1               5                   10                  15
Asp Phe Leu Arg Asn Asn Ala Lys Ser Phe Arg Cys Ala Leu Leu Ser
            20                  25                  30
His Arg Asp Gly Ala Lys Val His Leu Gly Thr Tyr Pro Thr Glu Lys
        35                  40                  45
Gln Tyr Glu Thr Leu Glu Asn Gln Leu Ala Phe Leu Cys Gln Gln Gly
    50                  55                  60
Phe Ser Leu Glu Asn Ala Met Arg Ala Leu Ala Ala Val Ala Met Phe
65                  70                  75                  80
Thr Leu
```

<210> SEQ ID NO 19
<211> LENGTH: 82
<212> TYPE: PRT
<213> ORGANISM: Artificial Sequence
<220> FEATURE:
<223> OTHER INFORMATION: Synthetic Sequence

<400> SEQUENCE: 19

Asp Arg His His Thr His Phe Cys Pro Leu Glu Gly Glu Ser Trp Gln
1               5                   10                  15

Asp Phe Leu Arg Asn Asn Ala Lys Ser Phe Arg Cys Ala Leu Leu Ser
                20                  25                  30

His Arg Asp Gly Ala Lys Val His Leu Gly Thr His Gly Thr Glu Lys
            35                  40                  45

Leu Tyr Glu Ile Ala Arg Asn Arg Ala Ala Phe Leu Cys Gln Gln Gly
        50                  55                  60

Phe Ser Leu Glu Asn Ala Leu Tyr Ala Leu Ser Ala Val Gly His Phe
65                  70                  75                  80

Thr Leu

<210> SEQ ID NO 20
<211> LENGTH: 47
<212> TYPE: PRT
<213> ORGANISM: Artificial Sequence
<220> FEATURE:
<223> OTHER INFORMATION: Synthetic Sequence

<400> SEQUENCE: 20

His Arg Asp Gly Ala Lys Val His Leu Gly Thr Arg Pro Thr Glu Lys
1               5                   10                  15

Gln Tyr Glu Thr Leu Glu Asn Gln Leu Ala Phe Leu Cys Gln Gln Gly
                20                  25                  30

Phe Ser Leu Glu Asn Ala Leu Tyr Ala Leu Ser Ala Val Gly His
            35                  40                  45

<210> SEQ ID NO 21
<211> LENGTH: 47
<212> TYPE: PRT
<213> ORGANISM: Artificial Sequence
<220> FEATURE:
<223> OTHER INFORMATION: Synthetic Sequence

<400> SEQUENCE: 21

His Arg Asp Gly Ala Lys Val Ala Leu Gly Thr Thr Gly Thr Glu Lys
1               5                   10                  15

Leu Arg Glu Val Gly Ala Asn Ile Leu Ala Phe Leu Cys Gln Gln Gly
                20                  25                  30

Phe Ser Leu Glu Asn Ala Leu Tyr Ala Leu Ser Ala Val Leu His
            35                  40                  45

<210> SEQ ID NO 22
<211> LENGTH: 47
<212> TYPE: PRT
<213> ORGANISM: Artificial Sequence
<220> FEATURE:
<223> OTHER INFORMATION: Synthetic Sequence

<400> SEQUENCE: 22

His Arg Asp Gly Ala Lys Val Ala Leu Gly Thr Thr Gly Phe Glu Lys
1               5                   10                  15

Leu Leu Glu Val Gly Ala Asn Asn Leu Ala Phe Leu Cys Gln Gln Gly
                20                  25                  30

Phe Ser Leu Glu Asn Ala Leu Tyr Ala Leu Ser Ala Val Leu His
            35                  40                  45

```
<210> SEQ ID NO 23
<211> LENGTH: 47
<212> TYPE: PRT
<213> ORGANISM: Artificial Sequence
<220> FEATURE:
<223> OTHER INFORMATION: Synthetic Sequence

<400> SEQUENCE: 23

His Arg Asp Gly Ala Lys Val Ala Leu Gly Thr Thr Gly Thr Glu Lys
1               5                   10                  15

Leu Leu Glu Ile Gly Leu Asn Asn Leu Ala Phe Leu Cys Gln Gln Gly
            20                  25                  30

Phe Ser Leu Glu Asn Ala Leu Tyr Ala Leu Ser Ala Val Leu His
        35                  40                  45

<210> SEQ ID NO 24
<211> LENGTH: 38
<212> TYPE: PRT
<213> ORGANISM: Artificial Sequence
<220> FEATURE:
<223> OTHER INFORMATION: Synthetic Sequence

<400> SEQUENCE: 24

Phe Leu Cys Gln Gln Gly Phe Ser Leu Glu Asn Ala Leu Tyr Ala Leu
1               5                   10                  15

Ser Ala Val Gly His Phe Thr Leu Gly Cys Val Leu Glu Asp Gln Glu
            20                  25                  30

His Gln Val Ala Lys Glu
        35

<210> SEQ ID NO 25
<211> LENGTH: 38
<212> TYPE: PRT
<213> ORGANISM: Artificial Sequence
<220> FEATURE:
<223> OTHER INFORMATION: Synthetic Sequence

<400> SEQUENCE: 25

Phe Leu Cys Gln Gln Gly Phe Ser Leu Glu Asn Ala Ser Tyr Ala Leu
1               5                   10                  15

Ala Ala Val Trp His Phe Thr Leu Gly Cys Val Leu His Asp Gln Glu
            20                  25                  30

Ser Gln Val Ala Lys Glu
        35

<210> SEQ ID NO 26
<211> LENGTH: 38
<212> TYPE: PRT
<213> ORGANISM: Artificial Sequence
<220> FEATURE:
<223> OTHER INFORMATION: Synthetic Sequence

<400> SEQUENCE: 26

Phe Leu Cys Gln Gln Gly Phe Ser Leu Glu Asn Ala Ser Lys Ala Leu
1               5                   10                  15

Ala Ala Val Trp His Phe Thr Ile Gly Cys Val Leu Ala Asp Gln Glu
            20                  25                  30

Arg Gln Val Ala Lys Glu
        35

<210> SEQ ID NO 27
<211> LENGTH: 38
```

<212> TYPE: PRT
<213> ORGANISM: Artificial Sequence
<220> FEATURE:
<223> OTHER INFORMATION: Synthetic Sequence

<400> SEQUENCE: 27

Phe Leu Cys Gln Gln Val Phe Ser Leu Glu Asn Ala Leu Tyr Ala Leu
1               5                   10                  15
Ser Ala Val Trp His Phe Thr Leu Gly Cys Val Leu His Asp Gln Glu
            20                  25                  30
Leu Gln Val Ala Lys Glu
        35

<210> SEQ ID NO 28
<211> LENGTH: 85
<212> TYPE: DNA
<213> ORGANISM: Artificial Sequence
<220> FEATURE:
<223> OTHER INFORMATION: Synthetic Sequence

<400> SEQUENCE: 28
tagggataac agggtaattg gcaaacagct attatgggta ttatgggtat ctatgtcggg      60
tgcggagaaa gaggtaatga aatgg                                           85

<210> SEQ ID NO 29
<211> LENGTH: 154
<212> TYPE: PRT
<213> ORGANISM: Artificial Sequence
<220> FEATURE:
<223> OTHER INFORMATION: Synthetic Sequence

<400> SEQUENCE: 29

Met Ala Ala Val Asp Leu Ala Thr His Pro Gly His Leu Ala Arg Arg
1               5                   10                  15
Leu Gln Gln Ala His Tyr Leu Leu Trp Asn Thr Met Val Ser Glu Glu
            20                  25                  30
Thr Thr Ser Pro Gln Tyr Ala Val Leu Asn Ala Leu Val Ala Glu Pro
        35                  40                  45
Gly Leu Asp Gln Arg Thr Val Gly Glu Arg Val Gly Leu Asp Arg Ser
    50                  55                  60
Thr Ile Ala Glu Val Val Ser Arg Leu Gly Arg Arg Gly Leu Leu Asp
65                  70                  75                  80
Lys Val Arg Asp Pro Gln Asp Gly Arg Arg Ser Leu Leu Arg Leu Thr
                85                  90                  95
Asp Glu Gly Leu Arg Val His Arg Arg Leu Gly Val Arg Ile Ala Arg
            100                 105                 110
Met Asn Gln Val Phe Leu Ala Pro Leu Ala Ala Asp Glu Gln Ala Val
        115                 120                 125
Phe Phe Asp Leu Ile Arg Arg Val Ala Asp Ala Glu Gly Leu Arg
    130                 135                 140
Asn Pro Ala Glu Pro Ala Val Ala Pro Gly
145                 150

<210> SEQ ID NO 30
<211> LENGTH: 188
<212> TYPE: PRT
<213> ORGANISM: Artificial Sequence
<220> FEATURE:
<223> OTHER INFORMATION: Synthetic Sequence

<400> SEQUENCE: 30

```
Met Asn Leu Lys Asp Lys Ile Leu Gly Val Ala Lys Glu Leu Phe Ile
1               5                   10                  15

Lys Asn Gly Tyr Asn Ala Thr Thr Thr Gly Glu Ile Val Lys Leu Ser
            20                  25                  30

Glu Ser Ser Lys Gly Asn Leu Tyr Tyr His Phe Lys Thr Lys Glu Asn
        35                  40                  45

Leu Phe Leu Glu Ile Leu Asn Ile Glu Glu Ser Lys Trp Gln Glu Gln
    50                  55                  60

Trp Lys Lys Glu Gln Ile Lys Ala Lys Thr Asn Arg Glu Lys Phe Tyr
65                  70                  75                  80

Leu Tyr Asn Glu Leu Ser Leu Thr Thr Glu Tyr Tyr Pro Leu Gln
                85                  90                  95

Asn Ala Ile Ile Glu Phe Tyr Thr Gly Tyr Tyr Lys Thr Asn Ser Ile
                100                 105                 110

Asn Glu Lys Met Asn Lys Leu Glu Asn Lys Tyr Ile Asp Ala Tyr His
            115                 120                 125

Val Ile Phe Lys Glu Gly Asn Leu Asn Gly Glu Trp Ser Ile Asn Asp
130                 135                 140

Val Asn Ala Val Ser Lys Ile Ala Ala Asn Ala Val Asn Gly Ile Val
145                 150                 155                 160

Thr Phe Thr His Glu Gln Asn Ile Asn Glu Arg Ile Lys Leu Met Asn
                165                 170                 175

Lys Phe Ser Gln Ile Phe Leu Asn Gly Leu Ser Lys
            180                 185
```

<210> SEQ ID NO 31
<211> LENGTH: 265
<212> TYPE: PRT
<213> ORGANISM: Artificial Sequence
<220> FEATURE:
<223> OTHER INFORMATION: Synthetic Sequence

<400> SEQUENCE: 31

```
Met Val Ile Ser Lys Pro Ile Asn Ala Arg Pro Leu Pro Ala Gly Leu
1               5                   10                  15

Thr Ala Ser Gln Gln Trp Thr Leu Leu Glu Trp Ile His Met Ala Gly
            20                  25                  30

His Ile Glu Thr Glu Asn Glu Leu Lys Ala Phe Leu Asp Gln Val Leu
        35                  40                  45

Ser Gln Ala Pro Ser Glu Arg Leu Leu Leu Ala Leu Gly Arg Leu Asn
    50                  55                  60

Asn Gln Asn Gln Ile Gln Arg Leu Glu Arg Val Leu Asn Val Ser Tyr
65                  70                  75                  80

Pro Ser Asp Trp Leu Asp Gln Tyr Met Lys Glu Asn Tyr Ala Gln His
                85                  90                  95

Asp Pro Ile Leu Arg Ile His Leu Gly Gln Gly Pro Val Met Trp Glu
                100                 105                 110

Glu Arg Phe Asn Arg Ala Lys Gly Ala Glu Lys Arg Phe Ile Ala
            115                 120                 125

Glu Ala Thr Gln Asn Gly Met Gly Ser Gly Ile Thr Phe Ser Ala Ala
        130                 135                 140

Ser Glu Arg Asn Asn Ile Gly Ser Ile Leu Ser Ile Ala Gly Arg Glu
145                 150                 155                 160
```

```
Pro Gly Arg Asn Ala Ala Leu Val Ala Met Leu Asn Cys Leu Thr Pro
                165                 170                 175

His Leu His Gln Ala Ala Ile Arg Val Ala Asn Leu Pro Pro Ala Ser
            180                 185                 190

Pro Ser Asn Met Pro Leu Ser Gln Arg Glu Tyr Asp Ile Phe His Trp
        195                 200                 205

Met Ser Arg Gly Lys Thr Asn Trp Glu Ile Ala Thr Ile Leu Asp Ile
    210                 215                 220

Ser Glu Arg Thr Val Lys Phe His Val Ala Asn Val Ile Arg Lys Leu
225                 230                 235                 240

Asn Ala Asn Asn Arg Thr His Ala Ile Val Leu Gly Met His Leu Ala
                245                 250                 255

Met Pro Pro Ser Thr Val Ala Asn Glu
            260                 265

<210> SEQ ID NO 32
<211> LENGTH: 210
<212> TYPE: PRT
<213> ORGANISM: Artificial Sequence
<220> FEATURE:
<223> OTHER INFORMATION: Synthetic Sequence

<400> SEQUENCE: 32

Met Val Arg Arg Thr Lys Glu Glu Ala Gln Glu Thr Arg Ala Gln Ile
1               5                   10                  15

Ile Glu Ala Ala Glu Arg Ala Phe Tyr Lys Arg Gly Val Ala Arg Thr
            20                  25                  30

Thr Leu Ala Asp Ile Ala Glu Leu Ala Gly Val Thr Arg Gly Ala Ile
        35                  40                  45

Tyr Trp His Phe Asn Asn Lys Ala Glu Leu Val Gln Ala Leu Leu Asp
    50                  55                  60

Ser Leu His Glu Thr His Asp His Leu Ala Arg Ala Ser Glu Ser Glu
65                  70                  75                  80

Asp Glu Leu Asp Pro Leu Gly Cys Met Arg Lys Leu Leu Leu Gln Val
                85                  90                  95

Phe Asn Glu Leu Val Leu Asp Ala Arg Thr Arg Arg Ile Asn Glu Ile
            100                 105                 110

Leu His His Lys Cys Glu Phe Thr Asp Asp Met Cys Glu Ile Arg Gln
        115                 120                 125

Gln Arg Gln Ser Ala Val Leu Asp Cys His Lys Gly Ile Thr Leu Ala
    130                 135                 140

Leu Ala Asn Ala Val Arg Arg Gly Gln Leu Pro Gly Glu Leu Asp Val
145                 150                 155                 160

Glu Arg Ala Ala Val Ala Met Phe Ala Tyr Val Asp Gly Leu Ile Gly
                165                 170                 175

Arg Trp Leu Leu Leu Pro Asp Ser Val Asp Leu Leu Gly Asp Val Glu
            180                 185                 190

Lys Trp Val Asp Thr Gly Leu Asp Met Leu Arg Leu Ser Pro Ala Leu
        195                 200                 205

Arg Lys
    210

<210> SEQ ID NO 33
<211> LENGTH: 210
<212> TYPE: PRT
<213> ORGANISM: Artificial Sequence
<220> FEATURE:
```

<223> OTHER INFORMATION: Synthetic Sequence

<400> SEQUENCE: 33

Met Val Arg Arg Thr Lys Glu Glu Ala Gln Glu Thr Arg Ala Gln Ile
1               5                   10                  15

Ile Glu Ala Ala Glu Arg Ala Phe Tyr Lys Arg Gly Val Ala Arg Thr
            20                  25                  30

Thr Leu Ala Asp Ile Ala Glu Leu Ala Gly Val Thr Arg Gly Ala Ile
        35                  40                  45

Tyr Trp His Phe Asn Asn Lys Ala Glu Leu Val Gln Ala Leu Leu Asp
    50                  55                  60

Ser Leu His Glu Thr His Asp His Leu Ala Arg Ala Ser Glu Ser Glu
65                  70                  75                  80

Asp Glu Leu Asp Pro Leu Gly Cys Met Arg Lys Leu Leu Gln Val
                85                  90                  95

Phe Asn Glu Leu Val Leu Asp Ala Arg Thr Arg Arg Ile Asn Glu Ile
                100                 105                 110

Leu His His Lys Cys Glu Phe Thr Asp Asp Met Cys Glu Ile Arg Gln
            115                 120                 125

Gln Arg Gln Ser Ala Val Leu Asp Cys His Lys Gly Ile Thr Leu Ala
130                 135                 140

Leu Ala Asn Ala Val Arg Arg Gly Gln Leu Pro Gly Glu Leu Asp Val
145                 150                 155                 160

Glu Arg Ala Ala Val Ala Met Phe Ala Tyr Val Asp Gly Leu Ile Gly
                165                 170                 175

Arg Trp Leu Leu Leu Pro Asp Ser Val Asp Leu Leu Gly Asp Val Glu
                180                 185                 190

Lys Trp Val Asp Thr Gly Leu Asp Met Leu Arg Leu Ser Pro Ala Leu
            195                 200                 205

Arg Lys
    210

<210> SEQ ID NO 34
<211> LENGTH: 210
<212> TYPE: PRT
<213> ORGANISM: Artificial Sequence
<220> FEATURE:
<223> OTHER INFORMATION: Synthetic Sequence

<400> SEQUENCE: 34

Met Val Arg Arg Thr Lys Glu Glu Ala Gln Glu Thr Arg Ala Gln Ile
1               5                   10                  15

Ile Glu Ala Ala Glu Arg Ala Phe Tyr Lys Arg Gly Val Ala Arg Thr
            20                  25                  30

Thr Leu Ala Asp Ile Ala Glu Leu Ala Gly Val Thr Arg Gly Ala Ile
        35                  40                  45

Tyr Trp His Phe Asn Asn Lys Ala Glu Leu Val Gln Ala Leu Leu Asp
    50                  55                  60

Ser Leu His Glu Thr His Asp His Leu Ala Arg Ala Ser Glu Ser Glu
65                  70                  75                  80

Asp Glu Leu Asp Pro Leu Gly Cys Met Arg Lys Leu Leu Gln Val
                85                  90                  95

Phe Asn Glu Leu Val Leu Asp Ala Arg Thr Arg Arg Ile Asn Glu Ile
                100                 105                 110

Leu His His Lys Cys Glu Phe Thr Asp Asp Met Cys Glu Ile Arg Gln
            115                 120                 125

Gln Arg Gln Ser Ala Val Leu Asp Cys His Lys Gly Ile Thr Leu Ala
            130                 135                 140

Leu Ala Asn Ala Val Arg Arg Gly Gln Leu Pro Gly Glu Leu Asp Val
145                 150                 155                 160

Glu Arg Ala Ala Val Ala Met Phe Ala Tyr Val Asp Gly Leu Ile Gly
                165                 170                 175

Arg Trp Leu Leu Leu Pro Asp Ser Val Asp Leu Leu Gly Asp Val Glu
            180                 185                 190

Lys Trp Val Asp Thr Gly Leu Asp Met Leu Arg Leu Ser Pro Ala Leu
            195                 200                 205

Arg Lys
    210

<210> SEQ ID NO 35
<211> LENGTH: 210
<212> TYPE: PRT
<213> ORGANISM: Artificial Sequence
<220> FEATURE:
<223> OTHER INFORMATION: Synthetic Sequence

<400> SEQUENCE: 35

Met Val Arg Arg Thr Lys Glu Glu Ala Gln Glu Thr Arg Ala Gln Ile
1               5                   10                  15

Ile Glu Ala Ala Glu Arg Ala Phe Tyr Lys Arg Gly Val Ala Arg Thr
            20                  25                  30

Thr Leu Ala Asp Ile Ala Glu Leu Ala Gly Val Thr Arg Gly Ala Ile
        35                  40                  45

Tyr Trp His Phe Asn Asn Lys Ala Glu Leu Val Gln Ala Leu Leu Asp
    50                  55                  60

Ser Leu His Glu Thr His Asp His Leu Ala Arg Ala Ser Glu Ser Glu
65                  70                  75                  80

Asp Glu Leu Asp Pro Leu Gly Cys Met Arg Lys Leu Leu Leu Gln Val
                85                  90                  95

Phe Asn Glu Leu Val Leu Asp Ala Arg Thr Arg Arg Ile Asn Glu Ile
            100                 105                 110

Leu His His Lys Cys Glu Phe Thr Asp Asp Met Cys Glu Ile Arg Gln
        115                 120                 125

Gln Arg Gln Ser Ala Val Leu Asp Cys His Lys Gly Ile Thr Leu Ala
    130                 135                 140

Leu Ala Asn Ala Val Arg Arg Gly Gln Leu Pro Gly Glu Leu Asp Val
145                 150                 155                 160

Glu Arg Ala Ala Val Ala Met Phe Ala Tyr Val Asp Gly Leu Ile Gly
                165                 170                 175

Arg Trp Leu Leu Leu Pro Asp Ser Val Asp Leu Leu Gly Asp Val Glu
            180                 185                 190

Lys Trp Val Asp Thr Gly Leu Asp Met Leu Arg Leu Ser Pro Ala Leu
            195                 200                 205

Arg Lys
    210

<210> SEQ ID NO 36
<211> LENGTH: 210
<212> TYPE: PRT
<213> ORGANISM: Artificial Sequence
<220> FEATURE:
<223> OTHER INFORMATION: Synthetic Sequence

<400> SEQUENCE: 36

```
Met Val Arg Arg Thr Lys Glu Glu Ala Gln Glu Thr Arg Ala Gln Ile
1               5                   10                  15

Ile Glu Ala Ala Glu Arg Ala Phe Tyr Lys Arg Gly Val Ala Arg Thr
            20                  25                  30

Thr Leu Ala Asp Ile Ala Glu Leu Ala Gly Val Thr Arg Gly Ala Ile
        35                  40                  45

Tyr Trp His Phe Asn Asn Lys Ala Glu Leu Val Gln Ala Leu Leu Asp
    50                  55                  60

Ser Leu His Glu Thr His Asp His Leu Ala Arg Ala Ser Glu Ser Glu
65                  70                  75                  80

Asp Glu Leu Asp Pro Leu Gly Cys Met Arg Lys Leu Leu Gln Val
                85                  90                  95

Phe Asn Glu Leu Val Leu Asp Ala Arg Thr Arg Ile Asn Glu Ile
                100                 105                 110

Leu His His Lys Cys Glu Phe Thr Asp Asp Met Cys Glu Ile Arg Gln
        115                 120                 125

Gln Arg Gln Ser Ala Val Leu Asp Cys His Lys Gly Ile Thr Leu Ala
    130                 135                 140

Leu Ala Asn Ala Val Arg Arg Gly Gln Leu Pro Gly Glu Leu Asp Val
145                 150                 155                 160

Glu Arg Ala Ala Val Ala Met Phe Ala Tyr Val Asp Gly Leu Ile Gly
                165                 170                 175

Arg Trp Leu Leu Leu Pro Asp Ser Val Asp Leu Leu Gly Asp Val Glu
            180                 185                 190

Lys Trp Val Asp Thr Gly Leu Asp Met Leu Arg Leu Ser Pro Ala Leu
        195                 200                 205

Arg Lys
    210
```

<210> SEQ ID NO 37
<211> LENGTH: 210
<212> TYPE: PRT
<213> ORGANISM: Artificial Sequence
<220> FEATURE:
<223> OTHER INFORMATION: Synthetic Sequence

<400> SEQUENCE: 37

```
Met Val Arg Arg Thr Lys Glu Glu Ala Gln Glu Thr Arg Ala Gln Ile
1               5                   10                  15

Ile Glu Ala Ala Glu Arg Ala Phe Tyr Lys Arg Gly Val Ala Arg Thr
            20                  25                  30

Thr Leu Ala Asp Ile Ala Glu Leu Ala Gly Val Thr Arg Gly Ala Ile
        35                  40                  45

Tyr Trp His Phe Asn Asn Lys Ala Glu Leu Val Gln Ala Leu Leu Asp
    50                  55                  60

Ser Leu Ile Glu Thr Ile Asp His Leu Ala Arg Ala Ser Glu Ser Glu
65                  70                  75                  80

Asp Glu Leu Asp Pro Leu Gly Cys Met Arg Lys Leu Leu Gln Val
                85                  90                  95

Phe Asn Glu Leu Val Leu Asp Ala Arg Thr Arg Ile Asn Glu Ile
                100                 105                 110

Leu His His Lys Cys Glu Phe Thr Asp Asp Met Cys Glu Ile Arg Gln
        115                 120                 125
```

```
Gln Arg Gln Ser Ala Val Leu Asp Cys His Lys Gly Ile Thr Leu Ala
    130                 135                 140

Leu Ala Asn Ala Val Arg Arg Gly Gln Leu Pro Gly Glu Leu Asp Val
145                 150                 155                 160

Glu Arg Ala Ala Val Ala Met Phe Ala Tyr Val Asp Gly Leu Ile Gly
                165                 170                 175

Arg Trp Leu Leu Leu Pro Asp Ser Val Asp Leu Leu Gly Asp Val Glu
            180                 185                 190

Lys Trp Val Asp Thr Gly Leu Asp Met Leu Arg Leu Ser Pro Ala Leu
        195                 200                 205

Arg Lys
    210

<210> SEQ ID NO 38
<211> LENGTH: 210
<212> TYPE: PRT
<213> ORGANISM: Artificial Sequence
<220> FEATURE:
<223> OTHER INFORMATION: Synthetic Sequence

<400> SEQUENCE: 38

Met Val Arg Arg Thr Lys Glu Glu Ala Gln Glu Thr Arg Ala Gln Ile
1               5                   10                  15

Ile Glu Ala Ala Glu Arg Ala Phe Tyr Lys Arg Gly Val Ala Arg Thr
            20                  25                  30

Thr Leu Ala Asp Ile Ala Glu Leu Ala Gly Val Thr Arg Gly Ala Ile
        35                  40                  45

Tyr Trp His Phe Asn Asn Lys Ala Glu Leu Val Gln Ala Leu Leu Asp
    50                  55                  60

Ser Leu His Glu Thr His Asp His Leu Ala Arg Ala Ser Glu Ser Glu
65                  70                  75                  80

Asp Glu Leu Asp Pro Leu Gly Cys Met Arg Lys Leu Leu Leu Gln Val
                85                  90                  95

Phe Asn Glu Leu Val Leu Asp Ala Arg Thr Arg Arg Ile Asn Glu Ile
            100                 105                 110

Leu His His Lys Cys Glu Phe Thr Asp Asp Met Cys Glu Ile Arg Gln
        115                 120                 125

Gln Arg Gln Ser Ala Val Leu Asp Cys His Lys Gly Ile Thr Leu Ala
    130                 135                 140

Leu Ala Asn Ala Val Arg Arg Gly Gln Leu Pro Gly Glu Leu Asp Val
145                 150                 155                 160

Glu Arg Ala Ala Val Ala Ser Leu Ala Phe Thr Trp Gly Leu Ile Gly
                165                 170                 175

Arg Trp Leu Leu Leu Pro Asp Ser Val Asp Leu Leu Gly Asp Val Glu
            180                 185                 190

Lys Trp Val Asp Thr Gly Leu Asp Met Leu Arg Leu Ser Pro Ala Leu
        195                 200                 205

Arg Lys
    210

<210> SEQ ID NO 39
<211> LENGTH: 219
<212> TYPE: PRT
<213> ORGANISM: Artificial Sequence
<220> FEATURE:
<223> OTHER INFORMATION: Synthetic Sequence
```

-continued

<400> SEQUENCE: 39

Met Pro Leu Thr Asp Thr Pro Pro Ser Val Pro Gln Lys Pro Arg Arg
1               5                   10                  15

Gly Arg Pro Arg Gly Ala Pro Asp Ala Ser Leu Ala His Gln Ser Leu
            20                  25                  30

Ile Arg Ala Gly Leu Glu His Leu Thr Glu Lys Gly Tyr Ser Ser Val
        35                  40                  45

Gly Val Asp Glu Ile Leu Lys Ala Ala Arg Val Pro Lys Gly Ser Phe
    50                  55                  60

Tyr His Tyr Phe Arg Asn Lys Ala Asp Phe Gly Leu Ala Leu Ile Glu
65                  70                  75                  80

Ala Tyr Asp Thr Tyr Phe Ala Arg Leu Leu Asp Gln Ala Phe Leu Asp
                85                  90                  95

Gly Ser Leu Ala Pro Leu Ala Arg Leu Arg Leu Phe Thr Arg Met Ala
            100                 105                 110

Glu Glu Gly Met Ala Arg His Gly Phe Arg Arg Gly Cys Leu Val Gly
        115                 120                 125

Asn Leu Gly Gln Glu Met Gly Ala Leu Pro Asp Asp Phe Arg Ala Ala
    130                 135                 140

Leu Ile Gly Val Leu Glu Thr Trp Gln Arg Arg Thr Ala Gln Leu Phe
145                 150                 155                 160

Arg Glu Ala Gln Ala Cys Gly Glu Leu Ser Ala Asp His Asp Pro Asp
                165                 170                 175

Ala Leu Ala Glu Ala Phe Trp Ile Gly Trp Glu Gly Ala Ile Leu Arg
            180                 185                 190

Ala Lys Leu Glu Leu Arg Pro Asp Pro Leu His Ser Phe Thr Arg Thr
        195                 200                 205

Phe Gly Arg His Phe Val Thr Arg Thr Gln Glu
    210                 215

<210> SEQ ID NO 40
<211> LENGTH: 219
<212> TYPE: PRT
<213> ORGANISM: Artificial Sequence
<220> FEATURE:
<223> OTHER INFORMATION: Synthetic Sequence

<400> SEQUENCE: 40

Met Pro Leu Thr Asp Thr Pro Pro Ser Val Pro Gln Lys Pro Arg Arg
1               5                   10                  15

Gly Arg Pro Arg Gly Ala Pro Asp Ala Ser Leu Ala His Gln Ser Leu
            20                  25                  30

Ile Arg Ala Gly Leu Glu His Leu Thr Glu Lys Gly Tyr Ser Ser Val
        35                  40                  45

Gly Val Asp Glu Ile Leu Lys Ala Ala Arg Val Pro Lys Gly Ser Phe
    50                  55                  60

Tyr His Tyr Phe Arg Asn Lys Ala Asp Phe Gly Leu Ala Leu Ile Glu
65                  70                  75                  80

Ala Tyr Asp Thr Tyr Phe Ala Arg Leu Leu Asp Gln Ala Phe Leu Asp
                85                  90                  95

Gly Ser Leu Ala Pro Leu Ala Arg Leu Arg Leu Phe Thr Arg Met Ala
            100                 105                 110

Glu Glu Gly Met Ala Arg His Gly Phe Arg Arg Gly Cys Leu Val Gly
        115                 120                 125

```
Asn Leu Gly Gln Glu Met Gly Ala Leu Pro Asp Asp Ile Arg Ala Ala
            130                 135                 140

Leu Ile Gly Val Leu Glu Thr Trp Gln Arg Arg Thr Ala Gln Leu Phe
145                 150                 155                 160

Arg Glu Ala Gln Ala Cys Gly Glu Leu Ser Ala Asp His Asp Pro Asp
                165                 170                 175

Ala Leu Ala Glu Ala Phe Trp Ile Gly Trp Glu Gly Ala Ile Leu Arg
                180                 185                 190

Ala Lys Leu Glu Leu Arg Pro Asp Pro Leu His Ser Phe Thr Arg Thr
                195                 200                 205

Phe Gly Arg His Phe Val Thr Arg Thr Gln Glu
            210                 215

<210> SEQ ID NO 41
<211> LENGTH: 219
<212> TYPE: PRT
<213> ORGANISM: Artificial Sequence
<220> FEATURE:
<223> OTHER INFORMATION: Synthetic Sequence

<400> SEQUENCE: 41

Met Pro Leu Thr Asp Thr Pro Pro Ser Val Pro Gln Lys Pro Arg Arg
1               5                   10                  15

Gly Arg Pro Arg Gly Ala Pro Asp Ala Ser Leu Ala His Gln Ser Leu
            20                  25                  30

Ile Arg Ala Gly Leu Glu His Leu Thr Glu Lys Gly Tyr Ser Ser Val
        35                  40                  45

Gly Val Asp Glu Ile Leu Lys Ala Ala Arg Val Pro Lys Gly Ser Phe
50                  55                  60

Tyr His Tyr Phe Arg Asn Lys Ala Asp Phe Gly Leu Ala Leu Ile Glu
65                  70                  75                  80

Ala Tyr Asp Thr Tyr Phe Ala Arg Leu Leu Asp Gln Ala Phe Leu Asp
                85                  90                  95

Gly Ser Leu Ala Pro Leu Ala Arg Leu Arg Leu Phe Thr Arg Met Ala
            100                 105                 110

Glu Glu Gly Met Ala Arg His Gly Phe Arg Arg Gly Cys Leu Val Gly
        115                 120                 125

Ser Leu Gly Gln Glu Met Gly Ala Leu Pro Asp Asp Phe Arg Ala Ala
            130                 135                 140

Leu Ile Gly Val Leu Glu Thr Trp Gln Arg Arg Thr Ala Gln Leu Phe
145                 150                 155                 160

Arg Glu Ala Gln Ala Cys Gly Glu Leu Ser Ala Asp His Asp Pro Asp
                165                 170                 175

Ala Leu Ala Glu Ala Phe Trp Ile Gly Trp Glu Gly Ala Val Leu Arg
                180                 185                 190

Ala Lys Leu Glu Leu Arg Pro Asp Pro Leu His Ser Phe Thr Arg Thr
                195                 200                 205

Phe Gly Arg His Phe Val Thr Arg Thr Gln Glu
            210                 215

<210> SEQ ID NO 42
<211> LENGTH: 219
<212> TYPE: PRT
<213> ORGANISM: Artificial Sequence
<220> FEATURE:
<223> OTHER INFORMATION: Synthetic Sequence
```

-continued

<400> SEQUENCE: 42

Met Pro Leu Thr Asp Thr Pro Pro Ser Val Pro Gln Lys Pro Arg Arg
1               5                   10                  15

Gly Arg Pro Arg Gly Ala Pro Asp Ala Ser Leu Ala His Gln Ser Leu
            20                  25                  30

Ile Arg Ala Gly Leu Glu His Leu Thr Glu Lys Gly Tyr Ser Ser Val
        35                  40                  45

Gly Val Asp Glu Ile Leu Lys Ala Ala Arg Val Pro Lys Gly Ser Phe
50                  55                  60

Tyr His Tyr Phe Arg Asn Lys Ala Asp Phe Gly Leu Ala Leu Ile Glu
65                  70                  75                  80

Ala Tyr Asp Thr Tyr Phe Ala Arg Leu Leu Asp Gln Ala Phe Leu Asp
                85                  90                  95

Gly Ser Leu Ala Pro Leu Ala Arg Leu Arg Leu Phe Thr Arg Met Ala
            100                 105                 110

Glu Glu Gly Met Ala Arg His Gly Phe Arg Arg Gly Cys Leu Val Gly
        115                 120                 125

Asn Leu Gly Gln Glu Met Gly Ala Leu Pro Asp Asp Phe Arg Ala Ala
130                 135                 140

Leu Ile Gly Val Leu Glu Thr Trp Gln Arg Arg Thr Ala Gln Leu Phe
145                 150                 155                 160

Arg Glu Ala Gln Ala Cys Gly Glu Leu Ser Ala Asp His Asp Pro Asp
                165                 170                 175

Ala Leu Ala Glu Ala Phe Trp Ile Gly Trp Glu Gly Ala Ile Leu Arg
            180                 185                 190

Ala Arg Leu Glu Leu Arg Pro Asp Pro Leu His Ser Phe Thr Arg Thr
        195                 200                 205

Phe Gly Arg His Phe Val Thr Arg Thr Gln Glu
210                 215

<210> SEQ ID NO 43
<211> LENGTH: 219
<212> TYPE: PRT
<213> ORGANISM: Artificial Sequence
<220> FEATURE:
<223> OTHER INFORMATION: Synthetic Sequence

<400> SEQUENCE: 43

Met Pro Leu Thr Asp Thr Pro Pro Ser Val Pro Gln Lys Pro Arg Arg
1               5                   10                  15

Gly Arg Pro Arg Gly Ala Pro Asp Ala Ser Leu Ala His Gln Ser Leu
            20                  25                  30

Ile Arg Ala Gly Leu Glu His Leu Thr Glu Lys Gly Tyr Ser Ser Ala
        35                  40                  45

Gly Val Asp Glu Ile Leu Lys Ala Ala Arg Val Pro Lys Gly Ser Phe
50                  55                  60

Tyr His Tyr Phe Arg Asn Lys Ala Asp Phe Gly Leu Ala Leu Ile Glu
65                  70                  75                  80

Ala Tyr Asp Thr Tyr Phe Ala Arg Leu Leu Asp Gln Ala Phe Leu Asp
                85                  90                  95

Gly Ser Leu Ala Pro Leu Ala Arg Leu Arg Leu Phe Thr Arg Met Ala
            100                 105                 110

Glu Glu Gly Met Val Arg His Gly Phe Arg Arg Gly Cys Leu Val Gly
        115                 120                 125

Asn Leu Gly Gln Glu Met Gly Ala Leu Pro Asp Asp Phe Arg Ala Ala
            130                 135                 140

Leu Ile Gly Val Leu Glu Thr Trp Gln Arg Arg Thr Ala Gln Leu Phe
145                 150                 155                 160

Arg Glu Ala Gln Ala Cys Gly Glu Leu Ser Ala Asp His Asp Pro Asp
                165                 170                 175

Ala Leu Ala Glu Ala Phe Trp Ile Gly Trp Glu Gly Ala Ile Leu Arg
                180                 185                 190

Ala Lys Leu Glu Leu Arg Pro Asp Pro Leu His Ser Phe Thr Arg Thr
            195                 200                 205

Phe Gly Arg His Phe Val Thr Arg Thr Gln Glu
    210                 215

<210> SEQ ID NO 44
<211> LENGTH: 219
<212> TYPE: PRT
<213> ORGANISM: Artificial Sequence
<220> FEATURE:
<223> OTHER INFORMATION: Synthetic Sequence

<400> SEQUENCE: 44

Met Pro Leu Thr Asp Thr Pro Pro Ser Val Pro Gln Lys His Arg Arg
1               5                   10                  15

Gly Arg Pro Arg Gly Ala Pro Asp Ala Ser Leu Ala His Gln Ser Leu
            20                  25                  30

Ile Arg Ala Gly Leu Glu His Leu Thr Glu Lys Gly Tyr Ser Ser Val
        35                  40                  45

Gly Val Asp Glu Ile Leu Lys Ala Ala Arg Val Pro Lys Gly Ser Phe
50                  55                  60

Tyr His Tyr Phe Arg Asn Lys Ala Asp Phe Gly Leu Ala Leu Ile Glu
65                  70                  75                  80

Ala Tyr Asp Thr Tyr Phe Ala Arg Leu Leu Asp Gln Ala Phe Leu Asp
                85                  90                  95

Gly Ser Leu Ala Pro Leu Ala Arg Leu Arg Leu Phe Thr Arg Met Ala
            100                 105                 110

Glu Glu Gly Met Ala Arg His Gly Phe Arg Arg Gly Cys Leu Val Gly
        115                 120                 125

Ser Leu Gly Gln Glu Met Gly Ala Leu Pro Asp Asp Phe Arg Ala Ala
            130                 135                 140

Leu Ile Gly Val Leu Glu Thr Trp Gln Arg Arg Thr Ala Gln Leu Phe
145                 150                 155                 160

Arg Glu Ala Gln Ala Cys Gly Glu Leu Ser Ala Asp His Asp Pro Asp
                165                 170                 175

Ala Leu Ala Glu Ala Phe Trp Ile Gly Trp Glu Gly Ala Ile Leu Arg
                180                 185                 190

Ala Lys Leu Glu Leu Arg Pro Asp Pro Leu His Ser Phe Thr Arg Thr
            195                 200                 205

Phe Gly Arg His Phe Val Thr Arg Thr Gln Asp
    210                 215

<210> SEQ ID NO 45
<211> LENGTH: 194
<212> TYPE: PRT
<213> ORGANISM: Artificial Sequence
<220> FEATURE:
<223> OTHER INFORMATION: Synthetic Sequence

<400> SEQUENCE: 45

```
Met Pro Arg Pro Lys Leu Lys Ser Asp Asp Glu Val Leu Glu Ala Ala
1               5                   10                  15

Thr Val Val Leu Lys Arg Cys Gly Pro Ile Glu Phe Thr Leu Ser Gly
            20                  25                  30

Val Ala Lys Glu Val Gly Leu Ser Arg Ala Ala Leu Ile Gln Arg Phe
        35                  40                  45

Thr Asn Arg Asp Thr Leu Leu Val Arg Met Met Glu Arg Gly Val Glu
    50                  55                  60

Gln Val Arg His Tyr Leu Asn Ala Ile Pro Ile Gly Ala Gly Pro Gln
65                  70                  75                  80

Gly Leu Trp Glu Phe Leu Gln Val Leu Val Arg Ser Met Asn Thr Arg
                85                  90                  95

Asn Asp Phe Ser Val Asn Tyr Leu Ile Ser Trp Tyr Glu Leu Gln Val
            100                 105                 110

Pro Glu Leu Arg Thr Leu Ala Ile Gln Arg Asn Arg Ala Val Val Glu
        115                 120                 125

Gly Ile Arg Lys Arg Leu Pro Pro Gly Ala Pro Ala Ala Ala Glu Leu
    130                 135                 140

Leu Leu His Ser Val Ile Ala Gly Ala Thr Met Gln Trp Ala Val Asp
145                 150                 155                 160

Pro Asp Gly Glu Leu Ala Asp His Val Leu Ala Gln Ile Ala Ala Ile
                165                 170                 175

Leu Cys Leu Met Phe Pro Glu His Asp Asp Phe Gln Leu Leu Gln Ala
            180                 185                 190

His Ala
```

<210> SEQ ID NO 46
<211> LENGTH: 207
<212> TYPE: PRT
<213> ORGANISM: Artificial Sequence
<220> FEATURE:
<223> OTHER INFORMATION: Synthetic Sequence

<400> SEQUENCE: 46

```
Met Ser Arg Leu Asp Lys Ser Lys Val Ile Asn Ser Ala Leu Glu Leu
1               5                   10                  15

Leu Asn Glu Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
        35                  40                  45

Arg Ala Leu Leu Asp Ala Leu Ala Ile Glu Met Leu Asp Arg His His
    50                  55                  60

Thr His Phe Cys Pro Leu Glu Gly Glu Ser Trp Gln Asp Phe Leu Arg
65                  70                  75                  80

Asn Asn Ala Lys Ser Phe Arg Cys Ala Leu Leu Ser His Arg Asp Gly
                85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125

Asn Ala Leu Tyr Ala Leu Ser Ala Val Gly His Phe Thr Leu Gly Cys
    130                 135                 140

Val Leu Glu Asp Gln Glu His Gln Val Ala Lys Glu Glu Arg Glu Thr
145                 150                 155                 160
```

```
Pro Thr Thr Asp Ser Met Pro Leu Leu Arg Gln Ala Ile Glu Leu
            165                 170                 175

Phe Asp His Gln Gly Ala Glu Pro Ala Phe Leu Phe Gly Leu Glu Leu
        180                 185                 190

Ile Ile Cys Gly Leu Glu Lys Gln Leu Lys Cys Glu Ser Gly Ser
        195                 200                 205

<210> SEQ ID NO 47
<211> LENGTH: 190
<212> TYPE: PRT
<213> ORGANISM: Artificial Sequence
<220> FEATURE:
<223> OTHER INFORMATION: Synthetic Sequence

<400> SEQUENCE: 47

Met Ser Arg Leu Asp Lys Ser Lys Val Ile Asn Ser Ala Leu Glu Leu
1               5                   10                  15

Leu Asn Glu Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
        35                  40                  45

Arg Ala Leu Leu Asp Ala Leu Ala Ile Glu Met Leu Asp Arg His His
    50                  55                  60

Thr His Phe Cys Pro Leu Glu Gly Glu Ser Trp Gln Asp Phe Leu Arg
65                  70                  75                  80

Asn Asn Ala Lys Ser Phe Arg Cys Ala Leu Leu Ser His Arg Asp Gly
                85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125

Asn Ala Leu Tyr Ala Leu Ser Ala Val Gly His Phe Thr Leu Gly Cys
    130                 135                 140

Val Leu Glu Asp Gln Glu His Gln Val Val Lys Lys Lys Gly Lys Leu
145                 150                 155                 160

Leu Leu Ile Val Cys Arg His Tyr Tyr Asp Lys Leu Ser Asn Tyr Leu
                165                 170                 175

Ile Thr Lys Val Gln Ser Gln Pro Thr Tyr Ser Ala Leu Asn
            180                 185                 190

<210> SEQ ID NO 48
<211> LENGTH: 207
<212> TYPE: PRT
<213> ORGANISM: Artificial Sequence
<220> FEATURE:
<223> OTHER INFORMATION: Synthetic Sequence

<400> SEQUENCE: 48

Met Ser Arg Leu Asp Lys Ser Lys Val Ile Asn Ser Ala Leu Glu Leu
1               5                   10                  15

Leu Asn Glu Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
        35                  40                  45

Arg Ala Leu Leu Asp Ala Leu Ala Ile Glu Met Leu Asp Arg His His
    50                  55                  60
```

```
Thr His Phe Cys Pro Leu Glu Gly Glu Ser Trp Gln Asp Phe Leu Arg
 65                  70                  75                  80

Asn Asn Ala Lys Ser Phe Arg Cys Ala Leu Leu Ser His Arg Asp Gly
                 85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125

Asn Ala Leu Tyr Ala Leu Ala Ala Ile Met His Phe Thr Leu Gly Cys
    130                 135                 140

Val Leu Trp Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Ser
        195                 200                 205
```

<210> SEQ ID NO 49

<400> SEQUENCE: 49

000

<210> SEQ ID NO 50
<211> LENGTH: 207
<212> TYPE: PRT
<213> ORGANISM: Artificial Sequence
<220> FEATURE:
<223> OTHER INFORMATION: Synthetic Sequence

<400> SEQUENCE: 50

```
Met Ser Arg Leu Asp Lys Ser Lys Val Ile Asn Ser Ala Leu Glu Leu
  1               5                  10                  15

Leu Asn Glu Val Gly Ile Glu Gly Leu Thr Thr Arg Lys Leu Ala Gln
             20                  25                  30

Lys Leu Gly Val Glu Gln Pro Thr Leu Tyr Trp His Val Lys Asn Lys
         35                  40                  45

Arg Ala Leu Leu Asp Ala Leu Ala Ile Glu Met Leu Asp Arg His His
     50                  55                  60

Thr His Phe Cys Pro Leu Glu Gly Glu Ser Trp Gln Asp Phe Leu Arg
 65                  70                  75                  80

Asn Asn Ala Lys Ser Phe Arg Cys Ala Leu Leu Ser His Arg Asp Gly
                 85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125

Asn Ala Leu Tyr Ala Leu His Ala Val Ala Met Phe Ala Leu Gly Cys
    130                 135                 140

Val Leu Tyr Asp Gln Glu Leu Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175
```

```
Phe Asp His Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Ser
        195                 200                 205

<210> SEQ ID NO 51
<211> LENGTH: 207
<212> TYPE: PRT
<213> ORGANISM: Artificial Sequence
<220> FEATURE:
<223> OTHER INFORMATION: Synthetic Sequence

<400> SEQUENCE: 51

Met Ser Arg Leu Asp Lys Ser Lys Val Ile Asn Ser Ala Leu Glu Leu
1               5                   10                  15

Leu Asn Glu Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
        35                  40                  45

Arg Ala Leu Leu Asp Ala Leu Ala Ile Glu Met Leu Asp Arg His His
    50                  55                  60

Thr His Phe Cys Pro Leu Glu Gly Glu Ser Trp Gln Asp Phe Leu Arg
65                  70                  75                  80

Asn Asn Ala Lys Ser Phe Arg Cys Ala Leu Leu Ser His Arg Asp Gly
                85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125

Asn Ala Leu Arg Ala Leu Ala Ala Val His Leu Phe Thr Leu Gly Cys
    130                 135                 140

Val Leu Tyr Ala Gln Glu Leu Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Ser
        195                 200                 205

<210> SEQ ID NO 52
<211> LENGTH: 207
<212> TYPE: PRT
<213> ORGANISM: Artificial Sequence
<220> FEATURE:
<223> OTHER INFORMATION: Synthetic Sequence

<400> SEQUENCE: 52

Met Ser Arg Leu Asp Lys Ser Lys Val Ile Asn Ser Ala Leu Glu Leu
1               5                   10                  15

Leu Asn Glu Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
        35                  40                  45

Arg Ala Leu Leu Asp Ala Leu Ala Ile Glu Met Leu Asp Arg His His
    50                  55                  60
```

```
Thr His Phe Cys Pro Leu Gly Glu Ser Trp Gln Asp Phe Leu Arg
 65                  70                  75                  80

Asn Asn Ala Lys Ser Phe Arg Cys Ala Leu Leu Ser His Arg Asp Gly
                 85                  90                  95

Ala Lys Val His Leu Gly Thr Tyr Pro Thr Glu Lys Gln Tyr Glu Thr
                100                 105                 110

Leu Glu Asn Gln Leu Ala Phe Leu Cys Gln Gln Gly Phe Ser Leu Glu
            115                 120                 125

Asn Ala Met Arg Ala Leu Ala Ala Val Ala Met Phe Thr Leu Gly Cys
        130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
                180                 185                 190

Ile Ile Cys Gly Leu Glu Lys Gln Leu Lys Cys Glu Ser Gly Ser
            195                 200                 205

<210> SEQ ID NO 53
<211> LENGTH: 207
<212> TYPE: PRT
<213> ORGANISM: Artificial Sequence
<220> FEATURE:
<223> OTHER INFORMATION: Synthetic Sequence

<400> SEQUENCE: 53

Met Ser Arg Leu Asp Lys Ser Lys Val Ile Asn Ser Ala Leu Glu Leu
  1               5                  10                  15

Leu Asn Glu Val Gly Ile Glu Gly Leu Thr Thr Arg Lys Leu Ala Gln
             20                  25                  30

Lys Leu Gly Val Glu Gln Pro Thr Leu Tyr Trp His Val Lys Asn Lys
         35                  40                  45

Arg Ala Leu Leu Asp Ala Leu Ala Ile Glu Met Leu Asp Arg His His
     50                  55                  60

Thr His Trp Lys Pro Leu Gly Glu Ser Trp Gln Asp Phe Leu Arg
 65                  70                  75                  80

Asn Arg Ala Lys Ser Leu Arg Cys Ala Ala Leu Ser His Arg Asp Gly
                 85                  90                  95

Ala Lys Val Met Leu Gly Ala Arg Pro Thr Glu Lys Gln Tyr Glu Thr
                100                 105                 110

Leu Glu Asn Gln Leu Ala Phe Leu Cys Gln Gln Gly Phe Ser Leu Glu
            115                 120                 125

Asn Ala Leu Tyr Ala Leu Ser Ala Val Gly His Phe Thr Leu Gly Cys
        130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
                180                 185                 190

Ile Ile Cys Gly Leu Glu Lys Gln Leu Lys Cys Glu Ser Gly Ser
            195                 200                 205

<210> SEQ ID NO 54
```

<211> LENGTH: 207
<212> TYPE: PRT
<213> ORGANISM: Artificial Sequence
<220> FEATURE:
<223> OTHER INFORMATION: Synthetic Sequence

<400> SEQUENCE: 54

Met Ser Arg Leu Asp Lys Ser Lys Val Ile Asn Ser Ala Leu Glu Leu
1               5                   10                  15

Leu Asn Glu Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
        35                  40                  45

Arg Ala Leu Leu Asp Ala Leu Ala Ile Glu Met Leu Asp Arg His His
    50                  55                  60

Thr His Phe Cys Pro Leu Glu Gly Glu Ser Trp Gln Asp Phe Leu Arg
65                  70                  75                  80

Asn Asn Ala Lys Ser Phe Arg Cys Ala Leu Leu Ser His Arg Asp Gly
                85                  90                  95

Ala Lys Val His Leu Gly Thr His Gly Thr Glu Lys Leu Tyr Glu Ile
            100                 105                 110

Ala Arg Asn Arg Ala Ala Phe Leu Cys Gln Gln Gly Phe Ser Leu Glu
        115                 120                 125

Asn Ala Leu Tyr Ala Leu Ser Ala Val Gly His Phe Thr Leu Gly Cys
    130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Ser
        195                 200                 205

<210> SEQ ID NO 55
<211> LENGTH: 207
<212> TYPE: PRT
<213> ORGANISM: Artificial Sequence
<220> FEATURE:
<223> OTHER INFORMATION: Synthetic Sequence

<400> SEQUENCE: 55

Met Ser Arg Leu Asp Lys Ser Lys Val Ile Asn Ser Ala Leu Glu Leu
1               5                   10                  15

Leu Asn Glu Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
        35                  40                  45

Arg Ala Leu Leu Asp Ala Leu Ala Ile Glu Met Leu Asp Arg His His
    50                  55                  60

Thr His Phe Cys Pro Leu Glu Gly Glu Ser Trp Gln Asp Phe Leu Arg
65                  70                  75                  80

Asn Asn Ala Lys Ser Phe Arg Cys Ala Leu Leu Ser His Arg Asp Gly
                85                  90                  95

Ala Lys Val Ala Leu Gly Thr Thr Gly Thr Glu Lys Leu Arg Glu Val
            100                 105                 110

Gly Ala Asn Ile Leu Ala Phe Leu Cys Gln Gln Gly Phe Ser Leu Glu
            115                 120                 125

Asn Ala Leu Tyr Ala Leu Ser Ala Val Leu His Phe Thr Leu Gly Cys
        130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Ser
            195                 200                 205

<210> SEQ ID NO 56
<211> LENGTH: 207
<212> TYPE: PRT
<213> ORGANISM: Artificial Sequence
<220> FEATURE:
<223> OTHER INFORMATION: Synthetic Sequence

<400> SEQUENCE: 56

Met Ser Arg Leu Asp Lys Ser Lys Val Ile Asn Ser Ala Leu Glu Leu
1               5                   10                  15

Leu Asn Glu Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
        35                  40                  45

Arg Ala Leu Leu Asp Ala Leu Ala Ile Glu Met Leu Asp Arg His His
    50                  55                  60

Thr His Phe Cys Pro Leu Glu Gly Glu Ser Trp Gln Asp Phe Leu Arg
65                  70                  75                  80

Asn Asn Ala Lys Ser Phe Arg Cys Ala Leu Leu Ser His Arg Asp Gly
                85                  90                  95

Ala Lys Val Ala Leu Gly Thr Thr Gly Thr Glu Lys Leu Leu Glu Ile
            100                 105                 110

Gly Leu Asn Asn Leu Ala Phe Leu Cys Gln Gln Gly Phe Ser Leu Glu
        115                 120                 125

Asn Ala Leu Tyr Ala Leu Ser Ala Val Leu His Phe Thr Leu Gly Cys
    130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Ser
            195                 200                 205

<210> SEQ ID NO 57
<211> LENGTH: 207
<212> TYPE: PRT
<213> ORGANISM: Artificial Sequence
<220> FEATURE:
<223> OTHER INFORMATION: Synthetic Sequence

<400> SEQUENCE: 57

```
Met Ser Arg Leu Asp Lys Ser Lys Val Ile Asn Ser Ala Leu Glu Leu
1               5                   10                  15

Leu Asn Glu Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
        35                  40                  45

Arg Ala Leu Leu Asp Ala Leu Ala Ile Glu Met Leu Asp Arg His His
    50                  55                  60

Thr His Phe Cys Pro Leu Glu Gly Glu Ser Trp Gln Asp Phe Leu Arg
65                  70                  75                  80

Asn Asn Ala Lys Ser Phe Arg Cys Ala Leu Leu Ser His Arg Asp Gly
                85                  90                  95

Ala Lys Val Ala Leu Gly Thr Thr Gly Phe Glu Lys Leu Leu Glu Val
            100                 105                 110

Gly Ala Asn Asn Leu Ala Phe Leu Cys Gln Gln Gly Phe Ser Leu Glu
        115                 120                 125

Asn Ala Leu Tyr Ala Leu Ser Ala Val Leu His Phe Thr Leu Gly Cys
    130                 135                 140

Val Leu Glu Asp Gln Glu His Gln Val Ala Lys Glu Arg Glu Thr
145                 150                 155                 160

Pro Thr Thr Asp Ser Met Pro Pro Leu Arg Gln Ala Ile Glu Leu
                165                 170                 175

Phe Asp His Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Ser
        195                 200                 205
```

<210> SEQ ID NO 58
<211> LENGTH: 207
<212> TYPE: PRT
<213> ORGANISM: Artificial Sequence
<220> FEATURE:
<223> OTHER INFORMATION: Synthetic Sequence

<400> SEQUENCE: 58

```
Met Ser Arg Leu Asp Lys Ser Lys Val Ile Asn Ser Ala Leu Glu Leu
1               5                   10                  15

Leu Asn Glu Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
        35                  40                  45

Arg Ala Leu Leu Asp Ala Leu Ala Ile Glu Met Leu Asp Arg His His
    50                  55                  60

Thr His Phe Cys Pro Leu Glu Gly Glu Ser Trp Gln Asp Phe Leu Arg
65                  70                  75                  80

Asn Asn Ala Lys Ser Phe Arg Cys Ala Leu Leu Ser His Arg Asp Gly
                85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125

Asn Ala Ser Tyr Ala Leu Ala Ala Val Trp His Phe Thr Leu Gly Cys
    130                 135                 140
```

Val Leu His Asp Gln Glu Ser Gln Val Ala Lys Glu Glu Arg Glu Thr
145                 150                 155                 160

Pro Thr Thr Asp Ser Met Pro Pro Leu Leu Arg Gln Ala Ile Glu Leu
            165                 170                 175

Phe Asp His Gln Gly Ala Glu Pro Ala Phe Leu Phe Gly Leu Glu Leu
        180                 185                 190

Ile Ile Cys Gly Leu Glu Lys Gln Leu Lys Cys Glu Ser Gly Ser
        195                 200                 205

<210> SEQ ID NO 59
<211> LENGTH: 207
<212> TYPE: PRT
<213> ORGANISM: Artificial Sequence
<220> FEATURE:
<223> OTHER INFORMATION: Synthetic Sequence

<400> SEQUENCE: 59

Met Ser Arg Leu Asp Lys Ser Lys Val Ile Asn Ser Ala Leu Glu Leu
1               5                   10                  15

Leu Asn Glu Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
        35                  40                  45

Arg Ala Leu Leu Asp Ala Leu Ala Ile Glu Met Leu Asp Arg His His
    50                  55                  60

Thr His Phe Cys Pro Leu Glu Gly Glu Ser Trp Gln Asp Phe Leu Arg
65                  70                  75                  80

Asn Asn Ala Lys Ser Phe Arg Cys Ala Leu Leu Ser His Arg Asp Gly
                85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125

Asn Ala Ser Lys Ala Leu Ala Ala Val Trp His Phe Thr Ile Gly Cys
    130                 135                 140

Val Leu Ala Asp Gln Glu Arg Gln Val Ala Lys Glu Glu Arg Glu Thr
145                 150                 155                 160

Pro Thr Thr Asp Ser Met Pro Pro Leu Leu Arg Gln Ala Ile Glu Leu
            165                 170                 175

Phe Asp His Gln Gly Ala Glu Pro Ala Phe Leu Phe Gly Leu Glu Leu
        180                 185                 190

Ile Ile Cys Gly Leu Glu Lys Gln Leu Lys Cys Glu Ser Gly Ser
        195                 200                 205

<210> SEQ ID NO 60
<211> LENGTH: 207
<212> TYPE: PRT
<213> ORGANISM: Artificial Sequence
<220> FEATURE:
<223> OTHER INFORMATION: Synthetic Sequence

<400> SEQUENCE: 60

Met Ser Arg Leu Asp Lys Ser Lys Val Ile Asn Ser Ala Leu Glu Leu
1               5                   10                  15

Leu Asn Glu Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
        35                  40                  45

```
Arg Ala Leu Leu Asp Ala Leu Ala Ile Glu Met Leu Asp Arg His His
    50                  55                  60

Thr His Phe Cys Pro Leu Glu Gly Glu Ser Trp Gln Asp Phe Leu Arg
65                  70                  75                  80

Asn Asn Ala Lys Ser Phe Arg Cys Ala Leu Leu Ser His Arg Asp Gly
                85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Val Phe Ser Leu Glu
            115                 120                 125

Asn Ala Leu Tyr Ala Leu Ser Ala Val Trp His Phe Thr Leu Gly Cys
            130                 135                 140

Val Leu His Asp Gln Glu Leu Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
                180                 185                 190

Ile Ile Cys Gly Leu Glu Lys Gln Leu Lys Cys Glu Ser Gly Ser
            195                 200                 205

<210> SEQ ID NO 61
<211> LENGTH: 207
<212> TYPE: PRT
<213> ORGANISM: Artificial Sequence
<220> FEATURE:
<223> OTHER INFORMATION: Synthetic Sequence

<400> SEQUENCE: 61

Met Ser Arg Leu Asp Lys Ser Lys Val Ile Asn Ser Ala Leu Glu Leu
1               5                   10                  15

Leu Asn Glu Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
        35                  40                  45

Arg Ala Leu Leu Asp Ala Leu Ala Ile Glu Met Leu Asp Arg His His
    50                  55                  60

Thr His Phe Cys Pro Leu Glu Gly Glu Ser Trp Gln Asp Phe Leu Arg
65                  70                  75                  80

Asn Asn Ala Lys Ser Phe Arg Cys Ala Leu Leu Ser His Arg Asp Gly
                85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
            115                 120                 125

Asn Ala Leu Tyr Ala Met Thr Ala Val Leu Trp Phe Thr Leu Gly Cys
            130                 135                 140

Val Leu Asp Asp Gln Glu Arg Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
                180                 185                 190

Ile Ile Cys Gly Leu Glu Lys Gln Leu Lys Cys Glu Ser Gly Ser
            195                 200                 205
```

<210> SEQ ID NO 62
<211> LENGTH: 207
<212> TYPE: PRT
<213> ORGANISM: Artificial Sequence
<220> FEATURE:
<223> OTHER INFORMATION: Synthetic Sequence

<400> SEQUENCE: 62

```
Met Ser Arg Leu Asp Lys Ser Lys Val Ile Asn Ser Ala Leu Glu Leu
1               5                   10                  15

Leu Asn Glu Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
        35                  40                  45

Arg Ala Leu Leu Asp Ala Leu Ala Ile Glu Met Leu Asp Arg His His
    50                  55                  60

Thr His Phe Cys Pro Leu Glu Gly Glu Ser Trp Gln Asp Phe Leu Arg
65                  70                  75                  80

Asn Asn Ala Lys Ser Phe Arg Cys Ala Leu Leu Ser His Arg Asp Gly
                85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125

Asn Ala Leu Tyr Ala Leu Thr Ala Val Phe Leu Phe Thr Leu Gly Cys
    130                 135                 140

Val Leu Gln Asp Gln Glu Ala Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Ser
        195                 200                 205
```

<210> SEQ ID NO 63
<211> LENGTH: 207
<212> TYPE: PRT
<213> ORGANISM: Artificial Sequence
<220> FEATURE:
<223> OTHER INFORMATION: Synthetic Sequence

<400> SEQUENCE: 63

```
Met Ser Arg Leu Asp Lys Ser Lys Val Ile Asn Ser Ala Leu Glu Leu
1               5                   10                  15

Leu Asn Glu Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
        35                  40                  45

Arg Ala Leu Leu Asp Ala Leu Ala Ile Glu Met Leu Asp Arg His His
    50                  55                  60

Thr His Phe Cys Pro Leu Glu Gly Glu Ser Trp Gln Asp Phe Leu Arg
65                  70                  75                  80

Asn Asn Ala Lys Ser Phe Arg Cys Ala Leu Leu Ser His Arg Asp Gly
                85                  90                  95
```

```
Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
            115                 120                 125

Asn Ala Met Arg Ala Leu Ala Ala Val Ile His Phe Thr Leu Gly Cys
            130                 135                 140

Val Leu Asp Asp Gln Glu Arg Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
                180                 185                 190

Ile Ile Cys Gly Leu Glu Lys Gln Leu Lys Cys Glu Ser Gly Ser
                195                 200                 205
```

<210> SEQ ID NO 64
<211> LENGTH: 207
<212> TYPE: PRT
<213> ORGANISM: Artificial Sequence
<220> FEATURE:
<223> OTHER INFORMATION: Synthetic Sequence

<400> SEQUENCE: 64

```
Met Ser Arg Leu Asp Lys Ser Lys Val Ile Asn Ser Ala Leu Glu Leu
1               5                   10                  15

Leu Asn Glu Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
            35                  40                  45

Arg Ala Leu Leu Asp Ala Leu Ala Ile Glu Met Leu Asp Arg His His
        50                  55                  60

Thr His Phe Cys Pro Leu Glu Gly Glu Ser Trp Gln Asp Phe Leu Arg
65                  70                  75                  80

Asn Asn Ala Lys Ser Phe Arg Cys Ala Leu Leu Ser His Arg Asp Gly
                85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
            115                 120                 125

Asn Ala Met Arg Asn Leu Ala Ala Val Trp His Phe Thr Leu Gly Cys
            130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
                180                 185                 190

Ile Ile Cys Gly Leu Glu Lys Gln Leu Lys Cys Glu Ser Gly Ser
                195                 200                 205
```

<210> SEQ ID NO 65
<211> LENGTH: 190
<212> TYPE: PRT
<213> ORGANISM: Artificial Sequence
<220> FEATURE:
<223> OTHER INFORMATION: Synthetic Sequence

<400> SEQUENCE: 65

```
Met Arg Gly Glu Thr Leu Lys Leu Lys Lys Asp Lys Arg Arg Glu Ala
1               5                   10                  15

Ile Arg Gln Gln Ile Asp Ser Asn Pro Phe Ile Thr Asp His Glu Leu
            20                  25                  30

Ser Asp Leu Phe Gln Val Ser Ile Gln Thr Ile Arg Leu Asp Arg Thr
        35                  40                  45

Tyr Leu Asn Ile Pro Glu Leu Arg Lys Arg Ile Lys Leu Val Ala Glu
50                  55                  60

Lys Asn Tyr Asp Gln Ile Ser Ser Ile Glu Glu Gln Glu Phe Ile Gly
65                  70                  75                  80

Asp Leu Ile Gln Val Asn Pro Asn Val Lys Ala Gln Ser Ile Leu Asp
                85                  90                  95

Ile Thr Ser Asp Cys Val Phe His Lys Thr Gly Ile Ala Arg Gly His
            100                 105                 110

Val Leu Phe Ala Gln Ala Asn Ser Leu Cys Val Ala Leu Ile Lys Gln
        115                 120                 125

Pro Thr Val Leu Thr His Glu Ser Ser Ile Gln Phe Ile Glu Lys Val
130                 135                 140

Lys Leu Asn Asp Thr Val Arg Ala Glu Ala Arg Val Val Asn Gln Thr
145                 150                 155                 160

Ala Lys Asn Tyr Tyr Val Glu Val Lys Ser Tyr Val Lys His Ala Leu
                165                 170                 175

Val Phe Lys Gly Asn Phe Lys Met Phe Tyr Asp Lys Arg Gly
            180                 185                 190
```

<210> SEQ ID NO 66
<211> LENGTH: 239
<212> TYPE: PRT
<213> ORGANISM: Artificial Sequence
<220> FEATURE:
<223> OTHER INFORMATION: Synthetic Sequence

<400> SEQUENCE: 66

```
Met Val Ile Lys Ala Gln Ser Pro Ala Gly Phe Ala Glu Glu Tyr Ile
1               5                   10                  15

Ile Glu Ser Ile Trp Asn Asn Arg Phe Pro Pro Gly Thr Ile Leu Pro
            20                  25                  30

Ala Glu Arg Glu Leu Ser Glu Leu Ile Gly Val Thr Arg Thr Thr Leu
        35                  40                  45

Arg Glu Val Leu Gln Arg Leu Ala Arg Asp Gly Trp Leu Thr Ile Gln
50                  55                  60

His Gly Lys Pro Thr Lys Val Asn Asn Phe Trp Glu Thr Ser Gly Leu
65                  70                  75                  80

Asn Ile Leu Glu Thr Leu Ala Arg Leu Asp His Glu Ser Val Pro Gln
                85                  90                  95

Leu Ile Asp Asn Leu Leu Ser Val Arg Thr Asn Ile Ser Thr Ile Phe
            100                 105                 110

Ile Arg Thr Ala Phe Arg Gln His Pro Asp Lys Ala Gln Glu Val Leu
        115                 120                 125

Ala Thr Ala Asn Glu Val Ala Asp His Ala Asp Ala Phe Ala Glu Leu
130                 135                 140

Asp Tyr Asn Ile Phe Arg Gly Leu Ala Phe Ala Ser Gly Asn Pro Ile
145                 150                 155                 160
```

```
Tyr Gly Leu Ile Leu Asn Gly Met Lys Gly Leu Tyr Thr Arg Ile Gly
                165                 170                 175

Arg His Tyr Phe Ala Asn Pro Glu Ala Arg Ser Leu Ala Leu Gly Phe
            180                 185                 190

Tyr His Lys Leu Ser Ala Leu Cys Ser Glu Gly Ala His Asp Gln Val
        195                 200                 205

Tyr Glu Thr Val Arg Arg Tyr Gly His Glu Ser Gly Glu Ile Trp His
    210                 215                 220

Arg Met Gln Lys Asn Leu Pro Gly Asp Leu Ala Ile Gln Gly Arg
225                 230                 235

<210> SEQ ID NO 67
<211> LENGTH: 225
<212> TYPE: PRT
<213> ORGANISM: Artificial Sequence
<220> FEATURE:
<223> OTHER INFORMATION: Synthetic Sequence

<400> SEQUENCE: 67

Met Lys Asn Tyr Tyr Ser Ser Asn Pro Thr Phe Tyr Leu Gly Ile Asp
1               5                   10                  15

Cys Ile Ile Phe Gly Phe Asn Glu Gly Ile Ser Leu Leu Leu Leu
            20                  25                  30

Lys Arg Asn Phe Glu Pro Ala Met Gly Glu Trp Ser Leu Met Gly Gly
        35                  40                  45

Phe Val Gln Lys Asp Glu Ser Val Asp Ala Ala Lys Arg Val Leu
    50                  55                  60

Ala Glu Leu Thr Gly Leu Glu Asn Val Tyr Met Glu Gln Val Gly Ala
65                  70                  75                  80

Phe Gly Ala Ile Asp Arg Asp Pro Gly Glu Arg Val Val Ser Ile Ala
                85                  90                  95

Tyr Tyr Ala Leu Ile Asn Ile Asn Glu Tyr Asp Arg Glu Leu Val Gln
            100                 105                 110

Lys His Asn Ala Tyr Trp Val Asn Ile Asn Glu Leu Pro Ala Leu Ile
        115                 120                 125

Phe Asp His Pro Glu Met Val Asp Lys Ala Arg Glu Met Met Lys Gln
    130                 135                 140

Lys Ala Ser Val Glu Pro Ile Gly Phe Asn Leu Leu Pro Lys Leu Phe
145                 150                 155                 160

Thr Leu Ser Gln Leu Gln Ser Leu Tyr Glu Ala Ile Tyr Gly Glu Pro
                165                 170                 175

Met Asp Lys Arg Asn Phe Arg Lys Arg Val Ala Glu Met Asp Phe Ile
            180                 185                 190

Glu Lys Thr Asp Lys Ile Asp Lys Leu Gly Ser Lys Arg Gly Ala Ala
        195                 200                 205

Leu Tyr Lys Phe Asn Gly Lys Ala Tyr Arg Lys Asp Pro Lys Phe Lys
    210                 215                 220

Leu
225

<210> SEQ ID NO 68
<211> LENGTH: 116
<212> TYPE: PRT
<213> ORGANISM: Artificial Sequence
<220> FEATURE:
<223> OTHER INFORMATION: Synthetic Sequence
```

<400> SEQUENCE: 68

Met Ala Glu Ile Pro Lys Glu Met Leu Arg Ala Gln Thr Asn Val Ile
1               5                   10                  15

Leu Leu Asn Val Leu Lys Gln Gly Asp Asn Tyr Val Tyr Gly Ile Ile
            20                  25                  30

Lys Gln Val Lys Glu Ala Ser Asn Gly Glu Met Glu Leu Asn Glu Ala
        35                  40                  45

Thr Leu Tyr Thr Ile Phe Lys Arg Leu Glu Lys Asp Gly Ile Ile Ser
    50                  55                  60

Ser Tyr Trp Gly Asp Glu Ser Gln Gly Gly Arg Arg Lys Tyr Tyr Arg
65                  70                  75                  80

Leu Thr Glu Ile Gly His Glu Asn Met Arg Leu Ala Phe Glu Ser Trp
                85                  90                  95

Ser Arg Val Asp Lys Ile Ile Glu Asn Leu Glu Ala Asn Lys Lys Ser
            100                 105                 110

Glu Ala Ile Lys
            115

<210> SEQ ID NO 69
<211> LENGTH: 360
<212> TYPE: PRT
<213> ORGANISM: Artificial Sequence
<220> FEATURE:
<223> OTHER INFORMATION: Synthetic Sequence

<400> SEQUENCE: 69

Met Lys Pro Val Thr Leu Tyr Asp Val Ala Glu Tyr Ala Gly Val Ser
1               5                   10                  15

Tyr Gln Thr Val Ser Arg Val Val Asn Gln Ala Ser His Val Ser Ala
            20                  25                  30

Lys Thr Arg Glu Lys Val Glu Ala Ala Met Ala Glu Leu Asn Tyr Ile
        35                  40                  45

Pro Asn Arg Val Ala Gln Gln Leu Ala Gly Lys Gln Ser Leu Leu Ile
    50                  55                  60

Gly Val Ala Thr Ser Ser Leu Ala Leu His Ala Pro Ser Gln Ile Val
65                  70                  75                  80

Ala Ala Ile Lys Ser Arg Ala Asp Gln Leu Gly Ala Ser Val Val Val
                85                  90                  95

Ser Met Val Glu Arg Ser Gly Val Glu Ala Cys Lys Ala Ala Val His
            100                 105                 110

Asn Leu Leu Ala Gln Arg Val Ser Gly Leu Ile Ile Asn Tyr Pro Leu
        115                 120                 125

Asp Asp Gln Asp Ala Ile Ala Val Glu Ala Ala Cys Thr Asn Val Pro
    130                 135                 140

Ala Leu Phe Leu Asp Val Ser Asp Gln Thr Pro Ile Asn Ser Ile Ile
145                 150                 155                 160

Phe Ser His Glu Asp Gly Thr Arg Leu Gly Val Glu His Leu Val Ala
                165                 170                 175

Leu Gly His Gln Gln Ile Ala Leu Leu Ala Gly Pro Leu Ser Ser Val
            180                 185                 190

Ser Ala Arg Leu Arg Leu Ala Gly Trp His Lys Tyr Leu Thr Arg Asn
        195                 200                 205

Gln Ile Gln Pro Ile Ala Glu Arg Glu Gly Asp Trp Ser Ala Met Ser
    210                 215                 220

```
Gly Phe Gln Gln Thr Met Gln Met Leu Asn Glu Gly Ile Val Pro Thr
225                 230                 235                 240

Ala Met Leu Val Ala Asn Asp Gln Met Ala Leu Gly Ala Met Arg Ala
                245                 250                 255

Ile Thr Glu Ser Gly Leu Arg Val Gly Ala Asp Ile Ser Val Val Gly
            260                 265                 270

Tyr Asp Asp Thr Glu Asp Ser Ser Cys Tyr Ile Pro Pro Leu Thr Thr
        275                 280                 285

Ile Lys Gln Asp Phe Arg Leu Leu Gly Gln Thr Ser Val Asp Arg Leu
    290                 295                 300

Leu Gln Leu Ser Gln Gly Gln Ala Val Lys Gly Asn Gln Leu Leu Pro
305                 310                 315                 320

Val Ser Leu Val Lys Arg Lys Thr Thr Leu Ala Pro Asn Thr Gln Thr
                325                 330                 335

Ala Ser Pro Arg Ala Leu Ala Asp Ser Leu Met Gln Leu Ala Arg Gln
            340                 345                 350

Val Ser Arg Leu Glu Ser Gly Gln
        355                 360

<210> SEQ ID NO 70
<211> LENGTH: 360
<212> TYPE: PRT
<213> ORGANISM: Artificial Sequence
<220> FEATURE:
<223> OTHER INFORMATION: Synthetic Sequence

<400> SEQUENCE: 70

Met Lys Pro Val Thr Leu Tyr Asp Val Ala Glu Tyr Ala Gly Val Ser
1               5                   10                  15

Tyr Gln Thr Val Ser Arg Val Val Asn Gln Ala Ser His Val Ser Ala
                20                  25                  30

Lys Thr Arg Glu Lys Val Glu Ala Ala Met Ala Glu Leu Asn Tyr Ile
            35                  40                  45

Pro Asn Arg Val Ala Gln Gln Leu Ala Gly Lys Gln Ser Leu Leu Ile
    50                  55                  60

Gly Val Ala Thr Ser Ser Leu Ala Leu His Ala Pro Ser Gln Ile Val
65                  70                  75                  80

Ala Ala Ile Lys Ser Arg Ala Asp Gln Leu Gly Ala Ser Val Val Val
                85                  90                  95

Ser Met Val Glu Arg Ser Gly Val Glu Ala Cys Lys Ala Ala Val His
            100                 105                 110

Asn Leu Leu Ala Gln Arg Val Ser Gly Leu Ile Ile Asn Tyr Pro Leu
        115                 120                 125

Asp Asp Gln Asp Ala Ile Ala Val Glu Ala Ala Cys Thr Asn Val Pro
    130                 135                 140

Ala Leu Phe Leu Asp Val Ser Asp Gln Thr Pro Ile Asn Ser Ile Ile
145                 150                 155                 160

Phe Ser Thr Glu Asp Ala Thr Arg Leu Gly Val Glu His Leu Val Ala
                165                 170                 175

Leu Gly His Gln Gln Ile Ala Leu Leu Ser Gly His Leu Ser Ser Val
            180                 185                 190

Met Ala Arg Leu Arg Leu Ala Gly Trp His Lys Tyr Leu Thr Arg Asn
        195                 200                 205

Gln Ile Gln Pro Ile Ala Glu Arg Glu Gly Asp Trp Ser Ala Met Ser
    210                 215                 220
```

Gly Phe Gln Gln Thr Met Gln Met Leu Asn Glu Gly Ile Val Pro Thr
225                 230                 235                 240

Ala Met Leu Val Ala Asn Asp Gln Met Ala Leu Gly Ala Met Arg Ala
                245                 250                 255

Ile Thr Glu Ser Gly Leu Arg Val Gly Ala Asp Ile Ser Val Val Gly
            260                 265                 270

Tyr Asp Asp Thr Glu Asp Ser Ser Cys Tyr Ile Pro Pro Leu Thr Thr
        275                 280                 285

Ile Lys Gln Asp Phe Arg Leu Leu Gly Gln Thr Ser Val Asp Arg Leu
    290                 295                 300

Leu Gln Leu Ser Gln Gly Gln Ala Val Lys Gly Asn Gln Leu Leu Pro
305                 310                 315                 320

Val Ser Leu Val Lys Arg Lys Thr Thr Leu Ala Pro Asn Thr Gln Thr
                325                 330                 335

Ala Ser Pro Arg Ala Leu Ala Asp Ser Leu Met Gln Leu Ala Arg Gln
            340                 345                 350

Val Ser Arg Leu Glu Ser Gly Gln
        355                 360

<210> SEQ ID NO 71
<211> LENGTH: 360
<212> TYPE: PRT
<213> ORGANISM: Artificial Sequence
<220> FEATURE:
<223> OTHER INFORMATION: Synthetic Sequence

<400> SEQUENCE: 71

Met Lys Pro Val Thr Leu Tyr Asp Val Ala Glu Tyr Ala Gly Val Ser
1               5                   10                  15

Tyr Gln Thr Val Ser Arg Val Val Asn Gln Ala Ser His Val Ser Ala
                20                  25                  30

Lys Thr Arg Glu Lys Val Glu Ala Ala Met Ala Glu Leu Asn Tyr Ile
            35                  40                  45

Pro Asn Arg Val Ala Gln Gln Leu Ala Gly Lys Gln Ser Leu Leu Ile
    50                  55                  60

Gly Val Ala Thr Ser Ser Leu Ala Leu His Ala Pro Ser Gln Ile Val
65                  70                  75                  80

Ala Ala Ile Lys Ser Arg Ala Asp Gln Leu Gly Ala Ser Val Val Val
                85                  90                  95

Ser Met Val Glu Arg Ser Gly Val Glu Ala Cys Lys Ala Ala Val His
            100                 105                 110

Asn Leu Leu Ala Gln Arg Val Ser Gly Leu Ile Ile Asn Tyr Pro Leu
        115                 120                 125

Asp Asp Gln Asp Ala Ile Ala Val Glu Ala Ala Cys Thr Asn Val Pro
    130                 135                 140

Ala Leu Phe Asn Asn Thr Ser Asn Gln Thr Pro Ile Asn Ser Ile Gly
145                 150                 155                 160

Phe Ser Gln Glu Asp Ala Thr Arg Leu Gly Val Glu His Leu Val Ala
                165                 170                 175

Leu Gly His Gln Gln Ile Ala Leu Leu Ala Gly Pro Leu Ser Ser Val
            180                 185                 190

Ser Ala Arg Leu Arg Leu Ala Gly Trp His Lys Tyr Leu Thr Arg Asn
        195                 200                 205

Gln Ile Gln Pro Ile Ala Glu Arg Glu Gly Asp Trp Ser Ala Met Ser
    210                 215                 220

```
Gly Phe Gln Gln Thr Met Gln Met Leu Asn Glu Gly Ile Val Pro Thr
225                 230                 235                 240

Ala Met Leu Val Ala Asn Asp Gln Met Ala Leu Gly Ala Met Arg Ala
            245                 250                 255

Ile Thr Glu Ser Gly Leu Arg Val Gly Ala Asp Ile Ser Val Val Gly
            260                 265                 270

Tyr Asp Asp Thr Glu Asp Ser Ser Cys Tyr Ile Pro Pro Leu Thr Thr
            275                 280                 285

Ile Lys Gln Asp Phe Arg Leu Leu Gly Gln Thr Ser Val Asp Arg Leu
            290                 295                 300

Leu Gln Leu Ser Gln Gly Gln Ala Val Lys Gly Asn Gln Leu Leu Pro
305                 310                 315                 320

Val Ser Leu Val Lys Arg Lys Thr Thr Leu Ala Pro Asn Thr Gln Thr
            325                 330                 335

Ala Ser Pro Arg Ala Leu Ala Asp Ser Leu Met Gln Leu Ala Arg Gln
            340                 345                 350

Val Ser Arg Leu Glu Ser Gly Gln
            355                 360

<210> SEQ ID NO 72
<211> LENGTH: 360
<212> TYPE: PRT
<213> ORGANISM: Artificial Sequence
<220> FEATURE:
<223> OTHER INFORMATION: Synthetic Sequence

<400> SEQUENCE: 72

Met Lys Pro Val Thr Leu Tyr Asp Val Ala Glu Tyr Ala Gly Val Ser
1               5                   10                  15

Tyr Gln Thr Val Ser Arg Val Val Asn Gln Ala Ser His Val Ser Ala
            20                  25                  30

Lys Thr Arg Glu Lys Val Glu Ala Ala Met Ala Glu Leu Asn Tyr Ile
        35                  40                  45

Pro Asn Arg Val Ala Gln Gln Leu Ala Gly Lys Gln Ser Leu Leu Ile
50                  55                  60

Gly Val Ala Thr Ser Ser Leu Ala Leu His Ala Pro Ser Gln Ile Val
65                  70                  75                  80

Ala Ala Ile Lys Ser Arg Ala Asp Gln Leu Gly Ala Ser Val Val Val
                85                  90                  95

Ser Met Val Glu Arg Ser Gly Val Glu Ala Cys Lys Ala Ala Val His
            100                 105                 110

Asn Leu Leu Ala Gln Arg Val Ser Gly Leu Ile Ile Asn Tyr Pro Leu
        115                 120                 125

Asp Asp Gln Asp Ala Ile Ala Val Glu Ala Ala Cys Thr Asn Val Pro
130                 135                 140

Ala Leu Phe Leu Asp Val Ser Asp Gln Thr Pro Ile Asn Ser Ile Thr
145                 150                 155                 160

Phe Ser His Glu Asp Glu Ala Arg Leu Gly Val Glu His Leu Val Ala
                165                 170                 175

Leu Gly His Gln Gln Ile Ala Leu Leu Ala Gly Asn Leu Ser Ser Val
            180                 185                 190

Gly Ser Arg Leu Arg Leu Ala Gly Trp His Lys Tyr Leu Thr Arg Asn
        195                 200                 205

Gln Ile Gln Pro Ile Ala Glu Arg Glu Gly Asp Trp Ser Ala Met Ser
210                 215                 220
```

-continued

```
Gly Phe Gln Gln Thr Met Gln Met Leu Asn Glu Gly Ile Val Pro Thr
225                 230                 235                 240

Ala Met Leu Val Ala Asn Asp Gln Met Ala Leu Gly Ala Met Arg Ala
                245                 250                 255

Ile Thr Glu Ser Gly Leu Arg Val Gly Ala Asp Ile Ser Val Val Gly
            260                 265                 270

Tyr Asp Asp Thr Glu Asp Ser Ser Cys Tyr Ile Pro Pro Leu Thr Thr
            275                 280                 285

Ile Lys Gln Asp Phe Arg Leu Leu Gly Gln Thr Ser Val Asp Arg Leu
        290                 295                 300

Leu Gln Leu Ser Gln Gly Gln Ala Val Lys Gly Asn Gln Leu Leu Pro
305                 310                 315                 320

Val Ser Leu Val Lys Arg Lys Thr Thr Leu Ala Pro Asn Thr Gln Thr
                325                 330                 335

Ala Ser Pro Arg Ala Leu Ala Asp Ser Leu Met Gln Leu Ala Arg Gln
            340                 345                 350

Val Ser Arg Leu Glu Ser Gly Gln
            355                 360
```

<210> SEQ ID NO 73
<211> LENGTH: 115
<212> TYPE: PRT
<213> ORGANISM: Artificial Sequence
<220> FEATURE:
<223> OTHER INFORMATION: Synthetic Sequence

<400> SEQUENCE: 73

```
Ala Leu Leu Asp Ser Leu His Glu Thr His Asp His Leu Ala Arg Ala
1               5                   10                  15

Ser Glu Ser Glu Asp Glu Leu Asp Pro Leu Gly Cys Met Arg Lys Leu
            20                  25                  30

Leu Leu Gln Val Phe Asn Glu Leu Val Leu Asp Ala Arg Thr Arg Arg
        35                  40                  45

Ile Asn Glu Ile Leu His His Lys Cys Glu Phe Thr Asp Asp Met Cys
    50                  55                  60

Glu Ile Arg Gln Gln Arg Gln Ser Ala Val Leu Asp Cys His Lys Gly
65                  70                  75                  80

Ile Thr Leu Ala Leu Ala Asn Ala Val Arg Arg Gly Gln Leu Pro Gly
                85                  90                  95

Glu Leu Asp Val Glu Arg Ala Ala Val Ala Met Phe Ala Tyr Val Asp
            100                 105                 110

Gly Leu Ile
        115
```

<210> SEQ ID NO 74
<211> LENGTH: 115
<212> TYPE: PRT
<213> ORGANISM: Artificial Sequence
<220> FEATURE:
<223> OTHER INFORMATION: Synthetic Sequence

<400> SEQUENCE: 74

```
Ala Leu Leu Asp Ser Leu Ile Glu Thr Ile Asp His Leu Ala Arg Ala
1               5                   10                  15

Ser Glu Ser Glu Asp Glu Leu Asp Pro Leu Gly Cys Met Arg Lys Leu
            20                  25                  30
```

```
Leu Leu Gln Val Phe Asn Glu Leu Val Leu Asp Ala Arg Thr Arg Arg
            35                  40                  45

Ile Asn Glu Ile Leu His His Lys Cys Glu Phe Thr Asp Asp Met Cys
 50                  55                  60

Glu Ile Arg Gln Gln Arg Gln Ser Ala Val Leu Asp Cys His Lys Gly
 65                  70                  75                  80

Ile Thr Leu Ala Leu Ala Asn Ala Val Arg Arg Gly Gln Leu Pro Gly
                85                  90                  95

Glu Leu Asp Val Glu Arg Ala Ala Val Ala Met Phe Ala Tyr Val Asp
                100                 105                 110

Gly Leu Ile
        115

<210> SEQ ID NO 75
<211> LENGTH: 115
<212> TYPE: PRT
<213> ORGANISM: Artificial Sequence
<220> FEATURE:
<223> OTHER INFORMATION: Synthetic Sequence

<400> SEQUENCE: 75

Ala Leu Leu Asp Ser Leu His Glu Thr His Asp His Leu Ala Arg Ala
 1               5                  10                  15

Ser Glu Ser Glu Asp Glu Leu Asp Pro Leu Gly Cys Met Arg Lys Leu
                20                  25                  30

Leu Leu Gln Val Phe Asn Glu Leu Val Leu Asp Ala Arg Thr Arg Arg
            35                  40                  45

Ile Asn Glu Ile Leu His His Lys Cys Glu Phe Thr Asp Asp Met Cys
 50                  55                  60

Glu Ile Arg Gln Gln Arg Gln Ser Ala Val Leu Asp Cys His Lys Gly
 65                  70                  75                  80

Ile Thr Leu Ala Leu Ala Asn Ala Val Arg Arg Gly Gln Leu Pro Gly
                85                  90                  95

Glu Leu Asp Val Glu Arg Ala Ala Val Ala Ser Leu Ala Phe Thr Trp
                100                 105                 110

Gly Leu Ile
        115

<210> SEQ ID NO 76
<211> LENGTH: 50
<212> TYPE: PRT
<213> ORGANISM: Artificial Sequence
<220> FEATURE:
<223> OTHER INFORMATION: Synthetic Sequence

<400> SEQUENCE: 76

Leu Asp Val Ser Asp Gln Thr Pro Ile Asn Ser Ile Ile Phe Ser Thr
 1               5                  10                  15

Glu Asp Ala Thr Arg Leu Gly Val Glu His Leu Val Ala Leu Gly His
                20                  25                  30

Gln Gln Ile Ala Leu Leu Ser Gly His Leu Ser Ser Val Met Ala Arg
            35                  40                  45

Leu Arg
    50

<210> SEQ ID NO 77
<211> LENGTH: 50
<212> TYPE: PRT
```

```
<213> ORGANISM: Artificial Sequence
<220> FEATURE:
<223> OTHER INFORMATION: Synthetic Sequence

<400> SEQUENCE: 77

Asn Asn Thr Ser Asn Gln Thr Pro Ile Asn Ser Ile Gly Phe Ser Gln
1               5                   10                  15

Glu Asp Ala Thr Arg Leu Gly Val Glu His Leu Val Ala Leu Gly His
            20                  25                  30

Gln Gln Ile Ala Leu Leu Ala Gly Pro Leu Ser Ser Val Ser Ala Arg
        35                  40                  45

Leu Arg
    50

<210> SEQ ID NO 78
<211> LENGTH: 40
<212> TYPE: PRT
<213> ORGANISM: Artificial Sequence
<220> FEATURE:
<223> OTHER INFORMATION: Synthetic Sequence

<400> SEQUENCE: 78

Ser Ile Thr Phe Ser His Glu Asp Glu Ala Arg Leu Gly Val Glu His
1               5                   10                  15

Leu Val Ala Leu Gly His Gln Gln Ile Ala Leu Leu Ala Gly Asn Leu
            20                  25                  30

Ser Ser Val Gly Ser Arg Leu Arg
        35                  40

<210> SEQ ID NO 79
<211> LENGTH: 116
<212> TYPE: PRT
<213> ORGANISM: Artificial Sequence
<220> FEATURE:
<223> OTHER INFORMATION: Synthetic Sequence

<400> SEQUENCE: 79

Ala Leu Leu Asp Ser Leu His Glu Thr His Asp His Leu Ala Arg Ala
1               5                   10                  15

Ser Glu Ser Glu Asp Glu Leu Asp Pro Leu Gly Cys Met Arg Lys Leu
            20                  25                  30

Leu Leu Gln Val Phe Asn Glu Leu Val Leu Asp Ala Arg Thr Arg Arg
        35                  40                  45

Ile Asn Glu Ile Leu His His Lys Cys Glu Phe Thr Asp Asp Met Cys
    50                  55                  60

Glu Ile Arg Gln Gln Arg Gln Ser Ala Val Leu Asp Cys His Lys Gly
65                  70                  75                  80

Ile Thr Ala Leu Ala Leu Ala Asn Ala Val Arg Arg Gly Gln Leu Pro
                85                  90                  95

Gly Glu Leu Asp Val Glu Arg Ala Ala Val Ala Met Phe Ala Tyr Val
            100                 105                 110

Asp Gly Leu Ile
        115

<210> SEQ ID NO 80
<211> LENGTH: 116
<212> TYPE: PRT
<213> ORGANISM: Artificial Sequence
<220> FEATURE:
<223> OTHER INFORMATION: Synthetic Sequence
```

```
<400> SEQUENCE: 80

Ala Leu Leu Asp Ser Leu Ile Glu Thr Ile Asp His Leu Ala Arg Ala
1               5                   10                  15

Ser Glu Ser Glu Asp Glu Leu Asp Pro Leu Gly Cys Met Arg Lys Leu
            20                  25                  30

Leu Leu Gln Val Phe Asn Glu Leu Val Leu Asp Ala Arg Thr Arg Arg
        35                  40                  45

Ile Asn Glu Ile Leu His His Lys Cys Glu Phe Thr Asp Asp Met Cys
    50                  55                  60

Glu Ile Arg Gln Gln Arg Gln Ser Ala Val Leu Asp Cys His Lys Gly
65                  70                  75                  80

Ile Thr Ala Leu Ala Leu Ala Asn Ala Val Arg Arg Gly Gln Leu Pro
                85                  90                  95

Gly Glu Leu Asp Val Glu Arg Ala Ala Val Ala Met Phe Ala Tyr Val
            100                 105                 110

Asp Gly Leu Ile
        115

<210> SEQ ID NO 81
<211> LENGTH: 116
<212> TYPE: PRT
<213> ORGANISM: Artificial Sequence
<220> FEATURE:
<223> OTHER INFORMATION: Synthetic Sequence

<400> SEQUENCE: 81

Ala Leu Leu Asp Ser Leu His Glu Thr His Asp His Leu Ala Arg Ala
1               5                   10                  15

Ser Glu Ser Glu Asp Glu Leu Asp Pro Leu Gly Cys Met Arg Lys Leu
            20                  25                  30

Leu Leu Gln Val Phe Asn Glu Leu Val Leu Asp Ala Arg Thr Arg Arg
        35                  40                  45

Ile Asn Glu Ile Leu His His Lys Cys Glu Phe Thr Asp Asp Met Cys
    50                  55                  60

Glu Ile Arg Gln Gln Arg Gln Ser Ala Val Leu Asp Cys His Lys Gly
65                  70                  75                  80

Ile Thr Ala Leu Ala Leu Ala Asn Ala Val Arg Arg Gly Gln Leu Pro
                85                  90                  95

Gly Glu Leu Asp Val Glu Arg Ala Ala Val Ala Ser Phe Ala Tyr Val
            100                 105                 110

Trp Gly Leu Ile
        115

<210> SEQ ID NO 82
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 82

Gly Ser Leu Ala Asn His Ala Ser Ser Gln Ala
1               5                   10

<210> SEQ ID NO 83
<211> LENGTH: 10
<212> TYPE: PRT
<213> ORGANISM: Artificial Sequence
<220> FEATURE:
```

<223> OTHER INFORMATION: Synthetic Sequence

<400> SEQUENCE: 83

Val Met Asn Asp Arg Met Gly Ser Gly Asp
1               5                   10

<210> SEQ ID NO 84
<211> LENGTH: 200
<212> TYPE: DNA
<213> ORGANISM: Artificial Sequence
<220> FEATURE:
<223> OTHER INFORMATION: Synthetic Sequence

<400> SEQUENCE: 84

```
gatataatgt gtggatactc agtgccctga ctatatctta atctagcggg ggaaggtttc    60
atatgcgtaa aggtgaagaa ctgttcaccg gtgttgttcc ctatattaca cacctatgag   120
tcacgggact gatatagaat tagatcgccc ccttccaaag tatacgcatt ccacttctt    180 gacaagtggc cacaacaagg                                              200
```

<210> SEQ ID NO 85
<211> LENGTH: 200
<212> TYPE: DNA
<213> ORGANISM: Artificial Sequence
<220> FEATURE:
<223> OTHER INFORMATION: Synthetic Sequence

<400> SEQUENCE: 85

```
gatataatgt gtggataatc cttatagacc gatcgcacgg tctataacca ttatcttaat    60
ctagcggggg aaggtttcat atgcgtaaag gtgaagaact ctatattaca cacctatgag   120
gaatatctgg ctagcgtgcc agatattggt aatagaatta gatcgccccc ttccaaagta   180
tacgcatttc cacttcttga                                              200
```

<210> SEQ ID NO 86
<211> LENGTH: 200
<212> TYPE: DNA
<213> ORGANISM: Artificial Sequence
<220> FEATURE:
<223> OTHER INFORMATION: Synthetic Sequence

<400> SEQUENCE: 86

```
gatataatgt gtggatacgt catgccctga cccttggaac agtattagcc aatcttaatc    60
tagcggggga aggtttcata tgcgtaaagg tgaagaactg ctatattaca cacctatgca   120
gtacgggact gggaaccttg tcataatcgg ttagaattag atcgcccct tccaaagtat    180 acgcatttcc acttcttgac                                              200
```

<210> SEQ ID NO 87
<211> LENGTH: 84
<212> TYPE: DNA
<213> ORGANISM: Artificial Sequence
<220> FEATURE:
<223> OTHER INFORMATION: Synthetic Sequence

<400> SEQUENCE: 87

```
atccctattg tccattaacc gtttgtcgat aataccata ataccatag atacagccca     60 cgcctctttc tccattactt tacc                                         84
```